United States Patent
Ueno et al.

(10) Patent No.: US 7,217,724 B2
(45) Date of Patent: May 15, 2007

(54) INDOLE, INDAZOLE, AND BENZAZOLE DERIVATIVE

(75) Inventors: Yoshihide Ueno, Osaka (JP); Tsuyoshi Noguchi, Takarazuka (JP); Kotaro Hirota, Toyonaka (JP); Nobuyuki Sawada, Nara-ken (JP); Takashi Umezome, Nishinomiya (JP)

(73) Assignee: Dainippon Sumitomo Pharma Co., Ltd., Osaka-shi (JP)

(*) Notice: Subject to any disclaimer, the term of this patent is extended or adjusted under 35 U.S.C. 154(b) by 104 days.

(21) Appl. No.: 10/517,446

(22) PCT Filed: Jun. 10, 2003

(86) PCT No.: PCT/JP03/07382

§ 371 (c)(1),
(2), (4) Date: Dec. 9, 2004

(87) PCT Pub. No.: WO03/106418

PCT Pub. Date: Dec. 24, 2003

(65) Prior Publication Data

US 2006/0063762 A1 Mar. 23, 2006

(30) Foreign Application Priority Data

Jun. 12, 2002 (JP) ............... 2002-171400
Feb. 4, 2003 (JP) ............... 2003-027529

(51) Int. Cl.
A61K 31/4439 (2006.01)
C07D 401/06 (2006.01)

(52) U.S. Cl. .................... 514/339; 546/277.4
(58) Field of Classification Search .............. None
See application file for complete search history.

(56) References Cited

U.S. PATENT DOCUMENTS

| | | | |
|---|---|---|---|
| 2,908,691 A | 10/1959 | Robinson | |
| 3,705,233 A | 12/1972 | Lunts | |
| 4,378,361 A | 3/1983 | Schromm et al. | |
| 4,540,581 A | 9/1985 | Nair | |
| 4,581,367 A | 4/1986 | Schromm et al. | |
| 4,647,563 A | 3/1987 | Schromm et al. | |
| 4,987,133 A | 1/1991 | Kurmeier et al. | |
| 4,990,509 A | 2/1991 | Arrowsmith et al. | |
| 5,030,640 A * | 7/1991 | Fisher et al. ............ | 514/339 |
| 5,114,952 A | 5/1992 | Arrowsmith et al. | |
| 5,817,689 A | 10/1998 | Kato et al. | |
| 6,310,050 B1 | 10/2001 | Advenier et al. | |
| 6,458,824 B1 | 10/2002 | Iwata et al. | |

FOREIGN PATENT DOCUMENTS

JP 8-165276 A 6/1996
JP 11-255743 A 9/1999
WO WO-96/16038 A1 5/1996
WO WO-01/17513 A2 3/2001
WO WO-02/64133 A1 8/2002
WO WO-02/74306 A1 9/2002

OTHER PUBLICATIONS

M.V. Sennitt et al., The Journal of Pharmacology and Experimental Therapeutics, vol. 285, No. 3, pp. 1084-1095, 1998.
J.E. Clifton et al., J. Med. Chem, vol. 25, No. 6, pp. 670-679, 1982.
Tetrahedron Lett., (2001), 42(43), p. 7671-4.
Chemical Abstracts, vol. 135, abs. No. 344399, RN=371752-47-5 (2003).
Chemical Abstracts, vol. 132, abs. No. 152006, RN=258267-67-3 (2003).
J. Org. Chem., (1991), 56(14), p. 4403-7.
J. Med. Chem., (1980), 23(11), p. 1268-9.
Can. Med. Chem., (1976), 54(8), p. 1262-77.
Chemical Abstracts, vol. 109, abs. No. 128763.
J. Med. Chem., (1982), 26(6), p. 670-9.

* cited by examiner

*Primary Examiner*—Joseph K. McKane
*Assistant Examiner*—Andrew B. Freistein
(74) *Attorney, Agent, or Firm*—Birch, Stewart, Kolasch & Birch, LLP

(57) ABSTRACT

The compound of the formula (I):

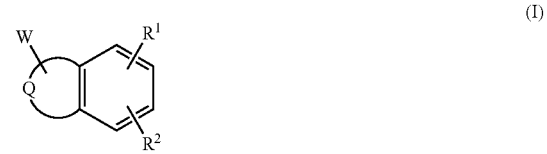

wherein W is a group of the following formula (VIII) binding to any possible position on the Q:

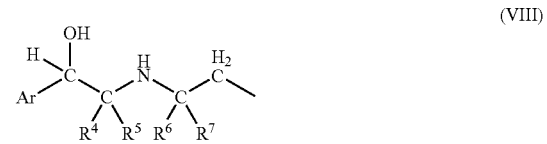

Q is, together with W, a group of the formula: —C(W)═C(R$^{3,4}$)—N(R$^3$)—, etc.; R$^{3,4}$ is H or optionally substituted lower alkyl; R$^4$, R$^5$, R$^6$, and R$^7$ are independently H or optionally substituted lower alkyl; R$^1$ is optionally substituted lower alkyl, etc.; R$^2$ is H, etc.; R$^3$ is H, etc.; Ar is phenyl, etc., or a pharmaceutically acceptable salt thereof, where these compounds exhibiting β3-adrenoceptor-stimulating activity and being useful as a medicament for treatment of obesity, etc.

11 Claims, No Drawings

INDOLE, INDAZOLE, AND BENZAZOLE DERIVATIVE

This is a National filing under 35 U.S.C. § 371 of PCT/JP03/07382, filed Jun. 10, 2003.

TECHNICAL FIELD

The present invention relates to a novel indole, indazole, and benzazole derivative, or a pharmaceutically acceptable salt thereof, which are useful as a medicament.

PRIOR ART

It has been known that β-adrenoceptor of sympathetic nerve has three subtypes, which are classified as β1, β2 and β3-receptors, and that these receptors distribute in specific tissues in the living body, and each exhibits inherent functions thereof.

For instance, β1-adrenoceptor mainly exists in the heart, and the stimulus mediated by β1-adrenoceptor may induce an increase in heart rate as well as the enhancement of cardiac contraction force. On the other hand, β2-adrenoceptors mainly exist in the smooth muscle of blood vessels, the bronchial tube and the uterus, and the stimulus mediated by β2-adrenoceptor may dilate blood vessels and widen the airways, or inhibit the uterine contraction, respectively. In addition, it has been reported that β3-adrenoceptor mainly exists in the adipocytes, the gallbladder and the intestine, and further in the brain, the liver, the stomach, the prostate gland, etc. as well. The stimulus mediated by β3-adrenoceptor may induce the increased lipolysis, the decreased intestinal motility, the increased glucose uptake, and the anti-depression effect, etc.

Further, it has been also reported recently that β3-adrenoceptor mainly exists in the human urinary bladder, which is relaxed by a β3-adrenoceptor-stimulating agent.

Hitherto, many β1-adrenoceptor-stimulating agents and β2-adrenoceptor-stimulating agents have been developed, and have been used as cardiotonic agents, bronchodilators, or protectants for threatened abortion/threatened premature labor.

On the other hand, β3-adrenoceptor-stimulating agents have been found to be useful as an agent for treatment or prophylaxis of obesity, hyperglycemia, diseases caused by increased intestinal motility, frequent urination or urinary incontinence, depression, bilestone, or diseases caused by the increased biliary tract motility. At the present, the research and development of excellent β3-adrenoceptor-stimulating agents have actively been done, and some compounds having β3-adrenoceptor-stimulating activity have been known (e.g., JP-A-11-255743), but none of these compounds has not been put on the market as a β3-adrenoceptor-stimulating agent.

Under the above circumstance, it has highly been desired to develop a novel β3-adrenoceptor-stimulating agent having an excellent β3-adrenoceptor-stimulating activity.

More preferably, it has been desired to develop a novel β3-adrenoceptor-stimulating agent with excellent adrenoceptor selectivity wherein side effects such as cardiopalmus or the finger tremor caused by β1 and/or β2-adrenoceptor-stimulating activity are reduced by having a more potent β3-adrenoceptor-stimulating activity than β1- and/or β2-adrenoceptor-stimulating activities.

DISCLOSURE OF INVENTION

An object of the present invention is to provide a novel β3-adrenoceptor-stimulating agent having an excellent β3-adrenoceptor-stimulating activity, more preferably a novel β3-adrenoceptor-stimulating agent with excellent adrenoceptor selectivity where side effects such as cardiopalmus or the finger tremor caused by β1- and/or β2-adrenoceptor-stimulating activities are reduced by having a more potent β3-adrenoceptor-stimulating activity than β1- and/or β2-adrenoceptor-stimulating activities.

The present inventors have intensively studied in order to solve the above problems, and have found that indole, indazole and benzazole derivatives of the following formula (I) and a pharmaceutically acceptable salt thereof may exhibit an excellent β3-adrenoceptor-stimulating activity, and they have finally accomplished the present invention.

Among the β3-adrenoceptor-stimulating agents of the present invention having β3-adrenoceptor-stimulating activity, the present inventors have further found the compounds of the following [2] as a compound having less β1- and/or β2-adrenoceptor-stimulating activities, which are explained below.

The present inventors have found that the compound disclosed in JP-A-11-255743 of the following formula:

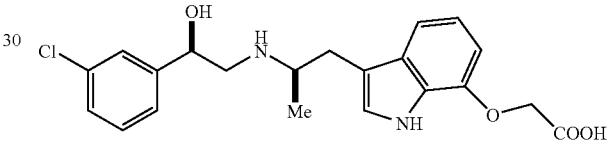

does not exhibit β1- and/or β2-adrenoceptor-stimulating activities in the conventional system for evaluating β1- and/or β2-adrenoceptor-stimulating activities (for example, by the method disclosed in Experiment 1 of the present invention), but exhibits β1- and/or β2-adrenoceptor-stimulating activities in the evaluation system using tissues (for example, by the method disclosed in Experiment 2 of the present invention). This fact is of a problem being pointed out by Sennitt et al. as a divergence in the results obtained with using cells and tissues (cf., J. Pharmacol. Exp. Ther. vol. 285, p. 1084–1095, (1998)).

Then, the present inventors have further studied, and have found that the compound of the following feature [2] wherein $R^1$ is a group of the formula: —X—$R^{1e}$—C(=O)N$R^{1a}R^{1b}$ or —X—$R^{1e}$—C(=O)O$R^{1a}$, X is a group of the formula: —O— or —S—, and $R^{1e}$ is a group of the formula: —C$R^{1f}R^{1g}$— ($R^{1f}$ and $R^{1g}$ are independently a hydrogen atom, an optionally substituted lower alkyl group, an optionally substituted aryl group, or an optionally substituted aralkyl group, or both combine each other together with the carbon atom to which they bond and form an optionally substituted cycloalkane ring, provided that $R^{1f}$ and $R^{1g}$ are not simultaneously a hydrogen atom) exhibits a low β1- and/or β2-adrenoceptor-stimulating activities even in the evaluation system using tissues, as compared to the compounds where $R^{1f}$ and $R^{1g}$ in the same partial structure are simultaneously a hydrogen atom such as the compounds disclosed in the above JP-A-11-255743.

From the above, it is confirmed that the compound of the following feature [2] is an excellent compound as a medicament, because the side effects such as cardiopalmus or the finger tremor are reduced due to the low β1- and/or β2-adrenoceptor-stimulating activities.

The present invention concerns the following features.

[1] A compound of the formula (I):

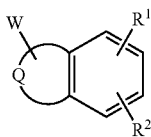

(I)

wherein W is a group of the following formula (VIII) binding to any possible position on the Q;

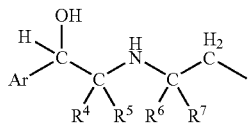

(VIII)

Q is, together with W, a group of the formula: —C(W)=C(R$^{3A}$)—N(R$^3$)—, —C(R$^{3A}$)=C(W)—N(R$^3$)—, —C(R$^{3A}$)=C(R$^{3B}$)—N(W)—, —C(W)=N—N(R$^3$)—, —C(R$^{3A}$)=N—N(W)—, —N=C(W)—N(R$^3$)—, —N=C(R$^{3A}$)—N(W)—, —C(W)=N—O—, or —C(W)=N—S—; R$^{3A}$ and R$^{3B}$ are independently a hydrogen atom or an optionally substituted lower alkyl group;

R$^4$, R$^5$, R$^6$, and R$^7$ are independently a hydrogen atom or an optionally substituted lower alkyl group;

R$^1$ is an optionally substituted lower alkyl group, or a group of the formula: —X—R$^{1e}$—C(=O)NR$^{1a}$R$^{1b}$, —X—R$^{1e}$—C(=O)OR$^{1a}$ or —X—R$^{1d}$ (wherein X is a direct bond or a group of the formula: —O—, —S—, —N(R$^{1c}$)—, —N(R$^{1c}$)C(=O)—, —C(=O)N(R$^{1c}$)—, —N(R$^{1c}$)SO$_2$—, —SO$_2$N(R$^{1c}$)—, or —C(=O)NHSO$_2$—, R$^{1e}$ is a direct bond or an optionally substituted lower alkylene group, R$^{1a}$, R$^{1b}$, and R$^{1c}$ are independently a hydrogen atom, an optionally substituted lower alkyl group, an optionally substituted aralkyl group, an optionally substituted aryl group, an optionally substituted cycloalkyl group, or an optionally substituted heterocyclic group, or R$^{1a}$ and R$^{1b}$ may combine each other, and with the adjacent nitrogen atom to which they bond, form a saturated 3- to 8-membered cyclic amino group optionally having a group of the formula: —O— or —NH— within the ring (said saturated cyclic amino group being substituted or unsubstituted), R$^{1d}$ is a hydrogen atom, an optionally substituted lower alkyl group, an optionally substituted phenyl group, or an optionally substituted cycloalkyl group (a —CH$_2$— moiety of said cycloalkyl group optionally being replaced by one or more groups of the formula: —O— or —N(R$^{1a}$)—, which are the same or different));

R$^2$ is a hydrogen atom, a halogen atom, an optionally substituted lower alkyl group, an optionally substituted lower alkenyl group, an optionally substituted amino group, a hydroxy group, a lower alkoxy group, or R$^1$ and R$^2$ may combine each other and form a methylenedioxy group and said methylenedioxy group may optionally be substituted by a carboxyl group or a lower alkoxycarbonyl group;

R$^3$ is a hydrogen atom or an optionally substituted lower alkyl group, or R$^1$ and R$^3$ may combine each other and form a divalent group of the formula: —X—R$^{1e}$—C(=O)— (provided that the bond at the carbonyl side of the above formula binds to the atom to which R$^3$ of the compound of the formula (I) attaches);

Ar is a group of the following formula (IX), formula (X), or formula (XIII);

A group of Formula (IX):

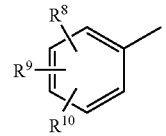

(IX)

(in which R$^8$ is a hydrogen atom, a halogen atom, a trifluoromethyl group, an optionally substituted lower alkyl group, a lower alkoxy group, a lower alkoxycarbonyl group, a carboxyl group, an optionally substituted benzyloxy group, a hydroxy group, a nitro group, an optionally substituted lower alkylsulfonyl group, an optionally substituted benzenesulfonyl group, an optionally substituted lower alkylthio group, an optionally substituted lower alkylsulfinyl group, a mercapto group, a cyano group, an amino group, an optionally substituted lower alkanoylamino group, an optionally substituted mono- or di-lower alkylamino group, an optionally substituted lower alkylsulfonylamino group, or an optionally substituted benzenesulfonyl-amino group;

R$^9$ and R$^{10}$ are independently a hydrogen atom, a halogen atom, an optionally substituted lower alkyl group, a lower alkoxy group, a lower alkoxycarbonyl group, a hydroxy group, an amino group or an optionally substituted mono- or di-lower alkylamino group, or two of R$^8$, R$^9$, and R$^{10}$ may combine each other and form a methylene-dioxy group, and said methylenedioxy group may optionally be substituted by a carboxyl group or a lower alkoxycarbonyl group, or two of R$^8$, R$^9$, and R$^{10}$ may combine each other and form a group of the formula: —NR$^{8a}$C(=O)CR$^{8b}$=CR$^{8c}$—(R$^{8a}$, R$^{8b}$, and R$^{8c}$ being the same or different and each a hydrogen atom or an optionally substituted lower alkyl group);

provided that when R$^1$ is a group of the formula: —O—CH$_2$—C(=O)OR$^{1a}$ and all of R$^4$, R$^5$, R$^9$, and R$^{10}$ are a hydrogen atom, then R$^8$ is not a halogen atom or a trifluoromethyl group substituting on the 3-position):

A group of Formula (X):

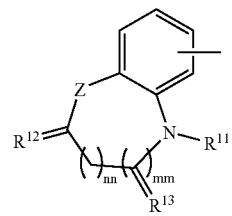

(X)

(in which Z is an oxygen atom or a sulfur atom;

R$^{11}$ is a hydrogen atom, a lower alkyl group, or a group of the formula: —SO$_2$R$^{14}$ or the formula: —NR$^{15}$R$^{16}$ (R$^{14}$ is an optionally substituted lower alkyl group, an optionally substituted phenyl group, an optionally substituted aralkyl group, R$^{15}$ and R$^{16}$ are independently a hydrogen atom, an optionally substituted lower alkyl group, or an optionally substituted benzyl group);

$R^{12}$ is an oxygen atom, a sulfur atom or $H_2$;
$R^{13}$ is an oxygen atom or $H_2$;
nn and mm are each 0 or 1): or
A group of Formula (XIII):

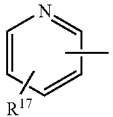

(XIII)

(in which $R^{17}$ is a hydrogen atom, a halogen atom, or a cyano group), or a pharmaceutically acceptable salt thereof.

[2] The compound according to the above [1], wherein $R^1$ is a group of the formula: —X—$R^{1e}$—C(=O)$NR^{1a}R^{1b}$ or the formula: —X—$R^{1e}$—C(=O)$OR^{1a}$, or $R^1$ and $R^3$ may combine each other and form a divalent group of the formula: —X—$R^{1e}$—C(=O)— (where X is a group of the formula: —O— or —S— and $R^{1e}$ is a group of the formula: —$CR^{1f}R^{1g}$— ($R^{1f}$ and $R^{1g}$ are independently a hydrogen atom, an optionally substituted lower alkyl group, an optionally substituted cycloalkyl group, an optionally substituted aryl group, or an optionally substituted aralkyl group, or both may combine each other, and with the carbon atom to which they bond, form an optionally substituted cycloalkane ring, provided that both $R^{1f}$ and $R^{1g}$ are not simultaneously a hydrogen atom)),
or a pharmaceutically acceptable salt thereof.

[3] The compound according to the above [1] or [2], which is a compound of the formula (I'):

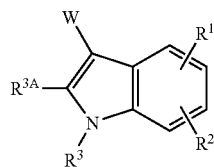

(I')

wherein $R^1$, $R^2$, $R^3$, $R^{3A}$, and W are as defined in the above [1],
or a pharmaceutically acceptable salt thereof.

[4] The compound according to the above [3], wherein $R^1$ binds to the 5-, 6- or 7-position of the indole ring of the compound of the formula (I'), and $R^2$ is a hydrogen atom,
or a pharmaceutically acceptable salt thereof.

[5] The compound according to the above [3], wherein $R^2$ is a group other than a hydrogen atom, and one of $R^1$ and $R^2$ binds to the 6-position of the indole ring of the compound of the formula (I'), and the other binds to the 7-position thereof,
or a pharmaceutically acceptable salt thereof.

[6] The compound according to any one of the above [1] to [5], wherein Ar is a group selected from the following substituents:

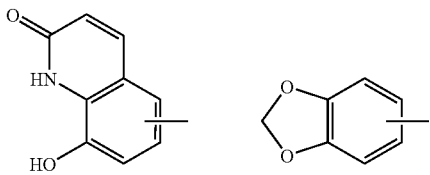

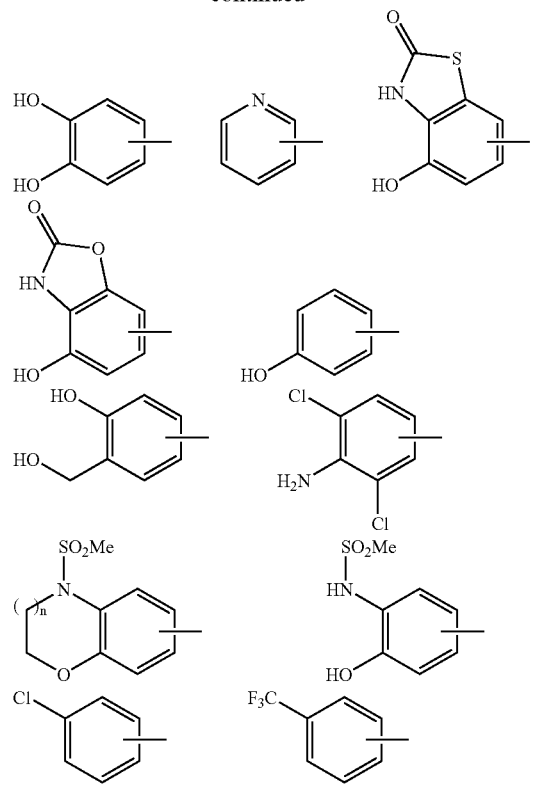

(wherein n is 0, 1, or 2),
or a pharmaceutically acceptable salt thereof.

[7] The compound according to any one of the above [1] to [6], wherein $R^1$ is a group of the formula: —X—$R^{1e}$—C(=O)$NR^{1a}R^{1b}$ or —X—$R^{1e}$—C(=O)$OR^{1a}$;
X is a direct bond or a group of the formula: —O—;
$R^{1a}$ and $R^{1b}$, when it exists, are independently selected from
(i) a hydrogen atom,
(ii) an unsubstituted lower alkyl group,
(iii) a lower alkyl group being substituted by one or more substituents, which are the same or different, and said substituent(s) are selected from a carboxyl group, a lower alkoxycarbonyl group, an amino group, a hydroxy group, an alkoxy group, a mercapto group, an alkylthio group, a carbamoyl group, an indolyl group, a guanidino group, an imidazolyl group, and a phenyl group optionally being substituted by a hydroxy group, or
(iv) a saturated 3- to 8-membered cyclic amino group which is formed by combining $R^{1a}$ and $R^{1b}$ together with the adjacent nitrogen atom to which they bond, and optionally has a group of the formula: —O— or —NH— within the ring (said saturated cyclic amino group being unsubstituted, or optionally being substituted by a carboxyl group or a lower alkoxycarbonyl group), or
a pharmaceutically acceptable salt thereof.

[8] The compound according to the above [7], wherein $R^1$ is a group of the formula: —X—$R^{1e}$—C(=O)$NR^{1a}R^{1b}$ (where the moiety of the formula: $NR^{1a}R^{1b}$ is an amino acid or amino acid ester residue binding to the carbonyl group of the above formula at the N-terminus thereof, and $R^{1a}$ binds to the nitrogen atom at the N-terminus thereof when $R^{1a}$ and $R^{1b}$ do not form a cyclic group), and
X and $R^{1e}$ are a direct bond,
or a pharmaceutically acceptable salt thereof.

[9] The compound according to any one of the above [1] to [3], wherein $R^1$ is a group of the formula: —C(=O)NR$^{1a}$R$^{1b}$, R$^{1a}$ and R$^{1b}$ are independently a hydrogen atom or an optionally substituted lower alkyl group, or R$^{1a}$ and R$^{1b}$ may combine each other, and with the adjacent nitrogen atom to which they bond, form a saturated 3- to 8-membered cyclic amino group optionally having a group of the formula: —O— or —NH— within the ring (said saturated cyclic amino group being unsubstituted, or optionally being substituted by a carboxyl group or a lower alkoxy-carbonyl group);
$R^2$ is a hydrogen atom, a halogen atom, an optionally substituted lower alkyl group, a hydroxy group, or a lower alkoxy group;
both of $R^4$ and $R^5$ are a hydrogen atom;
Ar is a group of the formula (XVI):

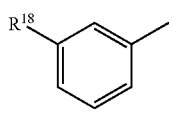

(XVI)

(in which $R^{18}$ is a halogen atom or a trifluoromethyl group), or a pharmaceutically acceptable salt thereof.
[10] The compound according to any one of the above [2] to [6], wherein $R^1$ is a group of the formula: —X—CR$^{1f}$R$^{1g}$—C(=O)OR$^{1a}$, or a pharmaceutically acceptable salt thereof.
[11] The compound according to any one of the above [2] to [6], wherein X is a group of the formula: —O—, or a pharmaceutically acceptable salt thereof.
[12] The compound according to any one of the above [1], [2], [6] to [11], wherein Q is, together with W, a group of the formula: —C(W)=C(R$^{3A}$)—N(R$^3$)— or —C(R$^{3A}$)=C(W)—N(R$^3$)—, or a pharmaceutically acceptable salt thereof.
[13] A pharmaceutical composition comprising as an active ingredient the compound as set forth in any one of the above [1] to [12], or a pharmaceutically acceptable salt thereof.
[14] An agent for treatment of obesity, hyperglycemia, frequent urination, urinary incontinence, depression, or bilestone, which comprises as an active ingredient the compound as set forth in any one of the above [1] to [12], or a pharmaceutically acceptable salt thereof.
[15] A method for treatment of obesity, hyperglycemia, frequent urination, urinary incontinence, depression, or bilestone, which comprises administering to a patient in need an effective amount of the compound as set forth in any one of the above [1] to [12], or a pharmaceutically acceptable salt thereof.
[16] A use of the compound as set forth in any one of the above [1] to [12], or a pharmaceutically acceptable salt thereof, in preparation of an agent for treatment of obesity, hyperglycemia, frequent urination, urinary incontinence, depression, or bilestone.

BEST MODE FOR CARRYING OUT THE INVENTION

Each group in the present invention is explained below. Unless defined otherwise, the definition for each group should be applied to cases wherein said group is a part of another substituent.

The "substituted benzene", the "substituted phenyl group" and the "substituted aryl group" may have one or more substituents, and such substituents include, for example, a halogen atom, a $C_1$–$C_8$ haloalkyl group, a $C_1$–$C_8$ alkyl group, a $C_2$–$C_8$ alkenyl group, a $C_1$–$C_8$ alkoxy group, a hydroxy group, a nitro group, a cyano group, a mercapto group, a group of the formula: —S(O)$_p$($C_1$–$C_8$ alkyl), a carboxyl group, a $C_1$–$C_8$ alkoxycarbonyl group, an aryloxycarbonyl group, an aralkyloxycarbonyl group, an optionally substituted amino group, an optionally substituted amido group, an optionally substituted urea group, an optionally substituted sulfonamido group, a group of the formula: —C(O)NHSO$_2$($C_1$–$C_8$ alkyl), etc. (in the above formula, p is 0, 1 or 2, hereinafter the same).

The "aryl group" includes, for example, an aryl group having not more than 10 carbon atoms such as phenyl, 1- or 2-naphthyl, etc.

The aryl moiety of the "aralkyl group" includes, for example, an aryl group having not more than 10 carbon atoms such as phenyl, 1- or 2-naphthyl, etc., and the alkyl moiety thereof includes, for example, an alkyl group having not more than 5 carbon atoms such as methyl, ethyl, propyl, butyl, etc. Representative aralkyl group is, for example, benzyl group, 1- or 2-phenetyl group, etc.

The "substituted aralkyl group" may have one or more substituents on the aryl moiety and/or the alkyl moiety, and such substituents include, for example, a halogen atom, a $C_1$–$C_8$ haloalkyl group, a $C_1$–$C_8$ alkyl group, a $C_2$–$C_8$ alkenyl group, a $C_1$–$C_8$ alkoxy group, a hydroxy group, a nitro group, a mercapto group, a group of the formula: —S(O)$_p$($C_1$–$C_8$ alkyl), a carboxyl group, a $C_1$–$C_8$ alkoxycarbonyl group, an aryloxycarbonyl group, an aralkyloxycarbonyl group, an optionally substituted amino group, an optionally substituted amido group, an optionally substituted urea group, an optionally substituted sulfonamido group, a group of the formula: —C(O)NHSO$_2$($C_1$–$C_8$ alkyl), etc.

The "alkyl group" includes "lower alkyl group". The "lower alkyl group" includes, unless defined otherwise, a straight chain or branched chain saturated $C_1$–$C_8$ hydrocarbon group, for example, methyl, ethyl, n-propyl, isopropyl, n-butyl, t-butyl, isobutyl, and sec-butyl, and further includes higher homologs and isomers such as n-pentyl, n-hexyl, 2-methylpentyl, etc.

The "substituted alkyl group", the "substituted alkenyl group", and the "substituted alkylene group" may have one or more substituents, and such substituents include, for example, a halogen atom, a $C_1$–$C_8$ alkoxy group, a $C_1$–$C_8$ alkoxycarbonyloxy group, a $C_3$–$C_8$ cycloalkyloxycarbonyloxy group, a hydroxy group, a mercapto group, a group of the formula: —S(O)$_p$($C_1$–$C_8$ alkyl), a $C_3$–$C_8$ cycloalkyl group, an optionally substituted amino group, a carboxyl group, a $C_1$–$C_8$ alkoxy-carbonyl group, an aryloxycarbonyl group, an aralkyloxycarbonyl group, an optionally substituted heterocyclic group, an optionally substituted aryl group, an oxo group, etc.

The "alkenyl group" includes "lower alkenyl group". The "lower alkenyl group" includes a straight chain or branched chain alkenyl group having not more than 8 carbon atoms, for example, vinyl, allyl, propenyl, 2-propenyl, butenyl, pentenyl, hexenyl, etc.

The "alkylene group" includes "lower alkylene group". The "lower alkylene group" includes a straight chain or branched chain alkylene group having not more than 8 carbon atoms, for example, methylene, ethylene, trimethylene, tetramethylene, pentamethylene, hexamethylene, etc.

The "optionally substituted alkoxy group" includes an optionally substituted alkyl group having an oxygen atom at the binding position thereof.

The "optionally substituted alkylthio group" includes an optionally substituted alkyl group having a sulfur atom at the binding position thereof.

The "optionally substituted alkylsulfinyl group" includes an optionally substituted alkyl group having a group of the formula: —SO— at the binding position thereof.

The "optionally substituted alkylsulfonyl group" includes an optionally substituted alkyl group having a group of the formula: —SO$_2$— at the binding position thereof.

The "optionally substituted alkoxycarbonyl group" includes an optionally substituted alkyl group having a group of the formula: —OC(=O)— at the binding position thereof via the oxygen atom side of the group of the formula: —OC(=O)—.

The "optionally substituted alkanoyl group" includes an optionally substituted alkyl group having a group of the formula: —C(=O)— at the binding position thereof.

The "optionally substituted alkanoylamino group" includes an optionally substituted alkyl group having a group of the formula: —NHC(=O)— at the binding position thereof via the carbon atom side of the group of the formula: —NHC(=O)—, wherein the nitrogen atom is optionally substituted by a $C_1$–$C_8$ haloalkyl group, a $C_1$–$C_8$ alkyl group, a $C_2$–$C_8$ alkenyl group, a $C_3$–$C_8$ cycloalkyl group, a phenyl group, an aralkyl group, a heterocyclic group, etc.

The "optionally substituted alkylaminocarbonyl group" includes an optionally substituted alkyl group having a group of the formula: —C(=O)NH— at the binding position thereof via the nitrogen atom side of the group of the formula: —C(=O)NH—, wherein the nitrogen atom is optionally substituted by a $C_1$–$C_8$ haloalkyl group, a $C_1$–$C_8$ alkyl group, a $C_2$–$C_8$ alkenyl group, a $C_3$–$C_8$ cycloalkyl group, a phenyl group, an aralkyl group, a heterocyclic group, etc.

The "halogen atom" includes chorine atom, bromine atom, fluorine atom, iodine atom, etc.

The "optionally substituted mono- or di-lower alkylamino group" includes an amino group where one or both of hydrogen atoms of the amino group are independently substituted by an optionally substituted alkyl group.

The "optionally substituted amido group" is a group of the formula: —NR$^{19}$COR$^{20}$, where R$^{19}$ is a hydrogen atom, a $C_1$–$C_8$ alkyl, etc., and R$^{20}$ is a $C_1$–$C_8$ haloalkyl group, a $C_1$–$C_8$ alkyl group, a $C_2$–$C_8$ alkenyl group, a $C_3$–$C_8$ cycloalkyl group, a phenyl group, an aralkyl group, a heterocyclic group, etc.

The "optionally substituted sulfonamido group" is a group of the formula: —NR$^{21}$SO$_2$R$^{22}$, where R$^{21}$ is a hydrogen atom, $C_1$–$C_8$ alkyl, etc., and R$^{22}$ is a $C_1$–$C_8$ haloalkyl group, a $C_1$–$C_8$ alkyl group, a $C_2$–$C_8$ alkenyl group, a $C_3$–$C_8$ cycloalkyl group, a phenyl group, an aralkyl group, a heterocyclic group, etc.

The "optionally substituted alkylsulfonylamino group" is a group of the formula: —NR$^{23}$SO$_2$R$^{24}$, where R$^{23}$ is a $C_1$–$C_8$ haloalkyl group, a $C_1$–$C_8$ alkyl group, a $C_2$–$C_8$ alkenyl group, a $C_3$–$C_8$ cycloalkyl group, a phenyl group, an aralkyl group, a heterocyclic group, etc., and R$^{24}$ is a $C_1$–$C_8$ alkyl group, etc.

The "substituted amino group" is an amino group where one or both of hydrogen atoms are independently substituted by a $C_1$–$C_8$ alkyl group, a $C_2$–$C_8$ alkenyl group, a $C_1$–$C_8$ alkoxy group, a hydroxy group, etc.

The cycloalkyl group includes, for example, a 3- to 8-membered cycloalkyl group such as cyclopropyl, cyclobutyl, cyclopentyl, cyclohexyl, cycloheptyl, etc.

The cycloalkane ring, which is formed by combining R$^{1f}$ and R$^{1g}$ of the group of the formula: —CR$^{1f}$R$^{1g}$— together with the nitrogen atom to which they bond, includes, for example, a 3- to 8-membered cyclo-alkane ring wherein two hydrogen atoms on the same carbon atom are replaced by two bonds, such as cyclopropane, cyclobutane, cyclo-heptane, cyclohexane, cycloheptane, etc.

The "substituted cycloalkyl group" and the "substituted cycloalkane ring" may have one or more substituents, and such substituents are, in addition to an alkyl group and an aralkyl group, the same substituents for the "substituted alkyl group" as mentioned above.

The "heterocycle" includes a 5-membered or 6-membered aromatic heterocycle or a saturated or unsaturated aliphatic heterocycle, for example, a 5-membered or 6-membered heterocyclic group consisting of 1 to 4 heteroatoms selected from a nitrogen atom, an oxygen atom and a sulfur atom and carbon atoms, such as pyridine ring, imidazole ring, pyrazine ring, pyrimidine ring, pyridazine ring, thiazole ring, isothiazole ring, isothiazoline ring, oxazole ring, isoxazole ring, isoxazoline ring, furan ring, thiophene ring, pyrrole ring, pyrroline ring, pyrrolidine ring, pyrazoline ring, imidazoline ring, tetrahydro-pyrane ring, tetrahydrofuran ring, tetrahydrothiophene ring, pyrrolidine ring, piperidine ring, etc.

The substituents of the "heterocycle" are 1 to 2 groups independently selected from a halogen atom, a $C_1$–$C_8$ alkyl group, a $C_2$–$C_8$ alkenyl group, a $C_1$–$C_8$ alkoxy group, a hydroxy group, a mercapto group, a group of the formula: —S(O)$_p$($C_1$–$C_8$ alkyl), a carboxyl group, a $C_1$–$C_8$ alkoxycarbonyl group, an aryloxycarbonyl group, an aralkyloxycarbonyl group, an amino group, an alkylamino group, an aryl group, an aralkyl group, and an oxo group, if the substitution is available.

The "heterocyclic group" includes a group where the hydrogen atom of the above "heterocycle" is replaced by a bond, and the substituents of the "heterocyclic group" are the same substituents as those for the above "heterocycle".

The 3- to 8-membered saturated cyclic amino group optionally having a group of the formula: —O— or —NH— within the ring includes, for example, 1-pyrrolidinyl, piperidino, 1-piperazinyl, morpholino, etc.

The substituents of the 3- to 8-membered saturated cyclic amino group optionally having a group of the formula: —O— or —NH— within the ring includes, for example, the same substituents as those for the "heterocycle" as mentioned above.

The "amino acid residue" includes a group where the hydrogen atom at the N-terminus of an amino acid is replaced by a bond. The "amino acid ester residue" includes a group where the hydrogen atom of the carboxyl group (at least one carboxyl group when two or more exist) of an amino acid residue is replaced by an alkyl group, an aryl group, or an aralkyl group.

The indolyl group includes 1-indolyl group and 2-indolyl group.

The imidazolyl group includes 2-imidazolyl group, 4-imidazolyl group, and 5-imidazolyl group.

When $R^1$ of the compound of the formula (I) is a group of the formula: $-X-R^{1e}-C(=O)OR^{1a}$, more concretely, such a group is a group of the following formula:

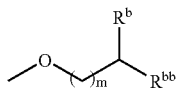

(III)

(in which $R^b$ is a hydrogen atom, an optionally substituted lower alkyl group, an optionally substituted lower alkoxycarbonyl group or a carboxyl group, $R^{bb}$ is an optionally substituted lower alkoxycarbonyl group or a carboxyl group, and m is an integer of 0–3)

When $R^1$ of the compound of the formula (I) is a group of the formula: $-X-R^{1d}$, more concretely, such a group is a group of $-O(CH_2)_p-R^c$ (in which $R^c$ is an optionally substituted lower alkanoyl group, a hydroxy group, a cyano group, an optionally substituted phenyl group, an optionally substituted heterocyclic group, an optionally substituted mono- or di-lower alkylaminocarbonyl group, or a group of the following formula (Va):

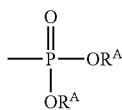

(Va)

(wherein $R^A$ is a hydrogen atom or a lower alkyl group), and p is an integer of 1 to 4).

The compounds of the present invention are prepared, for example, by the following Processes.

Process (a):

Among the present compounds, the compound wherein the substituents $R^4$ and $R^5$ in the formula (VIII) are a hydrogen atom, i.e., the compound of the following formula (I-a):

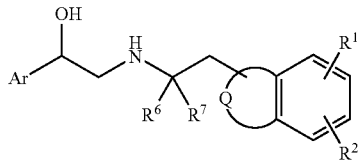

(I-a)

(in which $R^1$, $R^2$, $R^6$, $R^7$ and Ar are as defined above, and Q is the same as defined for the compound of the formula (I) except that W is replaced by a group of the formula: $ArCH(OH)CH_2NHCR^6(R^7)CH_2-$) may be prepared by reacting a compound of the following formula (XVII):

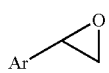

(XVII)

(in which Ar is as defined above), with a compound of the following formula (XVIII):

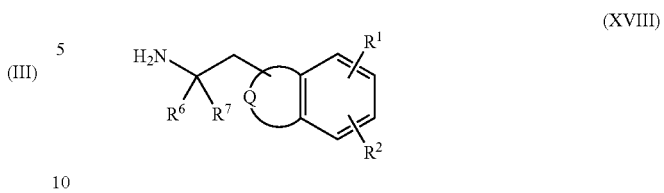

(XVIII)

(in which $R^1$, $R^2$, $R^6$, and $R^7$ are as defined above, and Q is the same as defined for the compound of the formula (I) except that W is replaced by a group of the formula: $NH_2CR^6(R^7)CH_2-$), or a salt thereof.

This reaction is carried out in a suitable solvent or without a solvent. The solvent to be used should be selected according to the kinds of the starting compounds, etc., and includes, for example, alcohols such as methanol, ethanol, isopropyl alcohol, ketones such as acetone, methyl ethyl ketone, halogenated hydrocarbons such as methylene chloride, chloroform, ethers such as diethyl ether, tetrahydrofuran, dioxane, aromatic hydrocarbons such as benzene, toluene, ethyl acetate, N,N-dimethylformamide, dimethylsulfoxide, etc., and these solvents may be used alone or in a mixture of two or more solvents.

Besides, when the compound of the formula (XVIII) is in the form of an acid addition salt, for example, a salt with an inorganic acid such as hydrochloride, hydrobromide, etc., or a salt with an organic acid such as oxalate, maleate, fumarate, etc., this reaction is carried out in the presence of a base. Example of base is an alkali metal hydrogen carbonate such as sodium hydrogen carbonate, potassium hydrogen carbonate, an alkali metal carbonate such as sodium carbonate, potassium carbonate, or an organic base such as triethylamine, tributylamine, diisopropyl ethyl-amine, N-methylmorpholine, etc.

The reaction temperature may vary according the kinds of the starting compounds, etc., but this reaction is usually carried out at a temperature of from room temperature to about 150° C., preferably at a temperature of from about 25° C. to about 100° C.

In this Process, when the starting compound of the formula (XVII) and the formula (XVIII) have an asymmetric carbon atom, the configuration based on said asymmetric carbon atom is maintained into the reaction product of the formula (I-a). That is, for example, the present compound in the (R,R)-configuration is obtained from the compound of the formula (XVII) in the R-configuration and the compound of the formula (XVIII) in the R-configuration.

The optically active compound of the above formula (XVII) may be prepared according to the method disclosed in the literatures (the method of Bloom, J. D. et al. (J. Med. Chem., 35, 3081–3084 (1992)), or the method of Eliel, E. L. and Delmonte, D. W. (J. Org. Chem., 21, 596–597 (1956))).

The optically active compound of the above formula (XVIII) may be prepared according to the method disclosed in the literatures (the method of Repke, D. B. and Ferguson, W. J. (J. Heterocycl. Chem., 13, 775–778 (1976))).

The starting compound of the above formula (XVIII) may be prepared, for example, by the method disclosed in the literature (J. Org. Chem., 25, 1548–1558 (1960)).

In addition, among the starting compounds of the above formula (XVIII), the compound having a partial structure of the following formula W':

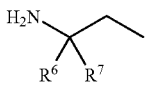

(wherein $R^6$ and $R^7$ are as defined above) being attached to the 3-position of the indole ring or the indazole ring may be prepared by the method disclosed in the literature (cf., J. Org. Chem., 51, 4294–4295 (1986), Tetrahedron Lett., 41, 4363–4366 (2000), etc.).

Further, among the starting compounds of the above formula (XVIII), the compound having the partial structure W' being attached to the 1-position of the indole ring, or to the 1- or 3-position of the benzimidazole ring, or to the 1-position of the indazole ring may be prepared by the method disclosed in the literature (cf., J. Med. Chem., 40, 2003–2010 (1997), Aust. J. Chem., 46, 1177–1191 (1993), etc.).

Moreover, among the starting compounds of the above formula (XVIII), the compound having the partial structure W' being attached to the 2-position of the indole ring may be prepared by the method disclosed in the literature (cf., J. Heterocyclic. Chem., 36, 921–926 (1999), etc.).

Process (b):

As an alternative process to Process (a), the compound of the present invention of the formula (I) may be prepared by reacting a compound of the formula (XIX):

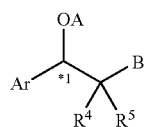

(wherein $R^4$, $R^5$, and Ar are as defined above, A is a protecting group for hydroxy group, B is a bromine atom or a iodine atom, and *1 means an asymmetric carbon atom) with the compound of the above formula (XVIII), followed by removing the protecting group A.

The protecting group for hydroxy group is not necessarily specified, and may be any conventional protecting groups. For example, the protecting groups being usually removed selectively and easily are a benzyl group or a tert-butyldimethylsilyl group, etc. These protecting groups for hydroxy group are introduced by a conventional method. For example, a benzyl group may be introduced by reacting benzyl bromide in an amount of equimolar or 2 moles with sodium iodide in an amount of 1.1 mole in a solvent such as dimethylformamide in the presence of potassium carbonate at room temperature. A triethylsilyl group may be introduced by reacting with a silylating agent such as triethylsilyl chloride in an amount of 1.2 to 2 moles in a solvent such as pyridine at a temperature of from 0° C. to 30° C. for 1 to 3 hours.

The coupling reaction of the compound of the formula (XIX) with the compound of the formula (XVIII) is carried out by heating the compound of the formula (XVIII) in an amount of 1 to 1.5 moles to 1 mole of the compound of the formula (XIX) in the presence of an amine such as triethylamine or diisopropyl ethylamine as a trapping agent for proton in a polar solvent such as dimethylformamide, dimethyl-acetamide or dimethylsulfoxide at a temperature of from room temperature to 90° C., preferably at 60° C. for 5 to 10 hours. The deprotection is usually carried out by a hydrogenation with a catalyst such as palladium or nickel in a solvent such as methanol when the protecting group A is a benzyl group. When the protecting group A is a benzyl group or methyl group, then the deprotection is usually carried out by treating with a Lewis acid such as boron tribromide in a solvent such as methylene chloride, etc. When the protecting group A is a triethylsilyl group, the deprotection is usually carried out by treating with acetic acid and tetrabutylammonium fluoride in an amount of 3 to 5 times by mole in tetrahydrofuran at room temperature for 30 minutes to 5 hours.

The compound of the formula (XIX) may be prepared, for example, by reducing a compound of the formula (XX):

(wherein $R^4$, $R^5$, Ar, and B are defined above) by the following methods, followed by protecting the hydroxy group.

Namely, the reduction of the compound of the formula (XX) is carried out by reducing with a reducing agent such as borane or sodium borohydride when the configuration (*1) of the hydroxy group of the desired compound of the formula (XIX) is racemic. The reaction is usually carried out in a solvent such as ethers (e.g., diethyl ether, tetrahydrofuran, etc.) or alcohols (e.g., methanol, ethanol, etc.) at a temperature of from 0° C. to a boiling point of the solvent.

Further, with respect to the configuration *1 in the formula (XIX), in order to obtain an optical isomer R or S, the reaction is carried out using a chiral auxiliary of the following formula:

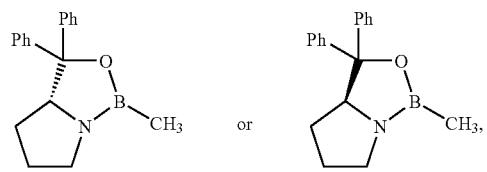

for example, by reducing the compound of the formula (XX) with boron in the presence of one of the above two chiral auxiliaries. The reduction is preferably carried out in a solvent such as tetrahydrofuran. The preparation and the reaction of these chiral auxiliaries are carried out according to the method disclosed in the literature (E. J. Corey et al., J. Org. Chem., vol. 56, p. 442, 1991).

When the bromine atom (bromine compound) should be converted into iodine atom after the reduction of the compound of the formula (XX), the compound obtained by the above reduction is additionally heated under reflux with a iodinating agent such sodium iodide in an amount of 3 to 10 moles to one mole of the bromine compound in a solvent such as acetone for 1 to 3 hours.

Then, by the method for protecting a hydroxy group as mentioned above, the hydroxy group is protected by a triethylsilyl group, etc. to give the compound of the formula (XIX).

The compound of the formula (XX) may be prepared by the method disclosed in the literature (A. A. Larsen et al., J. Med. Chem., 1967, vol. 10, p. 462 or C. Kaiser et al., J. Med. Chem., 1974, vol. 17, p. 49).

Process (c):

As an alternative method to Process (a) and Process (b), among the compounds of the present invention, the compound of the formula (I) wherein the substituent $R^7$ is a hydrogen atom, that is, the compound of the following formula (I-c):

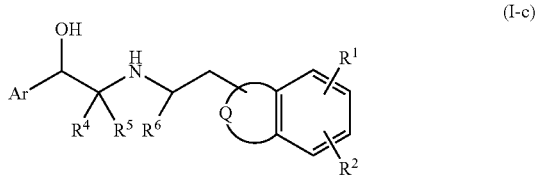

(I-c)

(wherein $R^1$, $R^2$, $R^4$, $R^5$, $R^6$, and Ar are as defined above, Q is the same as defined for the compound of the formula (I) except that W is replaced by a group of the formula: $ArCH(OH)CR^4(R^5)NHCH(R^6)CH_2$—) may be prepared by reacting a compound of the formula (XXII):

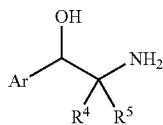

(XXII)

(wherein $R^4$, $R^5$, and Ar are as defined above)
with a compound of the following formula (XXIII):

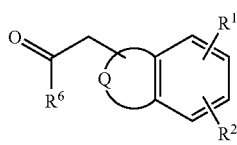

(XXIII)

(wherein $R^1$, $R^2$, $R^3$, and $R^6$ are as defined above, Q is the same as defined for the compound of the formula (I) except that W is replaced by a group of the formula: $R^6C(=O)CH_2$—)
under reduction conditions.

In this reaction, the method of "reaction under reduction conditions" means that the compound of the formula (XXII) and the compound of the formula (XXIII) are reacted in the presence of a reducing agent which may reduce only an imine moiety formed in course of the reaction without affecting the carbonyl group, or in the presence of a catalyst.

The reducing agent used in this reaction includes, for example, sodium cyanoborohydride, and the catalyst includes, for example, palladium, platinum oxide, etc.

This reaction is carried out in the presence of a reducing agent or a catalyst in a suitable solvent. The solvent is preferably alcohols such as methanol, ethanol, etc. The reaction temperature is usually in the range of about 20 to about 80° C. when a reducing agent is used. When a catalyst is used, the reaction temperature is usually in the range of about 10° C. to about 25° C.

The compound of the formula (XXII) used as a starting compound is prepared by the optical resolution of a commercially available enantiomer mixture by a conventional method, or by the method disclosed in the literature (cf., J. Med. Chem., vol. 20, no. 7, p. 978–981 (1977)).

Further, the starting compound of the formula (XXIII) may be prepared by the method disclosed in the literatures (J. Org. Chem., vol. 55, no. 4, p. 1390–1394 (1990), Chem. Pharm. Bull., vol. 45, no. 5, p. 932–935 (1997), Heterocycles, vol. 32, no. 10, p. 1923–1931 (1991)).

Process (d):

As an alternative to Process (a), Process (b), and Process (c), the compound of the formula (I-a) may be prepared by reducing a compound of the following formula (XXIV):

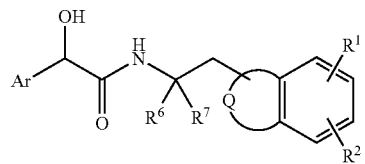

(XXIV)

(wherein $R^1$, $R^2$, $R^6$, $R^7$, and Ar are as defined above; Q is the same as defined for the compound of the formula (I) except that W is replaced by a group of the formula: $ArCH(OH)C(=O)NHCR^6(R^7)CH_2$—).

This process is carried out in the presence of a reducing agent in a solvent. The reducing agent to be used in this Process includes, for example, diborane, lithium aluminum hydride and an alkoxy complex thereof or a transition metal salt thereof, or a sodium borohydride with aluminum chloride, boron trifluoride, phosphorous 1s oxychloride or a carboxylic acid (e.g., acetic acid, trifluoroacetic acid), etc. The solvent includes, for example, ethers (e.g., diethyl ether, tetrahydrofuran, dimethoxyethane, dioxane, diglyme, etc.). The reaction temperature may vary according to the kinds of the reducing agent, etc., and it is usually in the range of from about 0° C. to about 160° C.

In this reaction, the configuration based on the asymmetric carbon atom of the starting compound of the formula (XXIV) is maintained into the product of the reaction.

The compound of the formula (XXIV), which is the starting compound of the above reaction, may be prepared, for example, by reacting a compound of the formula (XXV):

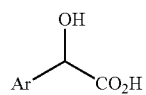

(XXV)

(wherein Ar is the same as defined above)
with the compound of the above formula (XVIII) or a salt thereof.

The reaction of the compound of the formula (XXV) with the compound of the formula (XVIII) is carried out in the presence of a condensing agent such as N,N'-dicyclohexylcarbodiimide, 1-ethyl-3-(3-dimethylaminopropyl)carbodiimide hydrochloride, N,N'-carbonyl-diimidazole, N,N'-carbonyldisuccinimide, 1-ethoxycarbonyl-2-ethoxy-1,2-dihydroquinoline, diphenylphosphorylazide, propanephosphoric anhydride, etc. When N,N'-dicyclohexylcarbodiimide or 1-ethyl-3-(3-dimethylaminopropyl)carbodiimide hydrochloride is used as a condensing agent, N-hydroxysuccinimide, 1-hydroxybenzotriazole, etc. may be added to the reaction system.

This reaction is carried out in a suitable solvent. The solvent includes, for example, the same solvents exemplified for Process (a). Further, the compound of the formula (XVIII) may be used in the form of an acid addition salt, as mentioned in Process (a). In these cases, the reaction is carried out in the presence of an organic base such as triethylamine, tributylamine, diisopropylethylamine, N-methyl-morpholine. The reaction temperature is usually in the range of about 20° C. to about 50° C.

The configuration based on the asymmetric carbon atom of the compound of the formula (XXV) and the compound of the formula (XVIII) is maintained into the product of this reaction (i.e., the compound of the formula (XXIV)).

The optically active compound of the formula (XXV) may be prepared according to the method disclosed in the literature (cf., the method of Collet, A. and Jacques, J. (Bull. Soc. Chim. France, 3330–3334 (1973))).

The optically active compound of the above formula (XVIII) may be prepared, for example, according to the method disclosed in JP-B-63-22559.

Process (e):

As an alternative to Process (a), Process (b), Process (c) and Process (d), the compound of the formula (I-a) may be prepared by reduction of a compound of the formula (XXVI):

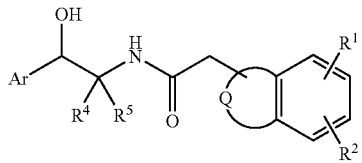

(XXVI)

(wherein $R^1$, $R^2$, $R^4$, $R^5$, and Ar are as defined above, Q is the same as defined in the compound of the formula (I) except that W is replaced by a group of the formula: $ArCH(OH)CR^4(R^5)NHC(=O)CH_2-$).

This process is carried out in a solvent in the presence of a reducing agent. The reducing agent to be used in this process includes, for example, diborane, lithium aluminum hydride and an alkoxy complex thereof or a transition metal salt thereof, or a sodium borohydride with aluminum chloride, boron trifluoride, phosphorous oxychloride or a carboxylic acid (e.g., acetic acid, trifluoroacetic acid), etc. The solvent includes, for example, ethers (e.g., diethyl ether, tetrahydrofuran, dimethoxyethane, dioxane, diglyme, etc.). The reaction temperature may vary according to the kinds of the reducing agent, etc., and it is usually in the range of about 0° C. to about 160° C.

In this process, the configuration based on the asymmetric carbon atom of the starting compound of the formula (XXIV) is maintained into the product of the reaction.

The compound of the formula (XXVI), which is a starting compound of the above reaction, may be prepared by reacting a compound of the formula (XXVII):

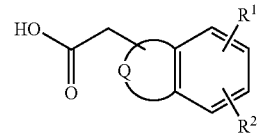

(XXVII)

(wherein $R^1$ and $R^2$ are as defined above, and Q is the same as defined for the compound of the formula (I) except that W is replaced by a group of the formula: $HOC(=O)CH_2-$) with the compound of the above formula (XXII) or a salt thereof. The reaction of the compound of the formula (XXVII) with the compound of the formula (XXII) is carried out in the presence of a condensing agent such as N,N'-dicyclohexylcarbodiimide, 1-ethyl-3-(3-dimethylaminopropyl)carbodiimide hydrochloride, N,N'-carbonyl-diimidazole, N,N'-carbonyldisuccinimide, 1-ethoxycarbonyl-2-ethoxy-1,2-dihydroquinoline, diphenylphosphorylazide, propanephosphoric anhydride, etc. When N,N'-dicyclohexylcarbodiimide or 1-ethyl-3-(3-dimethylaminopropyl)carbodiimide hydrochloride is used as a condensing agent, N-hydroxysuccinimide, 1-hydroxybenzotriazole, etc. may be added to the reaction system.

This reaction is carried out in a suitable solvent. The solvent includes, for example, the same solvents exemplified for Process (a). Further, the compound of the formula (XVIII) may be used in the form of an acid addition salt, as mentioned in Process (a). In these cases, the reaction is carried out in the presence of an organic base such as triethylamine, tributylamine, diisopropylethylamine, N-methyl-morpholine. The reaction temperature is usually in the range of about 20° C. to about 50° C.

The configuration based on the asymmetric carbon atom in the compound of the formula (XXVII) and the compound of the formula (XXII) is maintained into the product of this reaction (i.e., the compound of the formula (XXVI)).

Among the compounds of the formula (XXV), the compound of the formula (XXV) wherein the partial structure W" of the following formula:

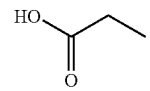

ataches to the 3-position of the indole ring or the benzisoxazole ring may be prepared by the method disclosed in the literature (cf., J. Biological Chemistry, 23, 12685–12689 (1985), J. Heterocycl. Chem., 6, 279–283 (1969)).

In addition, among the starting compounds of the above formula (XXV), the compound of the formula (XXV) wherein the partial structure W, attaches to the 2-position of the benzimidazole ring may be prepared by the method disclosed in the literature (cf., Bull. Soc. Chim. Belg, 100, 277–286 (1991), etc.).

Further, among the starting compounds of the above formula (XXV), the compound of the formula (XXV) wherein the partial structure W" ataches to the 3-position of the benzisothiazole ring may be prepared by the method disclosed in the literature (cf., J. Chem. Soc. Perkin Trans 1, 3006 (1972), etc.).

Process (f):

Among the compounds of the present invention, the compound of the formula (I) wherein $R^1$ is a group of the formula: $-X-R^{1e}-C(=O)-NR^{1a}R^{1b}$ or $-X-R^{1e}-C(=O)OR^{1a}$ (X is a group of the formula: $-O-$ or $-S-$) may be prepared by reacting a compound of the formula (XXVII):

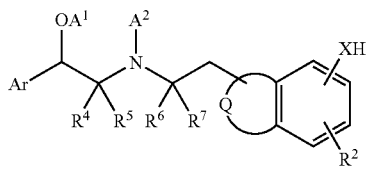

XXVII (wherein $A^1$ is a hydrogen atom or a protecting group for hydroxy group; $A^2$ is a hydrogen atom or a protecting group for amino group; X, $R^2$, $R^4$, $R^5$, $R^6$, $R^7$ and Ar are as defined above; Q is the same as defined for the compound of the formula (I) except that W is replaced by a group of the formula: $ArCH(OA^1)CR^4(R^5)NA^2CR^6(R^7)CH_2-$) with a compound of the formula: $YR^{1e}-C(=O)NR^{1a}R^{1b}$ or $YR^{1e}-C(=O)OR^{1a}$ (wherein Y is an alcoholic reactive residue, and $R^{1e}$, $R^{1a}$, $R^{1b}$ are as defined above), followed by removing the protecting group, if necessary.

The "alcoholic reactive residue" includes, for example, a halogen atom, a lower alkylsulfonyloxy group such as methanesulfonyloxy, ethanesulfonyloxy, etc., and an arylsulfonyloxy group such as benzenesulfonyloxy, p-toluenesulfonyloxy, etc.

The "protecting group for hydroxy group" may be any conventional ones, and the protecting groups being easily and selectively removed includes, for example, a benzyl group, a t-butyl-dimethylsilyl group, a triethylsilyl group, etc.

The "protecting group for amino group" may be any conventional ones, and includes, for example, a methoxycarbonyl group, an ethoxycarbonyl group, a 2,2,2-trichloroethoxycarbonyl group, a tert-butoxycarbonyl group, a benzyloxycarbonyl group, a vinyloxycarbonyl group, a 9-fluorenylmethoxycarbonyl group, a formyl group, an acetyl group, a trifluoroacetyl group, a benzoyl group, a phthalimide group, a p-toluenesulfonyl group, a benzenesulfonyl group, a methanesulfonyl group, and a benzyl group, etc., and preferable one is a tert-butoxy-carbonyl group.

The reaction temperature may vary according to the kinds of the starting compounds, and it is usually in the range of from about 50° C. to about 200° C. The solvent includes, for example, aromatic hydrocarbons such as benzene, toluene, etc., ketone such as acetone, methyl ethyl ketone, etc., ethers such as tetrahydrofuran, dioxane, etc., alcohols such as ethanol, isopropanol, etc., acetonitrile, N,N-dimethyl-formamide, 1,3-dimethyl-2-imidazolidinone, etc., and these solvents may be used alone or in a mixture of two or more solvents.

This reaction is preferably carried out in the presence of a base, and the base includes, for example, an inorganic base such as an alkali metal carbonate (e.g., sodium carbonate, potassium carbonate, etc.), an alkali metal hydrogen carbonate (e.g., sodium hydrogen carbonate, potassium hydrogen carbonate, etc.), an alkali metal hydroxide (e.g., sodium hydroxide, pottasium hydroxide, etc.), or an organic base such as triethylamine, tributylamine, N-methylmorpholine, etc. When the compound wherein Y is a chlorine atom or bromine atom is used, the reaction may smoothly proceed by addition of an alkali metal iodide (e.g., sodium iodide, potassium iodide, etc.), or a teteraalkylammonium halide (e.g., tetra-n-butylammonium chloride, etc.) into the reaction system.

Process (g):

Among the compounds of the present invention, the compound of the formula (I) wherein $R^1$ is a group of the formula: $-X-R^{1e}-C(=O)N-R^{1a}R^{1b}$ may be prepared by condensing a compound of the formula (XXVIII):

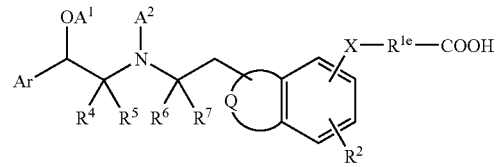

XXVIII (wherein X, $R^{1e}$, $A^1$, $A^2$, $R^2$, $R^4$, $R^5$, $R^6$, $R^7$ and Ar are as defined above; Q is the same as defined for the compound of the formula (I) except that W is replaced by a group of the formula: $ArCH(OA^1)CR^4(R^5)NA^2CR^6(R^7)-CH_2-$)
with a compound of the formula: $HNR^{1a}R^{1b}$ (wherein $R^{1a}$, $R^{1b}$ are as defined above), followed by removing the protecting group, if necessary.

In this condensation reaction, the organic solvent to be used may be any inert organic solvents, for example, halogenated hydrocarbons (e.g., carbon tetrachloride, dichloromethane, 1,2-dichloroethane, etc.), ethers (e.g., diethyl ether, tetrahydrofuran, 1,4-dioxane, etc.), and N,N-dimethylformamide, etc.

The condensing agent to be used in the reaction includes, for example, condensing agents usually used in the peptide-bond formation (e.g., dicyclohexylcarbodiimide (DCC), diisopropylcarbodiimide (DIPC), N-ethyl-N'-3-dimethylaminopropylcarbodiimide (EDC=WSCI) and a hydrochloride thereof (WSCI.HCl), benzotriazol-1-yl-tris(dimethylamino)phosphonium hexafluorophosphate salt (BOP), diphenyl-phosphoryl azide (DPPA), etc.), or carbonyl diimidazole (CDI), 2-ethoxyl-ethoxycarbonyl-1,2-dihydroquinoline (EEDQ), triphenylphosphine-carbon tetrachloride, diethyl cyanophosphate, diphenyl phosphoroazide, etc.

In order to accelerate the reaction speed of the condensing reaction or to avoid any side reactions, an additive such as N-hydroxy-succinimide (HONSu), 1-hydroxybenztriazole (HOBt), 3,4-dihydro-3-hydroxy-4-oxo-1,2,3-benzotriazine (HOOBt), etc. may be used. The reaction is preferably carried out at a temperature of from room temperature to a refluxing temperature, for 30 minutes to 24 hours.

Process (h):

Among the compounds of the present invention, the compound of the formula (I) wherein $R^1$ is a group of the formula: $-X-R^{1e}-C(=O)-NR^{1a}R^{1b}$ may also be prepared by activating the carboxyl group of the compound of the above formula (XXVIII) to give an acid halide, condensing said acid halide with a compound of the formula: $HNR^{1a}R^{1b}$ (wherein $R^{1a}$ and $R^{1b}$ are as defined above), following by removing the protecting group.

The compound of the formula (XXVIII) is converted into an acid halide by reacting the compound of the formula (XXVIII) with triamide hexamethyl phosphite—carbon tetrachloride, triphenylphospine-carbon tetrachloride, thionyl chloride, phosphorus oxychloride, phosphorus pentachloride, oxalyl chloride, etc. in a solvent. The reaction is usually carried out at room temperature for 30 minutes to 2 hours with stirring. The solvent used herein includes, for example, tetrahydrofuran, dichloromethane, N,N-dimethylformamide, toluene, benzene, etc.

The organic solvent used in the condensation reaction may be any inert organic solvents, for example, halogenated hydrocarbons (e.g., carbon tetrachloride, dichloromethane, 1,2-dichloroethane, etc.), ethers (e.g., diethyl ether, tetrahydrofuran, 1,4-dioxane, etc.), N,N-dimethyl-formamide, etc. The reaction may be carried out in the presence of a base. The reaction temperature is usually in the range of about −10° C. to 120° C., preferably in the range of about 0° C. to 100° C. The reaction is usually carried out for 1 to 48 hours, preferably for 1 to 24 hours. The base may be, for example, alkylamines (e.g., triethylamine, etc.), cyclic amines (e.g., N-methylmorpholine, pyridine, etc.), aromatic amines (e.g., N,N-dimethylaniline, N,N-diethylaniline, etc.), alkali metal carbonates (e.g., sodium carbonate, potassium carbonate, etc.), alkali metal hydrogen carbonates (e.g., sodium hydrogen carbonate, potassium hydrogen carbonate, etc.).

Process (i):

Among the present compounds, the compound of the formula (I) wherein $R^1$ and $R^3$ combine each other and form a divalent group of the formula: $-X-R^{1e}-C(=O)-$ may be prepared by subjecting a compound of the formula (XXIX):

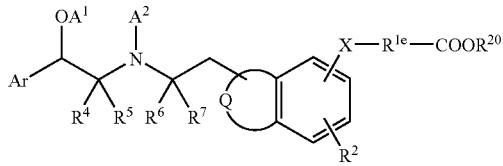

XXIX (wherein X, $R^{1e}$, $A^1$, $A^2$, $R^2$, $R^4$, $R^5$, $R^6$, $R^7$ and Ar are as defined above, $R^{20}$ is a lower alkyl group, Q is the same as defined for the compound of the formula (I) except that W is replaced by a group of the formula: $ArCH(OA^1)CR^4(R^5)NA^2CR^6(R^7)CH_2-$) to intramolecular cyclization reaction, followed by removing the protecting group, if necessary.

This reaction is preferably carried out in the presence of a base, and the base includes, for example, an alkali metal carbonate (e.g., sodium carbonate, potassium carbonate, etc.), an alkali metal hydrogen carbonate (e.g., sodium hydrogen carbonate, potassium hydrogen carbonate, etc.), an alkali metal hydroxide (e.g., sodium hydroxide, potassium hydroxide, etc.), and an organic base such as triethylamine, tributylamine, N-methylmorpholine, etc.

The reaction temperature may vary according to the kinds of the starting compound to be used, and it is usually in the range of about 50° C. to about 200° C. The solvent includes, for example, aromatic hydrocarbons (e.g., benzene, toluene, etc.), ketones (e.g., acetone, methyl ethyl ketone, etc.), ethers (e.g., tetrahydrofuran, dioxane, etc.), alcohols (e.g., ethanol, isopropanol, etc.), acetonitrile, N,N-dimethylformamide, 1,3-dimethyl-2-imidazolidinone, etc., and these solvents may be used alone or in a mixture of two or more thereof.

Process (j):

Among the present compounds, the compound of the formula (I) wherein $R^1$ and $R^3$ combine each other and form a divalent group of the formula: $-X-R^{1e}-C(=O)-$ may be prepared by subjecting a compound of the formula (XXX):

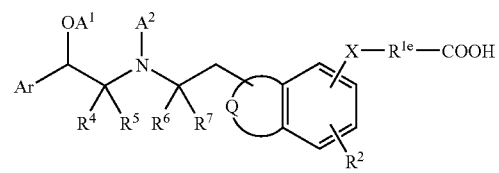

XXX (wherein X, $R^{1e}$, $A^1$, $A^2$, $R^2$, $R^3$, $R^4$, $R^5$, $R^6$, $R^7$ and Ar are as defined above, Q is the same as defined for the compound of the formula (I) except that W is replaced by a group of the formula: $ArCH(OA^1)CR^4(R^5)NA^2CR^6(R^7)-CH_2-$) to intramolecular cyclization reaction, followed by removing the protecting group, if necessary.

In this condensation reaction, the organic solvent may be an organic inert solvent, for example, halogenated hydrocarbons (e.g., carbon tetrachloride, dichloromethane, 1,2-dichloroethane, etc.), ethers (e.g., diethyl ether, tetrahydrofuran, 1,4-dioxane, etc.), N,N-dimethyl-formamide, etc.

The condensing agent to be used in the reaction includes, for example, condensing agents usually used in the peptide-bond formation (e.g., dicyclohexylcarbodiimide (DCC), diisopropylcarbodiimide (DIPC), N-ethyl-N'-3-dimethylaminopropylcarbodiimide (EDC=WSCI) and a hydrochloride thereof (WSCI.HCl), benzotriazol-1-yl-tris(dimethylamino)-phosphonium hexafluorophosphate salt (BOP), diphenylphosphoryl azide (DPPA), etc., or carbonyldiimidazole (CDI), 2-ethoxy-1-ethoxy-carbonyl-1,2-dihydroquinoline (EEDQ), triphenylphosphine-carbon tetrachloride, diethyl cyanophosphate, diphenyl phosphorazide, etc.

In order to accelerate the reaction speed of the condensing reaction or to avoid any side reactions, an additive such as N-hydroxy-succinimide (HONSu), 1-hydroxybenzotriazole (HOBt), 3,4-dihydro-3-hydroxy-4-oxo-1,2,3-benzotriazine (HOOBt), etc. may be used.

The reaction is preferably carried out at a temperature of from room temperature to a refluxing temperature, for 30 minutes to 24 hours.

The compound of the present invention of the above formula (I) may be converted into a pharmaceutically acceptable salt thereof by a conventional method. The pharmaceutically acceptable salt includes, for example, an acid addition salt with an inorganic acid such as hydrochloric acid, hydrobromic acid, hydroiodic acid, sulfuric acid, nitric acid, phosphoric acid, etc., an acid addition salt with an organic acid such as formic acid, acetic acid, methanesulfonic acid, benzene-sulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid, etc., a salt with an inorganic base such as sodium salt, potassium salt, calcium salt, etc., a salt with an organic base such as triethylamine, piperidine, morpholine, pyridine, lysine, etc.

The compound of the present invention includes solvates with a pharmaceutically acceptable solvent such as water or ethanol.

The compound of the present invention obtained in the above-mentioned Processes may be isolated and purified by a conventional isolation method such as recrystallization, a conventional purification method using chromatography, solvent extraction method, or reprecipitation.

The product obtained in any one of Processes may be in the form of an acid addition salt thereof or a free base, due to the reaction conditions. These products may be converted into a desired acid addition salt or a free base by a conventional method.

When the compound of the present invention or the starting compound obtained in any one of Processes are in the form of a racemic mixture or a mixture of diastereomers, each stereoisomer may be separated by a conventional method, for example, by the method disclosed in EP-A-455006.

In addition to the specific protecting groups as exemplified in Processes as explained above, when each starting compound has a reactive group such as a carboxyl group, a hydroxy group or an amino group, the desired compound may be obtained by protecting these groups in advance by a suitable protecting group, and removing these protecting groups after the reaction. The protection or deprotection can be carried out by a method disclosed in the literature: Green, T. W. and Wuts, P. G. M., PROTECTIVE GROUPS IN ORGANIC SYNTHESIS, JOHN WILEY & SONS, INC. (1999), which should be selected according to the kinds of the protecting group to be removed.

The compound of the present invention may be administered either parenterally or orally when used as a medicament. Namely, the present compounds may be administered orally in the form of a conventional administration form such as powders, granules, tablets, capsules, syrups, and suspensions, or administered parenterally in the form of an injection form such as solutions, emulsions, suspension, etc. Further, the present compounds may also be administered rectally in the form of a suppository. The above-mentioned pharmaceutical preparations can be formulated, for example, in a conventional manner by mixing the present compound with conventional pharmaceutically acceptable carriers, excipients, binding agents, stabilizers, or diluents. When the present compound is used in the form of an injection form, the injection form may further contain, for example, pharmaceutically acceptable buffering agents, solubilizing agents, and isotonic agents. The dosage and the frequency of administration of the present compounds may vary, for example, according to the diseases to be treated, the conditions, ages, body weights of the patients and the administration form, etc., but the present compounds can usually be administered in a dose of 0.1 to 2000 mg per day in adult, preferably in a dose of 1 to 200 mg per day in adult, once a day, or divided into several (e.g., 2–4) dosage units.

EXAMPLES

The present invention will be illustrated in more detail by Reference Examples, Examples and Experiments, but should not be construed to be limited thereto.

Reference Example 1

(R)-2—Chloro-1-pyridin-3-ylethanol

To a solution of (−)-B-chlorodiisopinocampheylborane [(−)-DIP-Cl] (25 g, 77.9 mmol) in tetrahydrofuran (90 ml) are added with stirring 3-(2-chloroacetyl)pyridine hydrochloride (Can. J. Chem., vol. 61, p. 334 (1983)) (3.0 g, 15.6 mmol) and triethylamine (2.39 ml, 17.2 mmol) at −25° C., and the reaction mixture is stirred at −25° C. for 3 days. To this mixture is added water (300 ml), and the mixture is warmed to room temperature. To the mixture is added ethyl acetate, and the organic phase is separated. The aqueous phase is neutralized with a saturated aqueous sodium hydrogen carbonate solution, and extracted 6 times with ethyl acetate. The combined organic phase is dried over sodium sulfate, and concentrated under reduced pressure to give yellow oil, which is purified by silica gel column chromatography (methanol/chloroform=1/20) to give the title compound (R)-2-chloro-1-pyridin-3-ylethanol (2.02 g, yield: 82%) as pale yellow oil.

$^1$H-NMR (CDCl$_3$) δ: 2.75 (1H, d, J=3.4 Hz), 3.67 (1H, dd, J=8.5, 11.3 Hz), 3.78 (1H, dd, J=3.5, 11.3 Hz), 4.96–5.00 (1H,m), 7.33 (1H, dd, J=4.9, 7.9 Hz), 7.75–7.78 (1H, m), 8.59 (1H, dd, J=1.6, 4.8 Hz), 8.64 (1H, d, J=2.2 Hz).

Reference Example 2

(R)-(Pyridin-3-yl)oxirane

To a solution of (R)-2-chloro-1-pyridin-3-ylethanol (2.0 g, 12.7 mmol) in acetonitrile (100 ml) is added potassium carbonate (7.02 g). The mixture is refluxed for 2.5 hours, and cooled to room temperature. The mixture is filtered, and the filtrate is distilled off under reduced pressure. The resultant is purified by silica gel column chromatography (methanol/chloroform=1/100) to give the title compound (R)-(pyridin-3-yl)oxirane (1.46 g, yield: 94%) as pale yellow oil.

$^1$H-NMR (CDCl$_3$) δ: 2.83 (1H, dd, J=2.5, 5.3 Hz), 3.21 (1H, dd, J=4.1, 5.3 Hz), 3.90 (1H, dd, J=2.6, 4.0 Hz), 7.29 (1H, dd, J=5.1, 8.3 Hz), 7.53–7.56 (1H, m), 8.57 (1H, dd, J=1.6, 4.8 Hz), 8.60 (1H, d, J=2.0 Hz).

Reference Example 3

N,N-Diethyl-2-(1H-indol-7-yloxy)acetamide

To a solution of 7-hydroxyindole (2.65 g, 20 mmol) in acetone (20 ml) are added potassium carbonate (3.32 g), chloroacetic acid diethylamide (3.29 g, 22 mmol) and potassium iodide (0.33 g), and the mixture is refluxed for 4 hours. After cooling with ice, the insoluble materials are removed by filtration, and the filtrate is concentrated under reduced pressure to remove the solvent. To the residue are added chloroform (40 ml) and water (20 ml), and the mixture is stirred. The chloroform layer is separated, and dried over anhydrous magnesium sulfate. The solvent is evaporated under reduced pressure, and isopropyl ether (100 ml) is added to the residue. The precipitated crystals are collected by filtration, and dried to give the title compound N,N-diethyl-2-(1H-indol-7-yloxy)acetamide (4.37 g, yield: 89%) as white crystals.

$^1$H-NMR (CDCl$_3$) δ: 1.18 (3H, t, J=7.1 Hz), 1.23 (3H, t, J=7.2 Hz), 3.36 (2H, q, J=7.2 Hz), 3.45 (2H, q, J=7.1 Hz), 4.81 (2H, s), 6.52 (1H, dd, J=2.2, 3.0 Hz), 6.68 (1H, d, J=7.6 Hz), 6.99 (1H, t, J=7.8 Hz), 7.22 (1H, t, J=2.7 Hz), 7.32 (1H, d, J=7.9 Hz), 9.59 (1H, s).

Reference Example 4

(R)-2-[3-(2-Aminopropyl)-1H-indol-7-yloxy]-N,N-diethylacetamide

To a suspension of N-(9-fluorenylmethoxycarbonyl)-D-alanine (8.17 g, 26.3 mmol), methylene chloride (88 ml) and N,N-dimethylformamide (0.14 ml) is added dropwise oxalyl chloride (2.44 ml, 28 mmol) at room temperature with stirring, and the mixture is further stirred for one hour. The reaction solution is concentrated to dryness under reduced pressure to give an oil containing 9-fluorenylmethoxycarbonyl-D-Ala-Cl. A solution of N,N-diethyl-2-(1H-indol-7-yloxy)acetamide (4.31 g, 17.5 mmol) in methylene chloride (44 ml) is cooled to −20° C., and thereto is added dropwise a 3M solution of methyl magnesium bromide in diethyl ether (20.5 ml, 61.4 mmol). After the addition, the mixture is further stirred at −15° C. for one hour. This reaction solution is cooled to −20 to −15° C., and thereto is added dropwise a solution of N-(9-fluorenylmethoxycarbonyl)-D-alanyl chloride in methylene chloride (53 ml) obtained above, and the mixture is further stirred at −20° C. for 5.5 hours. The mixture is warmed to about −5° C., and poured into 2N hydrochloric acid. The organic layer is collected, washed with water (25 ml), and dried over anhydrous magnesium sulfate. The solvent is evaporated under reduced pressure to give an oil (13.3 g) containing (R)-[2-(7-diethylcarbamoylmethoxy-1H-indol-3-yl)-1-methyl-2-oxoethyl]-carbamic acid 9H-fluoren-9-ylmethyl ester. To a solution of the obtained oil in a mixture of acetonitrile (70 mL) and 2-propanol (4.0 ml) is added sodium borohydride (1.98 g, 52 mmol) in portions at room temperature with stirring, and the mixture is refluxed for 5 hours. The reaction solution is cooled to room temperature, and thereto is added dropwise methanol (120 ml). The reaction mixture is concentrated to dryness under reduced pressure. To the residue are added ethyl acetate and water, and the mixture is stirred. The organic layer is separated, washed with a saturated brine, and dried over anhydrous sodium sulfate. The solvent is evaporated under reduced pressure, and the residue is purified by silica gel column chromatography (methanol/a saturated ammonia solution in chloroform=1/20) to give the desired (R)-2-[3-(2-aminopropyl)-1H-indol-7-yloxy]-N,N-diethyl-acetamide (1.33 g, yield: 25%).

$^1$H-NMR (CDCl$_3$) δ: 1.16 (3H, d, J=6.3 Hz), 1.17 (3H, t, J=7.1 Hz), 1.23 (3H, t, J=7.1 Hz), 2.63 (1H, dd, J=8.2, 14.2 Hz), 2.86 (1H, dd, J=4.4, 14.1 Hz), 3.24–3.29 (1H, m), 3.36 (2H, q, J=7.1 Hz), 3.45 (2H, q, J=7.1 Hz), 4.81 (2H, s), 6.68 (1H, d, J=7.6 Hz), 6.99 (1H, t, J=7.8 Hz), 7.06 (1H, d, J=1.8 Hz), 7.29 (1H, d, J=8.0 Hz), 9.36 (1H, s).

Example 1

N,N-Diethyl-2-{3-[(2R)-2-((2R)-2-hydroxy-2-pyridin-3-ylethylamino)-propyl]-1H-indol-7-yloxy}acetamide A solution of (R)-(pyridin-3-yl)oxirane (97 mg, 0.80 mmol) and (R)-2-[3-(2-aminopropyl)-1H-indol-7-yloxy]-N,N-diethylacetamide (243 mg, 0.80 mmol) in water (0.8 mL) and ethanol (8 mL) is refluxed for 5 hours. After concentrated, the resulting residue is purified by preparative TLC (SiO$_2$, 20×20 cm, 0.5 mm, iPrOH/saturated ammonia solution in chloroform=1/10) to give the desired N,N-diethyl-2-{3-[(2R)-2-((2R)-2-hydroxy-2-pyridin-3-ylethylamino)propyl]-1H-indol-7-yloxy}-acetamide (70 mg, yield: 21%).

$^1$H-NMR (CDCl$_3$) δ: 1.13 (3H, d, J=6.2 Hz), 1.17 (3H, t, J=7.2 Hz), 1.23 (3H, t, J=7.1 Hz), 2.67 (1H, dd, J=9.4, 12.2 Hz), 2.77–2.86 (2H, m), 2.89 (1H, dd, J=3.5, 12.2 Hz), 3.02–3.08 (1H, m), 3.35 (2H, q, J=7.1 Hz), 3.44 (2H, q, J=7.1 Hz), 4.57 (1H, dd, J=3.5, 9.3 Hz), 4.80 (2H, s), 6.66 (1H, d, J=1.5 Hz), 6.99 (1H, t, J=7.9 Hz), 7.02 (1H, d, J=1.5 Hz), 7.22–7.27 (2H, m), 7.65–7.68 (1H, m), 8.49 (1H, dd, J=1.6, 4.8 Hz), 8.54 (1H, d, J=2.1 Hz), 9.58 (1H, brs).

Example 2

{3-[(2 R)-2-((2R)-2-Hydroxy-2-pyridin-3-ylethylamino)propyl]-1 H-indol-7-yloxy}acetic acid.2 trifluoroacetate A solution of N,N-diethyl-2-{3-[(2R)-2-((2R)-2-hydroxy-2-pyridin-3-ylethylamino)propyl]-1H-indol-7-yloxy}acetamide (30 mg, 0.071 mmol) and potassium hydroxide (120 mg, 2.1 mmol) in water (1 mL)/ethanol (1 mL) is stirred at 60° C. for 6 hours. After cooling, to the mixture is added acetic acid (0.112 mL), and the mixture is concentrated. The residue is purified by preparative reversed phase HPLC (octadecylsilyl, trade name: Combiprep, ODS-A (YMC), inner diameter: 50×20 mm, particle size: 5 μm, pore size: 120 angstrom (hereinafter, this column is used in preparative reversed phase HPLC column), 0.05% trifluoroacetic acid/water-0.035% trifluoroacetic acid/acetonitrile) to give the desired {3-[(2R)-2-((2R)-2-hydroxy 2-pyridin-3-yl-ethylamino)propyl]-1H-indol-7-yloxy}acetic acid.2 trifluoroacetate (24 mg, yield: 57%).

$^1$H-NMR (CD$_3$OD) δ: 1.33 (3H, d, J=6.5 Hz), 3.02 (1H, dd, J=9.1, 14.2 Hz), 3.25–3.33 (2H, m), 3.40 (1H, dd, J=3.2, 12.8 Hz), 3.65–3.70 (1H, m), 4.80 (2H, s), 5.22 (1H, dd, J=3.2, 9.9 Hz), 6.62 (1H, d, J=7.6 Hz), 6.97 (1H, t, J=7.9 Hz), 7.20 (1H, s), 7.24 (1H, d, J=7.8 Hz), 7.80 (1H, dd, J=5.7, 8.0 Hz), 8.50 (1H, d, J=8.1 Hz), 8.79 (1H, d, J=5.1 Hz), 8.86 (1H, brs).

Reference Example 5

(R)-2-Bromo-1-[4-(phenylmethoxy)-3-[(methylsulfonyl)amino]phenyl]-ethanol

Under nitrogen atmosphere, a solution of 2-bromo-1-[4-(phenyl-methoxy)-3-[(methylsulfonyl)amino]phenyl]ethanone (J. Med. Chem., vol. 23, no. 7, p. 738 (1980)) (977 mg, 2.45 mmol) and (R)-5,5-diphenyl-2-methyl-3,4-propano-1,3,2-oxazaborolidine (170 mg, 0.61 mmol) in tetrahydrofuran is stirred for 30 minutes. The mixture is cooled to −30° C., and thereto is added a 2M borane-dimethylsulfide complex in tetrahydrofuran (1.84 mL, 3.68 mmol), and the mixture is stirred at −25° C. for 2 days. The reaction solution is warmed to room temperature, and ethyl acetate and a saturated aqueous ammonium chloride solution are added thereto, and the mixture is stirred. The organic layer is collected and dried over anhydrous sodium sulfate. The solvent is evaporated under reduced pressure, and the residue is purified by silica gel column chromatography (ethyl acetate/chloroform=1/50) to give the desired (R)-2-bromo-1-[4-(phenylmethoxy)-3-[(methylsulfonyl)-amino]phenyl]ethanol (881 mg, yield: 90%).

$^1$H-NMR (CDCl$_3$) δ: 2.64 (1H, d, J=3.3 Hz), 2.93 (3H, s), 3.53 (1H, dd, J=8.7, 10.4 Hz), 3.62 (1H, dd, J=3.5, 10.4 Hz), 4.89 (1H, ddt, J=3.3, 3.5, 8.7 Hz), 5.12 (2H,s), 6.82 (1H, brs), 7.00 (1H, d, J=8.5 Hz), 7.18 (1H, dd, J=2.1, 8.5 Hz), 7.36–7.44 (5H, m), 7.55 (1H, d, J=2.1 Hz).

Reference Example 6

(R)-2-Iodo-1-[4-(phenylmethoxy)-3-[(methylsulfonyl)amino]phenyl]-ethanol

A mixture of (R)-2-bromo-1-[4-(phenylmethoxy)-3-[(methyl-sulfonyl)amino]phenyl]ethanol (880 mg, 2.2 mmol) and NaI (3.66 g, 24.4 mmol) is refluxed in acetone (35 mL) for one hour. After the mixture is filtered, the filtrate is concentrated, and the residue is separated into ethyl acetate and water. The organic phase is washed with a 25% (w/w) aqueous sodium bisulfite solution, and dried over magnesium sulfate to give the desired (R)-2-iodo-1-[4-(phenyl-methoxy)-3-[(methyl-sulfonyl)amino]phenyl]ethanol (938 mg, yield: 95%).

$^1$H-NMR (CDCl$_3$) δ: 2.46 (1H, d, J=3.7 Hz), 2.94 (3H, s), 3.39 (1H, dd, J=8.4, 10.3 Hz), 3.48 (1H, dd, J=3.8, 10.3 Hz), 4.78 (1H, ddt, J=3.7, 3.8, 8.4 Hz), 5.11 (2H, s), 6.82 (1H, brs), 7.00 (1H, d, J=8.4 Hz), 7.17 (1H, dd, J=2.1, 8.4 Hz), 7.36–7.44 (5H, m), 7.54 (1H, d, J=2.1 Hz).

Reference Example 7

(R)—N-[2-Benzyloxy-5-(2-iodo-1-triethylsilyloxy-ethyl)phenyl]methane-sulfonamide To a solution of (R)-2-iodo-1-[4-(phenylmethoxy)-3-[(methyl-sulfonyl)amino]phenyl]ethanol (938 mg, 2.1 mmol), imidazole (393 mg, 5.77 mmol) and 4-dimethylaminopyridine (22.5 mg, 0.184 mmol) in dimethylformamide (10 mL) is added triethylsilyl chloride (0.38 mL, 2.2 mmol) with stirring. One hour thereafter, the reaction is complete, and the reaction solution is diluted with EtOAc (150 mL) and heptane (15 mL). The organic phase is washed with water, a saturated aqueous copper sulfate solution and a saturated brine, and dried over magnesium sulfate. The filtrate is concentrated under reduced pressure to give a solid, which is dissolved in ethyl acetate. The mixture is diluted with heptane, and the precipitated crystals are collected by filtration. The collected solid is washed with heptane and dried in vacuo to give the desired (R)—N-[2-benzyloxy-5-(2-iodo-1-triethylsilyloxyethyl)phenyl]methanesulfonamide (926 mg, yield: 79%).

$^1$H-NMR (CDCl3) δ: 0.52–0.62 (6H, m), 0.90 (9H, t, J=7.9 Hz), 2.91 (3H, s), 3.31 (1H, dd, J=5.3, 10.1 Hz), 3.34 (1H, dd, J=6.8, 10.1 Hz), 4.73 (1H, dd, J=5.3, 6.8 Hz), 5.10 (2H, s), 6.80 (1H, brs), 6.98 (1H, d, J=8.4 Hz), 7.13 (1H, dd, J=2.1, 8.4 Hz), 7.36–7.44 (5H, m), 7.53 (1H, d, J=2.1 Hz).

Reference Example 8

2-(3-{(2R)-2-[2-(4-Benzyloxy-3-methanesulfonylaminophenyl)-(2 R)-2-hydroxyethylamino]propyl}-1H-indol-7-yloxy)-N,N-diethylacetamide A solution of (R)—N-[2-benzyloxy-5-(2-iodo-1-triethylsilyloxy-ethyl)phenyl]methanesulfonamide (185 mg, 0.33 mmol), (R)-2-[3-(2-aminopropyl)-1H-indol-7-yloxy]-N,N-diethylacetamide (100 mg, 0.33 mmol) and diisopropylethylamine (287 μL, 1.65 mmol) in tetrahydrofuran (2 ml) is stirred at 110° C. for 18 hours in an autoclave. After cooling, to the mixture is added ethyl acetate, and the mixture is washed with a saturated brine, dried over sodium sulfate, and concentrated. The residue is dissolved in dichloromethane (2 mL), and thereto is added trifluoroacetic acid (0.5 mL), and the mixture is stirred at room temperature for one hour. After concentrated, the resulting residue is dissolved in ethyl acetate, washed wish a saturated aqueous sodium hydrogen carbonate solution, dried over sodium sulfate, and concentrated. The residue is purified by silica gel column chromatography (methanol/a saturated ammonia solution in chloroform=1/20) to give the desired 2-(3-{(2R)-2-[2-(4-benzyloxy-3-methanesulfonyl-aminophenyl)-(2R)-2-hydroxyethylamino]propyl}-1H-indol-7-yloxy)-N,N-diethylacetamide (144 mg, yield: 70%).

$^1$H-NMR (CDCl$_3$) δ: 1.12 (3H, d, J=6.2 Hz), 1.17 (3H, t, J=7.1 Hz), 1.23 (3H, t, J=7.2 Hz), 2.65 (1H, dd, J=8.9, 12.1 Hz), 2.76–2.89 (3H, m), 2.88 (3H, s), 2.98–3.05 (1H, m), 3.35 (2H, q, J=7.2 Hz), 3.44 (2H, q, J=7.1 Hz), 4.48 (1H, dd, J=3.9, 9.1 Hz), 4.80 (2H, s), 5.09 (2H, s), 6.67 (1H, d, J=7.6 Hz), 6.91–7.02 (3H, m), 7.11 (1H, dd, J=2.0, 8.5 Hz), 7.24–7.28 (1H, m), 7.35–7.44 (6H, m), 9.39 (1H, brs).

Example 3

N,N-Diethyl-2-(3-{(2 R)-2-[(2R)-2-hydroxy-2-(4-hydroxy-3-methane-sulfonylaminophenyl)ethylamino]propyl}-1 H-indol-7-yloxy)acetamide To a solution of 2-(3-{(2R)-2-[2-(4-benzyloxy-3-methanesulfonyl-aminophenyl)-(2R)-2-hydroxyethylamino]propyl}-1H-indol-7-yloxy)-N,N-diethylacetamide (110 mg, 0.177 mmol) in methanol (10 mL) is added 10% palladium on carbon (50% wet, 30 mg), and the mixture is stirred under atmospheric hydrogen atmosphere for 12 hours. The catalyst is filtered through celite, and the filtrate is concentrated. The resulting crude product is crystallized from diisopropyl ether to give the desired N,N-diethyl-2-(3-{(2R)-2-[(2R)-2-hydroxy-2-(4-hydroxy-3-methane-sulfonylaminophenyl)ethylamino]propyl}-1H-indol-7-yloxy)acetamide (80 mg, yield: 85%).

$^1$H-NMR (CD$_3$OD) δ: 1.12 (3H, d, J=6.2 Hz), 1.17 (3H, t, J=7.0 Hz), 1.25 (3H, t, J=7.1 Hz), 2.58 (1H, dd, J=6.7, 11.4 Hz), 2.70–2.80 (3H, m), 2.80 (3H, s), 2.93–2.99 (1H, m), 3.47 (2H, q, J=6.9 Hz), 3.59 (2H, q, J=7.0 Hz), 4.51 (1H, t, J=6.8 Hz), 4.90 (2H, s), 6.56–6.60 (2H, m), 6.75 (1H, dd, J=2.1, 8.3 Hz), 6.86–6.92 (2H, m), 7.10 (1H, d, J=8.0 Hz), 7.17 (1H, d, J=2.0 Hz).

Example 4

(3-{(2R)-2-[(2R)-2-Hydroxy-2-(4-hydroxy-3-methanesulfonylamino-phenyl)ethylamino]propyl}-1H-indol-7-yloxy)acetic acid.trifluoroacetate A solution of N,N-diethyl-2-(3-{(2R)-2-[(2R)-2-hydroxy-2-(4-hydroxy-3-methanesulfonylaminophenyl)ethylamino]propyl}-1H-indol-7-yloxy)acetamide (10 mg, 0.016 mmol) and potassium hydroxide (60 mg, 1.1 mmol) in water (0.5 mL)/ethanol (0.5 mL) is stirred at room temperature under argon atmosphere for one day. The mixture is purified by acetic acid (0.10 mL) preparative HPLC to give the desired (3-{(2R)-2-[(2R)-2-hydroxy-2-(4-hydroxy-3-methanesulfonylamino-phenyl)ethylamino]propyl}-1H-indol-7-yloxy) acetic acid trifluoroacetate (3 mg, yield: 32%).

$^1$H-NMR (CD$_3$OD) δ: 1.30 (3H, d, J=6.5 Hz), 2.92 (3H, s), 2.99 (1H, dd, J=9.0, 14.3 Hz), 3.16–3.18 (2H, m), 3.22 (2H, dd, J=5.8, 14.8 Hz), 3.60–3.64 (1H, m), 4.79 (2H, s), 4.82–4.88 (1H, m), 6.61 (1H, d, J=7.7 Hz), 6.88 (1H, d, J=8.3 Hz), 6.97 (1H, t, J=7.9 Hz), 7.10 (1H, dd, J=2.1, 8.4 Hz), 7.18 (1H, s), 7.22 (1H, d, J=8.0 Hz), 7.38 (1H, d, J=2.1 Hz).

Reference Example 9

2-[3-((2R)-2-{2-[4-(tert-Butyldimethylsilyloxy)phenyl]-(2R)-2-(triethylsilyloxy)ethylamino}propyl)-1H-indol-7-yloxy]-N,N-diethylacetamide (R)-1-(tert-Butyldimethylsilyloxy)-4-(2-iodo-1-triethylsilyloxy-ethyl)benzene (J. Org. Chem., vol. 56, p. 442 (1991)) (65 mg, 0.13 mmol) and (R)-2-[3-(2-aminopropyl)-1H-indol-7-yloxyl]-N,N-diethylacetamide (80 mg, 0.26 mmol) and $^i$Pr$_2$NEt (115 μL) are dissolved in tetrahydrofuran (2 mL), and the mixture is stirred at 110° C. for 10 hours. After cooling, the mixture is concentrated and the residue is purified by silica gel column chromatography (chloroform→a saturated ammonia solution in chloroform) to give the desired 2-[3-((2R)-2-{2-[4-(tert-butyl-dimethyl-silyloxy)phenyl]-(2R)-2-(triethylsilyloxy) ethylamino}propyl)-1H-indol-7-yloxy]-N,N-diethylacetamide (42 mg, yield: 48%).

$^1$H-NMR (CDCl$_3$) δ: 0.18 (6H, s), 0.31 (6H, q, J=7.5 Hz), 0.70 (9H, t, J=7.9 Hz), 0.97 (9H, s), 1.18 (3H, t, J=7.2 Hz), 1.23 (3H, t, J=7.2 Hz), 1.38 (3H, d, J=6.4 Hz), 2.92–3.14 (4H, m), 4.81 (2H, s), 4.96–4.99 (1H, m), 6.69 (1H, d, J=7.7 Hz), 6.76 (2H, d, J=8.4 Hz), 7.03 (1H, t, J=7.9 Hz), 7.12 (2H, d, J=8.6 Hz), 7.20 (1H, s), 7.27–7.30 (1H, m), 9.90 (1H, brs).

Example 5

N,N-Diethyl-2-(3-{(2R)-2-[(2R)-2-hydroxy-2-(4-hydroxyphenyl)ethyl-amino]propyl}-1H-indol-7-yloxy)acetamide A solution of 2-[3-((2R)-2-{2-[4-(tert-butyldimethylsilyloxy)-phenyl]-(2R)-2-(triethylsilyloxy)ethylamino}-propyl)-1H-indol-7-yloxy]-N,N-diethylacetamide (40 mg, 0.060 mmol) and TBAF (261 mg, 1 mmol) in tetrahydrofuran (1 mL) is stirred at room temperature for 8 hours. After concentrated, the resultant is purified by preparative TLC (thickness: 0.5 mm, methanol/(a saturated ammonia solution in chloroform)=1/10), extracted with saturated aqueous sodium hydrogen carbonate solution/chloroform. The organic layer is dried over sodium sulfate, and concentrated to give the desired N,N-diethyl-2-(3-{(2R)-2-[(2 R)-2-hydroxy-2-(4-hydroxyphenyl) ethylamino]propyl}-1H-indol-7-yl-oxy)acetamide (15 mg, yield: 55%).

$^1$H-NMR (CDCl$_3$) δ: 1.17 (3H, d, J=6.1 Hz), 1.20 (3H, t, J=7.2 Hz), 1.30 (3H, t, J=7.2 Hz), 2.47 (1H, dd, J=8.1, 10.4 Hz), 2.55 (1H, dd, J=10.1, 14.2 Hz), 2.81 (1H, dd, J=3.8, 14.2 Hz), 2.86–2.91 (1H, m), 3.10 (1H, dd, J=5.9, 10.5 Hz), 3.36 (2H, q, J=7.1 Hz), 3.44–3.52 (2H, m), 4.54 (1H, dd, J=6.1, 7.7 Hz), 4.81 (1H, d, J=14.7 Hz), 4.85 (1H, d, J=14.7 Hz), 4.96–4.99 (1H, m), 6.44 (1H, d, J=7.6 Hz), 6.45 (2H, d, J=8.5 Hz), 6.66 (1H, s), 6.78 (2H, d, J=8.5 Hz), 6.93 (1H, t, J=7.9 Hz), 7.15 (1H, d, J=8.0 Hz), 9.10 (1H, brs)

Example 6

(3-{(2R)-2-[(2 R)-2-Hydroxy-2-(4-hydroxyphenyl) ethylamino]propyl}-1H-indol-7-yloxy)acetic acid A solution of N,N-diethyl-2-(3-{(2R)-2-[(2R)-2-hydroxy-2-(4-hydroxyphenyl)ethylamino]propyl}-1H-indol-7-yloxy) acetamide (12 mg, 0.027 mmol) and potassium hydroxide (60 mg, 1.1 mmol) in water (0.5 mL) and ethanol (0.5 mL) is stirred at 60° C. for 6 hours. After cooling, the mixture is concentrated and acidified by addition of water (30 mL) and acetic acid. The resultant is purified by reversed phase column chromatography (COSMOSIL 75C18-OPN (Nacalai Tesque) (octadecyl-silica gel, particle diameter: 75 μm, hereinafter, the same), water→water/methanol=10/ 1) to give the desired (3-{(2R)-2-[(2R)-2-hydroxy-2-(4-hydroxyphenyl)ethylamino]propyl}-1H-indol-7-yloxy)acetic acid (7 mg, yield: 68%).

$^1$H-NMR (CD$_3$OD) δ: 1.27 (3H, d, J=6.5 Hz), 2.95 (1H, dd, J=8.1, 14.3 Hz), 3.02 (1H, dd, J=3.9, 12.4 Hz), 3.08–3.13 (2H, m), 3.48–3.53 (1H, m), 4.48 (2H, s), 4.76 (1H, dd, J=3.8, 9.4 Hz), 6.57 (1H, d, J=7.6 Hz), 6.72 (2H, d, J=8.6 Hz), 6.92 (1H, t, J=7.9 Hz), 7.09 (1H, s), 7.13 (2H, d, J=8.5 Hz), 7.14 (1H, d, J=7.8 Hz).

Reference Example 10 tert-Butyl (R)-[2-(7-diethylcarbamoylmethoxy-1H-indol-3-yl)-1-methyl-ethyl]carbamate A mixture of (R)-2-[3-(2-aminopropyl)-1H-indol-7-yloxy]-N,N-diethylacetamide (0.30 g, 1 mmol) and di-tert-butyl dicarbonate (0.44 g, 2 mmol) and potassium carbonate (0.28 g, 2 mmol) in water (40 mL) and ethyl acetate (40 mL) is stirred at room temperature for 2 hours. The mixture is separated, and the organic layer is washed with a saturated brine, dried over magnesium sulfate, and concentrated to give crystals. The resulting crystals are filtered, washed with hexane, and dried under reduced pressure to give tert-butyl (R)-[2-(7-diethyl-carbamoylmethoxy-1H-indol-3-yl)-1-methylethyl]carbamate (0.35 g, yield: 87%).

$^1$H-NMR (CDCl$_3$) δ: 1.10 (3H, d, J=6.6 Hz), 1.17 (3H, t, J=7.1 Hz), 1.23 (3H, d, J=7.1 Hz), 1.44 (9H, s), 2.84 (1H, dd, J=6.6, 14.1 Hz), 2.94 (1H, dd, J=6.0, 14.3 Hz), 3.35 (2H, q, J=7.1 Hz), 3.45 (2H, q, J=7.1 Hz), 4.00 (1H, brs), 4.45 (1H, brs), 4.80 (2H, s), 6.66 (1H, d, J=7.7 Hz), 6.99 (1H, t, J=7.8 Hz), 7.03 (1H, d, J=2.0 Hz), 7.30 (1H, d, J=8.0 Hz), 9.58 (1H, brs).

Reference Example 11

(R)-[3-(2-(tert-Butoxycarbonylamino)propyl)-1H-indol-7-yloxy]acetic acid

A solution of tert-butyl (R)-[2-(7-diethylcarbamoylmethoxy-1H-indol-3-yl)-1-methylethyl]carbamate (0.35 g, 0.87 mmol) and potassium hydroxide (0.39 g, 7 mmol) in water (4 mL) and ethanol (6 mL) is stirred at 60° C. for 8 hours. After cooling, the mixture is concentrated and acidified by addition of water (30 mL) and acetic acid. The resultant is extracted with chloroform, washed with water, dried over magnesium sulfate, and concentrated under reduced pressure to give the desired (R)-[3-(2-(tert-butoxycarbonylamino)propyl)-1H-indol-7-yloxy]acetic acid (0.30 g, yield: 100%).

$^1$H-NMR (CD$_3$OD) δ: 1.10 (3H, d, J=6.3 Hz), 1.43 (9H, s), 2.78 (1H, dd, J=7.5, 14.2 Hz), 2.92 (1H, dd, J=4.6, 13.6 Hz), 3.84–3.93 (1H, m), 4.79 (2H, s), 6.59 (1H, d, J=7.6 Hz), 6.93 (1H, t, J=7.8 Hz), 7.06 (1H, s), 7.26 (1H, d, J=8.0 Hz).

Reference Example 12 tert-Butyl (R)-{2-[7-(2-methanesulfonylamino-2-oxoethoxy)-1H-indol-3-yl]-1-methylethyl}carbamate A solution of (R)-[3-(2-(tert-butoxycarbonylamino)propyl)-1H-indol-7-yloxy]acetic acid (0.30 g, 0.86 mmol) and carbonyldiimidazole (0.21 g, 1.3 mmol) in dimethylformamide (10 mL) is stirred at room temperature for 3 days. To the mixture are added methanesulfonamide (0.16 g, 1.7 mmol) and 1,8-diazabicyclo[5.4.0]undeca-7-ene (0.26 mL, 1.7 mmol), and the mixture is stirred at 50° C. for 4 hours. After cooling, to the mixture is added water (0.1 mL), and the mixture is concentrated. The residue is purified by silica gel column chromatography (methanol/chloroform=1/ 10→1/3), and the resultant is dissolved in ethyl acetate, washed with a 0.05N hydrochloric acid (×2) and saturated brine, and further dried over magnesium sulfate and concentrated to give the desired tert-butyl (R)-{2-[7-(2-methanesulfonylamino-2-oxo-ethoxy)-1H-indol-3-yl]-1-methylethyl}carbamate (0.14 g, yield: 38%).

$^1$H-NMR (CD30D) δ: 1.07 (3H, d, J=6.3 Hz), 1.40 (9H, s), 2.75 (1H, dd, J=7.4, 14.2 Hz), 2.89 (1H, dd, J=3.8, 13.3 Hz), 3.17 (3H, s), 3.83–3.88 (1H, m), 4.64 (2H, s), 6.56 (1H, d, J=7.7 Hz), 6.89 (1H, t, J=7.9 Hz), 7.03 (1H, s), 7.22 (1H, d, J=7.9 Hz).

Reference Example 13

(R)—N-{2-[3-(2-Aminopropyl)-1H-indol-7-yloxy]acetyl}methanesulfonamide.trifluoroacetate A solution of tert-butyl (R)-{2-[7-(2-methanesulfonylamino-2-oxoethoxy)-1H-indol-3-yl]-1-methylethyl}carbamate (0.14 g, 0.33 mmol) and trifluoroacetic acid (1 mL) in methylene chloride (4 mL) is stirred at room temperature for 8 hours. The mixture is concentrated to give the desired (R)—N-{2-[3-(2-aminopropyl)-1H-indol-7-yloxy]acetyl}methane-sulfonamide.trifluoroacetate (0.13 g, yield: 90%).

$^1$H-NMR (CD$_3$OD) δ: 1.30 (3H, d, J=6.6 Hz), 2.98–3.06 (2H, m), 3.31 (3H, s), 3.55–3.60 (1H, m), 4.80 (2H, s), 6.64 (1H, d, J=7.7 Hz), 6.99 (1H, t, J=7.9 Hz), 7.18 (1H, s), 7.24 (1H, d, J=7.6 Hz)

Example 7

N-[2-(3-{(2 R)-2-[2-(3-Chlorophenyl)-(2R)-2-hydroxyethylamino]propyl}-1H-indol-7-yloxy)acetyl]methanesulfonamide.trifluoroacetate A mixture of (R)—N-{2-[3-(2-aminopropyl)-1H-indol-7-yloxy]-acetyl}methanesulfonamide.trifluoroacetate (40 mg, 0.091 mmol), (R)-(+)-3-chlorostyrene oxide (24 μL, 0.18 mmol) and $^i$Pr$_2$NEt (24 μL, 0.137 mmol) in acetonitrile (1 mL) is refluxed for 8 hours. After cooling, the mixture is concentrated and purified by preparative TLC (thickness: 0.5 mm, methanol/(a saturated ammonia solution in chloroform)=1/3) and preparative reversed phase HPLC (trifluoroacetic acid/water/acetonitrile) to give the desired N-[2-(3-{(2R)-2-[2-(3-chlorophenyl)-(2R)-2-hydroxyethylamino]propyl}-1H-indol-7-yloxy)acetyl]methanesulfonamide.trifluoroacetate (9 mg, yield: 21%).

$^1$H-NMR (CD$_3$OD) δ: 1.31 (3H, d, J=6.5 Hz), 3.01 (1H, dd, J=9.1, 14.3 Hz), 3.16 (1H, dd, J=10.1, 12.7 Hz), 3.21–3.28 (2H, m), 3.31 (3H, s), 3.62–3.67 (1H, m), 4.79 (2H, s), 4.93 (1H, dd, J=3.3, 9.9 Hz), 6.64 (1H, d, J=7.7 Hz), 6.99 (1H, t, J=7.9 Hz), 7.21 (1H, s), 7.27 (1H, d, J=7.9 Hz), 7.30–7.38 (3H, m), 7.44 (1H, s).

Example 8

N-(2-{3-[(2R)-2-((2R)-2-Hydroxy-2-pyridin-3-ylethylamino)propyl]-1H-indol-7-yloxy}acetyl)methanesulfonamide.2 trifluoroacetate A mixture of (R)—N-{2-[3-(2-aminopropyl)-1H-indol-7-yloxy]-acetyl}methanesulfonamide.trifluoroacetate (40 mg, 0.091 mmol), (R)-(pyridin-3-yl)oxirane (48 mg, 0.36 mmol) and $^i$Pr$_2$NEt (24 μL, 0.137 mmol) in acetonitrile (1 mL) is refluxed for 3 hours. After cooling, the mixture is concentrated and purified by preparative reversed phase HPLC (trifluoroacetic acid/water/acetonitrile) to give the desired N-(2-{3-[(2R)-2-((2R)-2-hydroxy-2-pyridin-3-ylethylamino)propyl]-1H-indol-7-yloxy}acetyl)methanesulfonamide.2 trifluoroacetate (3 mg, yield: 3%).

$^1$H-NMR (CD$_3$OD) δ: 1.32 (3H, d, J=6.5 Hz), 3.02 (1H, dd, J=9.1, 14.2 Hz), 3.26–3.33 (5H, m), 3.38 (1H, dd, J=3.4, 12.8 Hz), 3.65–3.70 (1H, m), 4.80 (2H, s), 5.18 (1H, dd, J=3.2, 9.9 Hz), 6.64 (1H, d, J=7.6 Hz), 6.99 (1H, t, J=7.9 Hz), 7.22 (1H, s), 7.27 (1H, d, J=8.0 Hz), 7.90 (1H, dd, J=5.5, 7.8 Hz), 8.39 (1H, d, J=8.1 Hz), 8.74 (1H, d, J=4.0 Hz), 8.81 (1H, s).

Reference Example 14

1H-Indole-7-carboxylic acid diethylamide

A solution of 1H-indole-7-carboxylic acid (0.48 g, 3 mmol), diethylamine (0.93 mL, 9 mmol), 1-ethyl-3-(3-dimethylaminopropyl)-carbodiimide hydrochloride (1.74 g, 9 mmol), 1-hydroxybenzotriazole (1.23 g, 9 mmol), triethylamine (1.26 mL, 12 mmol) in dimethylformamide (30 mL) is stirred at room temperature for 4 hours. The mixture is diluted with ethyl acetate, washed with 1N HCl, water, a saturated aqueous sodium hydrogen carbonate solution, water, and a saturated brine, dried over magnesium sulfate, and concentrated to give the desired 1H-indole-7-carboxylic acid diethylamide (0.64 g, yield: 99%).

$^1$H-NMR (CDCl$_3$) δ: 1.27 (6H, t, J=7.1 Hz), 3.56 (4H, q, J=7.1 Hz), 6.56 (1H, dd, J=2.2, 3.2 Hz), 7.09 (1H, t, J=7.5 Hz), 7.23 (1H, dd, J=0.7, 7.3 Hz), 7.25–7.27 (1H, m), 7.70 (1H, d, J=7.9 Hz), 9.06 (1H, brs).

Reference Example 15

(R)-[2-(7-Diethylcarbamoyl-1H-indol-3-yl)-1-methyl-2-oxoethyl]carbamic acid 9H-fluoren-9-ylmethyl ester To a suspension of N-(9-fluorenylmethoxycarbonyl)-D-alanine (21.61 g, 69.4 mmol), methylene chloride (230 ml) and N,N-dimethylformamide (0.37 ml) is added dropwise oxalyl chloride (6.46 ml, 74.0 mmol) at room temperature with stirring, and the mixture is further stirred for 2 hours. The reaction solution is concentrated to dryness under reduced pressure to give an oil containing N-(9-fluorenylmethoxy-carbonyl)-D-alanyl chloride. A solution of 1H-indole-7-carboxylic acid diethylamide (10.0 g, 46.3 mmol) in methylene chloride (120 ml) is cooled to −20° C., and thereto is added dropwise a 3M solution of methyl magnesium bromide/diethyl ether (54 ml, 162 mmol). After the addition, the mixture is further stirred at −20° C. for 2 hours. This reaction solution is cooled to −25--15° C., and thereto is added dropwise a solution of the above obtained N-(9-fluorenylmethoxycarbonyl)-D-alanyl in methylene chloride (140 ml), and the mixture is further stirred at −20° C. for 2 hours. The mixture is warmed to about −5° C., and poured into 2N hydrochloric acid. The organic layer is separated, washed with water (25 ml) and dried over anhydrous magnesium sulfate. The solvent is evaporated under reduced pressure, and the residue is purified by silica gel column chromatography (ethyl acetate/hexane=1/2→5/1) to give the desired (R)-[2-(7-diethylcarbamoyl-1H-indol-3-yl)-1-methyl-2-oxoethyl]carbamic acid 9H-fluoren-9-ylmethyl ester (10.24 g, yield: 43%).

$^1$H-NMR (CDCl$_3$) δ: 1.22–1.30 (6H, m), 1.38 (3H, d, J=7.0 Hz), 3.56 (brs, 4H), 4.22 (1H, t, J=7.2 Hz), 4.36 (2H, d, J=7.2 Hz), 4.96–4.99 (1H, m), 6.01 (1H, d, J=6.2 Hz), 7.27–7.33 (4H, m), 7.39 (2H, t, J=7.5 Hz), 7.59–7.62 (3H, m), 7.75 (2H, d, J=7.5 Hz), 8.42 (1H, dd, J=2.5, 6.3 Hz), 10.71 (1H, brs).

Reference Example 16

(R)-3-(2-Aminopropyl)-1H-indole-7-carboxylic acid diethylamide

A solution of (R)-[2-(7-diethylcarbamoyl-1H-indol-3-yl)-1-methyl-2-oxoethyl]carbamic acid 9H-fluoren-9-ylmethyl ester (10.24 g, 20.1 mmol) in a mixture of acetonitrile (134 mL) and 2-propanol (7.7 ml) is added sodium borohydride (3.80 g, 100 mmol) in portions at room temperature with stirring, and the mixture is refluxed for 4 hours. The reaction solution is cooled to room temperature, and thereto is added dropwise methanol (200 ml). The reaction mixture is concentrated to dryness under reduced pressure. To the residue are added ethyl acetate and water, and the mixture is stirred. The organic layer is separated, washed with a saturated brine, and dried over anhydrous sodium sulfate. The solvent is evaporated under reduced pressure, and the residue is purified by silica gel column chromatography (methanol/(a saturated ammonia solution in chloroform)=1/100) to give the desired (R)-3-(2-aminopropyl)-1H-indole-7-carboxylic acid diethylamide (3.60 g, yield: 66%).

$^1$H-NMR (CDCl$_3$) δ: 1.14 (3H, d, J=6.3 Hz), 1.24 (6H, t, J=6.9 Hz), 2.60–2.65 (1H, dd, J=8.1, 14.1 Hz), 2.82–2.87 (1H, dd, J=4.9, 14.2 Hz), 3.19–3.27 (1H, m), 3.51–3.53 (4H, m), 7.01 (1H, s), 7.04–7.08 (1H, m), 7.18 (1H, d, J=7.3 Hz), 7.64 (1H, d, J=6.3 Hz), 9.35 (1H, brs)

Example 9

3-{(2R)-2-[2-(3-Chlorophenyl)-(2R)-2-hydroxyethylamino]propyl}-1H-indole-7-carboxylic acid diethylamide A mixture of (R)-3-(2-aminopropyl)-1H-indole-7-carboxylic acid diethylamide (1.30 g, 4.76 mmol) and (R)-(+)-3-chlorostyrene oxide (1.21 mL, 9.52 mmol) in acetonitrile (15 mL) is refluxed for 10 hours. After cooling, the mixture is concentrated and the residue is purified by silica gel column chromatography (a saturated ammonia solution in chloroform) to give the desired 3-{(2R)-2-[2-(3-chlorophenyl)-(2R)-2-hydroxyethylamino]propyl}-1H-indole-7-carboxylic acid diethylamide (0.79 g, yield: 39%).

$^1$H-NMR (CDCl$_3$) δ: 1.10 (3H, d, J=6.2 Hz), 1.25 (6H, t, J=7.0 Hz), 2.63 (1H, dd, J=9.2, 12.0 Hz), 2.78–2.85 (3H, m), 2.98–3.03 (1H, m), 3.51–3.56 (4H, m), 4.49 (1H, dd, J=3.4, 9.0 Hz), 7.01 (1H, s), 7.07 (1H, t, J=7.7 Hz), 7.14–7.25 (4H, m), 7.32 (1H, s), 7.62 (1H, d, J=7.9 Hz), 9.17 (1H, brs).

Example 10

3-{(2R)-2-[2-(3-Chlorophenyl)-(2R)-2-hydroxyethylamino]propyl}-1H-indole-7-carboxylic acid A solution of 3-{(2 R)-2-[2-(3-chlorophenyl)-(2R)-2-hydroxyethyl-amino]propyl}-1H-indole-7-carboxylic acid diethylamide (175 mg, 0.41 mmol) in 1,4-dioxane (7 mL) and 6N hydrochloric acid (7 mL) is stirred with heating at 150° C. for 7 hours in a closed system. After cooling, the mixture is evaporated under reduced pressure to remove dioxane, and the resultant is neutralized with an aqueous Na$_2$CO$_3$ solution. The precipitates are filtered, and purified by reversed phase column (octa-decylsilyl, methanol/water=1/1→3/1) to give the desired 3-{(2R)-2-[2-(3-chlorophenyl)-(2R)-2-hydroxyethylamino]propyl}-1H-indole-7-carboxylic acid (45 mg, yield: 30%).

$^1$H-NMR (CD$_3$OD) δ: 1.30 (3H, d, J=6.4 Hz), 3.02 (1H, dd, J=8.1, 14.3 Hz), 3.11–3.21 (3H, m), 3.53–3.59 (1H, m), 7.07 (1H, t), J=7.8 Hz), 7.22–7.34 (4H, m), 7.42 (1H, s), 7.68 (1H, d, J=7.9 Hz), 7.78 (1H, d, J=7.4 Hz).

Example 11

Methyl (2S)-2-[(3-{(2R)-2-[2-(3-chlorophenyl)-(2R)-2-hydroxyethylamino]-propyl}-1H-indole-7-carbonyl)amino]-4-methylpentanoate.trifluoroacetate A solution of 3-{(2R)-2-[2-(3-chlorophenyl)-(2R)-2-hydroxyethyl-amino]propyl}-1H-indole-7-carboxylic acid (22 mg, 0.059 mmol), L-Leu-OMe.HCl (107 mg, 0.59 mmol), 1-ethyl-3-(3-dimethylaminopropyl)-carbodiimide hydrochloride (113 mg, 0.59 mmol), 1-hydroxybenztriazole (80 mg, 0.59 mmol), triethylamine (164 μL, 1.18 mmol) in dimethylformamide (2 mL) is stirred at room temperature for 18 hours. The mixture is diluted with ethyl acetate, washed with a saturated aqueous sodium hydrogen carbonate solution, water, and a saturated brine, dried over sodium sulfate, and concentrated. The residue is purified by silica gel column chromatography (a saturated ammonia solution in chloroform) and preparative reversed phase HPLC (octa-decylsilyl, trifluoroacetic acid/acetonitrile/water) to give the desired methyl (2S)-2-[(3-{(2R)-2-[2-(3-chlorophenyl)-(2R)-2-hydroxyethylamino]propyl}-1H-indole-7-carbonyl)amino]-4-methylpentanoate.trifluoroacetate (23 mg, yield: 63%).

$^1$H-NMR (CD$_3$OD) δ: 0.98 (3H, d, J=6.2 Hz), 1.00 (3H, d, J=6.3 Hz), 1.31 (3H, d, J=6.5 Hz), 1.69–1.88 (3H, m), 3.04 (1H, dd, J=9.2, 14.1 Hz), 3.14–3.30 (3H, m), 3.63–3.69 (1H, m), 3.73 (3H, s), 4.75 (1H, dd, J=4.4, 10.0 Hz), 4.95 (1H, dd, J=3.1, 9.9 Hz), 7.16 (1H, t, J=7.7 Hz), 7.30–7.37 (4H, m), 7.45 (1H, s), 7.72 (1H, d, J=7.5 Hz), 7.82 (1H, d, J=7.9 Hz).

Examples 12 to 23

The compounds of the following Examples 12 to 23 are obtained in a similar manner to Example 11.

Example 12

3-{(2R)-2-[2-(3-Chlorophenyl)-(2R)-2-hydroxyethylamino]propyl}-1H-indole-7-carboxylic acid dibutylamide trifluoroacetate $^1$H-NMR (CD$_3$OD) δ: 0.61 (3H, brs), 1.02 (5H, brs), 1.30 (3H, d, J=6.5 Hz), 1.46 (4H, brs), 1.73 (2H, brs), 3.01 (1H, dd, J=9.3, 14.2 Hz), 3.17 (1H, dd, J=10.1, 12.5 Hz), 3.25–3.31 (6H, m), 3.57 (2H, brs), 3.66 (1H, m), 4.95 (1H, dd, J=3.1, 10.0 Hz), 7.11 (2H, m), 7.26 (1H, s), 7.34 (3H, m), 7.47 (1H, m), 7.68 (1H, dd, J=1.7, 7.2 Hz).

Example 13

3-{(2R)-2-[2-(3-Chlorophenyl)-(2R)-2-hydroxyethylamino]propyl}-1H-indole-7-carboxylic acid (3-methylbutyl)amide.trifluoroacetate $^1$H-NMR (CD$_3$OD) δ: 0.97 (6H, d, J=6.6 Hz), 1.31 (3H, d, J=6.5 Hz), 1.55 (2H, dt, J=7.3, 8.7 Hz), 1.69 (1H, qq, J=6.7 Hz), 3.04 (2H, dd, J=9.1, 14.3 Hz), 3.27 (2H, m), 3.45 (1H, t, J=14.9 Hz), 3.66 (1H, m), 4.93 (1H, dd, J=3.3, 8.0 Hz), 7.13 (1H, t, J=7.7 Hz), 7.34 (4H, m), 7.45 (1H, m), 7.60 (1H, m), 7.79 (1H, m).

Example 14

(3-{(2R)-2-[2-(3-Chlorophenyl)-(2R)-2-hydroxy-ethylamino]propyl}-1H-indol-7-yl)-piperidin-1-yl-methanone.trifluoroacetate $^1$H-NMR (CD$_3$OD) δ: 1.30 (3H, d, J=6.5 Hz), 1.41–1.65 (6H, m), 3.02 (1H, dd, J=9.2, 14.2 Hz), 3.17 (1H, dd, J=10.1, 12.5 Hz), 3.27 (2H, m), 3.30–3.50 (2H, m), 3.66–3.88 (2H, m), 4.94 (1H, dd, J=3.1, 10.0 Hz), 7.15 (2H, m), 7.27 (1H, s), 7.34 (3H, m), 7.47 (1H, m), 7.70 (1H, dd, J=2.1, 6.9 Hz).

Example 15

(3-{(2R)-2-[2-(3-Chlorophenyl)-(2R)-2-hydroxy-ethylamino]propyl}-1H-indol-7-yl)-morpholin-4-ylmethanone.trifluoroacetate $^1$H-NMR (CD$_3$OD) δ: 1.31 (3H, d, J=6.5 Hz), 3.02 (1H, dd, J=9.2, 14.2 Hz), 3.17 (1H, dd, J=10.1, 12.5 Hz), 3.25–3.35 (4H, m), 3.66–3.76 (6H, m), 4.94 (1H, dd, J=3.1, 10.0 Hz), 7.17 (2H, m), 7.27 (1H, s), 7.34 (3H, m), 7.47 (1H, m), 7.72 (1H, dd, J=1.3, 7.7 Hz).

Example 16

3-{(2R)-2-[2-(3-Chlorophenyl)-(2 R)-2-hydroxy-ethylamino]propyl}-1H-indole-7-carboxylic acid ((1S)-1-hydroxymethyl-3-methylbutyl)amide.trifluoroacetate $^1$H-NMR (CD$_3$OD) δ: 0.97 (6H, d, J=6.6 Hz), 1.45 (3H, d, J=9.2 Hz), 1.49 (1H, m), 1.51 (1H, m), 1.56 (1H, m), 3.04 (2H, dd, J=9.1, 14.3 Hz), 3.27 (2H, m), 3.61 (3H, d, J=5.6 Hz), 3.66 (1H, m), 4.30 (1H, tt, J=4.7 Hz), 4.93 (1H, dd, J=3.2, 10.2 Hz), 7.14 (1H, t, J=7.7 Hz), 7.34 (4H, m), 7.45 (1H, m), 7.65 (1H, m), 7.79 (1H, m).

Example 17

3-{(2R)-2-[2-(3-Chlorophenyl)-(2R)-2-hydroxyethylamino]propyl}-1H-indole-7-carboxamide.trifluoroacetate $^1$H-NMR (CD$_3$OD) δ: 1.31 (3H, d, J=6.5 Hz), 3.04 (1H, dd, J=9.1, 14.3 Hz), 3.17 (2H, m), 3.25–3.35 (3H, m), 3.66 (1H, m), 4.94 (1H, dd, J=3.1, 10.0 Hz), 7.13 (1H, t, J=7.6 Hz), 7.45 (4H, m), 7.67 (1H, m), 7.82 (1H, dd, J=1.3, 7.7 Hz).

Example 18

3-{(2R)-2-[2-(3-Chlorophenyl)-(2R)-2-hydroxyethylamino]propyl}-1H-indole-7-carboxylic acid methylamide.trifluoroacetate $^1$H-NMR (CD$_3$OD) δ: 1.31 (3H, d, J=6.5 Hz), 2.96 (3H, s), 3.04 (2H, dd, J=9.1, 14.3 Hz), 3.27–3.35 (3H, m), 3.65 (3H, m), 4.93 (1H, dd, J=3.2, 10.2 Hz), 7.13 (1H, t, J=7.7 Hz), 7.34 (4H, m), 7.45 (1H, m), 7.57 (1H, m), 7.79 (1H, m).

Example 19

3-{(2R)-2-[2-(3-Chlorophenyl)-(2R)-2-hydroxyethylamino]propyl}-1H-indole-7-carboxylic acid dimethylamide.trifluoroacetate $^1$H-NMR (CD$_3$OD) δ: 1.31 (3H, d, J=6.5 Hz), 2.95 (3H, brs), 3.04 (2H, dd, J=9.1, 14.3 Hz), 3.10–3.35 (6H, m), 3.76 (1H, m), 4.93 (1H, dd, J=3.2, 10.2 Hz), 7.13 (1H, t, J=7.7 Hz), 7.27 (1H, m), 7.45 (3H, m), 7.47 (1H, m), 7.71 (1H, m).

Example 20

3-{(2R)-2-[2-(3-Chlorophenyl)-(2R)-2-hydroxyethylamino]propyl}-1H-indole-7-carboxylic acid ethylamide.trifluoroacetate $^1$H-NMR (CD$_3$OD) δ: 1.25 (3H, t, J=7.2 Hz), 1.31 (3H, d, J=6.5 Hz), 3.04 (1H, dd, J=9.1, 14.3 Hz), 3.16–3.35 (3H, m), 3.46 (2H, q, J=7.2 Hz), 3.76 (1H, m), 4.93 (1H, m), 7.13 (1H, t, J=7.7 Hz), 7.27 (3H, m), 7.45 (1H, m), 7.60 (1H, m), 7.79 (1H, m).

Example 21

Ethyl (2S)-2-[(3-{(2R)-2-[2-(3-chlorophenyl)-(2R)-2-hydroxyethylamino]-propyl}-1H-indole-7-carbonyl)amino]propionate.trifluoroacetate $^1$H-NMR (CD$_3$OD) δ: 1.27 (3H, t, J=7.2 Hz), 1.31 (3H, d, J=6.5 Hz), 1.52 (3H, d, J=7.3 Hz), 3.04 (1H, dd, J=9.1, 14.3 Hz), 3.16–3.35 (3H, m), 3.66 (1H, m), 4.18 (2H, q, J=7.2 Hz), 4.66 (1H, q, J=7.3 Hz), 4.93 (1H, d, J=3.7 Hz, 9.8 Hz), 7.16 (1H, t, J=7.7 Hz), 7.27 (3H, m), 7.45 (1H, m), 7.73 (1H, m), 7.81 (1H, m).

Example 22

Ethyl 3-[(3-{(2R)-2-[2-(3-chlorophenyl)-(2R)-2-hydroxyethylamino]-propyl}-1H-indole-7-carbonyl)amino]propionate.trifluoroacetate $^1$H-NMR (CD$_3$OD) δ: 1.23 (3H, t, J=7.1 Hz), 1.31 (3H, d, J=6.5 Hz), 2.68 (3H, d, J=6.9 Hz), 3.04 (1H, dd, J=9.1, 14.3 Hz), 3.16–3.35 (3H, m), 3.66 (1H, m), 3.69 (2H, t, J=6.9 Hz), 4.14 (2H, q, J=7.1 Hz), 4.93 (1H, d, J=3.3 Hz, 9.8 Hz), 7.14 (1H, t, J=7.7 Hz), 7.27 (3H, m), 7.45 (1H, m), 7.58 (1H,m), 7.81 (1H, m).

Example 23

Ethyl [(3-{(2R)-2-[2-(3-chlorophenyl)-(2R)-2-hydroxyethylamino]propyl}-1H-indole-7-carbonyl)amino]acetate.trifluoroacetate $^1$H-NMR (CD$_3$OD) δ: 1.27 (3H, t, J=7.1 Hz), 1.29 (3H, d, J=6.5 Hz), 3.04 (1H, dd, J=9.1, 14.3 Hz), 3.16–3.35 (3H, m), 3.66 (1H, m), 3.69 (2H, t, J=6.9 Hz), 4.15 (2H, s), 4.22 (2H, q, J=7.1 Hz), 4.93 (1H, d, J=3.3 Hz, 9.8 Hz), 7.14 (1H, t, J=7.7 Hz), 7.27 (3H, m),7.45 (1H, m), 7.66 (1H, m), 7.81 (1H, m).

Example 24

(2S)-2-[(3-{(2R)-2-[2-(3-Chlorophenyl)-(2R)-2-hydroxyethylamino]propyl}-1H-indole-7-carbonyl)amino]-4-methylpentanoic acid.trifluoroacetate A solution of methyl (2S)-2-[(3-{(2R)-2-[2-(3-chlorophenyl)-(2R)-2-hydroxyethylamino]propyl}-1H-indole-7-carbonyl)amino]-4-methyl-pentanoate.trifluoroacetate (20 mg, 0.0326 mmol) and potassium hydroxide (60 mg, 1.1 mmol) in water (0.5 mL) and methanol (2 mL) is stirred at room temperature for 3 hours. The mixture is acidified with 1N hydrochloric acid, and purified by preparative reversed phase HPLC (octadecylsilyl, trifluoroacetic acid/acetonitrile/water) to give the desired (2S)-2-[(3-{(2R)-2-[2-(3-chlorophenyl)-(2R)-2-hydroxyethyl-amino]propyl}-1H-indole-7-carbonyl)amino]-4-methylpentanoic acid.trifluoroacetate (18 mg, yield: 92%).

$^1$H-NMR (CD$_3$OD) δ: 0.98–1.01 (6H, m), 1.31 (3H, d, J=6.5 Hz), 1.72–1.89 (3H, m), 3.05 (1H, dd, J=9.0, 14.3 Hz), 3.14–3.31 (3H, m), 3.64–3.67 (1H, m), 4.74 (1H, dd, J=4.1, 10.2 Hz), 4.94 (1H, dd, J=3.3, 9.9 Hz), 7.16 (1H, t, J=7.7 Hz), 7.29–7.40 (4H, m), 7.45 (1H, s), 7.72 (1H, d, J=7.4 Hz), 7.82 (1H, d, J=7.9 Hz).

Examples 25 to 27

The compounds of the following Examples 25 to 27 are obtained in a similar manner to Example 24.

Example 25

Ethyl (2S)-2-[(3-{(2R)-2-[2-(3-chlorophenyl)-(2R)-2-hydroxyethyl-amino]propyl}-1H-indole-7-carbonyl) amino]propionate.trifluoroacetate $^1$H-NMR (CD$_3$OD) δ: 1.31 (3H, d, J=6.5 Hz), 3.04 (1H, dd, J=9.1, 14.3 Hz), 3.16–3.35 (3H, m), 3.66 (1H, m), 4.18 (2H, q, J=7.2 Hz), 4.67 (1H, q, J=7.4 Hz), 4.93 (1H, dd, J=3.4, 9.7 Hz), 7.16 (1H, t, J=7.7 Hz), 7.27 (3H, m), 7.45 (1H, m), 7.72 (1H, m), 7.81 (1H, m).

Example 26

3-[(3-{(2R)-2-[2-(3-Chlorophenyl)-(2R)-2-hydroxyethylamino]propyl}-1H-indole-7-carbonyl)amino] propionic acid.trifluoroacetate $^1$H-NMR (CD$_3$OD) δ: 1.31 (3H, d, J=6.5 Hz), 2.67 (3H, d, J=6.9 Hz), 3.04 (1H, dd, J=9.1, 14.3 Hz), 3.16–3.35 (3H, m), 3.66 (1H, m), 3.69 (2H, t, J=6.9 Hz), 4.93 (1H, dd, J=3.3, 9.8 Hz), 7.14 (1H, t, J=7.7 Hz), 7.27 (3H, m), 7.45 (1H, m), 7.58 (1H, m), 7.81 (1H, m).

Example 27

[(3-{(2R)-2-[2-(3-Chlorophenyl)-(2R)-2-hydroxyethylamino]propyl}-1H-indole-7-carbonyl)amino] acetic acid.trifluoroacetate $^1$H-NMR (CD$_3$OD) δ: 1.31 (3H, d, J=6.5 Hz), 3.04 (1H, dd, J=9.1, 14.3 Hz), 3.16–3.35 (3H, m), 3.66 (1H, m), 3.69 (2H, t, J=6.9 Hz), 4.15 (2H, s), 4.93 (1H, dd, J=3.3, 9.8 Hz), 7.14 (1H, t, J=7.7 Hz), 7.27 (3H, m), 7.45 (1H, m), 7.66 (1H, m), 7.81 (1H, m).

Example 28

3-[(2R)-2-((2R)-2-Hydroxy-2-pyridin-3-ylethylamino)propyl]-1H-indole-7-carboxylic acid diethylamide The title compound is prepared from (R)-3-(2-aminopropyl)-1H-indole-7-carboxylic acid diethylamide in a similar manner to Example 1.

$^1$H-NMR (CDCl$_3$) δ: 1.13 (3H, d, J=6.2 Hz), 1.27 (6H, t, J=7.1 Hz), 2.65 (1H, dd, J=9.4, 12.2 Hz), 2.83–2.90 (3H, m), 3.02–3.07 (1H, m), 3.55 (4H, q, J=7.0 Hz), 4.55 (1H, dd, J=3.5, 9.3 Hz), 7.06–7.10 (2H, m), 7.21–7.26 (2H, m), 7.63–7.68 (2H, m), 8.49 (1H, dd, J=1.6, 4.8 Hz), 8.54 (1H, d, J=2.1 Hz), 9.03 (1H, brs).

Reference Example 17

3-{(2R)-2-[(5R)-5-(3-Chlorophenyl)-2-oxooxazolidin-3-yl]propyl}-1H-indole-7-carboxylic acid diethylamide To a solution of 3-{(2R)-2-[2-(3-chlorophenyl)-(2R)-2-hydroxy-ethylamino]propyl}-1H-indole-7-carboxylic acid diethylamide.hydrochloride (47 mg, 0.1 mmol) and triethylamine (139 μL, 1 mmol) in tetrahydrofuran (3 mL) is added triphosgene (12 mg, 0.04 mmol), and the mixture is stirred at room temperature for 4 hours. To the mixture is added a saturated aqueous sodium hydrogen carbonate solution, and the mixture is extracted with ethyl acetate. The organic layer is washed with a saturated brine, dried over sodium sulfate, and concentrated. The residue is purified by silica gel column chromatography (methanol/chloroform=1/50) to give 3-{(2R)-2-[(5R)-5-(3-chlorophenyl)-2-oxooxazolidin-3-yl]propyl}-1H-indole-7-carboxylic acid diethylamide (45 mg, yield: 100%).

$^1$H-NMR (CDCl$_3$) δ: 1.25–1.30 (9H, m), 2.90–3.01 (2H, m), 3.26 (1H, dd, J=6.8, 8.6 Hz), 3.54 (4H, q, J=7.0 Hz), 3.83 (1H, t, J=6.8 Hz), 4.38–4.44 (1H, m), 5.36 (1H, dd, J=6.8, 8.9 Hz), 6.93 (1H, d, J=7.5 Hz), 7.02 (1H, d, J=2.2 Hz), 7.07 (1H, t, J=7.5 Hz), 7.15 (1H, m), 7.18–7.26 (4H, m), 7.66 (1H, d, J=7.9 Hz), 8.92 (1H, brs).

Example 29

3-{(2R)-2-[2-(3-Chlorophenyl)-(2R)-2-hydroxyethylamino]propyl}-1-methyl-1H-indole-7-carboxylic acid diethylamide A solution of 3-{(2 R)-2-[(5R)-5-(3-chlorophenyl)-2-oxooxazolidin-3-yl]propyl}-1H-indole-7-carboxylic acid diethylamide (10 mg, 0.022 mmol), methyl iodide (21 μL, 0.33 mmol), potassium carbonate (90 mg, 0.66 mmol) in acetone (2 mL) is refluxed for 24 hours. After cooling, the insoluble materials are removed by filtration, and the filtrate is concentrated under reduced pressure. The residue is purified by preparative TLC (silica gel, 0.5 mm, 20×20 cm, methanol/chloroform=1/30) to give 3-{(2R)-2-[(5R)-5-(3-chlorophenyl)-2-oxooxazolidin-3-yl]-propyl}-1-methyl-1H-indole-7-carboxylic acid diethylamide (3 mg). A solution of 3-{(2R)-2-[(5R)-5-(3-chlorophenyl)-2-oxooxazolidin-3-yl]-propyl}-1-methyl-1H-indole-7-carboxylic acid diethylamide (3 mg, 0.0064 mmol) and potassium hydroxide (0.6 g) in water (1 mL) and ethanol (1 mL) is stirred at 70° C. for 7 hours. After cooling, ethanol is removed by distillation, and water is added thereto. The mixture is extracted with ethyl acetate, and the organic layer is washed with a saturated aqueous sodium hydrogen carbonate solution, dried over sodium sulfate, and concentrated. The residue is purified by silica gel column chromatography (60, 2 g, a saturated ammonia solution in chloroform) to give 3-{(2R)-2-[2-(3-chlorophenyl)-(2R)-2-hydroxyethyl-amino]propyl}-1-methyl-1H-indole-7-carboxylic acid diethylamide (2 mg, yield: 71%).

$^1$H-NMR (CDCl$_3$, 40° C.) δ: 1.05 (3H, t, J=7.1 Hz), 1.12 (3H, d, J=5.5 Hz), 1.31 (3H, t, J=7.1 Hz), 2.63 (1H, m), 2.79–2.87 (3H, m), 3.00 (1H, m), 3.23 (2H, q, J=7.1 Hz), 3.55 (1H, m), 3.79 (1H, m), 4.50 (1H, dd, J=3.5, 8.9 Hz), 6.82 (1H, s), 7.03 (1H, dd, J=1.4, 7.2 Hz), 7.07 (1H, t, J=7.6 Hz), 7.16–7.23 (3H, m), 7.35 (1H, s), 7.56 (1H, dd, J=1.4, 7.6 Hz).

Reference Example 18

N-((7-Benzyloxy)-1H-indol-3-yl)methyl)-N,N-dimethylamine

To a solution of a 40% aqueous dimethylamine solution (7.88 g, 69.9 mmol) and a 37% aqueous formaldehyde solution (5.92 g, 72.9mmol) in acetic acid (70 mL) is added 7-(benzyloxy)-1H-indole (14.2 g, 63.6 mmol) at 0° C. under nitrogen atmosphere, and the mixture is stirred at room temperature for 3.5 hours. Water is added to the reaction solution, and the mixture is washed with diethyl ether. The pH value of the aqueous layer is adjusted to pH 12 with a 3N aqueous sodium hydroxide solution, and the mixture is extracted with chloroform. The organic layer is washed with a saturated brine, and dried over anhydrous potassium carbonate. The solvent is evaporated, and the obtained crude product is dissolved in ethyl acetate (100 mL), crystallized from n-hexane (100 mL), and collected by filtration to give N-((7-benzyloxy)-1H-indol-3-yl)methyl)-N,N-dimethylamine (14.3 g, 50.9 mmol, yield: 80%).

$^1$H-NMR (CDCl$_3$) δ: 8.35 (1H, brs), 7.47–7.49 (2H, m), 7.35–7.43 (3H, m), 7.32 (1H, d, J=8.0 Hz), 7.10 (1H, d, J=2.3 Hz), 7.03 (1H, dd, J=7.9, 7.7 Hz), 6.73 (1H, d, J=7.7 Hz), 5.20 (2H, s), 3.61 (2H, s), 2.27 (6H, s).

Reference Example 19

(7-(Benzyloxy)-1H-indol-3-yl)acetonitrile

To a solution of N-((7-benzyloxy)-1H-indol-3-yl)methyl)-N,N-dimethylamine (14.2 g, 50.6 mmol) in N,N-dimethylformamide (150 mL) is added a solution of potassium cyanide (13.2 g, 202.7 mmol) in water (25 ml) under nitrogen atmosphere, and after cooling thereto is added dropwise methyl iodide (34.5 g, 243.1 mmol), and the mixture is stirred at room temperature for 14 hours. The reaction solution is poured into water, and the mixture is extracted with ethyl acetate. The organic layer is washed successively with water and a saturated brine, and dried over anhydrous magnesium sulfate. The solvent is evaporated, and the obtained crude product is purified by silica gel column chromatography (n-hexane:ethyl acetate=2: 1) to give (7-(benzyloxy)-1H-indol-3-yl)acetonitrile (12.0 g, 45.7 mmol, yield: 90%).

$^1$H-NMR (CDCl$_3$) δ: 8.42 (1H, brs), 7.46–7.48 (2H, m), 7.34–7.43 (3H, m), 7.19–7.21 (2H, m), 7.08 (1H, t, J=7.9 Hz), 7.68 (1H, d, J=7.7 Hz), 5.21 (2H, s), 3.83 (2H, d, J=0.84 Hz).

Reference Example 20

(7-(Benzyloxy)-1H-indol-3-yl)acetic acid

Under nitrogen atmosphere, to a suspension of (7-(benzyloxy)-1H-indol-3-yl)acetonitrile (13.2 g, 50.3 mmol) in methanol (400 mL) is added 10N aqueous sodium hydroxide solution (130 mL), and the mixture is refluxed for 5 hours. The reaction solution is cooled to room temperature, and methanol alone is distilled off. The pH value of the resultant is adjusted to pH 1 with conc. hydrochloric acid while the mixture is cooled with ice. The precipitates are collected by filtration, and dissolved in chloroform, and dried over anhydrous sodium sulfate. The solvent is evaporated to give (7-(benzyloxy)-1H-indol-3-yl)acetic acid (12.2 g, 43.4 mmol, yield: 86%).

$^1$H-NMR (DMSO-d$_6$) δ: 12.09 (1H, brs), 11.04 (1H, s), 7.55–7.57 (2H, m), 7.39–7.42 (2H, m), 7.31–7.35 (1H, m), 7.14 (1H, d, J=2.4 Hz), 7.09 (1H, d, J=7.9 Hz), 6.88 (1H, dd, J=7.9, 7.6 Hz), 6.73 (1H, d, J=7.6 Hz), 5.26 (2H, s), 3.61 (2H, s).

Reference Example 21

2-(7-(Benzyloxy)-1H-indol-3-yl) ethanol

To a solution of (7-(benzyloxy)-1H-indol-3-yl)acetic acid (7.21 g, 27.4 mmol) in tetrahydrofuran (150 mL) is added a 1M solution of borane.tetrahydrofuran complex in tetrahydrofuran (55 ml, 55 mmol) under nitrogen atmosphere, and the mixture is stirred at room temperature for 17 hours. To the reaction solution is added methanol (100 mL), and the mixture is stirred at room temperature for one hour. The solvent is evaporated, and the resulting crude product is purified by silica gel column chromatography (n-hexane: ethyl acetate=2:1→1:1) to give 2-(7-(benzyloxy)-1H-indol-3-yl)ethanol (6.37 g, 23.8 mmol, yield: 87%).

$^1$H-NMR (CDCl$_3$) δ: 8.31 (1H, s), 7.47–7.49 (2H, m), 7.34–7.43 (3H, m), 7.24 (1H, d, J=8.1 Hz), 7.06 (1H, d, J=3.2 Hz), 7.03 (1H, dd, J=8.1, 7.7 Hz), 6.74 (1H, d, J=7.7 Hz), 5.21 (2H, s), 3.90 (2H, td, J=6.3, 5.3 Hz), 3.03 (2H, t, J=6.3 Hz), 1.48 (1H, t, J=5.3 Hz).

Reference Example 22

3-(2-Hydroxyethyl)-1H-indol-7-ol

To a solution of 2-(7-(benzyloxy)-1H-indol-3-yl)ethanol (6.31 g, 23.6 mmol) in ethanol (130 mL) are added ammonium formate (6.3 g, 99.9 mmol) and 10% palladium on carbon (50% wet, 555 mg), and the mixture is refluxed for one hour. The reaction solution is cooled to room temperature, and filtered through celite. The solvent is evaporated, and the obtained crude product is purified by silica gel column chromatography (n-hexane:ethyl acetate=1:1) to give 3-(2-hydroxyethyl)-1H-indol-7-ol (3.19 g, 18.0 mmol, yield: 76%).

$^1$H-NMR (DMSO-d$_6$) δ: 10.54 (1H, s), 9.39 (1H, s), 7.00 (1H, d, J=2.3 Hz), 6.94 (1H, d, J=7.9 Hz), 6.75 (1H, t, J=7.9 Hz), 6.46 (1H, d, J=7.9 Hz), 4.57 (1H, t, J=5.3 Hz), 3.61 (2H, td, J=7.4, 5.3 Hz), 2.79 (2H, t, J=7.4 Hz).

Reference Example 23

Ethyl (((3-(2-hydroxyethyl)-1H-indol-7-yl)oxy)acetate

To a solution of 3-(2-hydroxyethyl)-1H-indol-7-ol (124 mg, 0.70 mmol) in acetone (5 mL) are added potassium carbonate (106 mg, 0.77 mmol), potassium iodide (11 mg, 0.066 mmol) and ethyl bromoacetate (172 µL, 1.56 mmol) under nitrogen atmosphere, and the mixture is stirred at room temperature for 13 hours. The insoluble materials are removed by filtration, and the solvent is removed by distillation. The resultant residue is purified by silica gel column chromatography (n-hexane:ethyl acetate=5:1→3:1→1:2) to give ethyl (((3-(2-hydroxy-ethyl)-1H-indol-7-yl)oxy)acetate (122 mg, 0.46 mmol, yield: 66%).

$^1$H-NMR (CDCl$_3$) δ: 8.88 (1H, brs), 7.29 (1H, d, J=8.0 Hz), 7.09 (1H, d, J=2.3 Hz), 7.01 (1H, dd, J=8.0, 7.8 Hz), 6.60 (1H, d, J=7.8 Hz), 4.75 (2H, s), 4.28 (2H, q, J=7.1 Hz), 3.90 (2H, td, J=6.3, 5.6 Hz), 3.02 (2H, t, J=6.3 Hz), 1.57 (1H, t, J=5.6 Hz), 1.31 (3H, t, J=7.1 Hz).

Reference Example 24

Ethyl (((3-(2-oxoethyl)-1H-indol-7-yl)oxy)acetate

To a solution of ethyl (((3-(2-hydroxyethyl)-1H-indol-7-yl)oxy)-acetate (1.2 g, 4.56 mmol) in dimethyl sulfide (56 mL) are added triethylamine (1.9 mL, 13.7 mmol) and sulfur trioxide.pyridine complex (2.18 g, 13.7 mmol) under nitrogen atmosphere, and the mixture is stirred at room temperature for one hour. The reaction solution is poured into water, and the mixture is extracted with ethyl acetate. The organic layer is washed successively with 1N aqueous hydrochloric acid solution, a saturated aqueous sodium hydrogen carbonate solution, and a saturated brine, and dried over anhydrous magnesium sulfate. The solvent is evaporated, and the obtained crude product is purified by silica gel column chromatography (n-hexane:ethyl acetate=4:1) to give ethyl (((3-(2-oxoethyl)-1H-indol-7-yl)oxy)acetate (825 mg, 3.16 mmol, yield: 69%).

$^1$H-NMR (CDCl$_3$) δ: 9.75 (1H, t, J=2.5 Hz), 9.10 (1H, brs), 7.20 (1H, d, J=8.0 Hz), 7.16 (1H, d, J=2.4 Hz), 7.03 (1H, dd, J=8.0, 7.6 Hz), 6.62 (1H, d, J=7.6 Hz), 4.75 (2H, s), 4.28 (2H, q, J=7.2 Hz), 3.78 (1H, dd, J=2.5, 0.7 Hz), 1.30 (3H, t, J=7.2 Hz).

Example 30

Ethyl (((3-(2-(((1S,2R)-2-hydroxy-2-(4-hydroxyphenyl)-1-methylethyl)-amino)ethyl)-1H-indol-7-yl)oxy)acetate To a solution of ethyl (((3-(2-oxoethyl)-1H-indol-7-yl)oxy)acetate (103 mg, 0.394 mmol) in methylene chloride (10 mL) are added 4-((2S)-2-amino-(1R)-1-hydroxypropyl)phenol (J. Med. Chem., vol. 20, no. 7, p. 978 (1977)) (72 mg, 0.431 mmol), sodium triacetoxy borohydride (126 mg, 0.595 mmol) under nitrogen atmosphere, and the mixture is stirred at room temperature for 5 hours. The reaction solution is poured into water, and the mixture is extracted with chloroform. The organic layer is washed with a saturated brine, and dried over anhydrous magnesium sulfate. The solvent is evaporated, and the obtained crude product is purified by silica gel column chromatography (chloroform:methanol=50:1→30:1→10:1) to give ethyl (((3-(2-(((1S,2R)-2-hydroxy-2-(4-hydroxyphenyl)-1-methylethyl)amino)ethyl)-1H-indol-7-yl) oxy) acetate (119 mg, 0.288 mmol, yield: 73%).

$^1$H-NMR (CDCl$_3$) δ: 8.62 (1H, brs), 7.20 (1H, d, J=8.0 Hz), 6.96 (1H, dd, J=8.0, 7.7 Hz), 6.85 (2H, d, J=8.5 Hz), 6.72 (1H, d, J=1.9 Hz), 6.50 (1H, d, J=7.7 Hz), 6.45 (2H, d, J=8.5 Hz), 4.80 (1H, d, J=3.5 Hz), 4.32–4.38 (3H, m), 3.01–3.50 (1H, m), 2.90–2.96 (1H, m), 2.75–2.85 (2H, m), 2.68 (1H, dq, J=7.0, 6.3 Hz), 1.36 (1H, t, J=7.1 Hz), 1.09 (3H, d, J=6.3 Hz).

Example 31

(((3-(2-(((1S,2R)-2-Hydroxy-2-(4-hydroxyphenyl)-1-methylethyl)amino)-ethyl)-1H-indol-7-yl)oxy)acetic acid To a solution of ethyl (((3-(2-(((1S,2R)-2-hydroxy-2-(4-hydroxy-phenyl)-1-methylethyl)amino)ethyl)-1H-indol-7-yl)oxy)acetate (115 mg, 0.279 mmol) in tetrahydrofuran (5 mL) and water (0.5 mL) is added lithium hydroxide (10 mg, 0.418 mmol), and the mixture is stirred at room temperature for 11 hours. The pH value of the mixture is adjusted to pH 7 with 1N aqueous hydrochloric acid solution, and the solvent is distilled off. The obtained crude product is purified by octadecylsilyl (ODS) column chromatography (water→10% aqueous methanol) to give (((3-(2-(((1S,2R)-2-hydroxy-2-(4-hydroxyphenyl)-1-methylethyl)amino)ethyl)-1H-indol-7-yl)oxy)acetic acid (108 mg, 0.279 mmol, yield: 100%).

$^1$H-NMR (CD$_3$OD) δ: 7.15 (1H, d, J=7.9 Hz), 7.08 (1H, s), 7.03 (2H, d, J=8.5 Hz), 6.93 (1H, dd, J=7.9, 7.6 Hz), 6.70 (2H, d, J=8.5 Hz), 6.57 (1H, d, J=7.6 Hz), 4.83 (1H, d, J=3.7 Hz), 4.47 (2H, s), 3.20–3.37 (3H, m), 3.11 (2H, t, J=7.4 Hz), 0.90 (3H, d, J=6.8 Hz).

Reference Example 25

3-((Dimethylamino)methyl)-N,N-diethyl-1H-indole-7-carboxamide

The title compound is obtained from 1H-indole-7-carboxylic acid diethylamide in a similar manner to Reference Example 18.

$^1$H-NMR (CDCl$_3$) δ: 8.96 (1H, brs), 7.77 (1H, d, J=7.9 Hz), 7.22 (1H, dd, J=7.3, 0.9 Hz), 7.17 (1H, d, J=2.3 Hz), 7.08 (1H, dd, J=7.9, 7.3 Hz), 3.63 (2H, s), 3.55 (4H, q, J=7.1 Hz), 2.27 (6H, s), 1.27 (6H, t, J=7.1 Hz).

Reference Example 26

3-(Cyanomethyl)-N,N-diethyl-1H-indole-7-carboxyamide

The title compound is obtained from 3-((dimethylamino)methyl)-N,N-diethyl-1H-indole-7-carboxamide in a similar manner to Reference Example 19.

$^1$H-NMR (CDCl$_3$) δ: 9.23 (1H, brs), 7.65 (1H, d, J=7.9 Hz), 7.28 (1H, dd, J=7.3, 0.8 Hz), 7.21 (1H, m), 7.16 (1H, dd, J=7.9, 7.3 Hz), 3.84 (2H, d, J=0.9 Hz), 3.55 (4H, q, J=7.1 Hz), 1.27 (6H, t, J=7.1 Hz).

Reference Example 27

(7-((Diethylamino)carbonyl)-1H-indol-3-yl)acetic acid

The title compound is obtained from 3-(cyanomethyl)-N,N-diethyl-1H-indole-7-carboxamide in a similar manner to Reference Example 20.

$^1$H-NMR (CDCl$_3$) δ: 9.29 (1H, brs), 7.67 (1H, d, J=7.9 Hz), 7.19 (1H, dd, J=7.3, 0.8 Hz), 7.09 (1H, dd, J=7.9, 7.3 Hz), 7.01 (1H, d, J=2.3 Hz), 3.75 (2H, d, J=0.4 Hz), 3.51 (4H, q, J=7.0 Hz), 1.25 (6H, t, J=7.0 Hz).

Reference Example 28

Methyl (7-((diethylamino)carbonyl)-1H-indol-3-yl)acetate

To a solution of (7-((diethylamino)carbonyl)-1H-indol-3-yl)acetic acid (2.38 g, 8.68 mmol) in methanol (10 mL) is added a 10% hydrogen chloride solution in methanol (30 mL) under nitrogen atmosphere, and the mixture is refluxed for 30 minutes. The reaction solution is cooled to room temperature, and the solvent is distilled off. To the residue is added chloroform, and the mixture is washed with a saturated aqueous sodium hydrogen carbonate solution and a saturated brine, and dried over anhydrous magnesium sulfate. The solvent is removed by distillation, and the resultant crude product is purified by silica gel column chromatography (n-hexane:ethyl acetate=1:1→ethyl acetate) to give methyl (7-((diethylamino)carbonyl)-1H-indol-3-yl)acetate (1.93 g, yield: 77%).

$^1$H-NMR (CDCl$_3$) δ: 8.97 (1H, brs), 7.67 (1H, d, J=7.9 Hz), 7.22–7.25 (2H, m), 7.11 (1H, dd, J=7.9, 7.5 Hz), 3.79 (2H, s), 3.70 (3H, s), 3.55 (4H, q, J=7.0 Hz), 1.26 (6H, t, J=7.0 Hz).

Reference Example 29

N,N-Diethyl-3-(2-hydroxyethyl)-1H-indole-7-carboxyamide

To a solution of methyl (7-((diethylamino)carbonyl)-1H-indol-3-yl)acetate (1.87 g, 6.48 mmol) in tetrahydrofuran (30 mL) are added sodium borohydride (1.35 g, 35.7 mmol) and methanol (5 mL) under nitrogen atmosphere, and the mixture is stirred at room temperature for 24 hours, and then refluxed for 4 hours. The mixture is cooled to room temperature, and methanol is added to the reaction solution. The solvent is evaporated, and the residue is separated into water and chloroform. The organic layer is washed with a saturated brine, and dried over anhydrous magnesium sulfate. The solvent is evaporated, and the obtained crude product is purified by silica gel column chromatography (n-hexane: ethyl acetate=1:1→ethyl acetate ethyl acetate:methanol=5: 1) to give N,N-diethyl-3-(2-hydroxyethyl)-1H-indole-7-carboxyamide (1.56 g, 5.99 mmol, yield: 92%).

$^1$H-NMR (CDCl$_3$) δ: 8.94 (1H, brs), 7.67 (1H, d, J=7.9 Hz), 7.23 (1H, dd, J=7.3, 0.8 Hz), 7.13 (1H, d, J=2.2 Hz), 7.10 (1H, dd, J=7.9, 7.3 Hz), 3.90 (2H, td, J=6.0, 6.1 Hz), 3.55 (4H, q, J=7.1 Hz), 3.04 (2H, t, J=6.0 Hz), 1.49 (1H, t, J=6.1 Hz), 1.27 (6H, t, J=7.1 Hz).

Reference Example 30

N,N-Diethyl-3-(2-oxoethyl)-1H-indole-7-carboxyamide

The title compound is obtained from N,N-diethyl-3-(2-hydroxy-ethyl)-1H-indole-7-carboxyamide in a similar manner to Reference Example 24.

$^1$H-NMR (CDCl$_3$) δ: 9.75 (1H, t, J=2.5 Hz), 9.10 (1H, brs), 7.59 (1H, d, J=7.9 Hz), 7.26 (1H, dd, J=7.2, 0.7 Hz), 7.21 (1H, d, J=2.3 Hz), 7.12 (1H, dd, J=7.9, 7.2 Hz), 3.82 (2H, dd, J=2.5, 0.7 Hz), 3.56 (4H, q, J=7.1 Hz), 1.27 (6H, t, J=7.1 Hz).

Example 32

N,N-Diethyl-3-(2-(((1S,2R)-2-hydroxy-2-(4-hydroxyphenyl)-1-methyl-ethyl)amino)ethyl)-1H-indole-7-carboxyamide The title compound is obtained from N,N-diethyl-3-(2-oxoethyl)-1H-indole-7-carboxyamide in a similar manner to Example 30.

$^1$H-NMR (CDCl$_3$) δ: 8.28 (1H, brs), 7.59 (1H, d, J=7.9 Hz), 7.19 (1H, dd, J=7.3, 0.9 Hz), 7.09 (1H, dd, J=7.9, 7.3 Hz), 6.69 (2H, d, J=8.5 Hz), 6.66 (1H, d, J=2.2 Hz), 6.30 (2H, d, J=8.5 Hz), 4.15 (1H, d, J=8.3 Hz), 3.54 (4H, brs), 3.01–3.06 (1H, m), 2.92–2.97 (1H, m), 2.74–2.81 (1H, m), 2.64–2.70 (1H, m), 2.49–2.57 (1H, m), 1.26 (6H, brs), 1.24 (3H, d, J=6.1 Hz).

Reference Example 31

1H-Indole-6-carboxylic acid diethylamide

The title compound is obtained from indole-6-carboxylic acid in a similar manner to Reference Example 14.

$^1$H-NMR (CDCl$_3$) δ: 1.20 (6H, brs), 3.3–3.5 (4H, brs), 6.54 (1H, s), 7.11 (1H, d, J=6.8 Hz), 7.25 (1H, m), 7.47 (1H, s), 7.61 (1H, d, J=8.1 Hz), 8.80 (1H, brs).

Reference Example 32

(R)-[2-(6-Diethylcarbamoyl-1H-indol-3-yl)-1-methyl-2-oxoethyl]carbamic acid 9H-fluoren-9-ylmethyl ester The title compound is obtained from 1H-indole-6-carboxylic acid diethylamide in a similar manner to Reference Example 15.

$^1$H-NMR (CDCl$_3$) δ: 1.08 (3H, brs), 1.25 (3H, brs), 1.42 (3H, d, J=6.9 Hz), 3.25 (2H, brs), 3.56 (2H, brs), 4.21 (1H, t, J=7.1 Hz), 4.36 (2H, m), 4.96 (1H, dq, J=7.2, 7.2 Hz), 6.06 (1H, d, J=7.6 Hz), 7.21 (1H, m), 7.27 (2H, m), 7.37 (2H, dt, J=3.1, 7.4 Hz), 7.59 (2H, dd, J=3.8, 7.3 Hz), 7.67 (1H, d, J=3.0 Hz), 7.74 (1H, d, J=7.5 Hz), 8.31 (1H, d, J=8.2 Hz).

Reference Example 33

(R)-3-(2-Aminopropyl)-1H-indole-6-carboxylic acid diethylamide

The title compound is obtained from (R)-[2-(6-diethylcarbamoyl-1H-indol-3-yl)-1-methyl-2-oxoethyl]carbamic acid 9H-fluoren-9-yl-methyl ester in a similar manner to Reference Example 16.

$^1$H-NMR (CDCl$_3$) δ: 1.14 (3H, d, J=6.3 Hz), 1.20 (6H, brs), 2.60 (1H, d, J=8.3, 14.2 Hz), 2.84 (1H, dd, J=4.7, 14.2 Hz), 3.22 (1H, m), 3.3–3.5 (4H, brs), 7.00 (1H, s), 7.06 (1H, dd, J=1.3, 8.1 Hz), 7.39 (1H, s), 7.54 (1H, d, J=8.1 Hz).

Example 33

3-{(2R)-2-[2-(3-Chlorophenyl)-(2R)-2-hydroxyethylamino]propyl}-1H-indole-6-carboxylic acid diethylamide.trifluoroacetate The title compound is obtained from (R)-3-(2-aminopropyl)-1H-indole-6-carboxylic acid diethylamide in a similar manner to Example 9.

$^1$H-NMR (CD$_3$OD) δ: 1.14 (3H, brs), 1.26 (3H, brs), 1.31 (3H, d, J=6.5 Hz), 3.03 (1H, dd, J=9.3, 14.2 Hz), 3.16–3.35 (5H, m), 3.56 (2H, brs), 3.66 (1H, m), 4.95 (1H, dd, J=3.2 Hz, 10.0 Hz), 7.07 (1H, dd, J=1.4, 8.2 Hz), 7.3–7.4 (4H, m), 7.43 (1H, m), 7.47 (1H, m), 7.67 (1H, d, J=8.2 Hz), 10.9 (1H, brs).

Reference Example 34

3-{(2 R)-2-[2-(4-Benzyloxy-3-methanesulfonylaminophenylphenyl)-(2R)-2-hydroxyethylamino]propyl}-1H-indole-7-carboxylic acid diethylamide The title compound is obtained from (R)-3-(2-aminopropyl)-1H-indole-7-carboxylic acid diethylamide in a similar manner to Reference Example 8.

$^1$H-NMR (CDCl$_3$) δ: 8.88 (1H, s), 7.62 (1H, d, J=7.8 Hz), 7.31–7.43 (6H, m), 7.20 (1H, d, J=6.6 Hz), 7.03–7.12 (3H, m), 6.92 (1H, d, J=8.5 Hz), 5.07 (2H, s), 4.51 (1H, dd, J=8.5, 4.1 Hz), 3.54 (4H, q, J=7.1 Hz), 2.91–3.07 (1H, m), 2.85 (3H, s), 2.78–2.86 (3H, m), 2.71 (dd, J=11.8, 8.5 Hz), 1.26 (6H, t, J=7.1 Hz), 1.14 (3H, d, J=9.2 Hz).

Example 34

3-{(2R)-2-[(2R)-2-Hydroxy-2-(4-hydroxy-3-methanesulfonylamino-phenyl)ethylamino]propyl}-1H-indole-7-carboxylic acid diethylamide trifluoroacetate To a solution of 3-{(2R)-2-[2-(4-benzyloxy-3-methanesulfonyl-aminophenylphenyl)-(2R)-2-hydroxyethylamino]propyl}-1H-indole-7-carboxylic acid diethylamide (15.1 mg, 0.0255 mmol) in methanol (3 mL) is added 10% palladium on carbon (50% wet, 5 mg), and the mixture is stirred at room temperature under hydrogen atmosphere for 4 hours. The reaction solution is filtered through celite, and the filtrate is evaporated under reduced pressure to remove the solvent. The residue is purified by preparative TLC (a saturated ammonia solution in chloroform:a saturated ammonia solution in methanol=5:1) and preparative HPLC (trifluoroacetic acid-acetonitrile water) to give the desired 3-{(2R)-2-[(2R)-2-hydroxy-2-(4-hydroxy-3-methanesulfonyl-aminophenyl)ethylamino]propyl}-1H-indole-7-carboxylic acid diethyl-amide.trifluoroacetate (10.0 mg, 0.0 162 mmol, yield: 64%).

$^1$H-NMR (CD$_3$OD) δ: 10.7 (1H, s), 7.67–7.71 (1H, m), 7.40 (1H, d, J=2.1 Hz), 7.26 (1H, s), 7.07–7.20 (3H, m), 6.90 (1H, d, J=8.3 Hz), 4.80–4.86 (1H, m), 3.30–3.68 (5H, m), 3.18–3.28 (3H, m), 3.00–3.05 (1H, m), 2.92 (3H, s), 1.08–1.34 (9H, m).

Reference Example 35 tert-Butyl [2-(4-benzyloxy-3-methanesulfonylaminophenyl)-(2R)-2-hydroxyethyl]-[2-(7-diethylcarbamoyl-1H-indol-3-yl)-(1R)-1-methyl-ethyl]carbamate To a solution of 3-{(2R)-2-[2-(4-benzyloxy-3-methanesulfonyl-aminophenylphenyl)-(2R)-2-hydroxyethylamino]propyl}-1H-indole-7-carboxylic acid diethylamide (72.3 mg, 0.122 mmol) in tetrahydrofuran (3 mL) is added di-tert-butyl bicarbonate (40 mg, 0.183 mmol) under nitrogen atmosphere, and the mixture is stirred at room temperature for 17 hours. The reaction solution is poured into water, and the mixture is extracted with chloroform. The organic layer is washed with a saturated brine, and dried over anhydrous sodium sulfate. The solvent is distilled off, and the obtained crude product is purified by preparative TLC (chloroform:methanol=30: 1) to give the desired tert-butyl [2-(4-benzyloxy-3-methanesulfonylaminophenyl)-(2R)-2-hydroxyethyl]-[2-(7-diethylcarbamoyl-1H-indol-3-yl)-(1R)-1-methylethyl]carbamate (79 mg, 0.114 mmol, yield: 93%).

$^1$H-NMR (CDCl$_3$) δ: 8.88 (1H, s), 7.63 (1H, d, J=7.3 Hz), 7.49 (1H, brs), 7.35–7.43 (6H, m), 7.20 (1H, d, J=7.2 Hz), 7.09 (1H, dd, J=8.8, 7.7 Hz), 6.95–7.00 (2H, m), 6.82 (1H, s), 5.10 (2H, s), 4.71 (1H, d, J=8.3 Hz), 4.28–4.34 (1H, m), 3.50–3.62 (5H, m), 3.11–3.15 (1H, m), 2.90 (3H, s), 2.79 (2H, m), 1.22–1.26 (18H, m).

Reference Example 36 tert-Butyl [2-(7-diethylcarbamoyl-1H-indol-3-yl)-(1R)-1-methylethyl]-[(2R)-2-hydroxy-2-(4-methanesulfonyl-3,4-dihydro-2H-benzo[1,4]oxazin-6-yl)ethyl]carbamate To a solution of tert-butyl [2-(4-benzyloxy-3-methanesulfonyl-aminophenyl)-(2R)-2-hydroxyethyl]-[2-(7-diethylcarbamoyl-1H-indol-3-yl)-(1R)-1-methylethyl]carbamate (70.0 mg, 0.101 mmol) in methanol (3 mL) is added a 10% palladium on carbon (50% wet, 35 mg), and the mixture is stirred at room temperature under hydrogen atmosphere for one hour. The reaction solution is filtered through celite, and the solvent is evaporated to remove the solvent to give crude tert-butyl [2-(7-diethylcarbamoyl-1H-indol-3-yl)-(1R)-1-methylethyl]-[(2R)-2-hydroxy-2-(4-hydroxy-3-methanesulfonylaminophenyl)ethyl]carbamate (54.8 mg). To a solution of crude tert-butyl [2-(7-diethylcarbamoyl-1H-indol-3-yl)-(1R)-1-methylethyl]-[(2 R)-2-hydroxy-2-(4-hydroxy-3-methanesulfonyl-aminophenyl)ethyl]carbamate (54.8 mg) in N,N-dimethylformamide (3 mL) are added 1,2-dibromo-ethane (18 μL, 0.209 mmol) and potassium carbonate (27.9 mg, 0.202 mmol), and the mixture is stirred at 80° C. for 2.5 hours. The reaction solution is cooled to room temperature, and the mixture is poured into a saturated aqueous sodium hydrogen carbonate solution. The mixture is extracted with ethyl acetate, and the organic layer is washed with a saturated brine, and dried over anhydrous sodium sulfate. The solvent is distilled off, and the resulting crude product is purified by preparative TLC (ethyl acetate) to give the desired tert-butyl [2-(7-diethylcarbamoyl-1H-indol-3-yl)-(1R)-1-methylethyl]-[(2R)-2-hydroxy-2-(4-methanesulfonyl-3,4-dihydro-2H-benzo[1,4]oxazin-6-yl)ethyl]carbamate (54.2 mg, 0.0862 mmol, yield: 85%).

$^1$H-NMR (CDCl$_3$) δ: 8.85 (1H,s), 7.62–7.66 (2H, m), 7.21 (1H, d, J=7.0 Hz), 7.06–7.16 (2H, m), 6.89–6.95 (2H, m), 4.70 (1H, d, J=8.3 Hz), 4.23–4.35 (3H, m), 3.81–3.95 (2H, m), 3.48–3.65 (5H, m), 3.11–3.15 (1H, m), 2.96 (3H, s), 2.80 (3H, m), 1.22–1.27 (18H, m).

Example 35

3-{(2 R)-2-[(2R)-2-Hydroxy-2-(4-methanesulfonyl-3,4-dihydro-2H-benzo-[1,4]oxazin-6-yl)ethylamino]propyl}-1H-indole-7-carboxylic acid diethylamide.trifluoroacetate To a solution of tert-butyl [2-(7-diethylcarbamoyl-1H-indol-3-yl)-(1R)-1-methylethyl]-[(2R)-2-hydroxy-2-(4-methanesulfonyl-3,4-dihydro-2H-benzo[1,4]oxazin-6-yl)ethyl]carbamate (48.4 mg, 0.077 mmol) in methylene chloride (3 mL) is added trifluoroacetic acid (250 μL) under nitrogen atmosphere, and the mixture is stirred at room temperature for 18 hours, and to the mixture is added trifluoroacetic acid (1 mL). The mixture is stirred at room temperature for 3 hours, and thereto are added trifluoroacetic acid (1 mL) and thioanisole (50 μL). The mixture is stirred at room temperature for one hour. The pH value of the reaction solution is adjusted to pH 8 with a saturated aqueous sodium hydrogen carbonate solution, and the solvent is distilled off. The residue is dissolved in chloroform:methanol (2:1, 75 mL), and the insoluble materials are removed by filtration. The solvent is removed by distillation, and the crude product is purified by preparative TLC (a saturated ammonia solution in chloroform) and preprative HPLC (trifluoroacetic acid-acetonitrile-water) to give the desired 3-{(2R)-2-[(2R)-2-hydroxy-2-(4-methanesulfonyl-3,4-dihydro-2H-benzo[1,4]oxazin-6-yl)ethylamino]propyl}-1H-indole-7-carboxylic acid diethylamide trifluoroacetate (6.6 mg, 0.0103 mmol, yield: 13%).

$^1$H-NMR (CD$_3$OD) δ: 10.6 (1H, s), 7.67 (1H, d, J=7.7 Hz), 7.40 (1H, d, J=2.0 Hz), 7.08–7.16 (3H, m), 6.92 (1H, d, J=8.5 Hz), 6.87 (1H, dd, J=8.5, 2.0 Hz), 4.78 (1H, dd, J=6.7, 4.1 Hz), 4.25–4.32 (2H, m), 3.63–3.92 (5H, m), 3.32–3.59 (4H, m), 3.39 (1H, dd, J=16. 7,3 Hz), 3.07 (1H, dd, J=16.7, 11.4 Hz), 2.92 (3H, s), 1.51 (3H, d, J=6.6 Hz), 0.97–1.30 (6H, m).

Reference Example 37

Methyl (R)-3-(2-aminopropyl)-1H-indole-7-carboxylate (R)-3-(2-Aminopropyl)-1H-indole-7-carboxylic acid diethylamide (1.80 g, 6.59 mmol) is dissolved in a mixture of 6N hydrochloric acid (10 mL) and 1,4-dioxane (10 mL), and the mixture is stirred at 150° C. for 14 hours in a sealed vessel. After cooling, the mixture is concentrated, and the residue is dissolved in 10% HCl/methanol. The mixture is refluxed for 12 hours, cooled and concentrated. To the residue is added ethyl acetate, and the mixture is washed with a saturated aqueous sodium hydrogen carbonate solution and a saturated brine, dried over sodium sulfate, and concentrated to give the desired methyl (R)-3-(2-aminopropyl)-1H-indole-7-carboxylate (1.53 g, yield: 100%).

$^1$H-NMR (CDCl$_3$) δ: 1.18 (3H, d, J=6.3 Hz), 2.71 (1H, dd, J=8.1, 14.4 Hz), 2.90 (1H, ddd, J=0.7, 5.2, 14.3 Hz), 3.99 (3H, s), 7.15 (1H, dd, J=7.6, 7.6 Hz), 7.17 (1H, d, J=1.2 Hz), 7.84 (1H, J=7.8 Hz), 7.89 (1H, dd, J=0.9, 7.5 Hz), 9.69 (1H, brs).

Reference Example 38

Methyl 3-[(2R)-2-(2-pyridin-3-yl-(2R)-2-(triethylsilyloxy)ethylamino)-propyl]-1H-indole-7-carboxylate A solution of methyl (R)-(pyridin-3-yl)oxirane (1.17 g, 9.7 mmol) and methyl (R)-3-(2-aminopropyl)-1H-indole-7-carboxylate (1.50 g, 6.5 mmol) in methanol (10 mL) is stirred at 100° C. for 2 hours under sealed conditions, and the mixture is cooled and concentrated. The residue is dissolved in N,N-dimethylformamide (20 mL), and thereto are added imidazole (1.70 g, 25 mmol) and 4-dimethylaminopyridine (61 mg, 0.5 mmol) and triethylsilyl chloride (3.25 mL, 19.4 mmol). The mixture is stirred at room temperature for 3 hours, and thereto are added ethyl acetate. The mixture is washed with a saturated aqueous sodium hydrogen carbonate solution, water, and a saturated brine, dried over sodium sulfate, and concentrated. The residue is purified by silica gel column chromatography (methanol/chloroform=1/50) to give the desired methyl 3-[(2R)-2-(2-pyridin-3-yl-(2 R)-2-(triethylsilyloxy)ethyl-amino)propyl]-1H-indole-7-carboxylate (0.74 g, yield: 24%).

$^1$H-NMR (CDCl$_3$) δ: 0.43 (6H, dq, J=2.5, 8.3 Hz), 0.80 (9H, t, J=8.0 Hz), 1.09 (3H, d, J=6.2 Hz), 2.69–2.77 (2H, m), 2.84 (1H, dd, J=6.7, 14.4 Hz), 2.91–2.99 (2H, m), 3.99 (3H, s), 4.76 (1H, dd, J=5.0, 7.1 Hz), 7.05 (1H, d, J=2.1 Hz), 7.11–7.15 (2H, m), 7.53–7.56 (1H, m), 7.78 (1H, d, J=7.8 Hz), 7.88 (1H, dd, J=1.1, 7.6 Hz), 8.45 (1H, dd, J=1.7, 4.8 Hz), 8.52 (1H, d, J=2.1 Hz), 9.60 (1H, brs).

Example 36

Methyl 3-[(2R)-2-((2R)-2-hydroxy-2-pyridin-3-yl-ethylamino)propyl]-1H-indole-7-carboxylate methyl 3-[(2R)-2-(2-pyridin-3-yl-(2R)-2-(triethylsilyloxy)ethyl-amino)propyl]-1H-indole-7-carboxylate (0.72 g, 1.54 mmol) is dissolved in trifluoroacetic acid (20 mL), and the mixture is stirred at room temperature for one day. After concentrated, to the residue is added ethyl acetate, and the mixture is washed with a saturated aqueous sodium hydrogen carbonate solution and a saturated brine, dried over sodium sulfate, and concentrated. The residue is purified by silica gel column chromatography (methanol/chloroform=1/100→1/3) to give the desired methyl 3-[(2R)-2-((2R)-2-hydroxy-2-pyridin-3-ylethylamino)-propyl]-1H-indole-7-carboxylate (440 mg, yield: 81%).

$^1$H-NMR (CDCl$_3$) δ: 1.16 (3H, d, J=6.2 Hz), 2.70 (1H, dd, J=9.3, 12.2 Hz), 2.88–2.95 (3H, m), 3.06–3.11 (1H, m), 3.99 (3H, s), 4.61 (1H, dd, J=3.6, 9.2), 7.14–7.18 (2H, m), 7.22–7.26 (1H, m), 7.65–7.68 (1H, m), 7.81 (1H, d, J=7.8 Hz), 7.90 (1H, dd, J=0.8, 7.5 Hz), 8.49 (1H, dd, J=1.7, 4.8 Hz), 8.54 (1H, d, J=1.2 Hz), 9.71 (1H, brs).

Example 37

3-[(2R)-2-((2R)-2-Hydroxy-2-pyridin-3-ylethylamino)propyl]-1H-indole-7-carboxylic acid.2 trifluoroacetate A solution of methyl 3-[(2R)-2-((2R)-2-hydroxy-2-pyridin-3-yl-ethylamino)propyl]-1H-indole-7-carboxylate (440 mg, 1.24 mmol) and potassium hydroxide (1.14 g, 20 mmol) in water (2 mL)/methanol (10 mL) is stirred at room temperature for 19 hours. After concentrated, the resultant is purified by reversed phase column chromatography (octadecylsilyl, trifluoroacetic acid/water/methanol) to give the desired 3-[(2R)-2-((2R)-2-hydroxy-2-pyridin-3-ylethylamino)propyl]-1H-indole-7-carboxylic acid.2 trifluoroacetate (560 mg, yield: 80%).

$^1$H-NMR (CD$_3$OD) δ: 1.32 (3H, d, J=6.5 Hz), 3.05 (1H, dd, J=9.5, 14.2 Hz), 3.30–3.41 (3H, m), 3.65–3.73 (1H, m), 5.13 (1H, dd, J=3.3, 9.9 Hz), 7.16 (1H, dd, J=7.7, 7.7 Hz), 7.33 (1H, s), 7.67 (1H, dd, J=5.2, 8.0 Hz), 7.88 (1H, d, J=7.4 Hz), 7.89 (1H, d, J=7.8 Hz), 8.13–8.17 (1H, m), 8.62 (1H, dd, J=1.2, 5.1 Hz), 8.72 (1H, d, J=1.8 Hz), 10.67 (1H, brs).

Examples 38 to 41

The compounds of the following Examples are obtained from 3-[(2R)-2-((2R)-2-hydroxy-2-pyridin-3-ylethylamino)propyl]-1H-indole-7-carboxylic acid.2 trifluoroacetate in a similar manner to Example 11.

Example 38

(3-{(2R)-2-[(2R)-2-Hydroxy 2-pyridin-3-ylethylamino)propyl}-1H-indol-7-yl)-piperidin-1-ylmethanone.2 trifluoroacetate $^1$H-NMR (CD$_3$OD) δ: 1.32 (3H, d, J=6.6 Hz), 1.53–1.71 (6H, m), 3.04 (1H, dd, J=9.3, 14.2 Hz), 3.32–3.47 (4H, m), 3.44 (1H, dd, J=3.2, 12.8 Hz), 3.67–3.97 (3H, m), 5.26 (1H, dd, J=3.0, 9.9 Hz), 7.12–7.19 (2H, m), 7.28 (1H, s), 7.72 (1H, dd, J=1.8, 7.2 Hz), 8.03 (1H, dd, J=7.7, 8.1 Hz), 8.57 (1H, d, J=8.1 Hz), 8.81 (1H, d, J=5.5 Hz), 8.88 (1H, d, J=1.3 Hz).

Example 39

(3-{(2R)-2-[(2R)-2-Hydroxy-2-pyridin-3-ylethylamino]propyl}-1H-indol-7-yl)-morpholin-4-yl-methanone.2 trifluoroacetate $^1$H-NMR (CD$_3$OD) δ: 1.33 (3H, d, J=6.5 Hz), 2.85–3.12 (2H, m), 3.32–3.48 (2H, m), 3.68 (9H, m), 5.17 (1H, dd, J=3.1, 10.0 Hz), 7.10–7.21 (2H, m), 7.30 (1H, s), 7.73 (1H, dd, J=1.1, 7.8 Hz), 7.84 (1H, dd, J=5.2, 7.8 Hz), 8.34 (1H, d, J=8.1 Hz), 8.71 (1H, d, J=4.8 Hz), 8.79 (1H, s), 10.78 (1H, brs).

Example 40

3-{(2R)-2-[(2R)-2-Hydroxy-2-pyridin-3-ylethylamino]propyl}-1H-indole-7-carboxylic acid dimethylamide.2 trifluoroacetate $^1$H-NMR (CD$_3$OD) δ: 1.33 (3H, d, J=6.6 Hz), 2.87–3.33 (9H, m), 3.39 (1H, dd, J=3.3, 12.9 Hz), 3.68–3.72 (1H, m), 5.16 (1H, dd, J=3.2, 9.9 Hz), 7.14 (1H, dd, J=7.4, 7.7 Hz), 7.19 (1H, dd, J=0.9, 7.2 Hz), 7.29 (1H, s), 7.72 (1H, dd, J=1.1, 7.8 Hz), 7.83 (1H, dd, J=5.4, 8.1 Hz), 8.32 (1H, d, J=8.1 Hz), 8.70 (1H, d, J=4.8 Hz), 8.77 (1H, s), 10.72 (1H, brs).

Example 41

3-{(2R)-2-[(2R)-2-Hydroxy-2-pyridin-3-ylethylamino]propyl}-1H-indole-7-carboxylic acid ethylamide.2 trifluoroacetate $^1$H-NMR (CD$_3$OD) δ: 1.26 (3H, t, J=7.2 Hz), 1.33 (3H, d, J=6.6 Hz), 2.85–3.12 (2H, m), 3.31–3.49 (2H, m), 3.46 (2H, q, J=7.3 Hz), 3.68–3.72 (1H, m), 5.21 (1H, dd, J=3.1, 10.0 Hz), 7.13 (1H, dd, J=7.7, 7.7 Hz), 7.32 (1H, s), 7.60 (1H, d, J=7.0 Hz), 7.80 (1H, dd, J=0.8, 7.9 Hz), 7.92 (1H, dd, J=5.4, 8.0 Hz), 8.45 (1H, d, J=8.1 Hz), 8.75 (1H, d, J=5.4 Hz), 8.85 (1H, s).

Example 42

(1R)-1-(3-Chlorophenyl)-2-[2-(7-diethylaminomethyl-1H-indol-3-yl)-(1R)-1-(methyl)ethylamino]ethanol A solution of 3-{(2R)-2-[2-(3-chlorophenyl)-(2R)-2-hydroxyethyl-amino]propyl}-1H-indole-7-carboxylic acid diethylamide (30 mg, 0.07 mmol) in tetrahydrofuran (3 mL) is cooled to 0° C., and thereto is added LiAlH$_4$ (9 mg, 0.21 mmol), and the mixture is stirred at 0° C. for 4 hours. To the mixture are added water (10 μL), a 15% aqueous NaOH solution (10 μL) and water (30 μL), and the insoluble materials are removed by filtration, and the filtrate is concentrated. The residue is purified by preparative reversed phase HPLC (trifluoroacetic acid/water/acetonitrile) to give the desired (1R)-1-(3-chlorophenyl)-2-[2-(7-diethylaminomethyl-1H-indol-3-yl)-(1R)-1-(methyl)ethylamino]ethanol (16 mg, yield: 36%).

$^1$H-NMR (CD$_3$OD) δ: 1.30 (3H, d, J=6.6 Hz), 1.33 (3H, t, J=7.3 Hz), 3.03 (1H, dd, J=9.6, 14.2 Hz), 3.15–3.34 (3H, m), 3.26 (2H, q, J=7.3 Hz), 3.65–3.69 (1H, m), 4.61 (2H, s), 4.98 (1H, dd, J=3.1, 10.1 Hz), 7.20 (1H, dd, J=7.5, 7.7 Hz), 7.30–7.39 (5H, m), 7.47 (1H, s), 7.76 (1H, dd, J=0.7, 7.9).

Example 43

{3-[(2R)-2-((2R)-2-Hydroxy-2-pyridin-3-ylethylamino)propyl]-1H-indol-7-yloxy}acetic acid 1-(cyclohexyloxycarbonyloxy)ethyl ester {3-[(2R)-2-((2R)-2-Hydroxy-2-pyridin-3-ylethylamino) propyl]-1H-indol-7-yloxy}acetic acid (4 mg, 0.011 mmol) and potassium carbonate (3 mg, 0.022 mmol) are added to N,N-dimethylformamide (2 mL), and to the mixture is added at 0° C. 1-iodoethylcyclohexyl carbonate (J. Antibiot., vol. 40, no. 1, p. 81–90 (1987)) (7.8 mg, 0.026 mmol). The mixture is stirred at 0° C. for 2 hours, and thereto is added a saturated brine. The mixture is extracted with ethyl acetate, and the organic layer is washed with a saturated brine, dried over sodium sulfate, and concentrated. The residue is purified by silica gel column chromatography (methanol/chloroform=1/20 to 1/1) to give the desired {3-[(2R)-2-((2R)-2-hydroxy-2-pyridin-3-ylethylamino) propyl]-1H-indol-7-yloxy}-acetic acid 1-(cyclohexyloxycarbonyloxy)ethyl ester (1 mg, yield: 17%).

$^1$H-NMR (CDCl$_3$) δ: 1.23 (3H, d, J=6.2 Hz), 1.28–1.53 (6H, m), 1.56 (1H, d, J=5.4 Hz), 1.73 (2H, m), 1.91 (2H, m), 2.77–2.82 (1H, m), 2.89–3.01 (3H, m), 3.19–3.26 (1H, m), 4.60–4.66 (1H, m), 4.77 (2H, s), 4.81 (1H, m), 6.58 (1H, d, J=7.6 Hz), 6.87 (1H, q, J=5.3 Hz), 7.00 (1H, dd, J=7.8, 7.9 Hz), 7.09 (1H, s), 7.22–7.24 (2H, m), 7.68 (1H, d, J=7.8 Hz), 8.50 (1H, d, J=3.5 Hz), 8.55 (1H, s), 8.76 (1H, s).

Example 44

Ethyl {3-[(2R)-2-((2R)-2-hydroxy-2-pyridin-3-ylethylamino)propyl]-1H-indol-7-yloxy}acetate.2 hydrochloride {3-[(2R)-2-((2R)-2-Hydroxy-2-pyridin-3-ylethylamino) propyl]-1H-indol-7-yloxy}acetic acid (65 mg, 0.176 mmol) is dissolved in ethanol (5 mL), and thereto are added conc. sulfuric acid (0.1 mL) and Molecular Sieves 4A powder (trade name, 0.3 g), and the mixture is refluxed for 20 hours. After cooling, the insoluble materials are removed by filtration, and a saturated aqueous sodium hydrogen carbonate solution is added to the filtrate. The mixture is evaporated under reduced pressure to remove ethanol, and extracted with ethyl acetate. The organic layer is washed with a saturated brine, dried over sodium sulfate, and concentrated. The residue is purified by silica gel column chromatography (ethanol/chloroform=1/5→1/1). The obtained purified product is dissolved in ethanol (3 mL), and thereto is added 1N HCl/diethyl ether (0.5 mL). The mixture is concentrated under reduced pressure to give the desired ethyl {3-[(2R)-2-((2R)-2-hydroxy-2-pyridin-3-ylethylamino)propyl]-1H-indol-7-yloxy}acetate.2 hydrochloride (63 mg, yield: 76%).

$^1$H-NMR (DMSO-d$_6$) δ: 1.17 (3H, d, J=6.5 Hz), 1.22 (3H, t, J=7.1 Hz), 2.85 (1H, dd, J=10.2, 13.9 Hz), 3.25–3.39 (3H, m), 3.50 (1H, m), 4.18 (2H, q, J=7.1 Hz), 4.91 (2H, s), 5.11–5.16 (1H, m), 6.54 (1H, d, J=7.7 Hz), 6.89 (1H, dd, J=7.9, 7.9 Hz), 7.17 (1H, d, J=2.4 Hz), 7.24 (1H, d, J=7.9 Hz), 7.72 (1H, brs), 8.17 (1H, brs), 8.70 (1H, d, J=4.5 Hz), 8.78 (1H, s), 8.96 (1H, brs), 11.15 (1H, d, J=2.2 Hz).

Example 45

3-{(2R)-2-[2-(3-Chlorophenyl)-(2R)-2-hydroxyethylamino]propyl}-1H-indole-6-carboxylic acid diethylamide To a solution of (R)-3-(2-aminopropyl)-1H-indole-6-carboxylic acid diethylamide (960 mg, 3.51 mmol) in acetonitrile (10 ml) is added (R)-(+)-3-chlorostyrene oxide (1.09 g, 7.02 mmol), and the mixture is refluxed for 5 hours. The reaction solution is concentrated under reduced pressure, and the residue is purified by silica gel column chromatography (chloroform/methanol=20/1→(a saturated ammonia solution in chloroform)/methanol=20/1) to give 3-{(2R)-2-[2-(3-chloro-phenyl)-(2R)-2-hydroxyethylamino]propyl}-1H-indole-6-carboxylic acid diethylamide (950 mg, 2.22 mmol, 63%).

$^1$H-NMR (CDCl$_3$) δ: 1.12 (3H, d, J=6.2 Hz), 1.20 (6H, br), 2.64 (1H, dd, J=9.0, 12.1 Hz), 2.83 (2H, d, J=6.6 Hz), 2.88 (1H, dd, J=3.7, 12.1 Hz), 3.04 (1H, m), 3.30 (4H, br), 4.50 (1H, dd, J=3.5, 8.9 Hz), 7.08 (1H, d, J=2.2 Hz), 7.12 (1H, dd, J=2.2, 8.1 Hz), 7.21 (3H, m), 7.34 (1H, s), 7.43 (1H, s), 7.57 (1H, d, J=8.1 Hz), 8.16 (1H, br).

Example 46

3-{(2R)-2-[2-(3-Chlorophenyl)-(2R)-2-hydroxyethylamino]propyl}-1H-indole-6-carboxylic acid To a solution of 3-{(2R)-2-[2-(3-chlorophenyl)-(2R)-2-hydroxy-ethylamino]propyl}-1H-indole-6-carboxylic acid diethylamide (800 mg, 1.87 mmol) in 1,4-dioxane (10 ml) is added 6N—HCl (10 ml), and the mixture is refluxed for 24 hours. After allowed to cool, the reaction solution is concentrated under reduced pressure, and the residue is purified by octadecylsilyl column chromatography (trifluoroacetic acid/methanol/water), and further crystallized from aqueous methanol (pH 7) to give 3-{(2R)-2-[2-(3-chlorophenyl)-(2R)-2-hydroxyethylamino]-propyl}-1H-indole-6-carboxylic acid (304 mg, 0.815 mmol, 44%) as white crystals.

$^1$H-NMR (CD$_3$OD) δ: 1.28 (3H, d, J=6.5 Hz), 2.99 (1H, dd, J=8.7, 14.2 Hz), 3.18 (3H, m), 3.56 (1H, m), 4.92 (1H, m), 7.31 (4H, m), 7.43 (1H, s), 7.55 (1H, d, J=8.4 Hz), 7.71 (1H, dd, J=1.2, 8.3 Hz), 8.06 (1H, d, J=8.2 Hz).

Example 47

3-{(2R)-2-[2-(3-Chlorophenyl)-(2R)-2-hydroxyethylamino]propyl}-1H-indole-6-carboxylic acid trifluoroacetate 3-{(2R)-2-[2-(3-Chlorophenyl)-(2R)-2-hydroxyethylamino]propyl}-1H-indole-6-carboxylic acid (9.8 mg, 0.0263 mmol) is purified by preparative reversed phase HPLC (octadecylsilyl, trifluoroacetic acid/acetonitrile/water) to give 3-{(2R)-2-[2-(3-chlorophenyl)-(2R)-2-hydroxyethylamino]propyl}-1H-indole-6-carboxylic acid.trifluoroacetate (3.9 mg, 0.0080 mmol, 30%).

$^1$H-NMR (CD$_3$OD) δ: 1.30 (3H, d, J=6.5 Hz), 3.03 (1H, dd, J=9.3, 14.2 Hz), 3.18 (1H, dd, J=10.0, 12.5 Hz), 3.20 (2H, m), 3.66 (1H, m), 4.95 (1H, dd, J=9.2, 10.0 Hz), 7.31 (3H, m), 7.40 (1H, s), 7.45 (1H, s), 7.65 (1H, d, J=8.4 Hz), 7.75 (1H, dd, J=1.4, 8.4 Hz), 8.13 (1H, m).

Examples 48 to 59

The compounds of the following Examples are obtained from 3-{(2R)-2-[2-(3-chlorophenyl)-(2R)-2-hydroxyethylamino]propyl}-1H-indole-6-carboxylic acid in a similar manner to Example 11.

Example 48

3-{(2R)-2-[2-(3-Chlorophenyl)-(2R)-2-hydroxyethylamino]propyl}-1H-indole-6-carboxylic acid dibutylamide.trifluoroacetate $^1$H-NMR (CD$_3$OD) δ: 0.74 (3H, brs), 1.01 (3H, brs), 1.10 (2H, brs), 1.30 (3H, d, J=6.5 Hz), 1.42 (2H, brs), 1.54 (2H, brs), 1.68 (2H, brs), 3.02 (1H, dd, J=9.3, 14.2 Hz), 3.15–3.31 (4H, m), 3.52 (2H, brs), 3.66 (1H, m), 4.95 (1H, dd, J=3.1, 10.0 Hz), 7.06 (1H, dd, J=1.3, 8.2 Hz), 7.36 (4H, m), 7.41 (1H, m), 7.47 (1H, m), 7.67 (1H, d, J=8.0 Hz).

Example 49

3-{(2R)-2-[2-(3-Chlorophenyl)-(2R)-2-hydroxyethylamino]propyl}-1H-indole-6-carboxylic acid (3-methylbutyl)amide.trifluoroacetate $^1$H-NMR (CD$_3$OD) δ: 0.97 (6H, d, J=6.6 Hz), 1.29 (3H, d, J=6.5 Hz), 1.53 (2H, dt, J=7.2, 8.5 Hz), 1.69 (1H, m), 3.02 (2H, dd, J=9.3, 14.2 Hz), 3.27 (2H, m), 3.45 (2H, t, J=7.4 Hz), 3.66 (1H, m), 4.95 (1H, dd, J=3.2, 10.0 Hz), 7.34 (4H, m), 7.45 (1H, m), 7.53 (1H, dd, J=1.6, 8.4 Hz), 7.66 (1H, d, J=8.7 Hz), 7.91 (1H, m).

Example 50

(3-{(2R)-2-[2-(3-Chlorophenyl)-(2R)-2-hydroxyethylamino]propyl}-1H-indol-6-yl)-piperidin-1-ylmethanone.trifluoroacetate $^1$H-NMR (CD$_3$OD) δ: 1.30 (3H, d, J=6.5 Hz), 1.41–1.65 (6H, m), 3.02 (1H, dd, J=9.3, 14.2 Hz), 3.17 (1H, m), 3.27 (2H, m), 3.30–3.50 (2H, m), 3.66–3.88 (2H, m), 4.95 (1H, dd, J=3.2, 10.0 Hz), 7.10 (2H, dd, J=1.4, 8.2 Hz), 7.34 (4H, m), 7.45 (1H, m), 7.47 (1H, m), 7.66 (1H, d, J=8.2 Hz).

Example 51

(3-{(2R)-2-[2-(3-Chlorophenyl)-(2R)-2-hydroxyethylamino]propyl}-1H-indol-6-yl)-morpholin-4-ylmethanone.trifluoroacetate $^1$H-NMR (CD$_3$OD) δ: 1.30 (3H, d, J=6.5 Hz), 3.02 (1H, dd, J=9.4, 14.2 Hz), 3.17 (1H, dd, J=10.1, 12.5 Hz), 3.25–3.76 (6H, m), 4.95 (1H, dd, J=3.2, 10.0 Hz), 7.13 (1H, dd, J=1.4, 8.2 Hz), 7.27 (4H, m), 7.47 (1H, m), 7.50 (1H, m), 7.67 (1H, d, J=8.3 Hz).

Example 52

3-{(2R)-2-[2-(3-Chlorophenyl)-(2R)-2-hydroxyethylamino]propyl}-1H-indole-6-carboxylic acid ((1S)-1-hydroxymethyl-3-methylbutyl)amide.trifluoroacetate $^1$H-NMR (CD$_3$OD) δ: 0.97 (6H, d, J=6.6 Hz), 1.31 (3H, d, J=6.5 Hz), 1.49–1.57 (4H, m), 3.04 (2H, dd, J=9.1, 14.3 Hz), 3.27 (2H, m), 3.61 (3H, d, J=5.6 Hz), 3.66 (1H, m), 4.30 (1H, tt, J=4.7 Hz), 4.93 (1H, dd, J=3.2, 10.2 Hz), 7.34 (4H, m), 7.45 (1H, s), 7.54 (1H, m), 7.66 (1H, m), 7.91 (1H, d, J=16.2 Hz).

Example 53

3-{(2R)-2-[2-(3-Chlorophenyl)-(2R)-2-hydroxyethylamino]propyl}-1H-indole-6-carboxamide.trifluoroacetate $^1$H-NMR (CD$_3$OD) δ: 1.31 (3H, d, J=6.5 Hz), 3.04 (1H, dd, J=9.1, 14.3 Hz), 3.17 (2H, m), 3.25–3.35 (3H, m), 3.66 (1H, m), 4.94 (1H, dd, J=3.2, 9.9 Hz), 7.35 (4H, m), 7.45 (1H, m), 7.59 (1H, dd, J=1.5, 8.4 Hz), 7.98 (1H, m).

Example 54

3-{(2R)-2-[2-(3-Chlorophenyl)-(2R)-2-hydroxyethylamino]propyl}-1H-indole-6-carboxylic acid methylamide.trifluoroacetate $^1$H-NMR (CD$_3$OD) δ: 1.30 (3H, d, J=6.5 Hz), 2.94 (3H, s), 3.03 (2H, dd, J=9.3, 14.2 Hz), 3.27–3.35 (3H, m), 3.65 (3H, m), 4.94 (1H, dd, J=3.2, 10.0 Hz), 7.34 (4H, m), 7.46 (1H, m), 7.53 (1H, d, J=1.5, 8.3 Hz), 7.65 (1H, d, J=8.3 Hz), 7.91 (1H, m).

Example 55

3-{(2R)-2-[2-(3-Chlorophenyl)-(2R)-2-hydroxyethylamino]propyl}-1H-indole-6-carboxylic acid dimethylamide.trifluoroacetate $^1$H-NMR (CD$_3$OD) δ: 1.30 (3H, d, J=6.5 Hz), 3.10–3.35 (6H, m), 3.04 (4H, m), 3.66 (1H, m), 4.93 (1H, dd, J=3.2, 10.2 Hz), 7.13 (1H, dd, J=1.3, 8.2 Hz), 7.27 (3H, m), 7.47 (2H, m), 7.66 (1H, d, J=8.2 Hz).

Example 56

3-{(2R)-2-[2-(3-Chlorophenyl)-(2R)-2-hydroxyethylamino]propyl}-1H-indole-6-carboxylic acid ethylamide.trifluoroacetate $^1$H-NMR (CD$_3$OD) δ: 1.24 (3H, t, J=7.2 Hz), 1.31 (3H, d, J=6.5 Hz), 3.02 (1H, dd, J=9.3, 14.2 Hz), 3.16–3.35 (3H, m), 3.46 (2H, q, J=7.2 Hz), 3.65 (1H, m), 4.94 (1H, dd, J=3.2, 10.0 Hz), 7.35 (4H, m), 7.46 (1H, m), 7.54 (1H, dd, J=1.5, 8.3 Hz), 7.65 (1H, d, J=8.3 Hz), 7.91 (1H, m).

Example 57

Ethyl [(3-{(2R)-2-[2-(3-chlorophenyl)-(2R)-2-hydroxyethylamino]propyl}-1H-indole-6-carbonyl)amino]acetate.trifluoroacetate $^1$H-NMR (CD$_3$OD) δ: 1.31 (6H, m), 3.04 (1H, dd, J=9.3, 14.2 Hz), 3.17 (1H, dd, J=10.0, 12.5 Hz), 3.30 (2H, m), 3.66 (1H, m), 4.12 (2H, s), 4.20 (2H, q, J=7.2 Hz), 4.95 (1H, d, J=3.1 Hz, 9.9 Hz), 7.37 (4H, m), 7.46 (1H, m), 7.58 (1H, dd, J=1.5, 8.4 Hz), 7.67 (1H, d, J=8.4 Hz), 7.97 (1H, m).

Example 58

Ethyl (2S)-2-[(3-{(2R)-2-[2-(3-chlorophenyl)-(2 R)-2-hydroxyethylamino]-propyl}-1H-indole-6-carbonyl)amino]propionate.trifluoroacetate $^1$H-NMR (CD$_3$OD) δ: 1.27 (3H, t, J=7.1 Hz), 1.30 (3H, d, J=6.5 Hz), 1.51 (3H, d, J=7.3 Hz), 3.03 (1H, dd, J=9.3, 14.2 Hz), 3.17 (1H, dd, J=12.5 Hz), 3.20–3.35 (2H, m), 3.66 (1H, m), 4.19 (2H, q, J=7.1 Hz), 4.60 (1H, q, J=7.3 Hz), 4.93 (1H, d, J=3.2 Hz, 10.0 Hz), 7.37 (4H, m), 7.46 (1H, m), 7.59 (1H, dd, J=1.5,8.4 Hz), 7.67 (1H, d, J=8.4 Hz), 7.96 (1H, m).

Example 59

Ethyl 3-[(3-{(2R)-2-[2-(3-chlorophenyl)-(2 R)-2-hydroxyethylamino]-propyl}-1H-indole-6-carbonyl)amino]propionate.trifluoroacetate $^1$H-NMR (CD$_3$OD) δ: 1.24 (3H, t, J=7.1 Hz), 1.30 (3H, d, J=6.5 Hz), 2.66 (3H, d, J=6.8 Hz), 3.03 (1H, dd, J=9.3, 14.2 Hz), 3.16–3.35 (3H, m), 3.66 (1H, m), 3.66 (2H, t, J=6.8 Hz), 4.14 (2H, q, J=7.1 Hz), 4.95 (1H, d, J=1.8 Hz, 9.9 Hz), 7.27 (4H, m), 7.45 (1H, m), 7.52 (1H, dd, J=1.5, 8.4 Hz), 7.65 (1H, d, J=8.4 Hz), 7.90 (1H, m).

Examples 60 to 62

The compounds of the following Examples are obtained in a similar manner to Example 24.

Example 60

[(3-{(2R)-2-[2-(3-Chlorophenyl)-(2R)-2-hydroxyethylamino]propyl}-1H-indole-6-carbonyl)amino] acetic acid.trifluoroacetate $^1$H-NMR (CD$_3$OD) δ: 1.31 (3H, d, J=6.5 Hz), 3.04 (1H, dd, J=9.3, 14.2 Hz), 3.17 (1H, dd, J=10.0, 12.6 Hz), 3.20–3.35 (2H, m), 3.66 (1H, m), 4.11 (2H, s), 4.95 (1H, d, J=3.1 Hz, 10.0 Hz), 7.35 (4H, m), 7.47 (1H, m), 7.59 (1H, dd, J=1.5, 8.4 Hz), 7.67 (1H, d, J=8.4 Hz), 7.97 (1H, m).

Example 61

Ethyl (2 S)-2-[(3-{(2R)-2-[2-(3-chlorophenyl)-(2R)-2-hydroxyethylamino]-propyl}-1H-indole-6-carbonyl)amino]propionate.trifluoroacetate $^1$H-NMR (CD$_3$OD) δ: 1.31 (3H, d, J=6.5 Hz), 1.52 (3H, d, J=7.3 Hz), 3.03 (1H, dd, J=9.3, 14.2 Hz), 3.18 (1H, dd, J=10.0, 12.6 Hz), 3.20–3.35 (2H, m), 3.66 (1H, m), 4.62 (2H, q, J=7.3 Hz), 4.95 (1H, d, J=3.2 Hz, 10.0 Hz), 7.35 (4H, m), 7.46 (1H, m), 7.60 (1H, dd, J=1.5, 8.4 Hz), 7.66 (1H, d, J=8.4 Hz), 7.97 (1H, m).

Example 62

3-[(3-{(2R)-2-[2-(3-Chlorophenyl)-(2R)-2-hydroxyethylamino]propyl}-1H-indole-6-carbonyl)amino] propionic acid.trifluoroacetate $^1$H-NMR (CD$_3$OD) δ: 1.30 (3H, d, J=6.5 Hz), 2.65 (3H, d, J=6.8 Hz), 3.02 (1H, dd, J=9.3, 14.1 Hz), 3.16–3.35 (3H, m), 3.66 (1H, m), 3.69 (2H, t, J=6.8 Hz), 4.94 (1H, d, J=3.1 Hz, 10.0 Hz), 7.35 (4H, m), 7.45 (1H, m), 7.53 (1H, d, J=8.4 Hz), 7.65 (1H, d, J=8.4 Hz), 7.92 (1H, s)

Reference Example 39

3-{(2R)-2-[2-(4-Benzyloxy-3-methanesulfonylaminophenyl)-(2R)-2-(triethylsilyloxy)ethylamino]propyl}-1H-indole-6-carboxylic acid diethyl-amide To a solution of (R)-3-(2-aminopropyl)-1H-indole-6-carboxylic acid diethylamide (20.0 mg, 0.0742 mmol) in acetonitrile (1.0 ml) is added (R)—N-[2-benzyloxy-5-(2-iodo-1-triethylsilyloxyethyl)phenyl]-methanesulfonamide (41.1 mg, 0.0742 mmol), and the mixture is stirred at 110° C. for 21 hours in a sealed vessel. The reaction solution is concentrated under reduced pressure, and the residue is purified by preparative TLC (a saturated ammonia solution in chloroform/methanol=50/1) to give 3-{(2R)-2-[2-(4-benzyloxy-3-methanesulfonylamino-phenyl)-(2R)-2-(triethylsilyloxy) ethylamino]propyl}-1H-indole-6-carboxylic acid diethylamide (19.2 mg, 0.0272 mmol, 37%).

$^1$H-NMR (CDCl$_3$) δ: 0.44 (6H, m), 0.81 (9H, t, J=8.0 Hz), 1.09 (3H, d, J=6.2 Hz), 1.20 (6H, br), 2.63 (1H, dd, J=5.6, 11.3 Hz), 2.76 (2H, m), 2.85 (3H, s), 2.94 (2H, m), 3.30 (4H, br), 4.66 (1H, t, J=6.1 Hz), 5.07 (2H, s), 6.80 (1H, d, J=8.4 Hz), 6.93 (1H, dd, J=2.1, 8.4 Hz), 6.97 (1H, d, J=2.1 Hz), 7.05 (1H, dd, J=1.3, 8.1 Hz), 7.35 (1H, s), 7.40 (7H, m), 7.50 (1H, d, J=8.2 Hz), 8.41 (1H, br).

Example 63

3-{(2R)-2-[(2R)-2-Hydroxy-2-(4-hydroxy-3-methanesulfonylamino-phenyl)ethylamino]propyl}-1H-indole-6-carboxylic acid diethylamide trifluoroacetate To a solution of 3-{(2R)-2-[2-(4-benzyloxy-3-methanesulfonyl-aminophenyl)-(2R)-2-(triethylsilyloxy)ethylamino]propyl}-1H-indole-6-carboxylic acid diethylamide (18.0 mg, 0.0254 mmol) in methylene chloride (1.0 ml) is added trifluoroacetic acid (100 μl), and the mixture is stirred at room temperature for one hour. To the reaction solution is added a 5% aqueous potassium carbonate solution, and the mixture is extracted with chloroform. The organic layers are combined and washed with a saturated brine, dried over anhydrous sodium sulfate, and concentrated under reduced pressure to give the residue (19 mg). To a solution of the residue in methanol (1.0 ml) is added 10% palladium on carbon (50% wet, 5.0 mg), and the mixture is stirred under hydrogen atmosphere for 4 hours. The reaction solution is filtered through celite and the filtrate is concentrated under reduced pressure. The resulting residue is purified by preparative reversed phase HPLC (octadecylsilyl, trifluoroacetic acid/acetonitrile/water) to give 3-{(2R)-2-[(2R)-2-hydroxy-2-(4-hydroxy-3-methanesulfonylamino-phenyl) ethylamino]propyl)-1H-indole-6-carboxylic acid diethylamide trifluoroacetate (950 mg, 2.22 mmol, 63%).

$^1$H-NMR (CD$_3$OD) δ: 1.14–1.27 (6H, br), 1.30 (3H, d, J=6.6 Hz), 2.93 (3H, s), 3.01 (1H, dd, J=9.2, 14.2 Hz), 3.18 (2H, m), 3.27 (1H, m), 3.04 (1H, m), 3.30 (2H, br), 3.56 (2H, br), 3.66 (1H, m), 4.85 (1H, m), 6.89 (1H, d, J=8.3 Hz), 7.07 (1H, dd, J=1.4, 8.2 Hz), 7.11 (1H, dd, J=2.2, 8.5 Hz), 7.31 (1H, s), 7.39(1H, d, J=2.2 Hz), 7.43 (1H, m), 7.66 (1H, d, J=8.2 Hz).

Reference Example 40

3-[(2R)-2-(2-Pyridin-3-yl-(2R)-2-(triethylsilyloxy) ethylamino)propyl]-1H-indole-6-carboxylic acid diethylamide The title compound is obtained from (R)-3-(2-aminopropyl)-1H-indole-6-carboxylic acid diethylamide in a similar manner to Reference Example 38.

$^1$H-NMR (CDCl$_3$) δ: 0.44 (6H, m), 0.81 (9H, t, J=7.8 Hz), 1.08 (3H, d, J=6.2 Hz), 1.20 (6H, br), 2.70 (2H, m), 2.80 (1H, dd, J=6.8, 14.2 Hz), 2.96 (2H, m), 3.30 (4H, br), 4.76 (1H, m), 6.99 (1H, d, J=1.3 Hz), 7.07 (1H, dd, J=1.3, 8.1 Hz), 7.15 (1H, dd, J=4.9, 8.1 Hz), 7.41 (1H, s), 7.52 (1H, d, J=8.1 Hz), 7.56 (1H, m), 8.44 (1H, br), 8.46 (1H, dd, J=1.7, 4.8 Hz), 8.50 (1H, d, J=2.0 Hz).

Example 64

3-[(2R)-2-((2R)-2-Hydroxy-2-pyridin-3-ylethylamino) propyl]-1H-indole-7-carboxylic acid diethylamide The title compound is obtained from 3-[(2R)-2-(2-pyridin-3-yl-(2R)-2-(triethylsilyloxy)ethylamino)propyl]-1H-indole-6-carboxylic acid diethylamide in a similar manner to Example 36.

$^1$H-NMR (CDCl$_3$) δ: 1.13 (3H, d, J=6.2 Hz), 1.20 (6H, br), 2.66 (2H, dd, J=9.2, 12.2 Hz), 2.80 (2H, m), 2.87 (2H, d, J=3.7, 12.2 Hz), 3.05 (1H, m), 3.40 (4H, m), 4.54 (1H, dd, J=3.6, 9.1 Hz), 7.06 (1H, d, J=2.2 Hz), 7.10 (1H, dd, J=1.4, 8.2 Hz), 7.22 (1H, m), 7.43 (1H, s), 7.56 (1H, d, J=8.1 Hz), 7.64 (1H, dt, 7.9, 1.8 Hz), 8.47 (1H, dd, J=1.6, 4.8 Hz), 8.51 (1H, d, J=2.1 Hz), 8.68 (1H, brs).

Reference Example 41

3-((Dimethylamino) methyl)-N,N-diethyl-1H-indole-6-carboxamide

The title compound is obtained from 1H-indole-6-carboxylic acid diethylamide in a similar manner to Reference Example 18.

$^1$H-NMR (CDCl$_3$) δ: 1.18 (6H, brs), 2.27 (6H, s), 3.34–3.57 (4H, m), 3.60 (2H, s), 7.11 (1H, dd, J=8.1, 1.4 Hz), 7.15 (1H, d, J=1.4 Hz), 7.42 (1H, brs), 7.67 (1H, d, J=8.1 Hz), 8.80 (1H, brs).

Reference Example 42

3-(Cyanomethyl)-N,N-diethyl-1H-indole-6-carboxamide

The title compound is obtained from 3-((dimethylamino) methyl)-N,N-diethyl-1H-indole-6-carboxamide in a similar manner to Reference Example 19.

$^1$H-NMR (CDCl$_3$) δ: 1.14–1.25 (6H, m), 3.32–3.58 (4H, m), 3.83 (1H, d, J=0.9 Hz), 7.15 (1H, dd, J=8.1, 1.3 Hz), 7.23–7.24 (1H, m), 7.47 (1H, brs), 7.56 (1H, d, J=8.1 Hz), 8.97 (1H, brs).

Reference Example 43

(6-((Diethylamino)carbonyl)-1H-indol-3-yl)acetic acid

The title compound is obtained from 3-(cyanomethyl)-N,N-diethyl-1H-indole-6-carboxamide in a similar manner to Reference Example 20.

$^1$H-NMR (CDCl$_3$) δ: 1.08–1.29 (6H, m), 3.29–3.60 (4H, m), 3.58 (2H, s), 6.22 (1H, d, J=1.3 Hz), 7.01 (1H, dd, J=8.1, 1.3 Hz), 7.36 (1H, s), 7.45 (1H, d, J=8.1 Hz), 9.08 (1H, s).

Reference Example 44

Methyl (6-(((diethylamino)carbonyl)-1H-indol-3-yl)acetate

The title compound is obtained from (6-(((diethylamino)-carbonyl)-1H-indol-3-yl)acetic acid in a similar manner to Reference Example 28.

$^1$H-NMR (CDCl$_3$) δ: 1.19 (6H, brs), 3.35–3.54 (4H, m), 3.71 (3H, s), 3.78 (2H, s), 7.13 (1H, dd, J=8.2, 1.3 Hz), 7.22 (1H, m), 7.44 (1H, brs), 7.59 (1H, d, J=8.2 Hz), 8.67 (1H, brs).

Reference Example 45

N,N-Diethyl-3-(2-hydroxyethyl)-1H-indole-6-carboxamide

The title compound is obtained from methyl (6-(((diethylamino)-carbonyl)-1H-indol-3-yl)acetic acid in a similar manner to Reference Example 29.

$^1$H-NMR (CDCl$_3$) δ: 1.19 (6H, brs), 1.54 (1H, t, J=6.1 Hz), 3.02 (2H, t, J=6.3 Hz), 3.25–3.53 (4H, m), 3.90 (2H, td, J=6.3, 6.1 Hz), 7.11–7.13 (2H, m), 7.43 (1H, s), 7.60 (1H, d, J=8.1 Hz), 8.37 (1H, brs).

Reference Example 46

N,N-Diethyl-3-(2-oxoethyl)-1H-indole-6-carboxamide

The title compound is obtained from N,N-diethyl-3-(2-hydroxy-ethyl)-1H-indole-6-carboxamide in a similar manner to Reference Example 24.

$^1$H-NMR (CDCl$_3$) δ: 1.11–1.25 (6H, m), 3.31–3.59 (4H, m), 3.76 (2H, dd, J=2.4, 0.5 Hz), 7.07–7.10 (2H, m), 7.42 (1H, m), 7.47 (1H, d, J=8.2 Hz), 9.66 (1H, brs), 9.70 (1H, t, J=2.4 Hz).

Example 65

N,N-Diethyl-3-(2-(((1S,2R)-2-hydroxy-2-(4-hydroxyphenyl)-1-methyl-ethyl)amino)ethyl)-1H-indole-6-carboxamide The title compound is obtained from N,N-diethyl-3-(2-oxoethyl)-1H-indole-6-carboxamide in a similar manner to Example 30.

$^1$H-NMR (CDCl$_3$) δ: 1.15–1.32 (6H, m), 1.23 (3H, d, J=6.1 Hz), 2.50–2.65 (2H, m), 2.80–2.87 (1H, m), 2.91–2.96 (1H, m), 3.0–3.09 (1H, m), 3.38–3.64 (4H, m), 4.03 (1H, d, J=8.5 Hz), 6.21 (2H, d, J=8.5 Hz), 6.65 (2H, d, J=8.5 Hz), 6.91 (1H, d, J=2.1 Hz), 6.97 (1H, dd, J=8.1, 2.1 Hz), 7.35 (1H, s), 7.39 (1H, d, J=8.1 Hz), 8.30 (1H, brs).

Example 66

(R)—N,N-Diethyl-3-{2-[2-(3-chlorophenyl)-2-hydroxyethylamino]ethyl}-1H-indole-7-carboxamide The title compound is obtained from N,N-diethyl-3-(2-oxoethyl)-1H-indole-7-carboxamide and (R)-2-amino-1-(3-chlorophenyl)ethanol in a similar manner to Example 30.

$^1$H-NMR (CDCl$_3$) δ: 1.26 (6H, t, J=7.1 Hz), 2.65 (1H, dd, J=12.3, 9.2 Hz), 2.90 (1H, dd, J=12.3, 3.6 Hz), 2.92–3.06 (4H, m), 3.54 (4H, q, J=7.1 Hz), 4.65 (1H, dd, J=9.2, 3.6 Hz), 7.03 (1H, d, J=1.5 Hz), 7.08 (1H, dd, J=7.7, 7.5 Hz), 7.17–7.23 (4H, m), 7.35 (1H, s), 7.64 (1H, d, J=7.7 Hz), 9.02 (1H, s).

Example 67

(3-{(2R)-2-[2-(3-Chlorophenyl)-(2R)-2-hydroxy-ethylamino]propyl}-1H-indol-7-yl)-pyrrolidin-1-ylmethanone.trifluoroacetate The title compound is obtained in a similar manner to Example 11.

$^1$H-NMR (CD$_3$OD) δ:1.31 (3H, d, J=6.5 Hz), 1.85–2.03 (4H, m), 3.04 (1H, dd, J=9.2, 14.2 Hz), 3.17 (1H, dd, J=10.2, 12.6 Hz), 3.24–3.47 (3H, m), 3.68 (4H, m), 4.93 (1H, dd, J=6.7, 10.0 Hz), 7.14 (1H, dd, J=7.4, 7.4 Hz), 7.27–7.39 (5H, m), 7.47 (1H, s), 7.72 (1H, d, J=7.9 Hz).

Example 68

Ethyl 3-{2-[(1S,2R)-2-hydroxy-2-(4-hydroxyphenyl)-1-(methyl)ethyl-amino]ethyl}-1H-indole-7-carboxylate To a solution of N,N-diethyl-3-(2-(((1S,2R)-2-hydroxy-2-(4-hydroxyphenyl)-1-methylethyl)amino)ethyl)-1H-indole-7-carboxyamide (215.5 mg, 0.526 mmol) in acetonitrile (18 mL) is added disodium hydrogen phosphate (112 mg, 0.789 mmol) under nitrogen atmosphere, and thereto is further added a 1N solution of triethyloxonium tetra-fluoroborate in methylene chloride (1.58 mL, 1.58 mmol), and the mixture is stirred at room temperature for 15 hours. To the reaction solution are added a saturated aqueous sodium hydrogen carbonate solution (18 mL) and sodium hydrogen carbonate (200 mg), and the mixture is further stirred for 2 hours. The mixture is separated into water and chloroform, and the organic layer is washed with a saturated aqueous sodium hydrogen carbonate solution and dried over anhydrous sodium sulfate. The solvent is evaporated, and the obtained crude product is purified by silica gel column chromatography (chloroform: methanol=50:1 5:1) to give ethyl 3-{2-[(1S,2R)-2-hydroxy-2-(4-hydroxyphenyl)-1-(methyl) ethylamino]ethyl}-1H-indole-7-carboxylate (128.4 mg, 0.336 mmol, 64%).

$^1$H-NMR (CDCl$_3$) 5: 0.89 (3H, d, J=6.4 Hz), 1.45 (3H, t, J=7.1 Hz), 2.80–2.86 (1H, m), 2.89–2.97 (3H, m), 3.04–3.08 (1H, m), 4.45 (2H, q, J=7.1 Hz), 4.57 (1H, d, J=4.9 Hz), 6.68 (2H, d, J=8.6 Hz), 7.02 (1H, d, J=2.1 Hz), 7.06 (2H, d, J=8.6 Hz), 7.14 (1H, dd, J=7.8, 7.5 Hz), 7.80 (1H, d, J=7.8 Hz), 7.90 (1H, d, J=7.5 Hz), 9.60 (1H, brs).

Example 69

3-{2-[(1S,2R)-2-Hydroxy-2-(4-hydroxyphenyl)-1-(methyl)ethylamino]-ethyl}-1H-indole-7-carboxylic acid To a solution of ethyl 3-{2-[(1S,2R)-2-hydroxy-2-(4-hydroxy-phenyl)-1-(methyl) ethylamino]ethyl}-1H-indole-7-carboxylate (115 mg, 0.301 mmol) in tetrahydrofuran (10 mL) and water (5 mL) is added lithium hydroxide (36 mg, 1.51 mmol), and the mixture is stirred at room temperature for 15 hours. The pH value of the reaction solution is adjusted to pH 7 with 1N aqueous hydrochloric acid solution, and the solvent is distilled off. The residue is isolated by reversed phase column (octadecylsilyl, water→water-methanol=10:1→9:1→6:1) to give 3-{2-[(1S,2R)-2-hydroxy-2-(4-hydroxyphenyl)-1-(methyl)ethyl-amino]ethyl}-1H-indole-7-carboxylic acid (69.3 mg, 0.195 mmol, 65%).

¹H-NMR (CD₃OD) δ: 1.08 (3H, d, J=6.7 Hz), 3.20–3.26 (2H, m), 3.33–3.43 (3H, m), 5.01 (1H, d, J=3.1 Hz), 6.75 (2H, d, J=8.6 Hz), 7.03–7.15 (3H, m), 7.30 (1H, s), 7.74 (1H, d, J=7.8 Hz), 7.79 (1H, d, J=7.3 Hz).

Example 70

3-{2-[(1S,2R)-2-Hydroxy-2-(4-hydroxyphenyl)-1-(methyl)ethylamino]-ethyl}-1H-indole-7-carboxylic acid ethylamide To a solution of 3-{2-[(1S,2R)-2-hydroxy-2-(4-hydroxyphenyl)-1-(methyl)ethylamino]ethyl}-1H-indole-7-carboxylic acid (29.1 mg, 0.0821 mmol) in N,N-dimethylformamide (3 mL) are added ethylamine hydrochloride (67 mg, 0.822 mmol), triethylamine (171 μL, 1.23 mmol), 1-ethyl-3-(3-dimethylaminopropyl)carbodiimide (WSCI) hydrochloride (78.7 mg, 0.411 mmol) and 1-hydroxybenzotriazole (HOBt, 55.5 mg, 0.411 mmol), and the mixture is stirred at room temperature for 17 hours. The reaction solution is poured into a saturated aqueous sodium hydrogen carbonate solution, and the mixture is separated into chloroform. The organic layer is washed with a saturated brine and dried over anhydrous sodium sulfate. The solvent is removed by distillation, and the resulting crude product is purified by preparative TLC (a saturated ammonia solution in chloroform:methanol=20:1) to give 3-{2-[(1S,2R)-2-hydroxy-2-(4-hydroxyphenyl)-1-(methyl)ethyl-amino]ethyl}-1H-indole-7-carboxylic acid ethylamide (7.5mg, 0.0197 mmol, 24%).

¹H-NMR (CDCl₃) δ: 1.02 (3H, d, J=6.3 Hz), 1.31 (3H, t, J=7.3 Hz), 2.68 (1H, qd, J=6.3, 6.3 Hz), 2.76–2.90 (2H, m), 2.97 (1H, dt, J=14.3, 5.3 Hz), 3.02–3.08 (1H, m), 3.57 (2H, qd, J=7.3, -5.1 Hz), 4.39 (1H, d, J=6.3 Hz), 6.38 (1H, brt, J=5.1 Hz), 6.56 (2H, d, J=8.5 Hz), 6.85 (1H, d, J=2.1 Hz), 6.91 (2H, d, J=8.5 Hz), 7.10 (1H, dd, J=7.8, 7.2 Hz), 7.36 (1H, d, J=7.2 Hz), 7.72 (1H, d, J=7.8 Hz), 9.70 (1H, s).

Examples 71 to 74

The compounds of the following Examples are obtained from 3-{2-[(1S,2R)-2-hydroxy-2-(4-hydroxyphenyl)-l1-(methyl)ethylamino]ethyl}-1H-indole-7-carboxylic acid in a similar manner to Example 11.

Example 71

(3-{2-[(1S,2R)-2-Hydroxy-2-(4-hydroxyphenyl)-1-(methyl)ethylamino]-ethyl}-1H-indol-7-yl)-piperidin-1-ylmethanone.trifluoroacetate ¹H-NMR (CD₃OD) δ: 1.08 (3H, d, J=6.5 Hz), 1.50 (2H, brs), 1.70 (4H, m), 3.22 (2H, m), 3.41 (3H, m), 3.75 (4H, brs), 4.99 (1H, d, J=3.1 Hz), 6.76 (2H, m), 7.14 (4H, m), 7.27 (1H, s), 7.70 (1H, dd, J=2.4, 6.9 Hz).

Example 72

(3-{2-[(1S,2R)-2-Hydroxy-2-(4-hydroxyphenyl)-1-(methyl)ethylamino]-ethyl}-1H-indol-7-yl)morpholin-4-ylmethanone.trifluoroacetate ¹H-NMR (CD₃OD) δ: 1.08 (3H, d, J=6.5 Hz), 3.22 (2H, m), 3.41 (3H, m), 3.70 (8H, brs), 4.99 (1H, d, J=3.1 Hz), 6.76 (2H, m), 7.15 (2H, m), 7.18 (2H, m), 7.29 (1H, s), 7.73 (1H, dd, J=1.3, 7.7 Hz).

Example 73

(3-{2-[(1S,2R)-2-Hydroxy-2-(4-hydroxyphenyl)-1-(methyl)ethylamino]-ethyl}-1H-indol-7-yl)-(4-methylpiperazin-1-yl)methanone.2 trifluoroacetate ¹H-NMR (CD₃OD) δ: 1.08 (3H, d, J=6.5 Hz), 2.93 (3H, s), 3.29 (4H, m), 3.39 (3H, m), 3.50 (4H, brs), 4.43 (2H, brs), 5.00 (1H, d, J=3.1 Hz), 6.76 (2H, m), 7.15 (2H, d, J=8.4 Hz), 7.18 (1H, t, J=7.8 Hz), 7.28 (1H, d, J=6.9 Hz), 7.31 (1H, s), 7.78 (1H, d, J=8.0 Hz).

Example 74

3-{2-[(1S,2R)-2-Hydroxy-2-(4-hydroxyphenyl)-1-(methyl) ethylamino]-ethyl}-1H-indole-7-carboxylic acid dimethylamide.trifluoroacetate ¹H-NMR (CD₃OD) δ: 1.08 (3H, d, J=6.5 Hz), 2.98 (3H, brs), 3.16 (3H, brs), 3.22 (2H, m), 3.39 (3H, m), 5.00 (1H, d, J=3.0 Hz), 6.76 (2H, m), 7.16 (4H, m), 7.28 (1H, s), 7.88 (1H, dd, J=1.3, 7.7 Hz).

Examples 75 to 76

The compounds of the following Examples are obtained from 3-[(2R)-2-((2R)-2-hydroxy-2-pyridin-3-ylethylamino) propyl]-1H-indole-7-carboxylic acid.2 trifluoroacetate in a similar manner to Example 11.

Example 75

{3-[(2R)-2-((2R)-2-Hydroxy-2-pyridin-3-ylethylamino)propyl]-1H-indol-7-yl}-pyrrolidin-1-ylmethanone.2 trifluoroacetate ¹H-NMR (CD₃OD) δ: 1.32 (3H, d, J=6.5 Hz), 1.90 (2H, m), 2.01 (2H, m), 3.30 (1H, dd, J=9.3, 14.2 Hz), 3.34 (2H, m), 3.43 (3H, m), 3.69 (3H, m), 5.25 (1H, dd, J=3.0, 9.9 Hz), 7.13 (1H, t, J=7.8 Hz), 7.30 (2H, m), 7.71 (1H, m), 8.03 (1H, dd, J=5.7, 8.0 Hz), 8.58 (1H, m), 8.80 (1H, d, J=5.5 Hz), 8.89 (1H, s).

Example 76

Azepan-1-yl-{3-[(2R)-2-((2R)-2-hydroxy-2-pyridin-3-ylethylamino)propyl]-1H-indol-7-yl}methanone.2 trifluoroacetate ¹H-NMR (CD₃OD) δ: 1.32 (3H, d, J=6.5 Hz), 1.57 (4H, m), 1.68 (2H, m), 1.90 (2H, m), 3.03 (1H, dd, J=9.3, 14.2 Hz), 3.34 (2H, m), 3.43 (3H, m), 3.69 (3H, m), 3.76 (2H, m), 5.27 (1H, dd, J=3.0, 9.9 Hz), 7.13 (2H, m), 7.28 (1H, s), 7.71 (1H, dd, J=2.3, 6.7 Hz), 8.05 (1H, dd, J=5.7, 8.0 Hz), 8.58 (1H, m), 8.81 (1H, d, J=5.5 Hz), 8.89 (1H, s).

Examples 77 to 89

The compounds of the following Examples 77 to 89 are obtained in a similar manner to Example 11.

Example 77

N-Benzyl-3-((2R)-2-{[(2R)-2-(3-chlorophenyl)-2-hydroxyethyl]amino}-propyl)-1H-indole-7-carboxamide.trifluoroacetate ¹H-NMR (CD₃OD) δ: 1.31 (3H, d, J=6.5 Hz), 3.05 (1H, dd, J=9.0, 14.3 Hz), 3.16–3.31 (3H, m), 3.64–3.69 (1H, m), 4.63 (2H, s), 4.93 (1H, dd, J=3.3, 9.9 Hz), 7.15 (1H, dd, J=7.7, 7.7 Hz), 7.21–7.39 (9H, m), 7.67 (1H, d, J=7.0 Hz), 7.81 (1H, dd, J=0.8, 7.9 Hz).

Example 78

3-((2R)-2-{[(2R)-2-(3-Chlorophenyl)-2-hydroxyethyl]amino}propyl)-N-phenyl-1H-indole-7-carboxamide.trifluoroacetate $^1$H-NMR (CD$_3$OD) δ: 1.33 (3H, d, J=6.5 Hz), 3.07 (1H, dd, J=9.1, 14.3 Hz), 3.15–3.33 (3H, m), 3.65–3.71 (1H, m), 4.95 (1H, dd, J=3.6, 10.1 Hz), 7.12–7.17 (1H, m), 7.21 (1H, dd, J=7.7, 7.7 Hz), 7.31–7.39 (6H, m), 7.45–7.46 (1H, m), 7.72–7.75 (2H, m), 7.85 (2H, dd, J=7.6, 9.1 Hz).

Example 79

(1R)-2-[((1R)-2-{7-[(4-Benzylpiperazin-1-yl)carbonyl]-1H-indol-3-yl}-1-methylethyl)amino]-1-(3-chlorophenyl)ethanol.trifluoroacetate $^1$H-NMR (CD$_3$OD) δ: 1.29 (3H, d, J=6.6 Hz), 3.03 (1H, dd, J=9.5, 14.2 Hz), 3.18 (1H, dd, J=10.2, 12.6 Hz), 3.25–3.35 (6H, m), 3.65–3.69 (1H, m), 3.90 (4H, m), 4.37 (2H, s), 4.96 (1H, dd, J=3.1, 10.1 Hz), 7.17 (1H, t, J=7.4 Hz), 7.27 (1H, dd, J=0.8, 7.2 Hz), 7.31–7.39 (5H, m), 7.46–7.53 (6H, m), 7.78 (1H, dd, J=0.9, 7.9 Hz).

Example 80

(1R)-1-(3-Chlorophenyl)-2-[((1R)-1-methyl-2-{7-[(4-phenylpiperazin-1-yl)-carbonyl]-1H-indol-3-yl}ethyl)amino]ethanol.2 trifluoroacetate $^1$H-NMR (CD$_3$OD) δ: 1.32 (3H, d, J=6.5 Hz), 3.04 (1H, dd, J=9.2, 14.3 Hz), 3.15–3.32 (7H, m), 3.65–3.70 (1H, m), 3.80 (4H, m), 4.94 (1H, dd, J=2.8, 9.7 Hz), 6.88–6.92 (1H, m), 7.01 (2H, dd, J=0.9, 8.7 Hz), 7.15 (1H, t, J=7.3 Hz), 7.21–7.42 (8H, m), 7.48 (1H, m), 7.74 (1H, dd, J=1.0, 7.9 Hz).

Example 81

3-((2R)-2-{[(2R)-2-(3-Chlorophenyl)-2-hydroxyethyl]amino}propyl)-N-cyclopentyl-1H-indole-7-carboxamide.trifluoroacetate $^1$H-NMR (CD$_3$OD) δ: 1.31 (3H, d, J=6.5 Hz), 1.61–1.68 (4H, m), 1.78–1.80 (2H, m), 2.02–2.07 (2H, m), 3.04 (1H, dd, J=9.1, 14.4 Hz), 3.14–3.29 (3H, m), 3.63–3.69 (1H, m), 4.93 (1H, dd, J=3.1, 9.8 Hz), 7.13 (1H, t, J=7.7 Hz), 7.31–7.38. (4H, m), 7.44 (1H, m), 7.63 (1H, dd, J=0.6, 7.5 Hz), 7.79 (1H, dd, J=0.7, 7.9 Hz).

Example 82

3-((2R)-2-{[(2R)-2-(3-Chlorophenyl)-2-hydroxyethyl]amino}propyl)-N-cyclohexyl-1H-indole-7-carboxamide.trifluoroacetate $^1$H-NMR (CD$_3$OD) δ: 1.24–1.45 (6H, m), 1.31 (3H, d, J=6.6 Hz), 1.81–1.85 (2H, m), 1.97–2.02 (2H, m), 3.04 (1H, dd, J=9.1, 14.3 Hz), 3.14–3.27 (3H, m), 3.65–3.67 (1H, m), 3.93 (1H, m), 4.93 (1H, dd, J=3.4, 9.9 Hz), 7.13 (1H, dd, J=7.7, 7.7 Hz), 7.31–7.38 (4H, m), 7.44 (1H, s), 7.63 (1H, d, J=7.1 Hz), 7.78 (1H, d, J=7.9 Hz).

Example 83

(1R)-1-(3-Chlorophenyl)-2-[((1R)-1-methyl-2-{7-[(4-methylpiperidin-1-yl)-carbonyl]-1H-indol-3-yl}ethyl)amino]ethanol.trifluoroacetate $^1$H-NMR (CD$_3$OD) δ: 0.97 (3H, d, J=6.4 Hz), 1.31 (3H, d, J=6.5 Hz), 1.03–1.93 (5H, m), 2.81–3.20 (4H, m), 3.03 (1H, dd, J=9.1, 14.3 Hz), 3.17 (1H, dd, J=10.1, 12.6 Hz), 3.24–3.28 (2H, m), 3.64–3.69 (1H, m), 4.94 (1H, d, J=3.2, 10.1 Hz), 7.12–7.18 (2H, m), 7.27 (1H, m), 7.31–7.39 (3H, m), 7.47 (1H, m), 7.68–7.73 (1H, m).

Example 84

(1R)-2-({(1R)-2-[7-(Azepan-1-ylcarbonyl)-1H-indol-3-yl]-1-methylethyl}-amino)-1-(3-chlorophenyl)ethanol.trifluoroacetate $^1$H-NMR (CD$_3$OD) δ: 1.31 (3H, d, J=6.5 Hz), 1.57–1.69 (6H, m), 1.90 (2H, m), 3.03 (1H, dd, J=9.2, 14.3 Hz), 3.18 (1H, dd, J=10.2, 12.6 Hz), 3.25–3.28 (2H, m), 3.42 (2H, m), 3.63–3.69 (1H, m), 3.74–3.77 (2H, m), 4.94 (1H, dd, J=2.8, 9.7 Hz), 7.12–7.16 (2H, m), 7.27 (1H, s), 7.31–7.42 (3H, m), 7.47 (1H, s), 7.67–7.72 (1H, m).

Example 85

3-((2 R)-2-{[(2 R)-2-(3-Chlorophenyl)-2-hydroxyethyl]amino}propyl)-N-tetrahydro-2H-pyran-4-yl-1H-indole-7-carboxamide.trifluoroacetate $^1$H-NMR (CD$_3$OD) δ: 1.31 (3H, d, J=6.5 Hz), 1.67–1.77 (2H, m), 1.91–1.95 (2H, m), 3.04 (1H, dd, J=9.1, 14.3 Hz), 3.17–3.28 (3H, m), 3.51–3.57 (2H, m), 3.65 (1H, m), 3.98–4.02 (2H, m), 4.16–4.21 (1H, m), 4.94 (1H, dd, J=3.1, 9.9 Hz), 7.14 (1H, dd, J=7.7, 7.7 Hz), 7.31–7.36 (4H, m), 7.44 (1H, s), 7.65 (1H, d, J=7.5 Hz), 7.80 (1H, dd, J=0.8, 8.0 Hz).

Example 86

3-((2R)-2-{[(2R)-2-(3-Chlorophenyl)-2-hydroxyethyl]amino}propyl)-N-cyclohexyl-N-methyl-1H-indole-7-carboxamide.trifluoroacetate $^1$H-NMR (CD$_3$OD) δ: 0.87–1.15 (2H, m), 1.30 (3H, d, J=6.5 Hz), 1.46–1.93 (8H, m), 2.90 (3H, m), 3.03 (1H, dd, J=9.2, 14.2 Hz), 3.18 (1H, dd, J=10.2, 12.6 Hz), 3.25–3.28 (2H, m), 3.47 (1H, m), 3.64–3.69 (1H, m), 4.95 (1H, dd, J=3.1, 10.1 Hz), 7.12–7.16 (2H, m), 7.26 (1H, s), 7.32–7.40 (3H, m), 7.48 (1H, s), 7.70 (1H, d, J=8.9 Hz).

Example 87

3-((2R)-2-{[(2R)-2-(3-Chlorophenyl)-2-hydroxyethyl]amino}propyl)-N-methyl-N-(1-methylpiperidin-4-yl)-1H-indole-7-carboxamide.2 trifluoroacetate $^1$H-NMR (CD$_3$OD) δ: 1.30 (3H, d, J=6.6 Hz), 2.13–2.23 (4H, m), 2.85 (3H, s), 2.96 (3H, s), 3.03 (1H, dd, J=9.4, 14.2 Hz), 3.18 (1H, dd, J=10.2, 12.6 Hz), 3.25–3.31 (2H, m), 3.31–3.68 (3H, m), 4.96 (1H, dd, J=3.1, 10.0 Hz), 7.15 (1H, dd, J=7.3, 7.3 Hz), 7.18–7.20 (1H, m), 7.29 (1H, s), 7.32–7.38 (3H, m), 7.48 (1H, s), 7.74 (1H, dd, J=1.4, 7.5 Hz).

Example 88

(1R)-2-[((1R)-2-{7-[(4-Benzylpiperidin-1-yl)carbonyl]-1H-indol-3-yl}-1-methylethyl)amino]-1-(3-chlorophenyl)ethanol.trifluoroacetate $^1$H-NMR (CD$_3$OD) δ: 1.31 (3H, d, J=6.5 Hz), 1.15–1.89 (5H, m), 2.57 (2H, d, J=6.9 Hz), 3.00 (2H, m), 3.03 (1H, dd, J=9.1, 14.3 Hz), 3.17 (1H, dd, J=10.2, 12.5 Hz), 3.24–3.29 (2H, m), 3.64–3.69 (3H, m), 4.93 (1H, dd, J=3.1, 10.0 Hz), 7.13–7.16 (5H, m), 7.22–7.26 (3H, m), 7.31–7.37 (3H, m), 7.47 (1H, s), 7.70 (1H, dd, J=2.1, 6.7 Hz).

Example 89

(1R)-1-(3-Chlorophenyl)-2-[((1R)-2-{7-1(3,5-dimethylpiperidin-1-yl)-carbonyl]-1H-indol-3-yl}-1-methylethyl)amino}ethanol.trifluoroacetate $^1$H-NMR (CD$_3$OD) δ: 0.73–0.99 (8H, m), 1.31 (3H, d, J=6.5 Hz), 1.51–1.89 (2H, m), 2.36–2.60 (2H, m), 3.04 (1H, dd, J=9.2, 14.3 Hz), 3.18 (1H, dd, J=10.3, 12.6 Hz), 3.25–3.28 (2H, m), 3.53–3.97 (2H, m), 3.64–3.70 (1H, m), 4.94 (1H, dd, J=3.0, 9.9 Hz), 7.12–7.18 (2H, m), 7.27 (1H, s), 7.32–7.40 (3H, m), 7.48 (1H, s), 7.70–7.74 (1H, m).

Example 90

Ethyl 3-((2R)-2-{[(2 R)-2-(3-chlorophenyl)-2-hydroxyethyl]amino}propyl)-1H-indole-7-carboxylate 3-{(2R)-2-[2-(3-Chlorophenyl)-(2R)-2-hydroxyethylamino]propyl}-1H-indole-7-carboxylic acid (50 mg, 0.134 mmol) is dissolved in ethanol (5 mL), and thereto are added conc. sulfuric acid (0.05 mL) and Molecular Sieves 4A powder (trade name, 0.3 g), and the mixture is heated at 150° C. for 16 hours. After cooling, the insoluble materials are removed by filtration, and a saturated aqueous sodium hydrogen carbonate solution is added to the filtrate. The mixture is evaporated under reduced pressure to remove ethanol, and the resultant is extracted with ethyl acetate. The organic layer is washed with a saturated brine, dried over sodium sulfate, and concentrated. The residue is purified by silica gel column chromatography (chloroform/ethanol=4/1) to give the title compound (50 mg, yield: 93%).

$^1$H-NMR (CDCl$_3$) δ: 1.13 (3H, d, J=6.2 Hz), 1.45 (3H, t, J=7.1 Hz), 3.04 (1H, dd, J=6.4, 12.7 Hz), 2.85–2.89 (3H, m), 3.02–3.06 (1H, m), 4.45 (2H, q, J=7.1 Hz), 4.53 (1H, dd, J=3.7, 8.9 Hz), 7.12–7.17 (3H, m), 7.20–7.22 (2H, m), 7.32 (1H, s), 7.80 (1H, d, J=7.8 Hz), 7.91 (1H, d, J=7.4 Hz), 9.70 (1H, brs).

Reference Example 47

Ethyl 3-{(2R)-2-[(5R)-5-(3-chlorophenyl)-2-oxo-1,3-oxazolidin-3-yl]-propyl}-1H-indole-7-carboxylate The title compound is obtained from ethyl 3-((2R)-2-{[(2R)-2-(3-chlorophenyl)-2-hydroxyethyl]amino}propyl)-1H-indole-7-carboxylate in a similar manner to Reference Example 17.

$^1$H-NMR (CDCl$_3$) δ: 1.32 (3H, d, J=6.8 Hz), 1.46 (3H, t, J=7.1 Hz), 2.96–2.98 (2H, m), 3.22 (1H, dd, J=6.5, 8.5 Hz), 3.83 (1H, dd, J=8.7, 8.8 Hz), 4.42–4.49 (3H, m), 5.34 (1H, dd, J=6.6, 8.9 Hz), 6.86 (1H, d, J=7.7 Hz), 7.06–7.14 (4H, m), 7.20–7.23 (1H, m), 7.80 (1H, d, J=7.8 Hz), 7.89 (1H, dd, J=0.8, 7.5 Hz), 9.65 (1H, brs).

Reference Example 48

3-{(2R)-2-[(5R)-5-(3-Chlorophenyl)-2-oxo-1,3-oxazolidin-3-yl]propyl}-1H-indole-7-carboxylic acid A solution of ethyl 3-{(2R)-2-[(5R)-5-(3-chlorophenyl)-2-oxo-1,3-oxazolidin-3-yl]propyl}-1H-indole-7-carboxylate (55 mg, 0.129 mmol) and potassium hydroxide (70 mg, 1.3 mmol) in water (1 mL) and ethanol (2 mL) is stirred at room temperature for 3 days. The reaction mixture is neutralized with 1N hydrochloric acid, and the precipitated crystals are collected by filtration to give the title compound (44 mg, yield: 86%).

$^1$H-NMR (CD$_3$OD) δ:1.34 (3H, d, J=6.8 Hz), 2.98–3.00 (2H, m), 3.24–3.28 (1H, m), 3.95 (1H, dd, J=9.1, 9.1 Hz), 4.37–4.46 (1H, m), 5.42 (1H, dd, J=6.2, 9.1 Hz), 6.77 (1H, d, J=7.8 Hz), 7.02–7.13 (4H, m), 7.20–7.23 (1H, m), 7.79–7.82 (2H, m).

Example 91

(1R)-1-(3-Chlorophenyl)-2-[((1R)-2-{7-[(2,6-dimethylpiperidin-1-yl)-carbonyl]-1H-indol-3-yl}-1-methylethyl)amino]ethanol.trifluoroacetate To a solution of 3-{(2R)-2-[(5R)-5-(3-chlorophenyl)-2-oxo-1,3-oxazolidin-3-yl]propyl}-1H-indole-7-carboxylic acid (30 mg, 0.075 mmol) in tetrahydrofuran (5 mL) is added thionyl chloride (0.011 mL, 0.15 mmol), and the mixture is stirred at room temperature for 4 hours. The reaction solution is concentrated, and thereto are added tetra-hydrofuran (3 mL) and 2,6-dimethylpiperidine (85 mg, 0.75 mmol). The mixture is stirred at room temperature for one day. The reaction solution is concentrated, and thereto are added ethanol (1 mL)/water (1 mL) and potassium hydroxide (0.60 g). The mixture is stirred at 70° C. for 6.5 hours. The reaction solution is acidified with hydrochloric acid, and purified by preparative HPLC (trifluoroacetic acid-acetonitrile-water) to give the title compound (8 mg, yield: 18%).

$^1$H-NMR (CD$_3$OD) δ: 1.31 (9H, m), 1.46–1.61 (3H, m), 1.78 (2H, m), 1.88–1.98 (1H, m), 3.03 (1H, dd, J=9.2, 14.3 Hz), 3.18 (1H, dd, J=10.2, 12.5 Hz), 3.25–3.27 (2H, m), 3.34 (2H, m), 3.64–3.69 (1H, m), 4.94 (1H, dd, J=3.1, 10.1 Hz), 7.09–7.16 (2H, m), 7.26 (1H, m), 7.31–7.39 (3H, m), 7.47 (1H, m), 7.68 (1H,m).

Examples 92 to 95

The compounds of Examples 92 to 95 are obtained in a similar manner to Example 91.

Example 92

(1R)-1-(3-Chlorophenyl)-2-{[(1R)-2-(7-{[(2R,6S)-2,6-dimethylpiperidin-1-yl]carbonyl}-1H-indol-3-yl)-1-methylethyl]amino}ethanol.trifluoroacetate $^1$H-NMR (CD$_3$OD) δ: 1.31 (9H, m), 1.46–1.61 (3H, m), 1.78 (2H, m), 1.88–1.98 (1H, m), 3.03 (1H, dd, J=9.2, 14.3 Hz), 3.18 (1H, dd, J=10.3, 12.6 Hz), 3.25–3.27 (2H, m), 3.34 (2H, m), 3.64–3.69 (1H, m), 4.94 (1H, dd, J=3.1, 10.1 Hz), 7.09–7.18 (2H, m), 7.26 (1H, s), 7.31–7.39 (3H, m), 7.47 (1H, s), 7.68 (1H, dd, J=1.1, 7.7 Hz).

Example 93

3-((2 R)-2-{[(2R)-2-(3-Chlorophenyl)-2-hydroxyethyl]amino}propyl)-N,N-diisopropyl-1H-indole-7-carboxamide.trifluoroacetate ¹H-NMR (CDCl₃) δ: 1.12 (3H, d, J=6.2 Hz), 1.40 (9H, m), 2.62 (1H, dd, J=9.2, 12.1 Hz), 2.83 (2H, m), 2.87 (1H, dd, J=3.6, 12.1 Hz), 3.00–3.06 (1H, m), 3.97 (2H, m), 4.50 (1H, dd, J=3.5, 9.1 Hz), 7.05–7.24 (6H, m), 7.35 (1H, s), 7.61 (1H, d, J=7.7 Hz), 8.78 (1H,brs).

Example 94

(1R)-1-(3-Chlorophenyl)-2-{[(1R)-2-(7-{[(2R,5R)-2,5-dimethylpyrrolidin-1-yl]carbonyl}-1H-indol-3-yl)-1-methylethyl]amino}ethanol.trifluoroacetate ¹H-NMR (CD₃OD) δ: 0.68 (3H, d, J=6.2 Hz), 1.31 (3H, d, J=6.5 Hz), 1.36 (3H, d, J=6.2 Hz), 1.57–1.69 (2H, m), 2.17–2.39 (2H, m), 3.04 (1H, dd, J=9.0, 14.3 Hz), 3.17 (1H, dd, J=10.2, 12.6 Hz), 3.24–3.34 (2H, m), 3.64–3.69 (1H, m), 4.24–4.28 (1H, m), 4.49–4.52 (1H, m), 4.93 (1H, dd, J=3.2, 10.1 Hz), 7.13 (1H, dd, J=7.8, 8.4 Hz), 7.24–7.27 (2H, m), 7.31–7.40 (3H, m), 7.46–7.47 (1H, m), 7.71 (1H, dd, J=0.8, 7.9 Hz).

Example 95

(1R)-1-(3-Chlorophenyl)-2-[((1R)-2-{7-[(2,5-dimethylpyrrolidin-1-yl)-carbonyl]-1H-indol-3-yl}-1-methylethyl)amino]ethanol.trifluoroacetate ¹H-NMR (CD₃OD) δ: 1.21 (6H, m), 1.30 (3H, d, J=6.6 Hz), 1.73 (2H, m), 2.11 (2H, m), 3.02 (1H, dd, J=9.2, 14.3 Hz), 3.17 (1H, dd, J=10.2, 12.6 Hz), 3.25–3.34 (2H, m), 3.63–3.68 (1H, m), 4.10 (2H, m), 4.95 (1H, dd, J=3.1, 10.1 Hz), 7.13 (1H, dd, J=7.3, 7.6 Hz), 7.18 (1H, dd, J=1.2, 7.2 Hz), 7.26 (1H, s), 7.31–7.39 (3H, m), 7.47–7.48 (1H, m), 7.70 (1H, dd, J=1.2, 7.7 Hz).

Reference Example 49 tert-Butyl 3-((2R)-2-((5R)-5-(3-chlorophenyl)-2-oxo-1,3-oxazolidin-3-yl)-propyl)-1H-indol-7-ylcarbamate To a solution of 3-{(2R)-2-[(5R)-5-(3-chlorophenyl)-2-oxo-1,3-oxazolidin-3-yl]propyl}-1H-indole-7-carboxylic acid (504 mg, 1.26 mmol) in toluene (25 mL) and t-butyl alcohol (12.5 mL) are added diphenyl-phosphoryl azide (379 µL, 1.76 mmol) and triethylamine (245 µL, 1.76 mmol) under nitrogen atmosphere, and the mixture is stirred at room temperature for 30 minutes, and further stirred at 100° C. for 5 hours. The reaction solution is poured into a saturated aqueous ammonium chloride solution, and the mixture is extracted with ethyl acetate. The organic layer is washed with a saturated brine, and dried over anhydrous sodium sulfate. The solvent is evaporated, and the obtained crude product is purified by silica gel column chromatography (n-hexane:ethyl acetate=2:1→1:1) to give the title compound (427 mg, 72%).

¹H-NMR (CDCl₃) δ: 1.30 (3H, d, J=6.8 Hz), 1.56 (9H, s), 2.96 (2H, d, J=7.0 Hz), 3.22 (1H, dd, J=8.6, 6.8 Hz), 3.80 (1H, t, J=8.8 Hz), 4.37–4.36 (1H, m), 5.33 (1H, dd, J=8.9, 6.8 Hz), 6.68 (1H, brd, J=6.8 Hz), 6.74 (1H, brs), 6.87 (1H, d, J=7.6 Hz), 6.96 (1H, dd, J=7.9, 7.6 Hz), 7.02 (1H, d, J=2.3 Hz), 7.10–7.17 (2H, m), 7.22–7.24 (1H, m), 7.35 (1H, d, J=7.9 Hz), 9.78 (1H, brs).

Reference Example 50

(5R)-3-((1R)-2-(7-Amino-1H-indol-3-yl)-1-methylethyl)-5-(3-chloro-phenyl)-1,3-oxazolidin-2-one To a solution of tert-butyl 3-((2R)-2-((5R)-5-(3-chlorophenyl)-2-oxo-1,3-oxazolidin-3-yl)propyl)-1H-indol-7-ylcarbamate (419.2 mg, 0.894 mmol) in methanol (2 mL) is added a 10% solution of hydrochloric acid in methanol (10 mL) under nitrogen atmosphere, and the mixture is stirred at room temperature for 21 hours. The solvent is evaporated, and the residue is separated into a saturated ammonia solution in chloroform and water, and the organic layer is washed with a saturated brine, and dried over anhydrous sodium sulfate. The solvent is evaporated, and the obtained crude product is purified by silica gel column chromatography (a saturated ammonia solution in chloroform-methanol=1:0 20:1) to give the title compound (299 mg, 90%).

¹H-NMR (CDCl₃) δ: 1.33 (3H, d, J=6.8 Hz), 2.93 (2H, d, J=7.6 Hz), 3.24 (1H, dd, J=8.6, 6.8 Hz), 3.81 (1H, t, J=8.8 Hz), 4.42–4.51 (1H, m), 5.31 (1H, dd, J=9.0, 6.8 Hz), 6.55 (1H, dd, J=7.3, 0.6 Hz), 6.71 (1H, d, J=7.8 Hz), 6.91 (1H, t, J=7.9, 7.5 Hz), 7.00 (1H, d, J=2.4 Hz), 7.02–7.06 (2H, m), 7.16–7.19 (1H, m), 8.32 (1H, s).

Reference Example 51

N-(3-((2R)-2-((5R)-5-(3-Chlorophenyl)-2-oxo-1,3-oxazolidin-3-yl)propyl)-1H-indol-7-yl)propanamide To a solution of (5R)-3-((1R)-2-(7-amino-1H-indol-3-yl)-1-methylethyl)-5-(3-chlorophenyl)-1,3-oxazolidin-2-one (28.4 mg, 0.0768 mmol) in tetrahydrofuran (1 mL) are added triethylamine (13.5 µL, 0.0969 mmol) and propionyl chloride (8 µL, 0.0921 mmol) under nitrogen atmosphere, and the mixture is stirred at room temperature for 1 hour. The reaction solution is poured into water, and the mixture is extracted with ethyl acetate. The organic layer is washed with a saturated brine, and dried over anhydrous sodium sulfate. The solvent is evaporated, and the obtained crude product is purified by preparative thin layer chromatography (n-hexane:ethyl acetate=1:1) to give the title compound (34.3 mg, yield: 100%).

¹H-NMR (CDCl₃) δ: 1.21 (3H, t, J=7.5 Hz), 1.23 (3H, d, J=6.8 Hz), 2.40 (2H, q, J=7.5 Hz), 2.86 (2H, d, J=7.4 Hz), 3.19 (1H, dd, J=8.5, 7.0 Hz), 3.74 (1H, t, J=8.8 Hz), 4.29–4.38 (1H, m), 5.26 (1H, dd, J=8.8, 7.0 Hz), 6.78–6.82 (2H, m), 6.86–6.93 (2H, m), 7.01–7.02 (1H, m), 7.08 (1H, dd, J=7.9, 7.7 Hz), 7.14–7.17 (1H, m), 7.31 (1H, d, J=7.7 Hz), 7.72 (1H, s), 9.74 (1H, s).

Example 96

N-(3-((2R)-2-(((2R)-2-(3-Chlorophenyl)-2-hydroxyethyl) amino)propyl)-1 H-indol-7-yl)propanamide To a solution of N-(3-((2R)-2-((5R)-5-(3-chlorophenyl)-2-oxo-1,3-oxazolidin-3-yl)propyl)-1H-indol-7-yl)propanamide (28.4 mg, 0.0666 mmol) in ethanol (1 mL) is added a 5N aqueous sodium hydroxide solution (0.2 mL), and the mixture is stirred at room temperature for 15 hours, and further stirred at 60° C. for 11 hours. The ethanol is evaporated, and the resulting residue is separated into a saturated aqueous sodium hydrogen carbonate solution-and chloroform. The organic layer is washed with a saturated brine, and dried over anhydrous sodium sulfate. The solvent is evaporated, and the obtained crude product is purified by preparative HPLC (water-aceto-nitrile-trifluoroacetic acid), and preparative thin layer chromatography (1st; a saturated ammonia solution in chloroform-methanol=10:1, 2nd; chloroform:methanol=10: 1) to give the title compound (3.3 mg, 12.5%).

$^1$H-NMR (CDCl$_3$) δ: 1.09 (3H, d, J=6.2 Hz), 1.24 (3H, t, J=7.6 Hz), 2.45 (2H, q, J=7.6 Hz), 2.58 (1H, dd, J=12.2, 9.3 Hz), 2.79–2.83 (3H, m), 2.98–3.04 (1H, m), 4.48 (1H, dd, J=9.3, 3.4 Hz), 6.70 (1H, d, J=7.4 Hz), 6.94 (1H, t, J=7.7 Hz), 6.99 (1H, d, J=2.1 Hz), 7.07–7.16 (3H, m), 7.24 (1H, s), 7.35 (1H, d, J=7.8 Hz), 7.48 (1H, brs), 9.78 (1H, brs).

Reference Example 52

Tetrahydro-4H-pyran-4,4-dicarboxylic acid

Diethyl tetrahydro-2H-pyran-4,4-dicarboxylate (4.04 g, 20 mmol) is suspended in a 30% aqueous sodium hydroxide solution (10 mL), and the mixture is stirred at room temperature for 28 hours. The pH value of the reaction solution is adjusted to pH 1 with conc. hydrochloric acid, and the mixture is separated into water and ethyl acetate. The organic layer is dried over anhydrous sodium sulfate, and the solvent is evaporated. Ethyl acetate (30 mL) is added to the obtained crude product, and the mixture is washed by repulping, and the resulting solid is collected by filtration, and dried to give tetrahydro-4H-pyran-4,4-dicarboxylic acid (3.19 g, 18.3 mmol, 92%).

$^1$H-NMR (DMSO-d$_6$) δ: 1.90 (4H, t, J=5.3 Hz), 3.55 (4H, t, J=5.3 Hz), 12.93 (2H, s).

Reference Example 53

Tetrahydro-2H-pyran-4-carboxylic acid

Tetrahydro-4H-pyran-4,4-dicarboxylic acid (1.01 g, 5.80 mmol) is stirred at 185° C. for one hour. The resulting residue is crystallized from toluene (5 mL) to give tetrahydro-$^2$H-pyran-4-carboxylic acid (480.6 mg, 3.69 mmol, 64%).

$^1$H-NMR (DMSO-d$_6$) δ:1.48–1.58 (2H, m), 1.70–1.74 (2H, m), 2.42–2.48 (1H, m), 3.29–3.36 (2H,m), 3.78–3.83 (2H, m), 12.22 (1H, s).

Example 97

N-(3-((2R)-2-(((2R)-2-(3-Chlorophenyl)-2-hydroxyethyl) amino)propyl)-1H-indol-7-yl)cyclohexanecarboxamide.trifluoroacetate A solution of (5R)-3-((1R)-2-(7-amino-1H-indol-3-yl)-1-methyl-ethyl)-5-(3-chlorophenyl)-1,3-oxazolidin-2-one (30 mg, 0.08 mmol), cyclohexanecarboxylic acid (15 mg, 0.12 mmol), bis(2-oxo-3-oxazolidin-yl)phosphinic chloride (3.1 mg, 0.12 mmol) and triethylamine (0.033 mL, 0.24 mmol) in tetrahydrofuran (2 mL) is stirred at room temperature for 2.5 hours. The reaction solution is poured into a saturated aqueous sodium hydrogen carbonate solution, and the mixture is extracted with ethyl acetate. The organic layer is dried over anhydrous sodium sulfate and concentrated. The residue is purified by silica gel column chromatography (chloroform:methanol=20: 1). A solution of the purified residue and potassium hydroxide (0.5 g) in ethanol (2 mL)/water (1 mL) is stirred at 80° C. for 3.5 hours. The reaction solution is acidified with hydrochloric acid, and purified by preparative HPLC (trifluoroacetic acid-acetonitrile-water) to give the title compound (29 mg, yield: 65%).

$^1$H-NMR (CD$_3$OD) δ: 1.28–1.43 (3H, m), 1.31 (3H, d, J=6.5 Hz), 1.57–1.61 (2H, m), 1.73–1.76 (1H, m), 1.85–1.89 (2H, m), 1.96–2.02 (2H, m), 2.47–2.51 (1H, m), 3.02 (1H, dd, J=9.0, 14.3 Hz), 3.16 (1H, dd, J=10.1, 12.6 Hz), 3.12–3.27 (2H, m), 3.62–3.68 (1H, m), 4.92 (1H, dd, J=3.2, 9.9 Hz), 7.04 (1H, dd, J=7.7, 7.7 Hz), 7.15 (1H, dd, J=0.6, 7.5 Hz), 7.21 (1H, s), 7.30–7.38 (3H, m), 7.44–7.46 (2H, m).

Example 98

N-(3-((2R)-2-(((2R)-2-(3-Chlorophenyl)-2-hydroxyethyl) amino)propyl)-1H-indol-7-yl)tetrahydro-2H-pyran-4-carboxamide.trifluoroacetate The title compound is obtained in a similar manner to Example 97.

$^1$H-NMR (CD$_3$OD) δ: 1.31 (3H, d, J=6.5 Hz), 1.85–1.98 (4H, m), 2.74–2.80 (1H, m), 3.02 (1H, dd, J=8.9, 14.3 Hz), 3.16–3.28 (3H, m), 3.49–3.55 (2H, m), 3.63–3.68 (1H, m), 4.01–4.06 (2H, m), 4.93 (1H, m), 7.05 (1H, dd, J=7.7, 7.7 Hz), 7.14 (1H, d, J=0.8, 7.5 Hz), 7.30–7.38 (3H, m), 7.45 (1H, m), 7.47 (1H, dd, J=0.8, 7.9 Hz).

Example 99

N-(3-((2R)-2-(((2R)-2-(3-Chlorophenyl)-2-hydroxyethyl)amino)propyl)-1H-indol-7-yl)-1-methylpiperazine-4-carboxamide.trifluoroacetate A solution of (5R)-3-((1R)-2-(7-amino-1H-indol-3-yl)-1-methyl-ethyl)-5-(3-chlorophenyl)-1,3-oxazolidin-2-one (30 mg, 0.08 mmol), N-methylpiperidine-4-carboxylic acid (34 mg, 0.24 mmol), 1-ethyl-3-(3-dimethylaminopropyl)carbodiimide hydrochloride (46 mg, 0.24 mmol), 1-hydroxybenzotriazole (32 mg, 0.24 mmol) and triethylamine (67 μL, 0.48 mmol) in tetrahydrofuran (2 mL) is stirred at room temperature for 16 hours. The mixture is diluted with ethyl acetate, washed with a saturated aqueous sodium hydrogen carbonate solution, dried over sodium sulfate, and concentrated. The residue is purified by silica gel column chromatography (a saturated ammonia solution in chloroform:methanol=100:1→20:1). A solution of the purified residue and potassium hydroxide (0.5 g) in ethanol (2 mL)/water (1 mL) is stirred at 80° C. for 3.5 hours. The reaction solution is acidified with hydrochloric acid, and purified by preparative HPLC (trifluoroacetic acid-acetonitrile-water) and preparative thin layer chromatography (silica gel, a saturated ammonia solution in chloroform:methanol=10:1) to give the title compound (5 mg, yield: 13%).

$^1$H-NMR (CDCl$_3$) δ: 1.12 (3H, d, J=6.2 Hz), 1.90–2.07 (6H, m), 2.32 (3H, s), 2.36 (1H, m), 2.61 (1H, dd, J=9.2, 12.1 Hz), 2.81–2.88 (3H, m), 2.96–3.05 (3H, m), 4.49 (1H, dd, J=3.6, 9.2 Hz), 6.75 (1H, d, J=7.4 Hz), 7.01 (1H, dd, J=7.8, 7.8 Hz), 7.05 (1H, d, J=2.1 Hz), 7.15–7.18 (1H, m), 7.19–7.23 (2H, m), 7.33 (1H, s), 7.42 (1H, d, J=7.9 Hz), 7.57 (1H, s), 9.88 (1H, brs).

Reference Example 54

Methyl 3-[(2R)-2-({(2R)-2-{4-(benzyloxy)-3-[(methylsulfonyl)amino]-phenyl}-2-[(triethylsilyl)oxy]ethyl}amino)propyl]-1H-indole-7-carboxylate A solution of (R)-N-[2-benzyloxy-5-(2-iodo-1-triethylsilyloxy-ethyl)phenyl]methanesulfonamide (2.09 g, 3.72 mmol), methyl (R)-3-(2-aminopropyl)-1H-indole-7-carboxylate (1.00 g, 3.72 mmol), diisopropyl-ethylamine (1.9 ml, 11.2 mmol) in tetrahydrofuran (30 ml)-acetonitrile (20 ml) is stirred at 110° C. for 18 hours in a sealed vessel. After cooling, to the reaction solution are added a saturated aqueous sodium hydrogen carbonate solution and a saturated brine, and the mixture is extracted with ethyl acetate. The organic layer is dried over anhydrous sodium sulfate, and concentrated under reduced pressure. The residue is purified by silica gel column chromatography (chloroform/methanol=100/1→100/4) to give the title compound (1.05 g, yield: 42%).

$^1$H-NMR (CDCl$_3$) δ: 0.42 (6H, m), 0.73 (12H, m), 2.83 (3H, s), 3.00 (5H, m), 3.93 (3H, s), 5.05 (2H, s), 5.06 (1H, m), 6.7–7.5 (11H, m), 7.77 (1H, d, J=7.7 Hz), 7.86 (1H, d, J=7.4 Hz), 9.62 (1H, br).

Reference Example 55

3-{(2 R)-2-[((2R)-2-{4-(Benzyloxy)-3-[(methylsulfonyl)amino]phenyl}-2-hydroxyethyl)amino]propyl}-1H-indole-7-carboxylic acid To a solution of methyl 3-[(2R)-2-({(2R)-2-{4-(benzyloxy)-3-[(methylsulfonyl)amino]phenyl}-2-[(triethylsilyl)oxy]ethyl}amino)propyl]-1H-indole-7-carboxylate (400 mg, 0.601 mmol) in methanol (20 ml) is added a solution of potassium hydroxide (336 mg, 6.01 mmol) in water (2.0 ml), and the mixture is stirred at 40° C. for 9 hours. The reaction solution is neutralized with 1N hydrochloric acid at 0° C., and thereto is added a pH standard solution (pH 6.8, 5.0 ml). The resultant is purified by reversed phase column (octadecylsilyl, water/methanol 95/5→40/60) to give the title compound (296 mg, yield: 92%).

$^1$H-NMR (CD$_3$OD) δ: 1.31 (3H, d, J=6.5 Hz), 1.51 (2H, br), 1.71 (4H, brs), 3.03 (1H, dd, J=9.1, 14.2 Hz), 3.17 (1H, dd, J=10.1, 12.5 Hz), 3.25 (2H, m), 3.65 (1H, m), 3.70 (2H, br), 4.95 (1H, dd, J=3.2, 10.1 Hz), 7.15 (2H, m), 7.27 (1H, s), 7.34 (3H, m), 7.48 (1H, s), 7.71 (1H, dd, J=2.2, 6.9 Hz).

Example 100

N-{2-Hydroxy-5-[(1R)-1-hydroxy-2-({(1R)-1-methyl-2-[7-(pyrrolidin-1-yl-carbonyl)-1H-indol-3-yl]ethyl}amino)ethyl]phenyl}methane sulfonamide trifluoroacetate To a solution of 3-{(2R)-2-[((2R)-2-{4-(benzyloxy)-3-[(methyl-sulfonyl)amino]phenyl}-2-hydroxyethyl)amino]propyl}-1H-indole-7-carboxylic acid (40.0 mg, 0.0744 mmol) in dimethylformamide (1.5 ml) are added triethylamine (124 μl, 1.22 mmol), pyrrolidine (62.1 μl, 0.744 mmol), 1-ethyl-3-(3-dimethylaminopropyl)carbodiimide hydrochloride (143 mg, 0.744 mmol) and 1-hydroxybenzotriazole (101 mg, 0.744 mmol), and the mixture is stirred at room temperature for 16 hours. To the reaction solution are added a saturated aqueous sodium hydrogen carbonate solution and a saturated brine, and the mixture is extracted with chloroform. The organic layers are combined, dried over anhydrous sodium sulfate, and concentrated under reduced pressure. The obtained residue is purified by preparative thin layer chromatography (a 15% methanol solution in chloroform). The obtained compound is dissolved in methanol (2.0 ml), and thereto is added a 10% palladium on carbon (50% wet, 20 mg), and the mixture is stirred under hydrogen atmosphere for 30 minutes. The mixture is filtered through celite, and the filtrate is concentrated under reduced pressure. To a solution of the residue in acetonitrile is added trifluoroacetic acid (15 ml), and the mixture is purified by preparative reversed phase HPLC (trifluoroacetic acid/water/acetonitrile) to give the title compound (25.0 mg, yield: 55%).

$^1$H-NMR (CD$_3$OD) δ: 1.29 (3H, d, J=6.6 Hz), 1.88 (2H, m), 2.01 (2H, m), 2.93 (3H, s), 3.02 (1H, dd, J=9.0, 14.3 Hz), 3.20 (2H, m), 3.27 (1H, m), 3.43 (2H, m), 3.64 (3H, m), 4.83 (1H, m), 6.89 (1H, d, J=8.3 Hz), 7.1–7.2 (2H, m), 7.25 (2H, m), 7.39 (1H, d, J=2.1 Hz), 7.71 (1H, dd, J=0.9, 7.9 Hz).

Examples 101 to 104

The compounds of Examples 101 to 127 are obtained in a similar manner to Example 100.

Example 101

N-{2-Hydroxy-5-[(1R)-1-hydroxy-2-({(1R)-1-methyl-2-[7-(piperidin-1-yl-carbonyl)-1H-indol-3-yl]ethyl}amino)ethyl]phenyl}methanesulfonamide.trifluoroacetate $^1$H-NMR (CD$_3$OD) δ: 1.30 (3H, d, J=6.6 Hz), 1.5–1.7 (6H, m), 2.92 (3H, s), 3.02 (1H, dd, J=9.0, 14.3 Hz), 3.20 (2H, m), 3.27 (1H, m), 3.40 (2H, brs), 3.65 (1H, m), 3.70 (2H, brs), 4.83 (1H, m), 6.89 (1H, d, J=8.3 Hz), 7.1–7.2 (3H, m), 7.26 (1H, s), 7.39 (1H, d, J=2.1 Hz), 7.70 (1H, dd, J=2.2, 6.8 Hz).

Example 102

N-{2-Hydroxy-5-[(1R)-1-hydroxy-2-({(1R)-1-methyl-2-[7-(morpholin-4-yl-carbonyl)-1H-indol-3-yl]ethyl}amino)ethyl]phenyl}methanesulfonamide.trifluoroacetate $^1$H-NMR (CD$_3$OD) δ: 1.30 (3H, d, J=6.6 Hz), 2.93 (3H, s), 3.02 (1H, dd, J=9.0, 14.3 Hz), 3.20 (2H, m), 3.27 (1H, m), 3.65 (9H, m), 4.83 (1H, m), 6.89 (1H, d, J=6.9 Hz), 7.1–7.2 (3H, m), 7.28 (1H, s), 7.39 (1H, d, J=2.1 Hz), 7.71 (1H, dd, J=1.2, 7.7 Hz).

Example 103

N-(2-Hydroxy-5-{(1R)-1-hydroxy-2-[((1R)-1-methyl-2-{7-[(4-methyl-piperazin-1-yl) carbonyl]-1H-indol-3-yl}ethyl)amino]ethyl}phenyl)-methanesulfonamide-2 trifluoroacetate $^1$H-NMR (CD$_3$OD) δ: 1.30 (3H, d, J=6.5 Hz), 2.93 (3H, s), 2.93 (3H, s), 3.02 (1H, dd, J=9.1, 14.3 Hz), 3.20 (2H, m), 3.27 (1H, m), 3.45 (4H, m), 3.65 (2H, m), 4.83 (1H, m), 6.89 (1H, d, J=8.3 Hz), 7.11 (1H, dd, J=2.2, 8.4 Hz), 7.18 (1H, t, J=7.8 Hz), 7.27 (1H, m), 7.31 (1H, s), 7.37 (1H, d, J=2.1 Hz), 7.77 (1H, dd, J=1.0, 8.8 Hz).

Example 104

3-{(2R)-2-[((2R)-2-Hydroxy-2-{4-hydroxy-3-[(methylsulfonyl)amino]-phenyl}ethyl)amino]propyl}-N,N-dimethyl-1H-indole-7-carboxamide.trifluoroacetate $^1$H-NMR (CD$_3$OD) δ: 1.30 (3H, d, J=6.6 Hz), 2.92 (3H, s), 3.02 (4H, m), 3.20 (5H, m), 3.25 (1H, m), 3.40 (2H, brs), 3.65 (1H, m), 4.84 (1H, dd, J=4.8, 8.3 Hz), 6.89 (1H, d, J=8.3 Hz), 7.1–7.2 (3H, m), 7.27 (1H, s), 7.38 (1H, d, J=2.1 Hz), 7.70 (1H, dd, J=1.2, 7.8 Hz).

Reference Example 56

N-(3-{(1R)-2-Iodo-1-[(triethylsilyl)oxy]ethyl}phenyl)methanesulfonamide

The title compound is obtained from N-[3-(2-bromoacetyl)-phenyl]methanesulfonamide in a similar manner to Reference Example 5, Reference Example 6 and Reference Example 7.

$^1$H-NMR (CDCl$_3$) δ: 0.54–0.61 (6H, m), 0.91 (9H, t, J=7.7 Hz), 3.01 (3H, s), 3.33 (2H, d, J=6.1 Hz), 4.75 (1H, t, J=5.8 Hz), 7.15–7.18 (2H, m), 7.22–7.23 (1H, m), 7.33 (1H, dd, J=7.9, 7.9 Hz).

Example 105

N,N-Diethyl-3-{(2R)-2-[((2R)-2-hydroxy-2-{3-[(methylsulfonyl)amino]-phenyl}ethyl)amino]propyl}-1H-indole-7-carboxamide The title compound is obtained from N-(3-{(1R)-2-iodo-1-[(triethylsilyl)oxy]ethyl}phenyl)methanesulfonamide and (R)-3-(2-amino-propyl)-1H-indole-7-carboxylic acid diethylamide in a similar manner to Reference Example 8.

$^1$H-NMR (CDCl$_3$) δ: 1.15 (3H, d, J=6.1 Hz), 1.26 (6H, t, J=7.0 Hz), 2.59 (1H, dd, J=5.0, 11.8 Hz), 2.69–2.76 (2H, m), 2.82–2.87 (1H, m), 2.86 (3H, s), 2.95–3.03 (1H, m), 3.53 (4H, m), 4.45 (1H, dd, J=5.0, 7.9 Hz), 6.85 (1H, m), 6.99 (1H, m), 7.03–7.07 (3H, m), 7.14–7.19 (2H, m), 7.58 (1H, dd, J=0.6, 7.9 Hz), 9.00 (1H, brs).

Example 106

4-[(1R,2S)-1-Hydroxy-2-({2-[7-(pyrrolidin-1-ylcarbonyl)-1H-indol-3-yl]-ethyl}amino)propyl]phenol-.trifluoroacetate The title compound is obtained from 3-{2-[(1S,2R)-2-hydroxy-2-(4-hydroxyphenyl)-1-(methyl)ethylamino]ethyl}-1H-indole-7-carboxylic acid in a similar manner to Example 11.

$^1$H-NMR (CD$_3$OD) δ: 1.08 (3H, d, J=6.5 Hz), 1.88 (2H, m), 2.01 (2H, m), 3.22 (2H, m), 3.41 (3H, m), 3.68 (2H, t, J=6.9 Hz), 4.99 (1H, d, J=3.1 Hz), 6.76 (2H, m), 7.14 (3H, m), 7.30 (2H, m), 7.72 (1H, dd, J=0.9, 7.9 Hz).

Example 107

3-((2R)-2-{[(2R)-2-(4-Chlorophenyl)-2-hydroxyethyl]amino}propyl)-N,N-diethyl-1H-indole-7-carboxamide The title compound is obtained from (R)-4-chlorostyrene oxide in a similar manner to Example 9.

$^1$H-NMR (CDCl$_3$) δ: 1.12 (3H, d, J=6.2 Hz), 1.27 (6H, t, J=7.1 Hz), 2.61 (1H, dd, J=9.2, 12.1 Hz), 2.83–2.87 (m, 3H), 3.00–3.05 (1H, m), 3.55 (4H, q, J=6. Hz), 4.51 (1H, dd, J=3.6, 9.1 Hz), 7.04–7.10 (2H, m), 7.21–7.31 (5H, m), 7.63 (1H, d, J=7.9 Hz), 8.91 (1H, brs).

Reference Example 57

N,N-Diethyl-2-(2-nitrophenyl)acetamide

The title compound is obtained from 2-nitrophenylacetic acid in a similar manner to Reference Example 14.

$^1$H-NMR (CDCl$_3$) δ: 1.14 (3H, t, J=7.1 Hz), 1.30 (3H, t, J=7.2 Hz), 3.38–3.46 (4H, m), 4.05 (2H, s), 7.34 (1H, dd, J=1.1, 7.6 Hz), 7.42–7.46 (1H, m), 7.55–7.59 (1H, m), 8.09 (1H, dd, J=1.3, 8.2 Hz).

Reference Example 58

N,N-Diethyl-2-(1H-indol-7-yl)acetamide

N,N-Diethyl-2-(2-nitrophenyl)acetamide (87.2 g, 0.369 mol) is dissolved in tetrahydrofuran (1.5L), and the mixture is cooled to −70° C. To the mixture is added dropwise a 1M solution of vinylmagnesium bromide in tetrahydrofuran (1.11 L, 1.11 mol). After the addition, the mixture is stirred at −50° C. for additional 5 hours. The reaction solution is poured into an aqueous ammonium chloride solution, and the mixture is extracted with ethyl acetate. The organic layer is washed with a saturated brine, dried over anhydrous magnesium sulfate, and concentrated. The resulting residue is purified by silica gel column chromatography (chloroform, hexane/ethyl acetate=4/1) to give the title compound (4.02 g, yield: 5%).

$^1$H-NMR (CDCl$_3$) δ: 1.05 (3H, t, J=7.1 Hz), 1.13 (3H, t, J=7.2 Hz), 3.33 (2H, q, J=7.1 Hz), 3.42 (2H, q, J=7.2 Hz), 3.94 (2H, s), 6.52–6.53 (1H, m), 6.96 (1H, d, J=7.0 Hz), 7.04 (1H, dd, J=7.4, 7.6 Hz), 7.23–7.26 (2H, m), 7.57 (1H, d, J=7.8 Hz), 10.05 (1H, brs).

Reference Example 59

2-{3-[(2R)-2-Aminopropyl]-1H-indol-7-yl}-N,N-diethylacetamide

The title compound is obtained from N,N-diethyl-2-(1H-indol-7-yl)acetamide in a similar manner to Reference Example 4.

$^1$H-NMR (CDCl$_3$) δ: 1.06 (3H, t, J=7.1 Hz), 1.15 (3H, t, J=7.2 Hz), 1.16 (3H, d, J=6.3 Hz), 2.64 (1H, dd, J=8.2, 14.0 Hz), 2.87 (1H, dd, J=4.4, 14.2 Hz), 3.24–3.29 (1H, m), 3.34 (2H, q, J=7.1 Hz), 3.43 (2H, q, J=7.1 Hz), 3.92 (2H, s), 6.97 (1H, d, J=7.2 Hz), 7.04 (1H, dd, J=7.1, 7.8 Hz), 7.07 (1H, d, J=2.3 Hz), 7.53 (1H, d, J=7.9 Hz), 9.88 (1 Hbrs).

Example 108

2-[3-((2R)-2-{[(2R)-2-(3-Chlorophenyl)-2-hydroxyethyl]amino}propyl)-1H-indol-7-yl]-N,N-diethylacetamide To a solution of 2-{3-[(2R)-2-aminopropyl]-1H-indol-7-yl}-N,N-diethylacetamide (1.0 g, 3.48 mmol) in dimethylsulfoxide (5 mL) is added N-trimethylsilylacetamide (0.50 g, 3.83 mmol), and the mixture is stirred at room temperature for 1 hour. To the reaction solution is added (R)-(+)-3-chlorostyrene oxide (0.89 mL, 6.96 mmol), and the mixture is stirred at 110° C. for 2 hours. After cooling, a 2 N hydrochloric acid (5 mL) is added to the mixture, and the mixture is stirred at room temperature for 0.5 hour. To the mixture are added a saturated aqueous sodium hydrogen carbonate solution and a saturated brine, and the mixture is extracted with chloroform. The organic layer is dried over anhydrous sodium sulfate and concentrated. The residue is purified by silica gel column chromatography (a saturated ammonia solution in chloroform) to give the title compound (0.90 g, yield: 59%).

$^1$H-NMR (CDCl$_3$) δ: 1.06 (3H, t, J=7.1 Hz), 1.12 (3H, d, J=6.2 Hz), 1.14 (3H, t, J=7.2 Hz), 2.62 (1H, dd, J=9.2, 12.1 Hz), 2.82–2.90 (3H, m), 3.01–3.06 (1H, m), 3.34 (2H, q, J=7.1 Hz), 3.43 (2H, q, J=7.2 Hz), 3.92 (2H, s), 4.50 (1H, dd, J=3.6, 9.1 Hz), 6.97 (1H, d, J=7.0 Hz), 7.03–7.07 (2H, m), 7.16–7.25 (3H, m), 7.33–7.34 (1H, m), 7.51 (1H, d, J=7.9 Hz), 9.90 (1H, brs).

Reference Example 60

(1R)-2-(7-(Benzyloxy)-1H-indol-3-yl)-1-methyl-ethylamine

The title compound is obtained in a similar manner to Reference Example 4.

$^1$H-NMR (CDCl$_3$) δ: 1.16 (3H, d, J=6.3 Hz), 2.64 (1H, dd, J=14.1, 8.2 Hz), 2.86 (1H, d, J=14.1, 4.9 Hz), 3.24–3.32 (1H, m), 6.73 (1H, d, J=7.7 Hz), 7.01–7.04 (2H, m), 7.24 (1H, d, J=8 Hz), 7.34–7.43 (3H, m), 7.47–7.49 (2H, m), 8.30 (1H, s).

Reference Example 61

(2R)-N-((1R)-2-(7-(Benzyloxy)-1H-indol-3-yl)-1-methylethyl)-2-hydroxy-2-pyridin-3-ylacetamide To a solution of (1R)-2-(7-(benzyloxy)-1H-indol-3-yl)-1-methyl-ethylamine (5.0 g, 17.8 mmol) in tetrahydrofuran (100 mL) are added successively with stirring (R)-2-hydroxy-2-(3-pyridyl)acetic acid.sulfate (4.68 g, 11.6 mmol), triethylamine (3.22 mL, 23.1 mmol), 1-ethyl-3-(3-dimethylaminopropyl)carbodiimide.hydrochloride (4.78 g, 24.9 mmol), and 1-hydroxybenzotriazole (3.36 g, 24.9 mmol) under ice-cooling, and the mixture is stirred at room temperature for 2.5 hours. The reaction mixture is diluted with a mixture of a saturated aqueous sodium hydrogen carbonate solution and water (1:1, 100 mL), and extracted with ethyl acetate (2×100 mL). The organic layers are combined and washed with a mixture of a saturated brine and water (1:1, 100 mL), dried over magnesium sulfate, and separated by filtration. The filtrate is concentrated under reduced pressure, and the obtained pale brown solid is dispersed into chloroform (80 mL). The insoluble white solid is collected by filtration, washed with chloroform (40 mL), and dried under reduced pressure to give the title compound (6.38 g, yield: 86%).

$^1$H-NMR (CDCl$_3$) δ: 1.20 (3H, d, J=6.6 Hz), 2.85 (1H, dd, J=14.6, 5.5 Hz), 2.91 (1H, dd, J=14.6, 6.1 Hz), 4.32–4.39 (1H, m), 4.96 (1H, s), 5.20 (2H, s), 5.97 (1H, d, J=8.2 Hz), 6.72 (1H, d, 7.8 Hz), 6.73 (1H, s), 7.00 (1H, dd, J=8.0, 7.8 Hz), 7.13 (1H, d, J=8.0 Hz), 7.20 (1H, d, J=7.9, 4.8 Hz), 7.38–7.44 (3H, m), 7.48–7.50 (2H, m), 7.59 (1H, ddd, J=7.9, 2.2, 1.6 Hz), 8.34 (1H, brs), 8.53 (1H, dd, J=4.8, 1.6 Hz), 8.57 (1H, d, J=2.2 Hz).

Reference Example 62

(1R)-2-(((1R)-2-(7-(Benzyloxy)-1H-indol-3-yl)-1-methylethyl)amino)-1-pyridin-3-ylethanol To a solution of (2R)-N-((1R)-2-(7-(benzyloxy)-1H-indol-3-yl)-1-methylethyl)-2-hydroxy-2-pyridin-3-ylacetamide (283 mg, 0.681 mmol) in tetrahydrofuran (15 mL) is added a 2M solution of boranedimethyl sulfide complex in tetrahydrofuran (2.04 mL, 4.09 mmol), and the mixture is refluxed for 3 hours. To the reaction solution is added a 10% hydrogen chloride solution in methanol (30 mL), and the mixture is stirred for 30 minutes. The solvent is evaporated, and the residue is separated into a saturated aqueous sodium hydrogen carbonate solution and chloroform. The organic layer is washed with a saturated brine, and dried over sodium sulfate. The solvent is distilled off, and the obtained crude product is purified by silica gel column chromatography (a saturated ammonia solution in chloroform-methanol=100:1) to give the title compound (184.8 mg, yield: 68%).

$^1$H-NMR (CDCl$_3$) δ: 1.13 (3H, d, J=6.2 Hz), 2.65 (1H, dd, J=12.1, 9.2 Hz), 2.77–2.88 (3H, m), 3.01–3.08 (1H, m), 4.54 (1H, dd, J=9.2, 3.6 Hz), 5.19 (2H, s), 6.72 (1H, d, J=7.7 Hz), 6.97 (1H, d, J=2.1 Hz), 7.02 (1H, t, J=7.8 Hz), 7.20–7.22 (2H, m), 7.33–7.41 (3H, m), 7.46–7.48 (2H, m), 7.63–7.66 (1H, m), 8.45–8.50 (3H, m).

Reference Example 63 tert-Butyl (1R)-2-(7-(benzyloxy)-1H-indol-3-yl)-1-methylethyl-((2R)-2-hydroxy-2-pyridin-3-ylethyl)carbamate To a solution of (1R)-2-(((1R)-2-(7-(benzyloxy)-1H-indol-3-yl)-1-methylethyl)amino)-1-pyridin-3-ylethanol (182 mg, 0.453 mmol) in tetrahydrofuran (5 mL) is added di-tert-butyl bicarbonate (148 mg, 0.677 mmol), and the mixture is stirred at room temperature for one day. Without concentration, the reaction solution is purified by silica gel column chromatography (n-hexane n-hexane:ethyl acetate=2:1→1:1→1:2) to give the title compound (205.4 mg, yield: 91%).

$^1$H-NMR (CDCl$_3$) δ: 1.27 (3H, d, J=6.9 Hz), 1.29 (9H, s), 2.79–2.85 (2H, m), 3.10 (1H, m), 3.59–3.65 (1H, m), 4.26–4.31 (1H, m), 4.69 (1H, m), 5.20 (2H, s), 5.55 (1H, s), 6.72 (1H, d, J=7.6 Hz), 6.88 (1H, brs), 7.02 (1H, dd, J=8.0, 7.5 Hz), 7.20 (1H, d, J=7.5 Hz), 7.26–7.32 (1H, m), 7.32–7.41 (3H, m), 7.44–7.52 (2H, m), 7.74 (1H, m), 8.27 (1H, s), 8.51–8.53 (3H, m).

Reference Example 64 tert-Butyl (1R)-2-(7-(benzyloxy)-1H-indol-3-yl)-1-methylethyl((2R)-2-pyridin-3-yl-2-((triethylsilyl)oxy)ethyl)carbamate To a solution of tert-butyl (1R)-2-(7-(benzyloxy)-1H-indol-3-yl)-1-methylethyl((2R)-2-hydroxy-2-pyridin-3-yl-ethyl) carbamate (8.05 g, 16.1 mmol) in N,N-dimethylformamide (60 mL) are added imidazole (4.37 g, 64.2 mmol) and triethylsilane chloride (5.44 mL, 32.1 mmol) under nitrogen atmosphere, and the mixture is stirred at room temperature for 3 hours. The reaction solution is poured into water, and the mixture is extracted with ethyl acetate. The organic layer is washed with water and a saturated brine, and dried over anhydrous sodium sulfate. The solvent is evaporated, and the obtained crude product is purified by silica gel column chromatography (n-hexane:ethyl acetate=5:1→3:1) to give the title compound (7.94 g, yield: 80%).

IR (ATR/FT-IR, cm$^{-1}$): 1682, 1578, 1500, 1454, 1404, 1365, 1330, 1257, 1238, 1164, 1083, 1025, 1003.

Reference Example 65 tert-Butyl (1R)-2-(7-hydroxy-1H-indol-3-yl)-1-methylethyl((2R)-2-pyridin-3-yl-2-((triethylsilyl)oxy)ethyl)carbamate To a solution of tert-butyl (1R)-2-(7-(benzyloxy)-1H-indol-3-yl)-1-methylethyl((2R)-2-pyridin-3-yl-2-((triethylsilyl) oxy) ethyl)carbamate (2.5 g, 4.06 mmol) in methanol (50 mL) are added a phosphate standard buffer (pH 6.86, 2.5 mL) and a 10% palladium on carbon (50% wet, 2.5 g), and the mixture is stirred at room temperature for 1.5 hour under hydrogen atmosphere. The reaction solution is filtered through celite, and the filtrate is evaporated under reduced pressure to remove the solvent. To the residue are added water and ethyl acetate, and the organic layer is washed with a saturated brine, and dried over anhydrous sodium sulfate. The solvent is evaporated, and the obtained crude product is purified by silica gel column chromatography (n-hexane: ethyl acetate=3:1→3:2) to give the title compound (1.84 g, yield: 87%).

IR (ATR/FT-IR, cm$^{-1}$): 3336, 1681, 1577, 1454, 1430, 1407, 1365, 1331, 1238, 1164, 1083, 1003.

Example 109

2-((3-((2R)-2-(((2R)-2-Hydroxy-2-pyridin-3-ylethyl) amino)propyl)-1H-indol-7-yl)oxy)propanoic acid To a solution of tert-butyl (1R)-2-(7-hydroxy-1H-indol-3-yl)-1-methylethyl((2R)-2-pyridin-3-yl-2-((triethylsilyl) oxy)ethyl)carbamate (100 mg, 0.190 mmol) in acetone (10 mL) is added ethyl α-bromopropanoate (51.6 mg, 0.285 mmol), potassium carbonate (31.5 mg, 0.228 mmol) and potassium iodide (5 mg), and the mixture is refluxed for 16 hours. The reaction solution is allowed to cool, filtered, and concentrated. The residue is purified by silica gel column chromatography (n-hexane/ethyl acetate=10/1→1/1) to give ethyl 2-((3-((2R)-((tert-butoxycarbonyl)-((2R)-2-pyridin-3-yl-2-((triethyl)oxy)ethyl)amino)propyl)-1H-indol-7-yl)-oxy)propanoate (81.3 mg, yield: 68%).

Further, to a solution of ethyl 2-((3-((2R)-((tert-butoxycarbonyl)-((2R)-2-pyridin-3-yl-2-((triethyl)oxy)ethyl) amino)propyl)-1H-indol-7-yl)-oxy)propanoate (81.3 mg, 0.130 mmol) in ethanol (1.0 mL) is added a 4N hydrochloric acid in dioxane (1.0 mL), and the mixture is stirred at room temperature for 4 hours. Water (1.0 mL) is added to the mixture, and the mixture is further stirred for 1 hour. The mixture is concentrated under reduced pressure, and the residue is dissolved in a mixture of ethanol (1.25 mL) and water (0.25 mL), and thereto is added KOH (72.8 mg, 1.30 mmol). The mixture is stirred at room temperature overnight, and neutralized with 1N hydrochloric acid and a pH buffer (pH 6.8). The mixture is evaporated under reduced pressure to remove ethanol, and thereto is added a 0.1% aqueous trifluoroacetic acid solution (2.0 mL). The mixture is purified by reversed phase column (trade name; COSMOSIL 75C18-OPN (Nacalai Tesque), 0.1% aqueous trifluoroacetic acid solution/methanol=100/0→50/50) to give the title compound (80.1 mg, yield: 100%).

$^1$H-NMR (CD$_3$OD) δ: 1.31 and 1.32 (total 3H, d, J=6.5 Hz), 1.66 (3H, d, J=6.6 Hz), 3.03 (1H, m), 3.31 (2H, m), 3.40 (1H, m), 3.65 (1H, m), 3.70 (2H, br), 4.96 (1H, m), 5.26 (1H, m), 6.56 (1H, d, J=7.7 Hz), 6.94 (1H, t, J=7.9 Hz), 7.17 (1H, s), 7.21 (1H, dd, J=1.4, 8.0 Hz), 8.01 (1H, dd, J=5.7, 8.0 Hz), 8.53 (1H, d, J=8.1 Hz), 8.78 (1H, d, J=5.2 H), 8.88 (1H, m).

Example 110

N,N-Diethyl-2-((3-((2R)-2-(((2R)-2-hydroxy-2-pyridin-3-ylethyl)amino)-propyl)-1H-indol-7-yl)oxy) propanamide.2 trifluoroacetate To a solution of 2-((3-((2R)-2-(((2R)-2-hydroxy-2-pyridin-3-yl-ethyl)amino)propyl)-1H-indol-7-yl)oxy)propanoic acid (18.8 mg, 0.0490 mmol) in N,N-dimethylformamide (1.5 mL) are added triethylamine (170 μL, 1.22 mmol), diethylamine (50.7 μL, 0.490 mmol), N,N-bis(2-oxo-3-oxazolidinyl)phosphinic chloride (125 mg, 0.490 mmol), and the mixture is stirred at 0° C. for 2 hours. To the reaction solution are added a saturated aqueous sodium hydrogen carbonate solution and a saturated brine, and the mixture is extracted with chloroform. The organic layers are combined, dried over anhydrous sodium sulfate, and concentrated under reduced pressure. The obtained residue is dissolved in acetonitrile (2.0 mL). Trifluoroacetic acid (30 μl) is added to the mixture, and the mixture is purified by preparative reversed phase HPLC (octadecylsilyl, trifluoroacetic acid/ water/acetonitrile) to give the title compound (10.2 mg, yield: 31%).

$^1$H-NMR (CD$_3$OD) δ: 1.11 (3H, t, J=7.0 Hz), 1.17 (3H, m), 1.32 (3H, m), 1.60 (3H, m), 3.03 (1H, m), 3.29 (2H, m), 3.36 (2H, m), 3.39 (1H, m), 3.53 (2H, q, J=6.4 Hz), 3.67 (1H, m), 5.19 (1H, m), 5.30 (1H, m), 6.59 (1H, dd, J=2.6, 7.7 Hz), 6.94 (1H, dd, J=7.8, 7.8 Hz), 7.18 (1H, s), 7.22 (1H, dd, J=1.4, 7.9 Hz), 7.91 (1H, dd, J=5.6, 8.0 Hz), 8.41 (1H, d, J=8.1 Hz), 8.74 (1H, d, J=5.1 Hz), 8.78 (1H, m).

Example 111

2-((3-((2R)-2-(((2R)-2-Hydroxy-2-pyridin-3-ylethyl) amino) propyl)-1H-indol-7-yl) oxy)-N,N-dimethylpropanamide.2 trifluoroacetate The title compound is obtained in a similar manner to Example 110.

$^1$H-NMR (CD$_3$OD) δ: 1.32 (3H, m), 1.60 (3H, m), 2.97 (3H, s), 3.03 (1H, m), 3.19 (3H, s), 3.27 (2H, m), 3.35 (1H, m), 3.69 (1H, m), 3.52 (1H, m), 5.38 (1H, m), 6.53 (1H, dd, J-=2.5, 7.7 Hz), 6.94 (1H, dd, J=7.8, 7.8 Hz), 7.18 (1H, s), 7.21 (1H, dd, J=2.5, 8.0 Hz), 7.98 (1H, m), 8.48 (1H, m), 8.78 (2H, m).

Example 112

(1R)-$^2$-(((1R)-1-Methyl-2-(7-(1-methyl-2-oxo-2-piperidin-1-ylethoxy)-1H-indol-3-yl)ethyl)amino)-1-pyridin-3-ylethanol.2 trifluoroacetate The title compound is obtained in a similar manner to Example 11.

$^1$H-NMR (CD$_3$OD) δ: 1.31 and 1.32 (total 3H, d, J=6.5 Hz), 1.50 (4H, m), 1.60 (3H, d, J=6.6 Hz), 1.65 (2H, m), 3.03 (1H, m), 3.31 (2H, m), 3.38 (1H, m), 3.56 (2H, t, J=5.3 Hz), 3.65 (2H, m), 3.70 (1H, m), 5.23 (1H, m), 5.36 (1H, m), 6.57 (1H, dd, J=2.6, 7.7 Hz), 6.95 (1H, t, J=7.8 Hz), 7.18 (1H, s), 7.22 (1H, dd, J=2.2, 8.0 Hz), 8.01 (1H, dd, J=5.7, 8.0 Hz), 8.53 (1H, d, J=8.2 Hz), 8.80 (2H, m).

Example 113

(1R)-2-(((1R)-1-Methyl-2-(7-(1-methyl-2-morpholin-4-yl-2-oxoethoxy)-1H-indol-3-yl)ethyl)amino)-1-pyridin-3-ylethanol.2 trifluoroacetate The title compound is obtained in a similar manner to Example 11.

$^1$H-NMR (CD$_3$OD) δ: 1.31 and 1.32 (total 3H, d, J=6.5 Hz), 1.62 (3H, d, J=6.6 Hz), 3.03 (1H, m), 3.31 (1H, m), 3.40 (2H, m), 3.58 (6H, m), 3.70 (3H, m), 5.25 (1H, m), 5.34 (1H, m), 6.60 (1H, dd, J=1.7, 7.7 Hz), 6.96 (1H, t, J=7.9 Hz), 7.19 (1H, s), 7.23 (1H, dd, J=0.9, 7.9 Hz), 8.01 (1H, dd, J=5.7, 8.0 Hz), 8.55 (1H, d, J=8.1 Hz), 8.80 (1H, d, J=5.3 Hz), 8.86 (1H, m).

Example 114

2-((3-((2R)-2-(((2R)-2-Hydroxy-2-pyridin-3-ylethyl)amino)propyl)-1H-indol-7-yl)oxy)-2-methylpropanoic acid The title compound is obtained in a similar manner to Example 109.

$^1$H-NMR (CD$_3$OD) δ: 1.32 (3H, d, J=6.5 Hz), 1.63 (6H, s), 3.00 (1H, dd, J=9.1, 14.2 Hz), 3.31 (2H, m), 3.41 (1H, dd, J=4.3, 12.8 Hz), 3.65 (1H, m), 5.25 (1H, dd, J=3.0, 9.7 Hz), 6.63 (1H, d, J=7.7 Hz), 6.92 (1H, t, J=7.9 Hz), 7.17 (1H, s), 7.26 (1H, d, J=7.9Hz), 8.01 (1H, dd, J=5.7, 8.1 Hz), 8.53 (1H, d, J=8.1 Hz), 8.80 (1H, d, J=5.4 Hz), 8.89 (1H, brs).

Example 115

2-((3-((2 R)-2-(((2R)-2-Hydroxy-2-pyridin-3-yl-ethyl)amino)propyl)-1H-indol-7-yl) oxy)-N,N,2-trimethylpropanamide.2 trifluoroacetate The title compound is obtained in a similar manner to Example 110.

$^1$H-NMR (CD$_3$OD) δ: 1.32 (3H, d, J=6.5 Hz), 1.68 (6H, s), 2.95 (3H, s), 2.99 (1H, dd, J=9.4, 14.2 Hz), 3.21 (3H, s), 3.25–3.35 (2H, m), 3.38 (1H, dd, J=3.4, 12.8 Hz), 3.65–3.69 (1H, m), 5.15 (1H, dd, J=3.2, 10.0 Hz), 6.43 (1H, d, J=7.6 Hz), 6.89 (1H, t, J=7.9 Hz), 7.17 (1H, s), 7.23 (1H, d, J=7.7 Hz), 7.78 (1H, dd, J=5.3, 8.1 Hz), 8.28 (1H, d, J=8.0 Hz), 8.68 (1H, dd, J=1.3, 5.3 Hz), 8.77 (1H, d, J=1.8 Hz).

Example 116

N,N-Diethyl-2-((3-((2R)-2-(((2R)-2-hydroxy-2-pyridin-3-ylethyl)amino)-propyl)-1H-indol-7-yl)oxy)-2-methylpropanamide.2 trifluoroacetate The title compound is obtained in a similar manner to Example 110.

$^1$H-NMR (CDCl$_3$) δ: 0.88 (3H, t, J=7.1 Hz), 1.11–1.15 (6H, m), 1.71 (6H, s), 2.65 (1H, dd, J=9.3, 12.2 Hz), 2.80–2.83 (2H, m), 2.92 (1H, dd, J=3.6, 12.2 Hz), 3.04–3.09 (1H, m), 3.39 (2H, q, J=7.0 Hz), 3.69 (2H, d, J=7.1 Hz), 4.54 (1H, dd, J=3.6, 9.2 Hz), 6.59 (1H, d, J=7.7 Hz), 6.92 (1H, t, J=7.9 Hz), 7.01 (1H, d, J=2.2 Hz), 7.19 (1H, d, J=8.0 Hz), 7.22–7.24 (1H, m), 7.65–7.68 (1H, m), 8.24 (1H, brs), 8.50 (1H, dd, J=1.6, 4.8 Hz), 8.54 (1H, d, J=2.1 Hz).

Example 117

(1R)-2-(((1R)-2-(7-(1,1-Dimethyl-2-oxo-2-piperidin-1-ylethoxy)-1 H-indol-3-yl)-1-methylethyl)amino)-1-pyridin-3-ylethanol.2 trifluoroacetate The title compound is obtained in a similar manner to Example 11.

$^1$H-NMR (CD$_3$OD) δ: 1.10 (2H, brs), 1.30 (3H, d, J=6.5 Hz), 1.47 (4H, brs), 1.69 (6H, s), 2.97 (1H, dd, J=9.6, 14.1 Hz), 3.31 (2H, m), 3.45 (1H, dd, J=3.1, 12.7 Hz), 3.56 (2H, brs), 3.65 (1H, m), 3.84 (2H, brs), 5.26 (1H, d, J=3.0, 9.9 Hz), 6.50 (1H, d, J=7.7 Hz), 6.88 (1H, t, J=7.9 Hz), 7.17 (1H, s), 7.24 (1H, d, J=14.3 Hz), 8.01 (1H, m), 8.56 (1H, d, J=12.9 Hz), 8.80 (2H, d, J=5.3 Hz), 8.91 (1H, s).

Example 118

(1R)-2-(((1R)-2-(7-(1,1-Dimethyl-2-morpholin-4-yl-2-oxoethoxy)-1H-indol-3-yl)-1-methylethyl)amino)-1-pyridin-3-ylethanol.2 trifluoro-acetate The title compound is obtained in a similar manner to Example 11.

$^1$H-NMR (CD$_3$OD) δ: 1.30 (3H, d, J=6.5 Hz), 1.71 (6H, s), 3.00 (1H, dd, J=6.7, 16.4 Hz), 3.31 (2H, m), 3.45 (1H, dd, J=4.6, 12.8 Hz), 3.50 (2H, brs), 3.60 (2H, brs), 3.67 (1H, m), 3.89 (2H, brs), 5.26 (1H, dd, J=3.0, 10.0 Hz), 6.53 (1H, d, J=7.7 Hz), 6.92 (1H, t, J=7.9 Hz), 7.18 (1H, s), 7.25 (1H, d, J=7.9 Hz), 8.00 (1H, dd, J=5.6, 8.1 Hz), 8.56 (1H, d, J=8.1 Hz), 8.80 (1H, d, J=5.3 Hz), 8.91 (1H, s).

Example 119

(1R)-2-(((1R)-1-Methyl-2-(7-(((1R)-1-methyl-2-morpholin-4-yl-2-oxo-ethyl)oxy)-1H-indol-3-yl)ethyl)amino)-1-pyridin-3-ylethanol To a solution of tert-butyl (1R)-2-(7-hydroxy-1H-indol-3-yl)-1-methylethyl((2R)-2-pyridin-3-yl-2-((triethylsilyl)oxy)ethyl)carbamate (300 mg, 0.570 mmol) in N,N-dimethylformamide-(1.0 mL) are added potassium carbonate (98.5 mg, 0.714 mmol), (1S)-1-methyl-2-morpholin-4-yl-2-oxoethyl 4-methylbenzenesulfonate (JP-A-2000-273085) (196 mg, 0.627 mmol), and the mixture is stirred at 50° C. for one hour. To the reaction solution are added potassium carbonate (45 mg), (1S)-1-methyl-2-morpholin-4-yl-2-oxoethyl 4-methylbenzene-sulfonate (120 mg), and the mixture is stirred at 60° C. for 10 hours. After allowed to cool, to the reaction solution is added ethyl acetate (50 mL), and the mixture is filtered, washed with water and a saturated brine, and dried over anhydrous sodium sulfate, and concentrated under reduced pressure. The obtained residue is purified by silica gel column chromatography (chloroform/methanol=100/1→20/1) to give tert-butyl (1R)-1-methyl-2-(7-(((1R)-1-methyl-2-morpholin-4-yl-2-oxo-ethyl)oxy)-1H-indol-3-yl)ethyl((2R)-2-pyridin-3-yl-2-((triethylsilyl)oxy)-ethyl)carbamate (209 mg, yield: 55%).

Further, to a solution of tert-butyl (1R)-1-methyl-2-(7-(((1R)-1-methyl-2-morpholin-4-yl-2-oxoethyl)oxy)-1H-indol-3-yl)ethyl((2R)-2-pyridin-3-yl-2-((triethylsilyl)oxy)ethyl)carbamate (190 mg, 0.285 mmol) in ethanol (2.0 mL) is added a 4N hydrochloric acid/dioxane (2.0 mL, 8.0 mmol), and the mixture is stirred at room temperature for 14 hours. To the reaction solution are added a saturated aqueous sodium hydrogen carbonate solution and a saturated brine, and the mixture is extracted with chloroform, dried over anhydrous sodium sulfate, and concentrated under reduced pressure. The resulting residue is purified by silica gel column chromatography (a saturated ammonia solution in chloroform/methanol=100/1→100/4) to give the title compound (107 mg, yield: 83%).

$^1$H-NMR (CDCl$_3$) δ: 1.14 (3H, d, J=6.2 Hz), 1.65 (3H, d, J=6.6 Hz), 2.66 (1H, dd, J=9.3, 12.2 Hz), 2.83 (2H, m), 2.89 (1H, dd, J=3.6, 12.3 Hz), 3.05 (1H, m), 3.50 (2H, m), 3.60 (6H, m), 4.54 (1H, dd, J=3.4, 9.3 Hz), 5.14 (1H, q, J=6.7 Hz), 6.62 (1H, d, J=7.7 Hz), 6.99 (1H, t, J=7.9 Hz), 7.02 (1H, m), 7.24 (1H, m), 7.25 (1H, m), 7.66 (1H, dt, J=1.7, 7.9 Hz), 8.49 (1H, dd, J=1.6, 4.8 Hz), 8.52 (1H, d, J=2.2 Hz), 8.70 (1H, brs).

Example 120

(2R)-2-((3-((2R)-2-(((2R)-2-Hydroxy-2-pyridin-3-ylethyl)amino)propyl)-1H-indol-7-yl)oxy)propanoic acid.2 trifluoroacetate To a solution of (1R)-2-(((1R)-1-methyl-2-(7-((1R)-1-methyl-2-morpholin-4-yl-2-oxoethoxy)-1H-indol-3-yl)ethyl)amino)-1-pyridin-3-ylethanol (96.3 mg, 0.213 mmol) in methanol (850 μL) are added tetra-hydrofuran (850 μL) and a 2N lithium hydroxide (850 μL), and the mixture is stirred at 50° C. for one hour. The mixture is neutralized with 1N hydrochloric acid at 0° C., and thereto is added a pH standard solution (pH 6.8, 2.0 mL). The mixture is concentrated under reduced pressure, and purified by octadecylsilyl (ODS) column chromatography (Cosmosil, a 0.1% aqueous trifluoroacetic acid solution/methanol=100/1→70/30) to give the title compound (99.7 mg, yield: 77%).

$^1$H-NMR (CD$_3$OD) δ: 1.33 (3H, d, J=6.5 Hz), 1.67 (3H, d, J=6.6 Hz), 3.01 (1H, dd, J=8.8, 14.3 Hz), 3.30 (2H, m), 3.40 (1H, dd, J=3.3, 12.8 Hz), 3.70 (1H, m), 4.99 (1H, m), 5.23 (1H, dd, J=3.1, 9.6 Hz), 6.57 (1H, d, J=7.7 Hz), 6.95 (1H, t, J=7.9 Hz), 7.18 (1H, s), 7.21 (1H, d, J=7.7 Hz), 8.01 (1H, dd, J=5.7, 8.0 Hz), 8.51 (1H, m), 8.78 (1H, d, J=5.2 Hz), 8.87 (1H, m).

Example 121

(2R)-2-((3-((2R)-2-(((2R)-2-Hydroxy-2-pyridin-3-ylethyl)amino)propyl)-1H-indol-7-yl) oxy)-N,N-dimethylpropanamide.2 trifluoroacetate The title compound is obtained in a similar manner to Example 110.

$^1$H-NMR (CD$_3$OD) δ: 1.33 (3H, d, J=6.5 Hz), 1.60 (3H, d, J=6.6 Hz), 2.97 (3H, s), 3.02 (1H, dd, J=8.7, 14.3 Hz), 3.19 (3H, s), 3.30 (2H, m), 3.35 (1H, dd, J=3.4, 12.8 Hz), 3.68 (1H, m), 5.16 (1H, dd, J=3.2, 9.7 Hz), 5.36 (1H, q, J=6.6 Hz), 6.53 (1H, d, J=7.7 Hz), 6.94 (1H, t, J=7.9 Hz), 7.18 (1H, s), 7.21 (1H, d, J=7.7 Hz), 7.91 (1H, m), 8.51 (1H, m), 8.75 (2H, brs).

Example 122

(1R)-2-(((1R)-1-Methyl-2-(7-(((1R)-1-methyl-2-oxo-2-piperidin-1-ylethyl)-oxy)-1H-indol-3-yl)ethyl)amino)-1-pyridin-3-ylethanol.2 trifluoroacetate The title compound is obtained in a similar manner to Example 110.

$^1$H-NMR (CD$_3$OD) δ: 1.32 (3H, d, J=6.5 Hz), 1.5–1.7 (6H, m), 1.61 (3H, d, J=6.6 Hz), 3.00 (1H, dd, J=8.9, 14.3 Hz), 3.30 (2H,m), 3.39 (1H, dd, J=3.3, 12.8 Hz), 3.56 (2H, t, J=5.5 Hz), 3.66 (3H, m), 5.23 (1H, dd, J=3.0, 9.6 Hz), 5.35 (1H, q, J=6.6 Hz), 6.56 (1H, d, J=7.7 Hz), 6.95 (1H, t, J=7.9 Hz), 7.18 (1H, s), 7.21 (1H, d, J=7.8 Hz), 8.04 (1H, dd, J=5.7, 8.1 Hz), 8.57 (1H, m), 8.81 (2H, m).

Reference Example 66

(1R)-1-Methyl-2-morpholin-4-yl-2-oxoethyl 4-methylbenzenesulfonate

Under nitrogen atmosphere, to methyl D-(+)-lactate (20.8 g, 200 mmol) and morpholine (19.1 mL, 220 mmol) is added in portions a 60% sodium hydride (800 mg, 200 mmol) with stirring under ice-cooling, and the mixture is heated at 50° C. with stirring for 3 hours. The mixture is cooled to room temperature, and subjected to azeotropic distillation with toluene to remove excess morpholine. The resultant is dried under reduced pressure to give lactic morpholinamide (32.1 g).

Subsequently, to a suspension of 60% sodium hydride (8.41 g, 210 mmol) in tetrahydrofuran (120 mL) is added dropwise a solution of the above lactic morpholinamide (32.1 g) in tetrahydrofuran (150 mL) under nitrogen atmosphere with stirring under ice-cooling, and the mixture is heated with stirring at 50° C. for 30 minutes. After cooling with ice, to the mixture is added dropwise a solution of p-toluene-sulfonyl chloride (45.8 g, 234 mmol) in tetrahydrofuran (180 mL), and the mixture is stirred at room temperature for 4 hours. To the mixture is added 1N aqueous hydrochloric acid solution, and the mixture is extracted with ethyl acetate. The organic layer is washed with water and a saturated brine, dried over anhydrous magnesium sulfate, and the solvent is evaporated under reduced pressure. To the resulting oily residue is added diethyl ether, and the precipitated crystals are collected by filtration, washed with diethyl ether, and dried under reduced pressure to give the title compound (36.1 g, yield: 58%).

$^1$H-NMR (CDCl$_3$) δ: 7.81 (2H, d, J=8.0 Hz), 7.35 (2H, d, J=8.0 Hz), 5.27 (1H, q, J=6.8 Hz), 3.64–3.46 (8H, m), 2.46 (3H, s), 1.47 (3H, d, J=6.8 Hz).

Example 123

(1R)-2-(((1R)-1-Methyl-2-(7-(((1S)-1-methyl-2-morpholin-4-yl-2-oxoethyl-oxy)-1H-indol-3-yl)ethyl)amino)-1-pyridin-3-ylethanol The title compound is obtained in a similar manner to Example 119.

$^1$H-NMR (CDCl$_3$) δ: 1.15 (3H, d, J=6.2 Hz), 1.66 (3H, d, J=6.7 Hz), 2.67 (1H, dd, J=9.4, 12.2 Hz), 2.83 (2H, m), 2.91 (1H, dd, J=3.6, 12.2 Hz), 3.07 (1H, m), 3.50 (2H, m), 3.61 (6H, m), 4.59 (1H, dd, J=3.5, 9.3 Hz), 5.13 (1H, q, J=6.7 Hz), 6.63 (1H, d, J=7.7 Hz), 7.00 (1H, t, J=7.8 Hz), 7.03 (1H, m), 7.23 (1H, m), 7.25 (1H, m), 7.66 (1H, dt, J=1.7, 7.9 Hz), 8.49 (1H, dd, J=1.7, 4.8 Hz), 8.53 (1H, d, J=2.1 Hz), 8.60 (1H, brs).

Example 124

(2S)-2-((3-((2R)-2-(((2R)-2-Hydroxy-2-pyridin-3-ylethyl)amino)propyl)-1H-indol-7-yl)oxy)propanoic acid.2 trifluoroacetate The title compound is obtained in a similar manner to Example 120.

$^1$H-NMR (CD$_3$OD) δ: 1.32 (3H, d, J=6.5 Hz), 1.67 (3H, d, J=6.8 Hz), 3.00 (1H, dd, J=9.0, 14.2 Hz), 3.30 (2H, m), 3.40 (1H, dd, J=3.2, 12.6 Hz), 3.67 (1H, m), 4.97 (1H, q, J=6.8 Hz), 5.23 (1H, dd, J=3.0, 10.5 Hz), 6.57 (1H, d, J=7.7 Hz), 6.95 (1H, t, J=7.9 Hz), 7.18 (1H, s), 7.22 (1H, d, J=7.7 Hz), 7.98 (1H, dd, J=5.7, 8.0 Hz), 8.47 (1H, m), 8.78 (1H, d, J=5.2 Hz), 8.86 (1H, m).

Example 125

Ethyl(2S)-2-((3-((2R)-2-(((2R)-2-hydroxy-2-pyridin-3-ylethyl)amino)-propyl)-1H-indol-7-yl)oxy)propanoate To a suspension of (2S)-2-((3-((2R)-2-(((2R)-2-hydroxy-2-pyridin-3-ylethyl)amino)propyl)-1H-indol-7-yl)oxy)propanoic acid (6.72 g, 17.53 mmol) in ethanol (135 mL) is added a 4N solution of hydrogen chloride in dioxane (55 mL), and the mixture is stirred at room temperature for 2 hours. The reaction solution is evaporated to remove the solvent, and the residue is separated into a saturated aqueous sodium hydrogen carbonate solution and chloroform. The organic layer is washed with a saturated brine, and dried over anhydrous sodium sulfate. The mixture is evaporated to remove the solvent, and to the obtained crude product are added ethyl acetate (50 mL) and diisopropyl ether (50 mL). The product is crystallized and collected by filtration. The product on the filter is washed with diisopropyl ether, and dried to give the title compound (6.26 g, yield: 87%).

Example 126

(2 S)-6-(((2R)-2-(((2R)-2-Hydroxy-2-pyridin-3-yl-ethyl)amino)propyl)-2-methyl[1,4]oxazino[2,3,4-hi]indol-3 (2H)-one To a solution of ethyl (2S)-2-((3-((2R)-2-(((2R)-2-hydroxy-2-pyridin-3-ylethyl)amino)propyl)-1H-indol-7-yl)oxy)propanoate.2 hydrochloride (205 mg, 0.423 mmol) in acetonitrile (8.7 ml) is added potassium carbonate (294 mg, 2.13 mmol), and the mixture is stirred at 60° C. for 4 hours. After the reaction is completed, the mixture is cooled to room temperature, and filtered. The filtrate is evaporated under reduced pressure to remove the solvent, and the obtained residue is purified by preparative thin layer chromatography (chloroform/methanol=10/1) to give the title compound (131 mg, yield: 85%).

$^1$H-NMR (CDCl$_3$) δ: 1.16 (3H, d, J=6.3 Hz), 1.74 (3H, d, J=6.9 Hz), 2.74 (1H, dd, J=12, 9.3 Hz), 2.77 (1H, dd, J=14.3, 6.5 Hz), 2.88 (1H, dd, J=14.3, 6.6 Hz), 2.96 (1H, dd, J=12, 3.5 Hz), 3.10–3.15 (1H, m), 4.65 (1H, dd, J=9.3, 3.5 Hz), 5.10 (1H, q, J=6.9 Hz), 6.83 (1H, dd, J=6.6, 1.7 Hz), 7.13–7.18 (2H, m), 7.25–7.28 (1H, m), 7.41 (1H, s), 7.70 (1H, d, J=7.9 Hz), 8.50 (1H, dd, J=4.8, 1.4 Hz), 8.55 (1H, d, J=1.7 Hz).

Example 127

(2S)-2-((3-((2R)-2-(((2R)-2-Hydroxy-2-pyridin-3-ylethyl)amino)propyl)-1H-indol-7-yl)oxy)-N,N-dimethylpropanamide.2 trifluoroacetate The title compound is obtained in a similar manner to Example 110.

$^1$H-NMR (CD$_3$OD) δ: 1.32 (3H, d, J=6.5 Hz), 1.60 (3H, d, J=6.6 Hz), 2.97 (3H, s), 3.02 (1H, m), 3.19 (3H, s), 3.30 (2H, m), 3.39 (1H, dd, J=3.2, 12.8 Hz), 3.68 (1H, m), 5.22 (1H, dd, J=3.0, 9.7 Hz), 5.36 (1H, q, J=6.6 Hz), 6.54 (1H, d, J=7.7 Hz), 6.95 (1H, t, J=7.9 Hz), 7.18 (1H, s), 7.22 (1H, d, J=7.7 Hz), 8.00 (1H, dd, J=5.9, 8.0 Hz), 8.51 (1H, m), 8.80 (2H, m).

Example 128

(1R)-2-(((1R)-1-Methyl-2-(7-(((1 S)-1-methyl-2-oxo-2-piperidin-1-ylethy)-oxy)-1H-indol-3-yl)ethyl)amino)-1-pyridin-3-ylethanol.2 trifluoroacetate The title compound is obtained in a similar manner to Example 110.

$^1$H-NMR (CD$_3$OD) δ: 1.31 (3H, d, J=6.5 Hz), 1.5–1.7 (6H, m), 1.61 (3H, d, J=6.6 Hz), 3.00 (1H, dd, J=9.1, 14.2 Hz), 3.30 (2H, m), 3.42 (1H, dd, J=3.2, 12.8 Hz), 3.56 (2H, t, J=5.5 Hz), 3.66 (3H, m), 5.25 (1H, dd, J=3.0, 9.7 Hz), 5.34 (1H, q, J=6.6 Hz), 6.57 (1H, d, J=7.7 Hz), 6.95 (1H, t, J=7.9 Hz), 7.18 (1H, s), 7.22 (1H, d, J=7.9 Hz), 8.03 (1H, dd, J=5.7, 8.1 Hz), 8.56 (1H, m), 8.81 (2H, m).

Reference Example 67

4- (2-Bromobutanoyl)morpholine

To a solution of 2-bromobutanoic acid (0.3 mL, 2.81 mmol) in N,N-dimethylformamide (14 mL) are added morpholine (0.3 mL, 3.44 mmol), 1-ethyl-3-(3-dimethylaminopropyl)-carbodiimide hydrochloride (650 mg, 3.39 mmol) and 7-hydroxybenzotriazole (456 mg, 3.38 mmol), and the mixture is stirred at room temperature for 4.5 hours. After the reaction is completed, water is added to the mixture, and the mixture is extracted with ethyl acetate. The organic layer is washed with 1N-hydrochloric acid, a saturated aqueous sodium hydrogen carbonate solution, and a saturated brine, and dried over anhydrous magnesium sulfate. The solvent is evaporated, and the obtained residue is purified by silica gel column chromatography (n-hexane/ethyl acetate=3/1) to give the title compound (323 mg, yield: 49%).

$^1$H-NMR (CDCl$_3$) δ: 1.04 (3H, t, J=7.3 Hz), 1.96–2.16 (2H, m), 3.46–3.54 (2H, m), 3.62–3.74 (5H, m), 3.79–3.84 (1H, m), 4.28 (1H, dd, J=7.8, 6.2 Hz).

Example 129

(1R)-2-(((1R)-1-Methyl-2-(7-(1-(Morpholin-4-ylcarbonyl)propoxy)-1H-indol-3-yl) ethyl) amino)-1-pyridin-3-ylethanol.2 trifluoroacetate The title compound is obtained in a similar manner to Example 119.

$^1$H-NMR (CD$_3$OD) δ: 1.14 and 1.15 (total 3H, J, t=7.3 Hz), 1.33 and 1.34 (total 3H, d, J=6.5 Hz), 2.00–2.08 (2H, m), 3.02–3.05 (1H, m), 3.27–3.42 (3H, m), 3.52–3.82 (9H, m), 5.10–5.15 (1H, m), 5.21–5.25 (1H, m), 6.57 and 6.58 (total 1H, d, J=7.7 Hz), 6.96 (1H, t, J=7.8 Hz), 7.20 (s, 1H), 7.24 and 7.25 (total 1H, d, J=8.0 Hz), 8.00 (1H, m), 8.52 (1H, d, J=8.2 Hz), 8.80 (1H, d, J=4.2 Hz), 8.84 (s, 1H).

Example 130

2-((3-((2R)-2-(((2R)-2-Hydroxy-2-pyridin-3-ylethyl)amino)propyl)-1H-indol-7-yl)oxy)butanoic acid.2 trifluoroacetate The title compound is obtained in a similar manner to Example 120.

$^1$H-NMR (CD$_3$OD) δ: 1.14 (3H, t, J=7.4 Hz), 1.35 and 1.34 (total 3H, d, J=6.5 Hz), 1.99–2.14 (2H, m), 3.03–3.06 (1H, m), 3.25–3.36 (3H, m), 3.66–3.70 (1H, m), 4.81–4.88 (1H, m), 5.11–5.17 (m, 1H), 6.57 (1H, d, J=7.7 Hz), 6.95 (1H, t, J=7.9 Hz), 7.19 (1H, s), 7.22 (1H, d, J=8.1 Hz), 7.81 (dd, 1H, J=7.8, 5.6 Hz), 8.26 (1H, d, J=8.2 Hz), 8.69 (1H, s), 8.76 (1H, brs).

Example 131

2-((3-((2R)-2-(((2R)-2-Hydroxy-2-pyridin-3-ylethyl)amino)propyl)-1H-indol-7-yl)oxy)pentanoic acid.2 trifluoroacetate 6-((2 R)-2-(((2R)-2-Hydroxy-2-pyridin-3-ylethyl)amino)propyl)-2-propyl-[1,4]oxadino[2,3,4-hi]indol-3(2H)-one.2 trifluoroacetate To a solution of tert-butyl(1R)-2-(7-hydroxy-1H-indol-3-yl)-1-methylethyl((2R)-2-pyridin-3-yl-2-((triethylsilyl)oxy)

ethyl)carbamate (49.7 mg, 0.0945 mmol) in acetonitrile (2 ml) are added potassium carbonate (20.1 mg, 0.176 mmol), ethyl 2-bromo-n-valerate (0.03 ml, 0.176 mmol) and a catalytic amount of potassium iodide, and the mixture is stirred at 70° C. for 2 days. After the reaction is completed, the mixture is cooled to room temperature, filtered, and the solvent is evaporated under reduced pressure. The resulting residue is purified by preparative thin layer chromatography (n-hexane/ethyl acetate=2/1) to give ethyl 2-((3-((2R)-2-((tert-butoxycarbonyl)((2R)-2-pyridin-3-yl-2-((triethylsilyl)oxy)ethyl)amino)propyl)-1H-indol-7-yl)oxy)pentanoate (3.6 mg, yield: 5.7%) and tert-butyl(1R)-1-methyl-2-(3-oxo-2-propyl-2,3-dihydro[1,4]oxazino[2,3,4-hi]indol-6-yl)ethyl ((2R)-2-pyridin-3-yl-2-(triethylsilyl)oxy)ethyl)carbamate (9.5 mg, yield: 16%).

To a solution of the obtained ethyl 2-((3-((2R)-2-((tert-butoxy-carbonyl) ((2R)-2-pyridin-3-yl-2-(((triethylsilyl)oxy)ethyl)amino)propyl)-1H-indol-7-yl)oxy)pentanoate in ethanol (0.2 ml) is added a solution of 4N-hydrogen chloride in dioxane (0.2 ml), and the mixture is stirred at room temperature for 19 hours. After the reaction is completed, water (0.2 ml) is added to the mixture, and the solvent is evaporated under reduced pressure. To a solution of the obtained residue in ethanol (0.35 ml) is added a 5N aqueous potassium hydroxide solution (0.09 ml), and the mixture is stirred at room temperature for 4 hours. After the reaction is completed, the mixture is neutralized with 1N hydrochloric acid, and the solvent is evaporated under reduced pressure. The residue is purified by preparative high performance liquid chromatography (0.035% trifluoroacetic acid/acetonitrile-0.05% trifluoroacetic acid/water) to give 2-((3-((2R)-2-(((2R)-2-hydroxy-2-pyridin-3-ylethyl)-amino)propyl)-1H-indol-7-yl)oxy)pentanoic acid.2 trifluoroacetate (13.2 mg).

Further, to a solution of tert-butyl (1R)-1-methyl-2-(3-oxo-2-propyl-2,3-dihydro[1,4]oxazino[2,3,4-hi]indol-6-yl)ethyl((2R)-2-pyridin-3-yl-2-(triethylsilyl)oxy)ethyl)carbamate (9.5 mg, 0.0156 mmol) in ethanol (0.12 ml) is added a 4N solution of hydrogen chloride in dioxane (0.12 ml), and the mixture is stirred at room temperature for 15 hours. After the reaction is completed, water (0.12 ml) is added to the mixture, and the solvent is evaporated under reduced pressure. The obtained residue is purified by preparative high performance liquid chromatography (0.035% trifluoroacetic acid/acetonitrile-0.05% trifluoroacetic acid/water) to give 6-((2R)-2-(((2R)-2-hydroxy-2-pyridin-3-ylethyl)-amino)propyl)-2-propyl[1,4]oxazino[2,3,4-hi]indol-3(2H)-one.2 trifluoro-acetate (3.7 mg).

2-((3-((2R)-2-(((2R)-2-Hydroxy-2-pyridin-3-ylethyl)amino)propyl)-1H-indol-7-yl)oxy)pentanoic-2 trifluoroacetate $^1$H-NMR (CD$_3$OD) δ: 1.00 (3H, t, J=7.3 Hz), 1.34 (3H, t, J=5.5 Hz), 1.55–1.68 (2H, m), 1.96–2.09 (2H, m), 3.01 (1H, dt, J=14, 8.3 Hz), 3.24–3.41 (m, 2H), 3.64–3.67 (1H, m), 4.84–4.99 (2H, m), 5.20 (1H, t, J=9.4 Hz), 6.54 (1H, d, J=7.7 Hz), 6.94 (1H, t, J=7.7 Hz), 7.18 (1H, s), 7.20 (1H, d, J=7.8 Hz), 7.92 (1H, s), 8.40 (1H, s), 8.75 (1H, s), 8.82 (1H, s).

6-((2R)-2-(((2R)-2-Hydroxy-2-pyridin-3-ylethyl)amino)propyl)-2-propyl-[1,4]oxazino[2,3,4-hi]indol-3(2H)-one.2 trifluoroacetate $^1$H-NMR (CD$_3$OD) δ: 0.99 (3H, t, J=7.4 Hz), 1.35 (3H, d, J=6.5 Hz), 1.54–1.64 (2H, m), 1.96–2.04 (2H, m), 3.04 (1H, dd, J=14, 9.7 Hz), 3.30–3.48 (3H, m), 3.76–3.81 (1H, m), 5.09 (1H, dd, J=6.9, 5.1 Hz), 5.20 (1H, dd, J=9.7, 3.0 Hz), 6.86 (1H, d, J=7.7 Hz), 7.20 (1H, dd, J=7.9, 7.7 Hz), 7.26 (1H, d, J=7.9 Hz), 7.65 (1H, s), 7.79 (1H, dd, J=7.4, 5.6 Hz), 8.31 (1H, d, J=8.0 Hz), 8.70 (1H, brs), 8.81 (1H, brs).

Example 132

6-((2 R)-2-(((2R)-2-Hydroxy-2-pyridin-3-ylethyl)amino)propyl)-2-isopropyl-[1,4]oxazino[2,3,4-hi]indol-3(2H)-one.2 trifluoroacetate The title compound is obtained in a similar manner to Example 131.

$^1$H-NMR (CD$_3$OD) δ: 0.97 (3H, d, J=6.8 Hz), 1.17 (3H, d, J=7.0 Hz), 1.35, 1.36 (total 3H, d, J=6.5 Hz), 2.49–2.56 (1H, m), 3.04 (1H, dd, J=14, 10 Hz), 3.30–3.40 (2H, m), 3.50 (1H, dt, J=12, 3.1 Hz), 3.37–3.83 (2H, m), 4.94 (1H, dd, J=3.6, 0.9 Hz), 5.30 (1H, dd, J=9.8, 1.8 Hz), 6.86 (2H, t, J=7.6 Hz), 7.19 (1H, t, J=7.8 Hz), 7.25 (1H, d, J=7.8 Hz), 7.67 (1H, s), 8.01 (1H, dd, J=7.8, 5.7 Hz), 8.58 (1H, d, J=8.1 Hz), 8.80 (1H, d, J=5.2 Hz), 8.92 (1H, s).

Reference Example 68

3-Methyl-1-morpholin-4-yl-1-oxobutan-2-ol

To a solution of 2-hydroxy-1-valeric acid (501 mg, 4.24 mmol) in tetrahydrofuran (20 mL) are added 1-ethyl-3-(3-dimethylaminopropyl)-carbodiimide hydrochloride (976 mg, 5.09 mmol), 7-hydroxybenzo-triazole (691 mg, 5.11 mmol) and morpholine (0.44 mL, 5.05 mmol), and the mixture is stirred at room temperature for 9 hours. After the reaction is completed, the solvent is evaporated under reduced pressure, and the resulting residue is purified by silica gel column chromatography (n-hexane/ethyl acetate=2/1→1/1) to give the title compound (448 mg, yield: 56%).

$^1$H-NMR (CDCl$_3$) δ: 0.82 (3H, d, J=6.8 Hz), 1.08 (3H, d, J=6.9 Hz), 1.77–1.88 (1H, m), 3.38–3.48 (2H, m), 3.59–3.75 (6H, m), 4.23 (1H, d, J=2.8 Hz).

Reference Example 69

2-Methyl-1-(morpholin-4-ylcarbonyl)propyl 4-methylbenzenesulfonate

Under ice-cooling, to a solution of 60% sodium hydride (136 mg, 3.41 mmol) in tetrahydrofuran (5 mL) is added dropwise a solution of 3-methyl-1-morpholin-4-yl-1-oxobutan-2-ol (426 mg, 2.27 mmol) in tetrahydrofuran (15 mL), and the mixture is stirred at room temperature for 2 hours. To the reaction solution is added p-toluene-sulfonyl chloride (651 mg, 3.42 mmol), and the mixture is stirred at room temperature for 2 hours. After the reaction is completed, water is added to the mixture, and the mixture is extracted with ethyl acetate. This organic layer is washed with water, a saturated aqueous sodium hydrogen carbonate solution, and a saturated brine, and dried over anhydrous magnesium sulfate. The solvent is removed by distillation, and the obtained residue is purified by silica gel column chromatography (chloroform) to give the title compound (701 mg, yield: 90%).

$^1$H-NMR (CDCl$_3$) δ: 0.92 (3H, d, J=6.8 Hz), 0.97 (3H, d, J=6.6 Hz), 2.07–2.16 (1H, m), 2.45 (3H, s), 3.41–3.65 (8H, m), 4.74 (1H, d, J=8.4 Hz), 7.35 (2H, d, J=8.0 Hz), 7.81 (2H, d, J=8.4 Hz).

Example 133

(1R)-2-(((1R)-1-Methyl-2-(7-(2-methyl-1-(morpholin-4-ylcarbonyl)-propoxy)-1H-indol-3-yl)ethyl)amino)-1-pyridin-3-ylethanol.2 trifluoro-acetate The title compound is obtained in a similar manner to Example 119.

$^1$H-NMR (CD$_3$OD) δ: 1.13 and 1.10 (total 3H, d, J=6.4 Hz), 1.24 and 1.22 (total 3H, d, J=5.6 Hz), 2.30–2.35 (1H, m), 2.73–2.92 (4H, m), 3.04–3.07 (1H, m), 3.24–3.63 (8H, m), 3.76–3.77 (1H, m), 3.85–3.88 (1H, m), 4.69–4.74 (1H, m), 4.77–4.80 (1H, m), 6.55 and 6.54 (total 1H, d, J=7.6 Hz), 6.89 (1H, t, J=7.8 Hz), 7.02 (d, 1H, J=5.3 Hz), 7.16 (1H, d, J=7.9 Hz), 7.25–7.31 (1H, m), 7.67 and 7.65 (total 1H, Jd,=8.4 Hz), 8.37 and 8.36 (total 1H, d, J=5.2 Hz), 8.45 (1H, brs).

Example 134

2-((3-((2R)-2-(((2R)-2-Hydroxy-2-pyridin-3-ylethyl)amino)propyl)-1H-indol-7-yl)oxy)-3-methylbutanoic acid.2 trifluoroacetate The title compound is obtained in a similar manner to Example 120.

$^1$H-NMR (CD$_3$OD) δ: 1.19, 1.15 (total 3H, d, J=6.8 Hz), 1.33 and 1.34 (total 3H, d, J=6.5 Hz), 2.33–2.41 (1H, m), 2.98–3.06 (1H, m), 3.24–3.35 (2H, m), 3.37–3.44 (1H, m), 3.65–3.70 (1H, m), 4.61–4.62 (1H, m), 5.20–5.26 (1H, m), 6.54 (1H, d, J=7.7 Hz), 6.94 (1H, t, J=7.9 Hz), 7.19 (1H, s), 7.21 (1H, d, J=8.0 Hz), 7.97–8.00 (1H, m), 8.48 (1H, d, J=7.9 Hz), 8.78 (1H, d, J=4.8 Hz), 8.86 (1H, brs).

Reference Example 70

(2S)-3-Methyl-1-morpholin-4-yl-1-oxobutan-2-ol

The title compound is obtained in a similar manner to Reference Example 68.

$^1$H-NMR (CDCl$_3$) δ: 0.82 (3H, d, J=6.8 Hz), 1.07 (3H, d, J=6.9 Hz), 1.78–1.86 (1H, m), 3.42–3.44 (2H, m), 3.56 (1H, d, J=7.4 Hz), 3.61–3.75 (6H, m), 4.23 (1H, dd, J=7.4, 2.8 Hz).

Reference Example 71

(1S)-2-Methyl-1-(morpholin-4-ylcarbonyl)propyl 4-methylbenzene-sulfonate

The title compound is obtained in a similar manner to Reference Example 69.

$^1$H-NMR (CDCl$_3$) δ: 0.92 (3H, d, J=6.8 Hz), 0.97 (3H, d, J=6.6 Hz), 2.04–2.15 (1H, m), 2.45 (3H, s), 3.43–3.65 (8H, m), 4.74 (1H, d, J=8.4 Hz), 7.35 (2H, d, J=8.0 Hz), 7.81 (2H, d, J=8.3 Hz).

Example 135

(1R)-2-(((1R)-1-Methyl-2-(7-(((1R)-2-methyl-1-(morpholin-4-ylcarbonyl)-propyl)oxy)-1H-indol-3-yl)ethyl)amino)-1-pyridin-3-ylethanol The title compound is obtained in a similar manner to Example 119.

$^1$H-NMR (CDCl$_3$) δ: 1.11 (3H, d, J=6.8 Hz), 1.18 (3H, d, J=6.4 Hz), 1.20 (3H, d, J=6.7 Hz), 2.24–2.32 (1H, m), 2.71–2.78 (1H, m), 2.89–2.97 (4H, m), 3.14–3.19 (1H, m), 3.36 (2H, t, J=4.4 Hz), 3.48–3.67 (m, 6H), 4.65 (1H, d, J=7.6 Hz), 4.70 (1H, dd, J=9.3, 3.0 Hz), 6.64 (1H, d, J=7.7 Hz), 6.98 (1H, t, J=7.9 Hz), 7.03 (1H, d, J=1.7 Hz), 7.22–7.25 (1H, m), 7.67 (dt, J=7.9, 1.8 Hz), 8.53 (1H, d, 1H, J=1.9 Hz), 8.49 (1H, dd, J=4.8, 1.5 Hz), 8.81 (1H, brs).

Example 136

(2R)-2-((3-((2R)-2-(((2R)-2-Hydroxy-2-pyridin-3-ylethyl)amino)propyl)-1H-indol-7-yl)oxy)-3-methylbutanoic acid.2 trifluoroacetate The title compound is obtained in a similar manner to Example 120.

$^1$H-NMR (CD$_3$OD) δ: 1.15 (3H, d, J=6.9 Hz), 1.20 (3H, d, J=6.8 Hz), 1.35 (3H, d, J=6.5 Hz), 2.33–2.41 (1H, m), 3.03 (1H, dd, J=14, 8.8 Hz), 3.27–3.37 (3H, m), 3.66–3.74 (1H, m), 4.62 (1H, d, J=5.1 Hz), 5.15 (1H, dd, J=9.7, 2.9 Hz), 6.54 (1H, d, J=7.7 Hz), 6.94 (1H, t, J=7.9 Hz), 7.19 (1H, s), 7.21 (2H, d, J=8.0 Hz), 7.85 (1H, dd, J=7.4, 5.8 Hz), 8.30 (1H, d, J=8.0 Hz), 8.72 (1H, m), 8.78 (1H, brs).

Reference Example 72

(2R)-3-Methyl-1-morpholin-4-yl-1-oxobutan-2-ol

The title compound is obtained in a similar manner to Reference Example 68.

$^1$H-NMR (CDCl$_3$) δ: 0.82 (3H, d, J=6.8 Hz), 1.08 (3H, d, J=6.9 Hz), 1.78–1.86 (1H, m), 3.42–3.44 (2H, m), 3.55 (1H, d, J=7.4 Hz), 3.62–3.75 (m, 6H), 4.23 (1H, dd, J=7.4, 2.8 Hz).

Reference Example 73

(1R)-2-Methyl-1-(morpholin-4-ylcarbonyl)propyl 4-methylbenzene-sulfonate

The title compound is obtained in a similar manner to Reference Example 69.

$^1$H-NMR (CDCl$_3$) δ: 0.92 (3H, d, J=6.8 Hz), 0.97 (3H, d, J=6.6 Hz), 2.06–2.18 (1H, m), 2.45 (3H, s), 3.43–3.69 (8H, m), 4.74 (1H, d, J=8.4 Hz), 7.35 (2H, d, J=8.0 Hz), 7.81 (2H, d, J=8.3 Hz).

Example 137

(1R)-2-(((1R)-1-Methyl-2-(7-(((1S)-2-methyl-1-(morpholin-4-ylcarbonyl)-propyl)oxy)-1H-indol-3-yl)ethyl)amino)-1-pyridin-3-ylethanol The title compound is obtained in a similar manner to Example 119.

$^1$H-NMR (CDCl$_3$) δ: 1.11 (3H, d, J=6.8 Hz), 1.16 (3H, d, J=6.2 Hz), 1.20 (3H, d, J=6.6 Hz), 2.25–2.31 (1H, m), 2.70 (1H, dd, J=12, 9.5 Hz), 2.85 (2H, m), 2.91 (1H, dd, J=12, 3.4 Hz), 3.08–3.13 (1H, m), 3.34 (2H, m), 3.49–3.62 (6H, m), 4.61–4.64 (2H, m), 6.67 (1H, d, J=7.7 Hz), 6.99 (1H, t, J=7.8 Hz), 7.03 (1H, s), 7.22–7.26 (1H, m), 8.49 (1H, d, J=4.1 Hz), 8.53 (1H, d, J=1.2 Hz), 8.74 (1H, brs).

Example 138

(2S)-2-((3-((2R)-2-(((2 R)-2-Hydroxy-2-pyridin-3-ylethyl)amino)propyl)-1H-indol-7-yl)oxy)-3-methylbutanoic acid.2 trifluoroacetate The title compound is obtained in a similar manner to Example 120.
$^1$H-NMR (CDCl$_3$) δ: 1.15 (3H, d, J=6.9 Hz), 1.19 (3H, d, J=6.8 Hz), 1.33 (3H, d, J=6.5 Hz), 2.33–2.41 (1H, m), 3.01 (1H, dd, J=14, 9.0 Hz), 3.26–3.35 (2H, m), 3.42 (1H, dd, J=14, 3.2 Hz), 3.65–3.70 (1H, m), 4.61 (1H, d, J=5.1 Hz), 5.24 (1H, dd, J=9.0, 3.2 Hz), 6.54 (1H, d, J=7.7 Hz), 6.94 (1H, dd, J=7.8, 7.7 Hz), 7.19 (1H, s), 7.22 (1H, d, J=7.8 Hz), 7.99 (1H, dd, J=7.9, 5.7 Hz), 8.48 (1H, d, J=7.9 Hz), 8.79 (1H, d, J=5.7 Hz), 8.87 (1H, brs).

Example 139

Ethyl(2S)-2-((3-((2R)-2-(((2R)-2-Hydroxy-2-pyridin-3-ylethyl)amino)-propyl)-1H-indol-7-yl)oxy)-3-methylbutanoate.2 hydrochloride The title compound is obtained in a similar manner to Example 125.
$^1$H-NMR (CDCl$_3$) δ: 1.13 (3H, d, J=6.9 Hz), 1.18 (3H, d, J=6.8 Hz), 1.23 (3H, t, J=7.1 Hz), 1.34 (3H, d, J=6.1 Hz), 2.31–2.40 (1H, m), 3.02 (1H, dd, J=13.8, 9.2 Hz), 3.31–3.37 (2H, m), 3.47–3.50 (1H, m), 3.70 (1H, m), 4.21 (2H, q, J=7.1 Hz), 4.63 (1H, d, J=5.4 Hz), 5.38 (1H, m), 6.49 (1H, d, J=7.7 Hz), 6.93 (1H, dd, J=7.9, 7.7 Hz), 7.22 (1H, s), 7.26 (1H, d, J=7.9 Hz), 8.11 (1H, dd, J=7.7, 5.0 Hz), 8.68 (1H, d, J=7.7 Hz), 8.84 (1H, d, J=5.0 Hz), 8.99 (1H, brs).

Example 140

1-((3-((2R)-2-(((2R)-2-Hydroxy-2-pyridin-3-ylethyl)amino)propyl)-1H-indol-7-yl)oxy)cyclobutanecarboxylic acid.2 trifluoroacetate The title compound is obtained in a similar manner to Example 109.
$^1$H-NMR (CD$_3$OD) δ: 1.34 (3H, d, J=6.5 Hz), 1.97–2.14 (2H, m), 2.51–2.59 (2H, m), 2.77–2.86 (2H, m), 3.01 (1H, dd, J=14, 8.9 Hz), 3.24–3.35 (3H, m), 3.38 (1H, dd, J=13, 2.9 Hz), 3.63–3.71 (1H, m), 5.20 (1H, dd, J=9.6, 2.4 Hz), 6.21 (1H, d, J=7.7 Hz), 6.86 (1H, t, J=7.8 Hz), 7.17 (1H, s), 7.18 (1H, d, J=7.4 Hz), 7.93 (1H, m), 8.39 (1H, d, J=7.2 Hz), 8.75 (1H, brs), 8.82 (1H, brs).

Reference Example 74

(2R)-1-Morpholin-4-yl-1-oxo-3-phenylpropan-2-ol

The title compound is obtained in a similar manner to Reference Example 68.
$^1$H-NMR (CDCl$_3$) δ: 2.90 (3H, dd, J=14, 6.2 Hz), 2.96 (3H, dd, J=14, 6.8 Hz), 3.26–3.32 (2H, m), 3.51–3.74 (6H, m), 4.59 (1H, dt, J=8.4, 6.4 Hz), 7.21–7.33 (5H, m).

Reference Example 75

(1R)-1-Benzyl-2-morpholin-4-yl-2-oxoethyl 4-methylbenzenesulfonate

The title compound is obtained in a similar manner to Reference Example 69.
$^1$H-NMR (CDCl$_3$) δ: 2.43 (3H, s), 3.00–3.56 (10H, m), 5.26 (1H, dd, J=8.1, 6.8 Hz), 7.11–7.15 (2H, m), 7.23–7.29 (5H, m), 7.68 (2H, dt, J=8.3, 1.7 Hz).

Example 141

(1R)-2-(((1R)-1-Methyl-2-(7-(((1S)-1-benzyl-2-morpholin-4-yl-2-oxoethyl)-oxy)-1H-indol-3-yl)-1-methylethyl)amino)-1-pyridin-3-ylethanol The title compound is obtained in a similar manner to Example 119.
$^1$H-NMR (CDCl$_3$) δ: 1.14 (3H, d, J=6.2 Hz), 2.69 (1H, dd, J=12,9.5 Hz), 2.84 (2H, d, J=6.5 Hz), 2.91 (1H, dd, J=12, 3.5 Hz), 3.06–3.11 (2H, m), 3.27–3.62 (9H, m), 4.63 (1H, dd, J=9.2, 3.1 Hz), 5.16 (1H, t, J=6.8 Hz), 6.55 (1H, d, J=7.7 Hz), 6.95 (1H, t, J=7.9 Hz), 6.98 (1H, d, J=1.4 Hz), 7.21–7.26 (2H, m), 7.28–7.37 (5H, m), 7.66 (1H, d, J=7.8 Hz), 8.48 (1H, dd, J=4.7, 1.2 Hz), 8.53 (1H, d, J=1.6 Hz), 8.63 (1H, brs).

Example 142

(2S)-2-((3-((2R)-2-(((2R)-2-Hydroxy-2-pyridin-3-ylethyl)amino)propyl)-1H-indol-7-yl) oxy)-3-phenylpropanoic acid 2 trifluoro acetate The title compound is obtained in a similar manner to Example 120.
$^1$H-NMR (CD$_3$OD) δ: 1.33 (d, 3H, J=6.5 Hz), 3.01 (1H, dd, J=14, 8.9 Hz), 3.20–3.42 (5H, m), 3.64–3.69 (1H, m), 5.06 (1H, dd, J=7.5, 4.6 Hz), 5.22 (1H, dd, J=9.8, 2.9 Hz), 6.55 (1H, d, J=7.7 Hz), 6.93 (1H, t, J=7.9 Hz), 7.12–7.28 (4H, m), 7.35 (2H, d, J=7.2 Hz), 7.97 (1H, dd, J=7.9, 5.7 Hz), 8.47 (1H, d, J=8.1 Hz), 8.77 (1H, d, J=5.3 Hz), 8.86 (1H, brs).

Reference Example 76

(1R)-2-Morpholin-4-yl-2-oxo-1-phenylethanol

The title compound is obtained in a similar manner to Reference Example 68.
$^1$H-NMR (CDCl$_3$) δ: 3.05–3.10 (1H, m), 3.14–3.19 (1H, m), 3.28–3.32 (1H, m), 3.45–3.50 (1H, m), 3.55–3.82 (4H, m), 4.71 (1H, brs), 5.19 (1H, s), 7.29–7.41 (5H, m).

Reference Example 77

(1R)-2-Morpholin-4-yl-2-oxo-1-phenylethyl 4-methylbenzenesulfonate

The title compound is obtained in a similar manner to Reference Example 69.
$^1$H-NMR (CDCl$_3$) δ: 2.43 (3H, s), 3.35–3.61 (8H, m), 6.11 (1H, s), 7.31 (2H, d, J=8.1 Hz), 7.34 (5H, s), 7.81 (2H, d, J=8.1 Hz).

Example 143

(1R)-2-(((1R)-1-Methyl-2-(7-(((1S)-2-morpholin-4-yl-2-oxo-1-phenyl-ethyl)oxy)-1H-indol-3-yl)ethyl)amino)-1-pyridin-3-ylethanol The title compound is obtained in a similar manner to Example 119.
$^1$H-NMR (CDCl$_3$) δ: 1.16 (3H, d, J=6.2 Hz), 2.71 (1H, dd, J=12.2, 9.4 Hz), 2.86 (2H, m), 2.91 (1H, dd, J=12.2, 3.4 Hz), 3.07–3.15 (1H, m), 3.19–3.22 (1H, m), 3.34–3.36 (1H, m), 3.50–3.63 (6H, m), 4.64 (1H, dd, J=9.4, 3.4 Hz), 6.03 (1H, s), 6.74 (1H, d, J=7.8 Hz), 6.98 (1H, t, J=7.8 Hz), 7.03 (1H, s), 7.21–7.26 (2H, m), 7.36–7.45 (3H, m), 7.56–7.58 (2H, m), 7.66 (1H, dt, J=6.2, 1.7 Hz), 8.48 (1H, dd, J=4.7, 1.3 Hz), 8.53 (1H, d, J=1.7 Hz), 8.90 (1H, brs).

Example 144

(2S)-((3-((2R)-2-(((2R)-2-Hydroxy-2-pyridin-3-yl-ethyl)amino) propyl)-1H-indol-7-yl)oxy)(phenyl) acetic acid.2 trifluoroacetate The title compound is obtained in a similar manner to Example 120.
$^1$H-NMR (CD$_3$OD) δ: 1.33 (3H, d, J=6.5 Hz), 3.02 (1H, dd, J=14.3, 8.8 Hz), 3.23–3.37 (3H, m), 3.62–3.69 (1H, m), 5.13 (1H, dd, J=9.9, 3.1 Hz), 5.93 (1H, s), 6.59 (1H, d, J=7.7 Hz), 6.89 (1H, dd, J=8.0, 7.7 Hz), 7.20 (1H, d, J=,8.0 Hz), 7.21 (1H, s), 7.33–7.43 (3H, m), 7.64–7.66 (2H, m), 7.78 (1H, dd, J=8.0, 4.3 Hz), 8.24 (1H, d, J=8.0 Hz), 8.68 (1H, d, J=4.3 Hz), 8.75 (1H, s).

Reference Example 78

3-(2-Azidethyl)-7-(benzyloxy)-1H-indole

To a solution of 2-(7-(benzyloxy)-1H-indol-3-yl)ethanol (1.65 g, 6.17 mmol) in methylene chloride (20 mL) are added triethylamine (1.72 mL, 12.3 mmol) and methanesulfonyl chloride (0.6 mL, 7.78 mmol) under nitrogen atmosphere, and the mixture is stirred at room temperature for 16 hours. The reaction solution is poured into water, and the mixture is extracted with chloroform. The organic layer is washed successively with a 1N aqueous hydrocloric acid solution, a saturated aqueous sodium hydrogen carbonate solution and a saturated brine, and dried over anhydrous magnesium sulfate. The solvent is evaporated, and the obtained crude product is dissolved in N,N-dimethylformamide (20 mL), and thereto is added sodium azide (1.00 g, 15.4 mmol), and the mixture is reacted at 60° C. for 3 hours. The reaction solution is poured into water, and the mixture is extracted with ethyl acetate. The organic layer is washed successively with a 1N aqueous hydrochloric acid solution, a saturated aqueous sodium hydrogen carbonate solution, and a saturated brine, and dried over anhydrous magnesium sulfate. The solvent is removed by distillation, and the obtained crude product is purified by silica gel column chromatography (n-hexane:ethyl acetate=10:1→3:1→1:1) to give the title compound (1.52 g, yield: 84%).
$^1$H-NMR (CDCl$_3$) δ: 3.05 (2H, t, J=7.2 Hz), 3.56 (2H, t, J=7.2 Hz), 5.20 (2H, s), 6.74 (1H, d, J=7.7 Hz), 7.02–7.06 (2H, m), 7.21 (1H, d, J=8.0 Hz), 7.34–7.43 (3H, m), 7.47–7.49 (2H, m), 8.42 (1H, brs).

Reference Example 79

2-(7-(Benzyloxy)-1H-indol-3-yl)ethylamine

To a solution of 3-(2-azidethyl)-7-(benzyloxy)-1H-indole (5.10 g, 17.4 mmol) in pyridine (100 mL)-water (100 mL) is added triphenyl-phosphine (5.02 g, 19.1 mmol) under nitrogen atmosphere, and the mixture is stirred at room temperature for 18 hours. The reaction solution is poured into water, and the mixture is extracted with chloroform. The organic layer is washed with a saturated brine, and dried over anhydrous magnesium sulfate. The solvent is evaporated under reduced pressure, and the obtained crude product is purified by silica gel column chromatography (a saturated ammonia solution in chloroform a saturated ammonia solution in chloroform-methanol 50:1→10:1) to give the title compound (4.38 g, yield: 95%).
$^1$H-NMR (CDCl$_3$) δ: 2.89 (2H, t, J=6.8 Hz), 3.02 (2H, t, J=6.8 Hz), 5.21 (2H, s), 6.73 (1H, d, J=7.7 Hz), 7.01 (1H, d, J=2.1 Hz), 7.02 (1H, dd, J=8.0, 7.7 Hz), 7.24 (1H, d, J=8.0 Hz), 7.34–7.43 (3H, m), 7.47–7.49 (2H, m), 8.29 (1H, brs).

Reference Example 80

(2R)-N-(2-(7-(Benzyloxy)-1H-indol-3-yl)ethyl)-2-hydroxy-2-pyridin-3-ylacetamide

The title compound is obtained in a similar manner to Reference Example 61.
$^1$H-NMR (CDCl$_3$) δ: 2.82–2.97 (2H, m), 3.54–3.65 (2H, m), 4.99 (1H, s), 5.20 (2H, s), 6.37 (1H, t, J=5.3 Hz), 6.73 (1H, d, J=7.6 Hz), 6.80 (1H, d, J=2.2 Hz), 7.02 (1H, dd, J=8.0, 7.6 Hz), 7.16 (1H, d, J=8.0 Hz), 7.22 (1H, dd, J=7.9, 4.8 Hz), 7.33–7.42 (3H, m), 7.47–7.49 (2H, m), 7.65 (1H, dt, J=7.9, 1.8 Hz), 8.44 (1H, brs), 8.47 (1H, dd, J=4.8, 1.6 Hz), 8.52 (1H, d, J=2.1 Hz).

Reference Example 81 tert-Butyl 2-(7-(benzyloxy)-1H-indol-3-yl) ethyl ((2R)-2-hydroxy-2-pyridin-3-ylethyl)carbamate The title compound is obtained in a similar manner to Reference Example 62 and Reference Example 63.
IR (ATR (total reflection absorption method)/FT-IR, cm$^{-1}$): 3320, 1670, 1577, 1411, 1365, 1257, 1226, 1161, 1045, 1026.

Reference Example 82 tert-Butyl 2-(7-(benzyloxy)-1H-indol-3-yl)ethyl ((2R)-2-pyridin-3-yl-2-((triethylsilyl)oxy)ethyl)carbamate The title compound is obtained in a similar manner to Reference Example 64.
IR (ATR (total reflection absorption method)/FT-IR, cm$^{-1}$): 1685, 1577, 1454, 1408, 1365, 1230, 1164, 1087.

Reference Example 83 tert-Butyl 2-(7-hydroxy-1H-indol-3-yl)ethyl((2R)-2-pyridin-3-yl-2-((triethylsilyl)oxy)ethyl)carbamate The title compound is obtained in a similar manner to Reference Example 65.
IR (ATR (total reflection absorption method)/FT-IR, cm$^{-1}$): 3340, 1670, 1577, 1473, 1457, 1411, 1365, 1238, 1161, 1088.

Example 145

(1R)-2-((2-(7-(((1S)-1-Methyl-2-morpholin-4-yl-2-oxoethyl)oxy)-1H-indol-3-yl)ethyl)amino)-1-pyridin-3-ylethanol The title compound is obtained in a similar manner to Example 119.
$^1$H-NMR (CDCl$_3$) δ: 1.65 (3H, d, J=6.6 Hz), 2.69 (1H, dd, J=12.2, 9.3 Hz), 2.93 (1H, dd, J=12.2, 3.4 Hz), 2.94–3.08 (4H, m), 3.41–3.61 (8H, m), 4.70 (1H, dd, J=9.3, 3.4 Hz), 5.15 (1H, q, J=6.6 Hz), 6.63 (1H, d, J=7.7 Hz), 6.99 (1H, dd, J=8.0, 7.7 Hz), 7.01 (1H, d, J=1.8 Hz), 7.23–7.26 (2H, m), 7.69 (1H, d, J=7.9 Hz), 8.49 (1H, dd, J=4.8, 1.3 Hz), 8.55 (1H, d, J=1.8 Hz), 8.83 (1H, brs).

Example 146

(2S)-2-((3-(2-(((2R)-2-Hydroxy-2-pyridin-3-ylethyl) amino)ethyl)-1H-indol-7-yl)oxy)propanoic acid The title compound is obtained in a similar manner to Example 120.
$^1$H-NMR (DMSO-$d_6$) δ: 1.55 (3H, d, J=6.6 Hz), 2.60–2.90 (5H, m), 3.02 (1H, dd, J=12.3, 3.3 Hz), 4.60 (1H, q, J=6.6 Hz), 4.93 (1H, dd, J=9.9, 3.3 Hz), 6.50 (1H, d, J=7.7 Hz), 6.70 (1H, dd, J=7.9, 7.7 Hz), 6.78 (1H, d, J=1.8 Hz), 6.91 (1H, d, J=7.9 Hz), 7.38 (1H, dd, J=7.7, 4.7 Hz), 7.79 (1H, ddd, J=7.7, 1.8, 1.5 Hz), 8.49 (1H, dd, J=4.7, 1.5 Hz), 8.59 (1H, d, J=1.8 Hz), 10.87 (1H, d, J=1.6 Hz).

Example 147

(1R)-2-((2-(7-(((1S)-2-Methyl-1-(morpholin-4-ylcarbonyl)propyl)oxy)-1H-indol-3-yl)ethyl) amino)-1-pyridin-3-ylethanol The title compound is obtained in a similar manner to Example 119.
$^1$H-NMR (CDCl$_3$) δ: 1.11 (3H, d, J=6.8 Hz), 1.20 (3H, d, J=6.6 Hz), 2.23–2.32 (1H, m), 2.70 (1H, dd, J=12.3, 9.5 Hz), 2.95 (1H, dd, J=12.3, 3.5 Hz), 2.96–3.07 (3H, m), 3.36–3.37 (2H, m), 3.48–3.67 (6H, m), 3.76–3.79 (1H, m), 4.62 (1H, d, J=7.8 Hz), 4.73 (1H, dd, J=9.5, 3.5 Hz), 6.67 (1H, d, J=7.7 Hz), 6.99 (1H, dd, J=8.0, 7.7 Hz), 7.03 (1H, d, J=1.9 Hz), 7.25 (1H, dd, J=7.9, 4.8 Hz), 7.25 (1H, d, J=8.0 Hz), 7.68 (1H, ddd, J=7.9, 2.0, 1.6 Hz), 8.49 (1H, dd, J=4.8, 1.6 Hz), 8.55 (1H, d, J=2.0 Hz), 8.69 (1H, brs).

Example 148

(2S)-2-((3-(2-(((2R)-2-Hydroxy-2-pyridin-3-ylethyl) amino)ethyl)-1H-indol-7-yl)oxy)-3-methylbutanoic acid.2 trifluoroacetate The title compound is obtained in a similar manner to Example 120.
$^1$H-NMR (CD$_3$OD) δ: 1.19 (3H, d, J=6.9 Hz), 1.24 (3H, d, J=6.9 Hz), 2.35–2.45 (1H, m), 3.23–3.31 (3H, m), 3.41–3.47 (3H, m), 4.66 (1H, d, J=5.1 Hz), 5.28 (1H, dd, J=9.9, 3.0 Hz), 6.58 (1H, d, J=7.7 Hz), 6.99 (1H, dd, J=7.9, 7.7 Hz), 7.22 (1H, s), 7.26 (1H, d, J=7.9 Hz), 8.04 (1H, brt, J=6 Hz), 8.50 (1H, d, J=8.1 Hz), 8.84–8.90 (2H, m).

Reference Example 84

2-(7-{[(1S)-1-Methyl-2-morpholin-4-yl-2-oxoethyl] oxy}-1H-indol-3-yl)-ethanol

To a solution of 3-(2-hydroxyethyl)-1H-indol-7-ol (1.05 g, 5.93 mmol) in N,N-dimethylformamide (20 mL) are added (1R)-1-methyl-2-morpholin-4-yl-2-oxoethyl-4-methylbenzenesulfonate (2.79 g, 8.90 mmol) and potassium carbonate (1.3 g, 9.41 mmol), and the mixture is stirred at 60° C. for 5 hours. The reaction solution is cooled to room temperature, and the mixture is poured into water. The mixture is extracted with ethyl acetate, and the organic layer is washed with a saturated aqueous sodium hydrogen carbonate solution, and dried over anhydrous sodium sulfate. The solvent is removed by distillation, and the obtained crude product is purified by silica gel column chromatography (chloroform→chloroform:methanol=50:1→30:1) to give the title compound (1.29 g, yield: 68%).
$^1$H-NMR (DMSO-$d_6$) δ: 1.63 (1H, t, J=6.1 Hz), 1.66 (3H, d, J=6.7 Hz), 3.02 (2H, td, J=6.3, 0.4 Hz), 3.43–3.74 (8H, m), 3.90 (1H, td, J=6.3, 6.1 Hz), 5.15 (1H, q, J=6.7 Hz), 6.64 (1H, d, J=7.7 Hz), 7.00 (1H, dd, J=7.9, 7.7 Hz), 7.07 (1H, d, J=2.3 Hz), 7.29 (1H, d, J=7.9 Hz), 8.73 (1H, brs).

Reference Example 85

(7-{[(1S)-1-Methyl-2-morpholin-4-yl-2-oxoethyl] oxy}-1H-indol-3-yl)acet-aldehyde The title compound is obtained in a similar manner to Reference Example 24.
$^1$H-NMR (CDCl$_3$) δ: 1.65 (3H, d, J=6.7 Hz), 3.42–3.62 (8H, m), 3.78 (2H, dd, J=2.5, 0.7 Hz), 5.15 (1H, q, J=6.7 Hz), 7.02 (1H, dd, J=8.0, 7.7 Hz), 7.12 (1H, d, J=2.4 Hz), 7.18 (1H, d, J=8.0 Hz), 9.00 (1H, brs), 9.74 (1H, t, J=2.5 Hz).

Example 149

4-((1R,2S)-1-Hydroxy-2-{[2-(7-{[(1S)-1-methyl-2-morpholin-4-yl-2-oxo-ethyl]oxy}-1H-indol-3-yl) ethyl]amino}propyl)phenol The title compound is obtained in a similar manner to Example 30.
$^1$H-NMR (CDCl$_3$) δ: 1.18 (3H, d, J=6.3 Hz), 1.68 (3H, d, J=6.7 Hz), 2.59–2.65 (2H, m), 2.74–2.81 (1H, m), 2.86–2.92 (1H, m), 3.00–3.05 (1H m), 3.61–3.83 (8H, m), 4.19 (1H, d, J=7.8 Hz), 5.19 (1H, q, J=6.7 Hz), 6.30 (2H, d, J=8.5 Hz), 6.32 (1H, d, J=7.5 Hz), 6.64 (1H, d, J=2.2 Hz), 6.75 (2H, d, J=8.5 Hz), 6.90 (1H, dd, J=8.0, 7.6 Hz), 7.18 (1H, d, J=8.0 Hz), 8.59 (1H, brs).

Example 150

(2S)-2-{[3-(2-{[(1S,2R)-2-Hydroxy-2-(4-hydroxyphenyl)-1-methylethyl]-amino}ethyl)-1H-indol-7-yl]oxy}propanoic acid The title compound is obtained in a similar manner to Example 120.
$^1$H-NMR (DMSO-$d_6$) δ: 0.89 (3H, d, J=6.6 Hz), 1.54 (3H, d, J=6.8 Hz), 2.49–2.53 (1H, m), 2.62–2.75 (1H, m), 2.94–3.04 (2H, m), 3.16 (1H, brs), 4.58 (1H, q, J=6.8 Hz), 4.99 (1H, brs), 6.51 (1H, d, J=7.6 Hz), 6.67 (2H, d, J=8.3 Hz), 6.73 (1H, s), 6.75 (1H, dd, J=7.9, 7.6 Hz), 6.90 (1H, d, J=7.9 Hz), 7.08 (2H, d, J=8.3 Hz), 9.49 (1H, brs), 10.82 (1H, s).

Reference Example 86

2-(7-{[(1R)-1-Methyl-2-morpholin-4-yl-2-oxoethyl] oxy}-1H-indol-3-yl)ethanol

The title compound is obtained in a similar manner to Reference Example 84.
$^1$H-NMR (CDCl$_3$) δ: 1.63 (1H, t, J=6.1 Hz), 1.65 (3H, d, J=6.7 Hz), 3.02 (2H, t, J=6.2 Hz), 3.43–3.63 (m, 8H), 3.90 (2H, td, J=6.2, 6.1 Hz), 5.14 (1H, q, J=6.7 Hz), 6.64 (1H, d, J=7.7 Hz), 7.00 (1H, t, J=7.8 Hz), 7.06 (1H, d, J=2.2 Hz), 7.27 (1H, d, J=7.4 Hz), 8.70 (brs, 1H).

Reference Example 87

(7-{[(1R)-1-Methyl-2-morpholin-4-yl-2-oxoethyl]oxy}-1H-indol-3-yl)acet-aldehyde

The title compound is obtained in a similar manner to Reference Example 24.

$^1$H-NMR (CDCl$_3$) δ: 1.66 (3H, d, J=6.7 Hz), 3.43–3.63 (8H, m), 3.79 (2H, dd, J=2.4, 0.65 Hz), 5.15 (1H, q, J=6.7 Hz), 6.67 (1H, d, J=7.7 Hz), 7.03 (1H, t, J=7.8 Hz), 7.16 (1H, d, J=2.4 Hz), 7.19 (1H, d, J=8.0 Hz), 9.76 (t, 1H, J=2.5 Hz).

Example 151

4-((1R,2 S)-1-Hydroxy-2-{[2-(7-{[(1R)-1-methyl-2-morpholin-4-yl-ethyl]oxy}-1H-indol-3-yl)ethyl]amino}propyl)phenol The title compound is obtained in a similar manner to Example 30.

$^1$H-NMR (CDCl$_3$) δ: 1.24 (3H, d, J=6.1 Hz), 1.69 (3H, d, J=6.7 Hz), 2.47–2.54 (1H, m), 2.61–2.73 (2H, m), 2.61–2.73 (2H, m), 2.97–3.03 (2H, m), 3.65–3.91 (8H, m), 4.12 (1H, d, J=8.5 Hz), 5.22 (1H, q, J=6.7 Hz), 6.25 (1H, d, J=7.6 Hz), 6.27–6.31 (2H, m), 6.60 (1H, d, J=7.6 Hz), 6.66–6.70 (2H, m), 6.91 (1H, t, J=7.8 Hz), 7.13 (1H, d, J=8.0 Hz), 8.26 (brs, 1H).

Example 152

(2R)-2-{[3-(2-{[(1S,2R)-2-Hydroxy-2-(4-hydroxyphenyl)-1-methylethyl]-amino}ethyl)-1H-indol-7-yl]oxy}propanoic acid The title compound is obtained in a similar manner to Example 120.

$^1$H-NMR (CD$_3$OD) δ: 1.07 (3H, d, J=6.7 Hz), 1.68 (3H, d, J=6.8 Hz), 3.17–3.20 (2H, m), 3.35–3.42 (3H, m), 4.91–5.00 (2H, m), 6.59 (1H, d, J=7.7 Hz), 6.76 (2H, d, J=8.6 Hz), 6.96 (1H, t, J=7.9 Hz), 7.11 (2H, d, J=8.6 Hz), 7.18 (1H, s), 7.23 (1H, d, J=7.9 Hz).

Reference Example 88 tert-Butyl (1R)-2-[7-(benzyloxy)-1H-indol-3-yl]-1-methylethylcarbamate

To a solution of (1R)-2-[7-(benzyloxy)-1H-indol-3-yl]-1-methyl-ethylamine (3.09 g, 11.0 mmol) in tetrahydrofuran (100 mL) is added di-tert-butyl bicarbonate (3.80 mL, 16.5 mmol) under nitrogen atmosphere, and the mixture is stirred at room temperature for 60 hours. The reaction solution is poured into a mixture of a saturated brine and water (1:1), and the mixture is extracted with ethyl acetate. The organic layer is washed with a saturated brine, and dried over anhydrous magnesium sulfate. The solvent is evaporated, and the obtained crude product is purified by silica gel column chromatography (n-hexane:ethyl acetate=3:1) to give the title compound (3.70 g, yield: 88%).

$^1$H-NMR (CDCl$_3$) δ: 1.11 (3H, d, J=6.4 Hz), 1.43 (9H, s), 2.84 (1H, dd, J=14.8, 7.2 Hz), 2.95 (1H, dd, J=14.8, 5.2 Hz), 4.01 (1H, brs), 4.45 (1H, brs), 5.20 (2H, s), 6.72 (1H, d, J=7.2 Hz), 6.99 (1H, d, J=2.4 Hz), 7.02 (1H, dd, J=7.6, 7.2 Hz), 7.34–7.43 (3H, m), 7.46–7.49 (2H, m), 8.28 (1H, brs).

Reference Example 89 tert-Butyl (1R)-1-methyl-2-(7-{[(1S)-1-methyl-2-morpholin-4-yl-2-oxo-ethyl]oxy}-1H-indol-3-yl)ethylcarbamate To a solution of tert-butyl (1R)-2-[7-(benzyloxy)-1H-indol-3-yl]-1-methylethylcarbamate (1.0 g, 2.63 mmol) in methanol (30 mL) is added a 10% palladium on carbon (50% wet, 1.0 g), and the mixture is stirred under hydrogen atmosphere for one hour. The reaction solution is filtered through celite, and the filtrate is evaporated under reduced pressure to remove the solvent. The resulting residue is dissolved in N,N-dimethylformamide (5 mL), and thereto are added potassium carbonate (581 mg, 4.21 mmol) and (1R)-1-methyl-2-morpholin-4-yl-2-oxoethyl 4-methylbenzenesulfonate (1.24 g, 3.95 mmol), and the mixture is stirred at 55° C. The reaction solution is cooled to room temperature, and the mixture is poured into a mixture of a saturated brine and water (1:1), and extracted with ethyl acetate. The organic layer is washed with a saturated aqueous sodium hydrogen carbonate solution, and dried over anhydrous potassium carbonate. The solvent is distilled off, and the obtained crude product is purified by silica gel column chromatography (chloroform→chloroform:methanol=100:1) to give the title compound (1.03 g, yield: 63%).

$^1$H-NMR (CDCl$_3$) δ: 1.11 (3H, d, J=6.4 Hz), 1.43 (9H, s), 1.66 (3H, d, J=6.8 Hz), 2.83 (1H, dd, J=14, 6.8 Hz), 2.94 (1H, dd, J=5.2 Hz), 3.39–3.51 (2H, m), 3.55–3.65 (6H, m), 4.00 (1H, brs), 4.45 (1H, brs), 5.13 (1H, q, J=6.8 Hz), 6.63 (1H, d, J=7.6 Hz), 6.99 (1H, dd, J=8.0, 7.6 Hz), 7.01 (1H, s), 7.29 (1H, d, J=8 Hz), 8.55 (1H, brs).

Reference Example 90

(1R)-1-Methyl-2-(7-{[(1S)-1-methyl-2-morpholin-4-yl-2-oxoethyl]oxy}-1H-indol-3-yl)ethylamine To a solution of tert-butyl (1R)-1-methyl-2-(7-{[(1S)-1-methyl-2-morpholin-4-yl-2-oxoethyl]oxy}-1H-indol-3-yl)ethylcarbamate (1.03 g, 2.39 mmol) in acetonitrile (10 mL) is added oxalic acid (860 mg, 9.55 mmol), and the mixture is refluxed for 5 hours. The reaction solution is evaporated under reduced pressure to remove the solvent, and to the residue are added a 10% aqueous potassium carbonate solution and a mixture of chloroform:methanol (10:1) for separation. The organic layer is dried over anhydrous potassium carbonate, and the solvent is removed by distillation to give the title compound (626 mg, yield: 79%).

$^1$H-NMR (CDCl$_3$) δ: 1.16 (3H, d, J=6.4 Hz), 1.66 (3H, d, J=6.8 Hz), 2.63 (1H, dd, J=8.4, 14.8 Hz), 2.86 (1H, ddd, J=0.8, 4.8, 14.4 Hz), 3.25–3.30 (1H, m), 3.40–3.52 (2H, m), 3.58–3.62 (6H, m), 5.13 (1H, q, J=6.8 Hz), 6.64 (1H, d, J=7.6 Hz), 6.99 (1H, dd, J=8.0, 8.0 Hz), 7.27 (1H, d, J=8.0 Hz), 8.55 (1H, brs).

Example 153

(1R)-1-(3-Chlorophenyl)-2-{[(1R)-1-methyl-2-(7-{[(1S)-1-methyl-morpholin-4-yl-2-oxoethyl]oxy}-1H-indol-3-yl)ethyl]amino}ethanol.hydrochloride The title compound is obtained in a similar manner to Example 108.

$^1$H-NMR (CD$_3$OD) δ: 1.31 (3H, d, J=6.5 Hz), 1.63 (3H, d, J=6.6 Hz), 3.00 (1H, dd, J=9.0, 14.3 Hz), 3.16–3.27 (3H, m), 3.40–3.43 (1H, m), 3.57–3.72 (8H, m), 4.93 (1H, dd, J=3.3, 9.9 Hz), 5.35 (1H, q, J=6.6 Hz), 6.62 (1H, d, J=8.0

Hz), 6.96 (1H, dd, J=7.9, 7.9 Hz), 7.18 (1H, s), 7.23 (1H, d, J=8.0 Hz), 7.29–7.40 (3H, m), 7.45 (1H, s).

Example 154

(2S)-2-{[3-((2R)-2-{[(2R)-2-(3-Chlorophenyl)-2-hydroxyethyl]amino}-propyl)-1H-indol-7-yl]oxy}propanoic acid The title compound is obtained in a similar manner to Example 120.

$^1$H-NMR (CD$_3$OD) δ: 1.16 (3H, d, J=6.4 Hz), 1.60 (3H, d, J=6.7 Hz), 2.78–2.98 (4H, m), 3.21–3.26 (1H, m), 4.70–4.76 (2H, m), 6.57 (1H, d, J=7.7 Hz), 6.86 (1H, dd, J=7.8, 7.9 Hz), 7.00 (1H, s), 7.07 (1H, d, J=7.7 Hz), 7.14–7.16 (1H, m), 7.22–7.25 (2H, m), 7.34 (1H, s).

Reference Example 91 tert-Butyl (1R)-1-methyl-2-(7-{[(1R)-1-methyl-2-morpholin-4-yl-2-oxo-ethyl]oxy}-1H-indol-3-yl)ethylcarbamate The title compound is obtained in a similar manner to Reference Example 89.

$^1$H-NMR (CDCl$_3$) δ: 1.11 (3H, d, J=6.6 Hz), 1.44 (9H, s), 1.66 (3H, d, J=6.7 Hz), 2.83 (1H, dd, J=14, 6.9 Hz), 2.94 (1H, dd, J=14, 5.2 Hz), 3.48–3.57 (8H, m), 4.40 (1H, m), 4.38–4.48 (1H, m), 5.14 (1H, q, J=6.7 Hz), 6.63 (1H, d, J=7.7 Hz), 6.99 (1H, t, J=7.9 Hz), 7.01 (1H, d, J=2.1 Hz), 7.29 (1H, d, J=8.0 Hz), 8.57 (1H, brs).

Reference Example 92

(1R)-1-Methyl-2-(7-{[(1R)-1-methyl-2-morpholin-4-yl-2-oxoethyl]oxy}-1H-indol-3-yl) ethylamine The title compound is obtained in a similar manner to Reference Example 90.

$^1$H-NMR (CDCl$_3$) δ: 1.16 (3H, d, J=6.3 Hz), 1.66 (3H, d, J=6.7 Hz), 2.64 (1H, dd, J=14, 8.2 Hz), 2.85 (1H, dd, J=14, 5.0 Hz), 3.23–3.31 (1H, m), 3.41–3.62 (8H, m), 5.14 (1H, q, J=6.7 Hz), 6.64 (1H, d, J=7.7 Hz), 6.99 (1H, t, J=7.8 Hz), 7.04 (1H, d, J=2.1 Hz), 7.27 (1H, d, J=7.9 Hz), 8.55 (1H, s).

Example 155

(1R)-1-(3-Chlorophenyl)-2-{[(1R)-1-methyl-2-(7-{[(1R)-1-methyl-2-morpholin-4-yl-2-oxoethyl]oxy}-1H-indol-3-yl)ethyl]amino}ethanol The title compound is obtained in a similar manner to Example 108.

$^1$H-NMR (CDCl$_3$) δ: 1.11 (3H, d, J=6.2 Hz), 1.63 (3H, d, J=6.6 Hz), 2.66 (1H, dd, J=12, 9.1 Hz), 2.75–2.84 (2H, m), 2.85 (1H, dd, J=12, 3.6 Hz), 3.00–3.05 (1H, m), 3.39–3.59 (8H, m), 4.51 (1H, dd, J=9.0, 3.4 Hz), 5.14 (1H, q, J=6.7 Hz), 6.60 (1H, d, J=7.7 Hz), 6.97 (1H, s), 6.98 (1H, t, J=7.9 Hz), 7.14–7.24 (4H, m), 7.32 (1H, s), 8.92 (brs, 1H).

Example 156

(2R)-2-{[3-((2R)-2-{[(2R)-2-(3-Chlorophenyl)-2-hydroxyethyl]amino}-propyl)-1H-indol-7-yl]oxy}propanoic acid The title compound is obtained in a similar manner to Example 120.

$^1$H-NMR (DMSO-d$_6$) δ: 0.91 (3H, d, J=6.2 Hz), 1.55 (3H, d, J=6.7 Hz), 2.50–2.55 (1H, m), 2.77–2.85 (2H, m), 2.94–2.97 (1H, m), 3.04 (2H, m), 4.65–4.70 (1H, m), 4.79–4.82 (1H, m), 6.76 (1H, t, J=7.8 Hz), 6.91 (1H, s), 7.00 (1H, d, J=8.0 Hz), 7.30–7.38 (3H, m), 7.43 (1H, s), 7.48 (1H, d, J=7.7 Hz), 10.9 (s, 1H).

Reference Example 93

(1S)-2-Morpholin-4-yl-2-oxo-1-phenylethanol

The title compound is obtained in a similar manner to Reference Example 68.

$^1$H-NMR (CDCl$_3$) δ: 3.05–3.10 (1H, m), 3.14–3.19 (1H, m), 3.28–3.33 (1H, m), 3.45–3.50 (1H, m), 3.54–3.83 (4H, m), 4.70 (1H, brs), 5.19 (1H, s), 7.30–7.41 (5H, m).

Reference Example 94

(1S)-2-Morpholin-4-yl-2-oxo-1-phenylethyl 4-methylbenzenesulfonate

The title compound is obtained in a similar manner to Reference Example 69.

$^1$H-NMR (CDCl$_3$) δ: 2.43 (3H, s), 3.35–3.61 (8H, m), 6.12 (1H, s), 7.31 (2H, d, J=8.4 Hz), 7.34 (5H, s), 7.81 (2H, d, J=8.4 Hz).

Example 157

(2 R)-{[3-((2R)-2-{[(2R)-2-Hydroxy-2-pyridin-3-ylethyl]amino}propyl)-1H-indol-7-yl]oxy}(phenyl)acetic acid.2 trifluoroacetate The title compound is obtained in a similar manner to Example 119 and Example 120.

$^1$H-NMR (CD$_3$OD) δ: 1.33 (3H, d, J=6.5 Hz), 3.20 (1H, dd, J=14, 9.0 Hz), 3.25–3.31 (2H, m), 3.39 (1H, ddd, J=13, 4.1, 3.4 Hz), 3.62–3.70 (1H, m), 5.21 (1H, dd, J=9.8, 2.9 Hz), 5.93 (1H, s), 6.59 (1H, d, J=7.9 Hz), 6.87 (1H, t, J=7.9 Hz), 7.19–7.21 (1H, m), 7.21 (1H, s), 7.33–7.45 (3H, m), 7.64–7.66 (2H, m), 7.93 (1H, dd, J=7.4, 6.0 Hz), 8.43 (1H, d, J=7.9 Hz), 8.76 (1H, d, J=4.2 Hz), 8.84 (1H, s).

Reference Example 95

(2S)-1-Morpholin-4-yl-1-oxo-3-phenylpropan-2-ol

The title compound is obtained in a similar manner to Reference Example 68.

$^1$H-NMR (CDCl$_3$). δ: 2.90 (1H, dd, J=14, 6.7 Hz), 2.96 (1H, dd, J=14, 6.7 Hz), 3.27–3.30 (2H, m), 3.51–3.68 (6H, m), 4.59 (1H, dd, J=14, 6.7 Hz), 7.21–7.33 (5H, m).

Reference Example 96

(1S)-1-Benzyl-2-morpholine-4-yl-2-oxoethyl 4-methylbenzenesulfonate

The title compound is obtained in a similar manner to Reference Example 69.

$^1$H-NMR (CDCl$_3$) δ: 2.43 (3H, s), 2.97–3.02 (1H, m), 3.07–3.13 (2H, m), 3.16–3.27 (2H, m), 3.30–3.43 (3H, m), 3.48–3.59 (2H, m), 5.26 (1H, dd, J=8.1, 6.9 Hz), 7.12–7.14 (2H, m), 7.24–7.29 (5H, m), 7.68 (2H, d, J=8.3 Hz).

Example 158

(1R)-2-{[(1R)-2-(7-{[(1R)-1-Benzyl-2-morpholin-4-yl-2-oxoethyl]oxy}-1H-indol-3-yl)-1-methylethyl]amino}-1-pyridin-3-ylethanol The title compound is obtained in a similar manner to Example 119.

$^1$H-NMR (CD$_3$OD) δ: 1.14 (3H, d, J=6.2 Hz), 2.75–2.92 (5H, m), 3.02–3.12 (1H, m), 3.24–3.56 (9H, m), 4.71 (1H, dd, J=8.1, 4.7 Hz), 5.43 (1H, t, J=7.0 Hz), 6.53 (1H, d, J=7.7 Hz), 6.88 (1H, dd, J=8.0, 7.7 Hz), 7.02 (1H, s), 7.15 (1H, d, J=8.0 Hz), 7.23–7.27 (2H, m), 7.30–7.34 (2H, m), 7.36–7.38 (2H, m), 7.64 (1H, d, J=7.9 Hz), 7.88 (1H, s), 8.33 (1H, d, J=4.8 Hz), 8.44 (1H, d, J=1.8 Hz).

Reference Example 97

(1R)-1-Cyclohexyl-2-morpholin-4-yl-2-oxoethanol

The title compound is obtained in a similar manner to Reference Example 68.

$^1$H-NMR (CDCl$_3$) δ: 1.14–1.22 (5H, m), 1.41–1.44 (3H, m), 1.64–1.67 (1H, m), 1.78–1.81 (2H, m), 3.43–3.44 (2H, m), 3.63–3.74 (6H, m), 4.19 (1H, brs).

Reference Example 98

(1R)-1-Cyclohexyl-2-morpholin-4-yl-2-oxoethyl 4-methylbenzene-sulfonate

The title compound is obtained in a similar manner to Reference Example 69.

$^1$H-NMR (CDCl$_3$) δ: 0.90–1.27 (5H, m), 1.49–1.91 (6H, m), 2.45 (3H, s), 3.43–3.70 (8H, m), 4.79 (1H, d, J=8.7 Hz), 7.34 (2H, d, J=8.2 Hz), 7.80 (2H, d, J=8.2 Hz).

Example 159

(1R)-2-{[(1R)-2-(7-{[(1S)-1-Cyclohexyl-2-morpholin-4-yl-2-oxoethyl]oxy}-1H-indol-3-yl)-1-methylethyl]amino}-1-pyridin-3-ylethanol The title compound is obtained in a similar manner to Example 119.

$^1$H-NMR (CDCl$_3$) δ: 1.17 (3H, d, J=6.1 Hz), 1.10–1.31 (6H, m), 1.71–1.74 (2H, m), 1.81–1.84 (2H, m), 1.97–2.05 (1H, m), 2.14–2.21 (1H, m), 2.70–2.75 (1H, m), 2.87 (1H, d, J=6.2 Hz), 2.93 (1H, dd, J=12, 2.9 Hz), 3.11–3.14 (1H, m), 3.35 (2H, m), 3.51–3.70 (6H, m), 4.63 (1H, d, J=6.9 Hz), 4.68 (1H, d, J=8.0 Hz), 6.66 (1H, d, J=7.7 Hz), 6.98 (1H, t, J=7.8 Hz), 7.03 (1H, s), 7.22 (1H, d, J=8.2 Hz), 7.23 (1H, d, J=7.4 Hz), 7.66 (1H, d, J=7.7 Hz), 8.49 (1H, d, J=3.9 Hz), 8.52 (1H, s), 8.63 (1H, brs).

Example 160

(2S)-Cyclohexyl{[3-((2R)-2-{[(2R)-2-hydroxy-2-pyridin-3-ylethyl]amino}-propyl)-1H-indol-7-yl]oxy}acetic acid.2 trifluoroacetate The title compound is obtained in a similar manner to Example 120.

$^1$H-NMR (CD$_3$OD) δ: 1.33 (3H, d, J=6.5 Hz), 1.29–1.49 (6H, m), 1.71–1.74 (1H, m), 1.83 (3H, m), 1.95–2.05 (2H, m), 3.01 (1H, dd, J=14, 9.0 Hz), 3.25–3.32 (1H, m), 3.37 (1H, dd, J=13, 3.3 Hz), 3.66–3.68 (1H, m), 4.60 (1H, d, J=5.4 Hz), 5.16 (1H, dd, J=9.9, 3.1 Hz), 6.53 (1H, d, J=7.7 Hz), 6.94 (1H, t, J=7.9 Hz), 7.18 (1H, s), 7.21 (1H, d, J=7.8 Hz), 7.83 (1H, dd, J=7.9, 5.5 Hz), 8.29 (1H, d, J=8.1 Hz), 8.71 (1H, d, J=4.4 Hz), 8.78 (1H, brs).

Reference Example 99

(2R)-1-Morpholin-4-yl-1-oxobutan-2-ol

The title compound is obtained in a similar manner to Reference Example 68.

$^1$H-NMR (CDCl$_3$) δ: 1.00 (3H, t, J=7.4 Hz), 1.46–1.56 (1H, m), 1.65–1.73 (1H, m), 3.41–3.43 (2H, m), 3.63–3.74 (6H, m), 4.28–4.32 (1H, m).

Reference Example 100

(1R)-1-(Morpholin-4-ylcarbonyl)propyl 4-methylbenzenesulfonate

The title compound is obtained in a similar manner to Reference Example 69.

$^1$H-NMR (CDCl$_3$) δ: 0.93 (3H, t, J=7.4 Hz), 1.81–1.88 (2H, m), 2.45 (3H, s), 3.43–3.64 (8H, m), 5.00 (1H, t, J=6.7 Hz), 7.35 (2H, d, J=8.0 Hz), 7.81 (2H, d, J=8.3 Hz).

Example 161

(1R)-2-{[(1R)-1-Methyl-2-(7-{[(1S)-1-(morpholin-4-ylcarbonyl)propyl]oxy}-1H-indol-3-yl)ethyl]amino}-1-pyridin-3-ylethanol The title compound is obtained in a similar manner to Example 119.

$^1$H-NMR (CDCl$_3$) δ: 1.14–1.18 (6H, m), 2.02–2.07 (2H, m), 2.65 (1H, dd, J=9.4, 12.2 Hz), 2.81–2.92 (2H, m), 3.04–3.07 (1H, m), 3.39–3.49 (2H, m), 3.57–3.63 (6H, m), 4.55 (1H, dd, J=3.5, 9.3 Hz), 4.88 (1H, dd, J=5.8, 7.6 Hz), 6.65 (1H, d, J=7.7 Hz), 7.00 (1H, dd, J=7.8, 7.9 Hz), 7.03 (1H, d, J=2.0 Hz), 7.23–7.26 (2H, m), 7.66–7.68 (1H, m), 8.50 (1H, dd, J=1.6, 4.8 Hz), 8.54 (1H, d, J=2.0 Hz), 8.58 (1H, brs).

Example 162

(2S)-2-{[3-((2R)-2-{[(2R)-2-Hydroxy-2-pyridin-3-ylethyl]amino}propyl)-1H-indol-7-yl]oxy}butanoic acid.2 trifluoroacetate The title compound is obtained in a similar manner to Example 120.

$^1$H-NMR (CD$_3$OD) δ: 1.13 (3H, t, J=7.5 Hz), 1.32 (3H, d, J=6.5 Hz), 2.01–2.13 (2H, m), 3.00 (1H, dd, J=9.1, 14.3 Hz), 3.25–3.32 (2H, m), 3.63–3.68 (1H, m), 4.80 (1H, dd, J=5.2, 6.7 Hz), 5.26 (1H, dd, J=3.0, 9.7 Hz), 6.55 (1H, d, J=7.7 Hz), 6.94 (1H, dd, J=7.9, 7.9 Hz), 7.18 (1H, s), 7.22 (1H, d, J=7.8 Hz), 8.00 (1H, dd, J=5.7, 8.0 Hz), 8.51 (1H, d, J=8.2 Hz), 8.78 (1H, d, J=4.9 Hz), 8.88 (1H, brs).

Reference Example 101

(2R)-1-Morpholin-4-yl-1-oxopentan-2-ol

The title compound is obtained in a similar manner to Reference Example 68.
$^1$H-NMR (CDCl$_3$) δ: 0.95 (3H, t, J=7.2 Hz), 1.47–1.58 (4H, m), 3.40–3.42 (2H, m), 3.61–3.74 (6H, m), 4.31–4.36 (1H, m).

Reference Example 102

(1R)-1-(Morpholin-4-ylcarbonyl)butyl 4-methylbenzenesulfonate

The title compound is obtained in a similar manner to Reference Example 69.
$^1$H-NMR (CDCl$_3$) δ: 0.87 (3H, t, J=7.4 Hz), 1.24–1.33 (1H, m), 1.39–1.48 (1H, m), 1.69–1.87 (2H, m), 2.45 (3H, s), 3.41–3.64 (8H, m), 5.06 (1H, dd, J=5.3, 8.7 Hz), 7.35 (2H, d, J=8.4 Hz), 7.81 (2H, d, J=8.3 Hz).

Example 163

(1R)-2-{[(1R)-1-Methyl-2-(7-{[(1S)-1-(morpholin-4-ylcarbonyl)butyl]oxy}-1H-indol-3-yl)ethyl]amino}-1-pyridin-3-ylethanol The title compound is obtained in a similar manner to Example 119.
$^1$H-NMR (CDCl$_3$) δ: 1.03 (3H, t, J=7.4 Hz), 1.14 (3H, d, J=6.2 Hz), 1.58–1.72 (2H, m), 1.89–2.05 (2H, m), 2.65 (1H, dd, J=9.3, 12.2 Hz), 2.79–2.92 (3H, m), 3.03–3.08 (1H, m), 3.38–3.47 (2H, m), 3.58–3.62 (6H, m), 4.55 (1H, dd, J=3.5, 9.2 Hz), 4.95 (1H, dd, J=4.8, 8.6 Hz), 6.64 (1H, d, J=7.6 Hz), 6.99 (1H, dd, J=7.8, 7.9 Hz), 7.02 (1H, d, J=1.9 Hz), 7.23–7.26 (2H, m), 7.65–7.67 (1H, m), 8.50 (1H, dd, J=1.6, 4.8 Hz), 8.54 (2H, m).

Example 164

(2S)-2-{[3-((2R)-2-{[(2R)-2-Hydroxy-2-pyridin-3-ylethyl]amino}propyl)-1H-indol-7-yl]oxy}pentanoic acid.2 trifluoroacetate The title compound is obtained in a similar manner to Example 120.
$^1$H-NMR (CD$_3$OD) δ: 0.99 (3H, t, J=7.4 Hz), 1.32 (3H, d, J=6.5 Hz), 1.57–1.67 (2H, m), 1.98–2.05 (2H, m), 3.99 (1H, dd, J=9.0, 14.3 Hz), 3.25–3.32 (2H, m), 3.42 (1H, dd, J=3.2, 12.7 Hz), 3.63–3.69 (1H, m), 4.84 (1H, dd, J=5.3, 7.0 Hz), 5.25 (1H, dd, J=3.0, 9.7 Hz), 6.54 (1H, d, J=7.7 Hz), 6.94 (1H, dd, J=7.9, 7.9 Hz), 7.17 (1H, s), 7.21 (1H, d, J=7.9 Hz), 7.99 (1H, dd, J=5.7, 8.0 Hz), 8.50 (1H, d, J=8.2 Hz), 8.78 (1H, d, J=5.2 Hz), 8.87 (1H, brs).

Example 165

(1R)-2-{[2-(7-{[(1R)-1-Methyl-2-morpholin-4-yl-2-oxoethyl]oxy}-1H-indol-3-yl) ethyl]amino}-1-pyridin-3-ylethanol The title compound is obtained in a similar manner to Example 119.
$^1$H-NMR (CDCl$_3$) δ: 1.64 (3H, d, J=6.7 Hz), 2.67–2.72 (1H, m), 2.89–3.04 (5H, m), 3.42–3.66 (8H, m), 4.70 (1H, m), 5.13 (1H, q, J=6.7 Hz), 6.62 (1H, d, J=7.6 Hz), 6.97–7.01 (2H, m), 7.23–7.26 (2H, m), 7.68 (1H, d, J=7.8 Hz), 8.48 (1H, d, J=4.6 Hz), 8.55 (1H, s), 8.91 (1H, brs).

Example 166

(2R)-2-{[3-(2-{[(2R)-2-Hydroxy-2-pyridin-3-ylethyl]amino}ethyl)-1H-indol-7-yl]oxy}propanoic acid.2 trifluoroacetate The title compound is obtained in a similar manner to Example 120.
$^1$H-NMR (CD$_3$OD) δ: 1.67 (3H, d, J=6.8 Hz), 3.18–3.28 (3H, m), 3.35–3.41 (3H, m), 4.93–5.00 (1H, m), 5.23 (1H, dd, J=9.7, 2.7 Hz), 6.58 (1H, d, J=7.7 Hz), 6.95 (1H, dd, J=7.9, 7.7 Hz), 7.17 (1H, s), 7.72 (1H, d, J=7.9 Hz), 7.96 (1H, brs), 8.45 (1H, d, J=8.1 Hz), 8.77 (1H, brs), 8.85 (1H, brs).

Example 167

(1R)-2-{[2-(7-{[(1R)-2-Methyl-1-(morpholin-4-ylcarbonyl)propyl]oxy}-1H-indol-3-yl)ethyl]amino}-1-pyridin-3-ylethanol The title compound is obtained in a similar manner to Example 119.
$^1$H-NMR (CDCl$_3$) δ: 1.10 (3H, d, J=6.8 Hz), 1.19 (3H, d, J=6.8 Hz), 2.23–2.32 (1H, m), 2.68 (1H, dd, J=12.3, 9.3 Hz), 2.88–3.06 (5H, m), 3.33–3.36 (2H, m), 3.47–3.68 (6H, m), 4.62 (1H, d, J=7.8 Hz), 4.69 (1H, dd, J=9.3, 3.5 Hz), 6.66 (1H, d, J=7.7 Hz), 6.97–7.00 (2H, m), 7.23–7.26 (2H, m), 7.68 (1H, ddd, J=7.9, 2.0, 1.6 Hz), 8.48 (1H, dd, J=4.8, 1.6 Hz), 8.55 (1H, d, J=2.0 Hz), 8.78 (1H, brs).

Example 168

(2R)-2-{[3-(2-{[(2R)-2-Hydroxy-2-pyridin-3-ylethyl]amino}ethyl)-1H-indol-7-yl]oxy}-3-methylbutanoic acid.2 trifluoroacetate The title compound is obtained in a similar manner to Example 120.
$^1$H-NMR (CD$_3$OD) δ: 1.14 (3H, d, J=6.8 Hz), 1.18 (3H, d, J=6.8 Hz), 2.32–2.40 (1H, m), 3.18–3.27 (3H, m), 3.32–3.40 (3H, m), 4.60 (1H, d, J=5.1 Hz), 5.21–5.23 (1H, m), 6.53 (1H, d, J=7.7 Hz), 6.93 (1H, dd, J=7.9, 7.7 Hz), 7.18 (1H, s), 7.20 (1H, d, J=7.9 Hz), 7.96 (1H, brs), 8.44 (1H, brs), 8.77 (1H, brs), 8.85 (1H, brs).

Example 169

(1R)-2-{[2-(7-{[(1S)-1-Benzyl-2-morpholin-4-yl-2-oxoethyl]oxy}-1H-indol-3-yl)ethyl]amino}-1-pyridin-3-ylethanol The title compound is obtained in a similar manner to Example 119.
$^1$H-NMR (CDCl$_3$) δ: 2.68 (1H, dd, J=12.2, 9.3 Hz), 2.89–3.09 (6H, m), 3.28–3.36 (5H, m), 3.51–3.60 (4H, m), 4.70 (1H, dd, J=9.3, 3.4 Hz), 5.15 (1H, t, J=6.9 Hz), 6.56 (1H, d, J=7.6 Hz), 6.93–6.97 (2H, m), 7.22–7.36 (6H, m), 7.68 (1H, ddd, J=7.9, 2.1, 1.6 Hz), 8.49 (1H, dd, J=4.8, 1.6 Hz), 8.55 (1H, d, J=2.1 Hz), 8.60 (1H, brs).

Example 170

(2S)-2-{[3-(2-{[(2R)-2-Hydroxy-2-pyridin-3-yl-ethyl]amino}ethyl)-1H-indol-7-yl]oxy}-3-phenyl-propanoic acid.2 trifluoroacetate The title compound is obtained in a similar manner to Example 120.
$^1$H-NMR (CD30D) δ: 3.17–3.48 (8H, m), 5.06 (1H, dd, J=7.5, 4.6 Hz), 5.24 (1H, dd, J=9.8, 2.9 Hz), 6.55 (1H, d, J=7.9 Hz), 6.92 (1H, t, J=7.9 Hz), 7.17–7.27 (5H, m), 7.34–7.36 (2H, m), 7.99–8.02 (1H, m), 8.50 (1H, d, J=7.8 Hz), 8.79 (1H, brs), 8.87 (1H, brs).

Example 171

(1R)-2-{[2-(7-{[(1S)-2-Morpholin-4-yl-2-oxo-1-phenylethyl]oxy}-1H-indol-3-yl)ethyl]amino}-1-pyridin-3-ylethanol The title compound is obtained in a similar manner to Example 119.
$^1$H-NMR (CDCl$_3$) δ: 2.68 (1H, dd, J=12.3, 9.3 Hz), 2.88–3.05 (5H, m), 3.19–3.22 (1H, m), 3.33–3.36 (1H, m), 3.49–3.63 (6H, m), 4.70 (1H, dd, J=9.3, 3.5 Hz), 6.02 (1H, s), 6.74 (1H, dd, J=7.7, 1.6 Hz), 6.98 (1H, dd, J=7.8, 7.7 Hz), 6.99 (1H, d, J=1.6 Hz), 7.24 (1H, dd, J=7.9, 4.8 Hz), 7.26 (1H, d, J=7.8 Hz), 7.36–7.45 (3H, m), 7.55–7.57 (2H, m), 7.68 (1H, ddd, J=7.9, 1.9, 1.6 Hz), 8.48 (1H, dd, J=4.8, 1.6 Hz), 8.55 (1H, d, J=1.9 Hz), 8.94 (1H, brs).

Example 172

(2S)-{[3-(2-{[(2R)-2-Hydroxy-2-pyridin-3-ylethyl]amino}ethyl)-1H-indol-7-yl]oxy}(phenyl)acetic acid.2 trifluoroacetate The title compound is obtained in a similar manner to Example 120.
$^1$H-NMR (CD$_3$OD) δ: 3.17–3.27 (3H, m), 3.37–3.40 (3H, m), 5.23 (1H, d, J=9.7 Hz), 5.92 (1H, s), 6.58 (1H, d, J=7.8 Hz), 6.88 (1H, t, J=7.8 Hz), 7.18–7.20 (2H, m), 7.31–7.40 (3H, m), 7.63–7.64 (2H, m), 7.98 (1H, brs), 8.47–8.50 (1H, m), 8.78 (1H, brs), 8.86 (1H, brs).

Example 173

(1R)-2-{[2-(7-{[(1S)-1-(Morpholin-4-ylcarbonyl)propyl]oxy}-1H-indol-3-yl)ethyl]amino}-1-pyridin-3-ylethanol The title compound is obtained in a similar manner to Example 119.
$^1$H-NMR (CD$_3$OD) δ: 1.14 (3H, t, J=7.4 Hz), 2.00–2.08 (2H, m), 2.83 (2H, d, J=6.5 Hz), 2.94–3.03 (4H, m), 3.31–3.35 (1H, m), 3.47–3.61 (5H, m), 3.68–3.74 (1H, m), 3.77–3.83 (1H, m), 4.81 (1H, t, J=6.5 Hz), 5.07 (1H, t, J=6.1 Hz), 6.55 (1H, d, J=7.7 Hz), 6.90 (1H, dd, J=8.0, 7.7 Hz), 7.06 (1H, s), 7.19 (1H, d, J=8.0 Hz), 7.36 (1H, dd, J=7.8, 4.9 Hz), 7.76 (1H, ddd, J=7.8, 2.1, 1.6 Hz), 8.41 (1H, dd, J=4.9, 1.6 Hz), 8.51 (1H, d, J=2.1 Hz).

Example 174

(1R)-2-{[2-(7-{[(1S)-1-(Morpholin-4-ylcarbonyl)butyl]oxy}-1H-indol-3-yl)-ethyl]amino}-1-pyridin-3-ylethanol The title compound is obtained in a similar manner to Example 119.
$^1$H-NMR (CDCl$_3$) δ: 1.02 (3H, t, J=7.4 Hz), 1.52–1.58 (1H, m), 1.65–1.70 (1H, m), 1.87–1.94 (1H, m), 1.98–2.08 (1H, m), 2.68 (1H, dd, J=12.3, 9.4 Hz), 2.92–3.06 (5H, m), 3.37–3.49 (2H, m), 3.58–3.62 (6H, m), 4.70 (1H, dd, J=9.4, 3.5 Hz), 4.94 (1H, dd, J=8.6, 4.8 Hz), 6.64 (1H, d, J=7.4 Hz), 6.97–7.02 (2H, m), 7.23–7.27 (2H, m), 7.69 (1H, ddd, J=7.9, 2.1, 1.6 Hz), 8.51 (1H, dd, J=4.8, 1.6 Hz), 8.56 (1H, d, J=2.1 Hz), 8.56 (1H, brs).

Example 175

6-(2-{[(2R)-2-Hydroxy-2-pyridin-3-ylethyl]amino}ethyl)-2,2-dimethyl-[1,4]oxazino[2,3,4-hi]indol-3(2H)-one-2 hydrochloride The title compound is obtained in a similar manner to Example 131.
$^1$H-NMR (CD$_3$OD) δ: 1.65 (6H, s), 3.23–3.36 (3H, m), 3.47–3.53 (3H, m), 6.38 (1H, dd, J=9.9, 2.8 Hz), 6.84 (1H, d, J=7.8 Hz), 7.20 (1H, t, J=7.8 Hz), 7.30 (1H, d, J=7.8 Hz), 7.63 (1H, s), 8.14 (1H, dd, J=8.1, 5.8 Hz), 8.75 (1H, d, J=8.1 Hz), 8.86 (1H, d, J=5.8 Hz), 9.01 (1H, s).

Example 176

(2S)-2-{[3-(2-{[(2R)-2-Hydroxy-2-pyridin-3-yl-ethyl]amino}ethyl)-1H-indol-7-yl]oxy}butanoic acid.2 trifluoroacetate The title compound is obtained in a similar manner to Example 120.
$^1$H-NMR (CD$_3$OD) δ: 1.13 (3H, t, J=7.4 Hz), 2.02–2.11 (2H, m), 3.18–3.24 (3H, m), 3.30–3.35 (1H, m), 3.38–3.42 (2H, m), 4.81 (1H, dd, J=6.7, 5.2 Hz), 5.11 (1H, dd, J=10, 3.1 Hz), 6.56 (1H, d, J=7.7 Hz), 6.95 (1H, t, J=7.9 Hz), 7.17 (1H, s), 7.21 (1H, d, J=7.9Hz), 7.72 (1H, dd, J=7.7, 5.3 Hz), 8.15 (1H, d, J=8.0 Hz), 8.64 (1H, d, J=4.7 Hz), 8.70 (1H, brs).

Example 177

(2S)-2-{[3-(2-{[(2R)-2-Hydroxy-2-pyridin-3-yl-ethyl]amino}ethyl)-1H-indol-7-yl]oxy}pentanoic acid.2 trifluoroacetate The title compound is obtained in a similar manner to Example 120.
$^1$H-NMR (CD$_3$OD) δ: 1.00 (3H, t, J=7.4 Hz), 1.59–1.65 (2H, m), 1.99–2.05 (2H, m), 3.18–3.25 (3H, m), 3.32–3.42 (3H, m), 4.83–4.89 (1H, m), 5.14 (1H, dd, J=10, 3.1 Hz), 6.55 (1H, d, J=7.9 Hz), 6.95 (1H, t, J=7.9 Hz), 7.17 (1H, s), 7.21 (1H, d, J=8.0 Hz), 7.78 (1H, dd, J=7.7, 5.5 Hz), 8.21 (1H, d, J=8.1 Hz), 8.67 (1H, d, J=5.1 Hz), 8.73 (1H, brs).

Example 178

2-{[3-(2-{[(2R)-2-Hydroxy-2-pyridin-3-ylethyl]amino}ethyl)-1H-indol-7-yl]oxy}-2-methylpropanoic acid.2 trifluoroacetate The title compound is obtained in a similar manner to Example 120.
$^1$H-NMR (CD$_3$OD) δ: 1.62 (6H, s), 3.17–3.25 (3H, m), 3.32–3.41 (3H, m), 5.09 (1H, dd, J=10, 3.0 Hz), 6.65 (1H, d, J=7.7 Hz), 6.92 (1H, t, J=7.9 Hz), 7.14 (1H, s), 7.26 (1H, d, J=7.9 Hz), 7.65–7.68 (1H, m), 8.10 (1H, d, J=7.3 Hz), 8.61 (1H, d, J=4.1 Hz), 8.68 (1H, brs).

Example 179

(1R)-2-[(2-{7-[(1S)-1-Cyclohexyl-2-morpholin-4-yl-2-oxoethoxy]-1H-indol-3-yl}ethyl)amino]-1-pyridin-3-ylethanol The title compound is obtained in a similar manner to Example 119.

$^1$H-NMR (CDCl$_3$) δ: 1.17–1.34 (5H, m), 1.71–1.74 (2H, m), 1.81–1.84 (2H, m), 1.97–1.99 (1H, m), 2.14–2.17 (1H, m), 2.66 (1H, dd, J=9.4, 12.3 Hz), 2.92–3.05 (5H, m), 3.34 (2H, m), 3.49–3.67 (6H, m), 4.65–4.69 (2H, m), 6.68 (1H, d, J=7.6 Hz), 6.99 (1H, dd, J=7.8, 7.9 Hz), 7.01 (2H, d, J=1.9 Hz), 7.24–7.27 (2H, m), 7.68–7.71 (1H, m), 8.48 (1H, brs), 8.51 (1H, dd, J=1.6, 4.8 Hz), 8.57 (1H, d, J=2.1 Hz).

Example 180

(2S)-Cyclohexyl{[3-(2-{[(2R)-2-hydroxy-2-pyridin-3-ylethyl]amino}ethyl)-1H-indol-7-yl]oxy}acetic acid The title compound is obtained in a similar manner to Example 120.

$^1$H-NMR (CD$_3$OD) δ: 1.23–1.41 (5H, m), 1.69–1.71 (1H, m), 1.81 (3H, m), 1.95–1.98 (1H, m), 2.07–2.09 (1H, m), 2.93–3.14 (6H, m), 4.35 (1H, d, J=6.3 Hz), 4.99 (1H, dd, J=3.2, 10.3 Hz), 6.58 (1H, d, J=7.7 Hz), 6.79 (1H, dd, J=7.8, 7.9 Hz), 6.98 (1H, s), 7.01 (1H, d, J=7.7 Hz), 7.45 (1H, dd, J=4.8, 7.9 Hz), 7.84–7.87 (1H, m), 8.49 (1H, dd, J=1.5, 4.9 Hz), 8.56 (1H, d, J=2.0 Hz).

Example 181

Ethyl 1-{[3-(2-{[(2R)-2-hydroxy-2-pyridin-3-yl-ethyl]amino}ethyl)-1H-indol-7-yl]oxy}cyclobutanecarboxylate The title compound is obtained in a similar manner to Example 119.

$^1$H-NMR (CD$_3$OD) δ: 1.13 (3H, t, J=7.1 Hz), 1.99–2.07 (2H, m), 2.51–2.59 (2H, m), 2.75–2.82 (2H, m), 3.17–3.26 (3H, m), 3.31–3.48 (3H, m), 4.17 (2H, q, J=7.1 Hz), 5.13 (1H, dd, J=10, 3.1 Hz), 6.15 (1H, d, J=7.7 Hz), 6.86 (1H, t, J=7.9 Hz), 7.17 (1H, s), 7.19 (1H, d, J=7.9 Hz), 7.74 (1H, dd, J=7.9, 5.3 Hz), 8.20 (1H, d, J=7.9 Hz), 8.66 (1H, d, J=4.7 Hz), 8.74 (1H, brs).

Example 182

1-{[3-(2-{[(2R)-2-Hydroxy-2-pyridin-3-ylethyl]amino}ethyl)-1H-indol-7-yl]oxy}cyclobutanecarboxylic acid The title compound is obtained in a similar manner to Example 120.

$^1$H-NMR (CD$_3$OD) δ: 1.97–2.13 (2H, m), 2.50–2.58 (2H, m), 2.76–2.83 (2H, m), 3.17–3.25 (3H, m), 3.31–3.41 (3H, m), 5.14 (1H, dd, J=10, 3.1 Hz), 6.21 (1H, d, J=7.7 Hz), 6.87 (1H, t, J=7.9 Hz), 7.17. (1H, s), 7.18 (1H, d, J=8.0 Hz), 7.78 (1H, dd, J=7.9, 5.4 Hz), 8.23 (1H, d, J=8.0 Hz), 8.67 (1H, d, J=4.8 Hz), 8.74 (1H, brs).

Reference Example 103

1-[7-(Benzyloxy)-1H-indol-3-yl]-2-methylpropan-2-amine

The title compound is obtained in a similar manner to Reference Example 4.

$^1$H-NMR (CDCl$_3$) δ: 1.17 (6H, s), 2.80 (2H, s), 5.21 (2H, s), 6.72 (1H, d, J=7.6 Hz), 7.02 (1H, dd, J=8.2, 7.6 Hz), 7.02 (1H, d, J=2.7 Hz), 7.25 (1H, d, J=8.2 Hz), 7.34–7.43-(3H, m), 7.48–7.50 (2H, m), 8.37 (1H, brs).

Reference Example 104 tert-Butyl {2-[7-(benzyloxy)-1H-indol-3-yl]-1,1-dimethylethyl}carbamate

The title compound is obtained in a similar manner to Reference Example 88.

$^1$H-NMR (CDCl$_3$) δ: 1.32 (6H, s), 1.46 (9H, s), 3.09 (2H, s), 4.43 (1H, s), 5.20 (2H, s), 6.71 (1H, d, J=7.6 Hz), 6.97 (1H, d, J=2.3 Hz), 7.01 (1H, dd, J=8.1, 7.6 Hz), 7.25 (1H, d, J=8.1 Hz), 7.34 (3H, m), 7.47–7.49 (2H, m), 8.32 (1H, brs).

Reference Example 105 tert-Butyl (1,1-dimethyl-2-{7-[(1S)-1-methyl-2-morpholin-4-yl-2-oxo-ethoxy]-1H-indol-3-yl}ethyl)carbamate The title compound is obtained in a similar manner to Reference Example 89.

$^1$H-NMR (CDCl$_3$) δ: 1.31 (3H, s), 1.32 (3H, s), 1.47 (9H, s), 1.66 (3H, d, J=6.7 Hz), 3.09 (2H, s), 3.40–3.66 (8H, m), 4.41 (1H, s), 5.13 (1H, q, J=6.7 Hz), 6.62 (1H, d, J=7.7 Hz), 6.98 (1H, dd, J=7.9, 7.7 Hz), 6.99 (1H, d, J=2.5 Hz), 7.27 (1H, d, J=7.9 Hz), 8.50 (1H, brs).

Reference Example 106

2-Methyl-1-{7-[(1S)-1-methyl-2-morpholin-4-yl-2-oxoethoxy]-1H-indol-3-yl}propan-2-amine To a solution of tert-butyl (1,1-dimethyl-2-{7-[(1S)-1-methyl-2-morpholin-4-yl-2-oxoethoxy]-1H-indol-3-yl}ethyl)carbamate (166 mg, 0.373 mmol) in methylene chloride (2 mL) is added a 4N hydrogen chloride solution in dioxane (0.5 mL), and the mixture is stirred at room temperature for 3 hours. The reaction solution is poured into a saturated aqueous sodium hydrogen carbonate solution, and the mixture is extracted with chloroform. The organic layer is dried over anhydrous magnesium sulfate, and the solvent is evaporated. The obtained crude product is purified by silica gel column chromatography (a saturated ammonia solution in chloroform ) a saturated ammonia solution in chloroform-methanol=50:1) to give the title compound (68.4 mg, yield: 53%).

$^1$H-NMR (CDCl$_3$) δ: 1.17 (6H, s), 1.67 (3H, d, J=6.7Hz), 2.76 (2H, s), 3.40–3.70 (8H, m), 5.14 (1H, q, J=6.7Hz), 6.62 (1H, d, J=7.7Hz), 6.99 (1H, dd, J=8.1, 7.7 Hz), 7.04 (1H, d, J=2.1 Hz), 7.27 (1H, d, J=8.1 Hz), 8.61 (1H, brs).

Example 183

(2S)-2-{[3-(2-{[(2R)-2-Hydroxy-2-pyridin-3-yl-ethyl]amino}-2-methyl-propyl)-1H-indol-7-yl]oxy}propanoic acid.2 trifluoroacetate To a solution of 2-methyl-1-{7-[(1S)-1-methyl-2-morpholin-4-yl-2-oxoethoxy]-1H-indol-3-yl}propan-2-amine (68.4 mg, 0.198 mmol) in ethanol (4 mL)- water (0.4 mL) is added (R)-(pyridin-3-yl)oxirane (36.0 mg, 0.297 mmol), and the mixture is refluxed for 8 hours. To the reaction solution is added (R)-(pyridin-3-yl)oxirane (144.0 mg, 1.19 mmol) in 4 portions, and the mixture is heated with stirring at 100 to 110° C. in a sealed tube for 18 hours. After the reaction is completed, the solvent is evaporated under reduced pressure, and the obtained residue is purified by silica gel column chromatography (chloroform/methanol=20/1→10/1→chloroform/a saturated ammonia methanol=10/1) to give (1R)-2-[(1,1-dimethyl-2-{7-[(1S)-1-methyl-2-morpholin-4-yl-2-oxoethoxy]-1H-indol-3-yl}ethyl)amino]-1-pyridin-3-ylethanol (23.1 mg).

To a solution of (1R)-2-[(1,1-dimethyl-2-{7-[(1S)-1-methyl-2-morpholin-4-yl-2-oxoethoxy]-1H-indol-3-yl}ethyl)amino]-1-pyridin-3-yl-ethanol (23.1 mg, 0.0495 mmol) in methanol (0.3 mL)-tetrahydrofuran (0.3 mL) is added a 2M aqueous lithium hydroxide solution (0.3 mL), and the mixture is stirred at room temperature overnight. After the reaction is completed, the mixture is neutralized with a 1N hydrochloric acid solution, and the solvent is evaporated under reduced pressure. The obtained residue is purified by preparative high performance liquid chromatography (0.035% trifluoroacetic acid/acetonitrile-0.05% trifluoroacetic acid/water) to give the title compound (12.6 mg, yield: 10%).

$^1$H-NMR (CD$_3$OD) δ: 1.40 (s, 3H), 1.41 (s, 3H), 1.68 (s, 3H), 3.13–3.17 (m, 2H), 3.21–3.31 (m, 1H), 3.45 (dd, 1H, J=13, 2.7Hz), 4.98–5.01 (m, 1H), 5.21 (dd, 1H, J=10, 2.5 Hz), 6.58 (d, 1H, J=7.8 Hz), 6.97 (dd, 1H, J=8.0, 7.8 Hz), 7.22 (s, 1H), 7.24 (d, 1H, J=8.0 Hz), 8.03 (dd, 1H, J=6.9, 6.4 Hz), 8.50 (d, 1H, J=8.1 Hz), 8.81 (m, 1H), 8.88 (brs, 1H).

Reference Example 107

4-{[tert-Butyl(dimethyl)silyl]oxy}-1H-indole

To a suspension of 4-hydroxyindole (5.65 g, 42.4 mmol) in chloroform (200 mL) are added imidazole (4.33 g, 63.6 mmol) and tert-butylchlorodimethylsilane (7.03 g, 46.6 mmol), and the mixture is stirred at room temperature for 2.5 hours. The reaction mixture is washed with a mixture of a saturated brine and water (1:1, 100 mL), and the organic layer is dried over anhydrous potassium carbonate, filtered, and the filtrate is concentrated to about 50 mL under reduced pressure. The resultant is purified by silica gel column (300 g, ethyl acetate:hexane=1:5→1:1) to give the title compound as a white solid (3.90 g, yield: 37%), and the starting compound (2.62g, recovery rate: 46%).

$^1$H-NMR (CDCl$_3$) δ: 0.24 (6H, s), 1.06 (9H, s), 6.52 (1H, dd, J=6.0, 2.0 Hz), 6.58–6.59 (1H, m), 7.00–7.03 (2H, m), 7.09 (1H, dd, J=3.2, 2.4 Hz), 8.10 (1H, brs).

Reference Example 108

(4-{[tert-Butyl(dimethyl)silyl]oxy}-1H-indol-1-yl)acetonitrile

Under nitrogen atmosphere, to a suspension of sodium hydride (60% dispersion in mineral oil, 750 mg, 18.8 mmol) in dimethyl-formamide (30 mL) is added dropwise a solution of 4-{[tert-butyl-(dimethyl)silyl]oxy}-1H-indole (2.32 g, 9.38 mmol) in dimethylformamide (10 mL)-with stirring under ice-cooling, and the mixture is stirred at the same temperature for 15 minutes. To the mixture is added dropwise acetonitrile bromide (1.96 mL, 28.1 mmol), and the mixture is stirred at room temperature for 15 hours. The reaction mixture is diluted with a mixture of a saturated brine and water (1:1, 400 mL), and the mixture is extracted with ethyl acetate (2×100 mL). The combined organic layer is washed with a mixture of a saturated brine and water (1:1, 100 mL), dried over anhydrous potassium carbonate, and filtered. The filtrate is concentrated under reduced pressure, and the obtained residue is purified by silica gel column (ethyl acetate:hexane=10:1→5:1) to give the title compound as a pale brown solid (803 mg, yield: 39%).

$^1$H-NMR (CDCl$_3$) δ: 0.23 (6H, s), 1.06 (9H, s), 4.98 (2H, s), 6.60 (1H, dd, J=8, 0.8 Hz), 6.64 (1H, dd, J=3.2, 0.8 Hz), 6.98 (1H, d, J=8.4 Hz), 7.00 (1H, d, J=3.2 Hz), 7.16 (1H, dd, J=8.4, 8.0 Hz).

Reference Example 109

2-(4-{[tert-Butyl(dimethyl)silyl]oxy}-1H-indol-1-yl)ethylamine

To a solution of (4-{[tert-butyl(dimethyl)silyl]oxy}-1H-indol-1-yl)acetonitrile (259 mg, 0.904 mmol) in tetrahydrofuran (20 mL) are added a 2.0M hydrochloric acid in ethanol (1 mL) and active Raney-nickel (manufactured by Kawaken Fine Chemicals Co., Ltd., about 1 mL), and the mixture is vigorously stirred under hydrogen atmosphere under pressure (0.5 Pa) at room temperature for 1 hour. To the mixture is further added active Raney-nickel (about 1.5 mL), and the mixture is vigorously stirred under the same conditions for 4 hours. The catalyst is removed by filtration through celite, and the filtrate is concentrated under reduced pressure. The obtained residue is purified by silica gel column (ammonia-chloroform:methanol=100:1→50:1→30:1) to give the title compound as pale brown oil (207 mg, yield: 79%).

$^1$H-NMR (CDCl$_3$) δ: 0.24 (6H, s), 1.06 (9H, s), 3.12 (2H, t, J=6.0 Hz), 4.17 (2H, t, J=6.0 Hz), 6.51 (1H, d, J=7.2 Hz), 6.54 (1H, d, J=3.2 Hz), 6.96–7.07 (3H, m).

Reference Example 110

(2R)-N-[2-(4-{[tert-Butyl(dimethyl)silyl]oxy}-1H-indol-1-yl)ethyl]-2-hydroxy-2-pyridin-3-ylacetamide The title compound is obtained in a similar manner to Reference Example 61.

$^1$H-NMR (CDCl$_3$) δ: 0.24 (6H, s), 1.06 (9H, s), 3.59–3.73 (3H, m), 4.22–4.25 (2H, m), 6.40 (1H, t, J=6 Hz), 6.50–6.53 (2H, m), 6.80 (1H, d, J=3.6 Hz), 6.91 (1H, d, J=8.0 Hz), 7.04 (1H, t, J=8.0 Hz), 7.25 (1H, ddd, J=0.8, 4.8, 8.0 Hz), 7.60 (1H, dt, J=7.6, 2.0 Hz), 8.51–8.52 (2H, m).

Reference Example 111 tert-Butyl [2-(4-{[tert-butyl(dimethyl)silyl]oxy}-1H-indol-1-yl)ethyl][(2R)-2-hydroxy-2-pyridin-3-yl-ethyl]carbamate To a solution of (2R)-N-[2-(4-{[tert-butyl(dimethyl)silyl]oxy}-1H-indol-1-yl)ethyl]-2-hydroxy-2-pyridin-3-ylacetamide (498 mg, 1.17 mmol) in tetrahydrofuran (5 mL) is added a 2.0 M solution of borane dimethylsulfide complex in tetrahydrofuran (1.76 mL, 3.51 mmol), and the mixture is refluxed for 3.5 hours. To the reaction solution is added piperidine (1.0 mL), and the mixture is further refluxed for 2 hours. The reaction mixture is separated into a mixture of a saturated brine and water (1:1, 30 mL) and chloroform (30 mL). The aqueous layer is extracted with ethyl acetate (2×30 mL), and the combined organic layer is washed with a mixture of a saturated brine and water (1:1, 30 mL), dried over anhydrous potassium carbonate, and filtered. The filtrate is concentrated under reduced pressure, and the obtained residue is subjected to azeotropic distillation with toluene to remove piperidine. To a solution of the yellow residue thus obtained in tetrahydrofuran (5.0 mL) is added di-tert-butyl bicarbonate (296 μL, 1.29 mmoL), and the mixture is stirred at room temperature for 3.5 hours. The reaction mixture is concentrated under reduced pressure, and the obtained orange residue is purified by silica gel column (ethyl acetate:hexane 1:1) to give the title compound as oil (316 mg, yield: 53%).

$^1$H-NMR (CDCl$_3$) δ: 0.18 (6H, s), 1.02 (9H, s), 1.40 (9H, s), 2.55–2.64 (1H, m), 3.06–3.16 (1H, m), 3.32–3.52 (2H, m), 4.09–4.34 (2H, m), 4.72 (1H, m), 6.85–7.00 (2H, m), 7.05 (1H, dd, J=8.0, 7.6Hz), 7.21–7.24 (1H, m), 7.42–7.55 (1H, m), 8.35–8.42 (1H, m), 8.46–8.47 (1H, m).

Reference Example 112 tert-Butyl [2-(4-hydroxy-1H-indol-1-yl)ethyl][(2R)-2-hydroxy-2-pyridin-3-ylethyl]carbamate To a solution of tert-butyl [2-(4-{[tert-butyl(dimethyl)silyl]oxy}-1H-indol-1-yl)ethyl][(2R)-2-hydroxy-2-pyridin-3-ylethyl]carbamate (316 mg, 0.618 mmol) in tetrahydrofuran (5 mL) is added a 1.0M solution of tetrabutylammonium fluoride in tetrahydrofuran (927 μL, 1.5 equivalent), and the mixture is stirred at room temperature for 3 hours. Further, to the mixture is added a 1.0 M solution of tetrabutylammonium fluoride in tetrahydrofuran (927 μL, 1.5 equivalent), and the mixture is stirred for 15 hours. The reaction mixture is concentrated under reduced pressure, and the obtained brown residue is purified by silica gel column (ammonia-chloroform:methanol=100:1→50:1→20:1) to give the title compound as oil (239 mg, yield: 97%).

LC/MS M+1:398, retention time: 2.89 min.
Conditions for analysis:
Body: API 150EX (Applied Biosystems)
Method for ionization: ESI
Column: CombiScreen Hydrosphere C18 S-5 μm (4.6×50 mm) (YMC)
Mobile phase: Solution A: 0.05% aqueous trifluoroacetic acid
Solution B: 0.035% trifluoroacetic acid in acetonitrile
Flow rate: 3.5 mL/min.
Conditions for HPLC: 0.0 min→0.5 min: 90% Solution A constant
0.5 min→4.2 min: 90% Solution A→1%
4.2 min→4.4 min: 1% Solution A constant Example 184

(1R)-2-[(2-{4-[(1S)-1-Methyl-2-morpholin-4-yl-2-oxoethoxy]-1H-indol-1-yl}ethyl)amino]-1-pyridin-3-ylethanol The title compound is obtained in a similar manner to Example 119.

$^1$H-NMR (CDCl$_3$) δ: 1.71 (3H, d, J=6.8 Hz), 2.64 (1H, dd, J=12, 9.2 Hz), 2.88 (1H, dd, J=12, 3.6 Hz), 3.04–3.17 (2H, m), 3.49–3.68 (8H, m), 4.26 (2H, t, J=6.0 Hz), 4.63 (1H, dd, J=9.2, 3.6 Hz), 5.14 (1H, q, J=6.8 Hz), 6.55 (1H, d, J=8.0 Hz), 6.59 (1H, d, J=3.2 Hz), 7.02 (1H, d, J=8.0 Hz), 7.04 (1H, d, J=3.2 Hz), 7.11 (1H, t, J=8.0 Hz), 7.23–7.26 (1H, m), 7.64 (1H, ddd, J=7.6, 2.0, 1.6 Hz), 8.51 (1H, dd, J=4.8, 1.2 Hz), 8.53 (1H, d, J=2.4 Hz).

Example 185

(2S)-2-{[1-(2-{[(2R)-2-Hydroxy-2-pyridin-3-ylethyl]amino}ethyl)-1H-indol-4-yl]oxy}propanoic acid The title compound is obtained in a similar manner to Example 120.

$^1$H-NMR (DMSO-d$_6$) δ: 1.57 (3H, d, J=6.8 Hz), 3.04–3.35 (4H, m), 4.57 (2H, t, J=6.8 Hz), 4.89 (1H, q, J=6.8 Hz), 5.04 (1H, d, J=9.6 Hz), 6.41 (1H, d, J=8.0 Hz), 6.41 (1H, brs), 6.51 (1H, dd, J=3.2, 0.8 Hz), 7.07 (1H, t, J=8.0 Hz), 7.22 (1H, d, J=8.0 Hz), 7.31 (1H, d, J=2.8 Hz), 7.46 (1H, dd, J=8.0, 4.8 Hz), 7.80 (1H, ddd, J=8.0, 2.0, 1.6 Hz), 8.55 (1H, dd, J=4.8, 1.6 Hz), 8.60 (1H, d, J=2.0 Hz), 9.14 (1H, brs), 9.44 (1H, brs).

Reference Example 113

N-(2-Methoxy-6-methylphenyl)acetamide

To a solution of 3-methyl-2-nitroanisole (10.00 g, 59.8 mmol) in ethanol (60 mL)-tetrahydrofuran (60 mL) is added a 10% palladium on carbon (50% wet, 2.00 g), and the mixture is subjected to hydrogenation, and stirred at room temperature for 1.5 hour. After the reaction is completed, the reaction solution is filtered through celite, and the solvent is evaporated under reduced pressure. To a solution of the residue in ethyl acetate (110 ml) is added acetic anhydride (9.0 mL, 95.2 mmol), and the mixture is refluxed for 5 hours. The reaction solution is cooled with ice, and the precipitated solid is collected by filtration, and washed with hexane to give the title compound (9.28 g, yield: 87%).

$^1$H-NMR (CDCl$_3$) δ: 2.21 (3H, s), 2.24 (3H, s), 3.81 (3H, s), 6.75 (1H, d, J=8.0 Hz), 6.85 (1H, d, J=8.0 Hz), 7.13 (1H, t, J=8.0 Hz).

Reference Example 114

7-Methoxy-1H-indazole

To a solution of N-(2-methoxy-6-methylphenyl)acetamide (9.28 g, 51.8 mmol) in ethyl acetate (100 ml) are added acetic anhydride (14.7 mL, 156 mmol), tetrabutylammonium bromide (0.84 g, 2.61 mmol), potassium acetate (10.16 g, 104 mmol), and isoamyl nitrite (9.1 mL, 67.7 mmol), and the mixture is refluxed for 9 hours. After the reaction is completed, the solvent is evaporated under reduced pressure, and to the obtained residue is added 6N aqueous sodium hydroxide solution (100 mL). The mixture is stirred at room temperature for 1 hour. After the reaction is completed, the pH value of the mixture is adjusted to pH 7–8 with 3N hydrochloric acid, and the mixture is extracted with chloroform. The organic layer is dried over anhydrous magnesium sulfate, and the solvent is evaporated under reduced pressure. The obtained residue is purified by silica gel column chromatography (n-hexane/ethyl acetate=3/1→1/1) to give the title compound (3.95 g, yield: 51%).

$^1$H-NMR (DMSO-d$_6$) δ: 3.94 (3H, s), 6.82 (1H, d, J=7.5 Hz), 7.02 (1H, dd, J=8.0, 7.5 Hz), 7.30 (1H, d, J=8.0 Hz), 8.01 (1H, d, J=1.5 Hz), 13.27 (brs, 1H).

Reference Example 115

3-Iodo-7-methoxy-1H-indazole

To a solution of 7-methoxy-1H-indazole (2.60 g, 17.5 mmol) in N,N-dimethylformamide (50 mL) are added iodine (6.68 g, 26.3 mmol) and potassium hydroxide (2.79 g, 49.7 mmol), and the mixture is stirred at room temperature for 0.5 hour. The reaction solution is poured into a 10% aqueous sodium hydrogen sulfite solution (200 mL), and the mixture is extracted with diethyl ether. The organic layer is washed with water and a saturated brine, and dried over anhydrous magnesium sulfate. The solvent is evaporated under reduced pressure, and the obtained residue is purified by silica gel column chromato-graphy (n-hexane/ethyl acetate=5/1) to give the title compound (3.97 g, yield: 83%).

$^1$H-NMR (CDCl$_3$) δ: 3.99 (3H, s), 6.80 (1H, d, J=7.4 Hz), 7.09 (1H, d, J=8.1 Hz), 7.15 (1H, dd, J=8.1, 7.4 Hz), 10.24 (1H, brs).

Reference Example 116 tert-Butyl 3-iodo-7-methoxy-1H-indazole-1-carboxylate

To a solution of 3-iodo-7-methoxy-1H-indazole (1.33 g, 4.86 mmol) in acetonitrile (20 mL) are added di-t-butyl bicarbonate (1.34 mL, 5.83 mmol), triethylamine (0.81 mL, 5.81 mmol) and N,N-dimethyl-aminopyridine (60.0 mg, 0.491 mmol), and the mixture is stirred at room temperature for 3 hours. To the reaction solution is added water, and the mixture is extracted with ethyl acetate. The organic layer is washed with a saturated brine, and dried over anhydrous magnesium sulfate. The solvent is evaporated under reduced pressure, and the obtained residue is purified by silica gel column chromatography (n-hexane/ethyl acetate=5/1) to give the title compound (1.79 g, yield: 98%).

$^1$H-NMR (CDCl$_3$) δ: 1.68 (9H, s), 3.99 (3H, s), 7.01 (1H, d, J=7.8 Hz), 7.10 (1H, dd, J=8.0, 0.7 Hz), 7.30 (1H, dd, J=8.0, 7.8 Hz).

Reference Example 117 tert-Butyl 7-methoxy-3-[(1E)-3-methoxy-3-oxopropyl-1-en-1-yl]-1 H-indazole-1-carboxylate To a solution of tert-butyl 3-iodo-7-methoxy-1H-indazole-1-carboxylate (484 mg, 1.29 mmol) in N,N-dimethylformamide:water (11:1, 76 mL) are added triethylamine (1.76 mL, 12.6 mmol), methyl acrylate (1.17 mL, 13.0 mmol), dichloro[1,1'-bis(diphenylphosphono)ferrocene]-palladium (190 mg, 0.259 mmol) and tetra-n-butylammonium iodide (954 mg, 2.58 mmol), and the mixture is refluxed at 50° C. for 4 hours. After the reaction is completed, the excess methyl acrylate is removed by distillation under reduced pressure, and to the residue is added water (100 mL). The precipitates are collected by filtration, dissolved in ethyl acetate, and filtered through celite. The solvent is evaporated under reduced pressure, and the obtained residue is purified by silica gel column chromatography (n-hexane/ethyl acetate=3/1) to give the title compound (145 mg, yield: 38%).

$^1$H-NMR (CDCl$_3$) δ: 1.69 (9H, s), 3.84 (3H, s), 3.99 (3H, s), 6.99 (1H, d, J=16.3 Hz), 6.98 (1H, d, J=7.7 Hz), 7.32 (1H, dd, J=8.0, 7.7 Hz), 7.49 (1H, dd, J=8.0, 0.6 Hz), 7.96 (1H, d, J=16.3 Hz).

Reference Example 118

Methyl (2E)-3-(7-methoxy-1H-indazol-3-yl)acrylate

To a solution of tert-butyl 7-methoxy-3-[(1E)-3-methoxy-3-oxo-propyl-1-en-1-yl]-1H-indazole-1-carboxylate (147 mg, 0.442 mmol) in tetrahydrofuran (2 mL) is added a solution of sodium methoxide in methanol (0.2 mL), and the mixture is stirred at room temperature overnight. To the reaction solution is added water, and the mixture is extracted with diethyl ether. The organic layer is washed with a saturated brine, and dried over anhydrous magnesium sulfate. The solvent is evaporated under reduced pressure, and the obtained residue is purified by silica gel column chromatography (n-hexane/ethyl acetate=3/1) to give the title compound (98.5 mg, yield: 96%).

$^1$H-NMR (CDCl$_3$) δ: 3.85 (3H, s), 4.01 (3H, s), 6.79 (1H, d, J=16.3 Hz), 6.80 (1H, d, J=7.6 Hz), 7.20 (1H, dd, J=8.1, 7.6 Hz), 7.50 (1H, d, J=8.1 Hz), 8.02 (1H, d, J=16.3 Hz), 10.46 (1H, brs).

Reference Example 119

Methyl 3-(7-methoxy-1H-indazol-3-yl)propanoate

To a solution of m-ethyl (2E)-3-(7-methoxy-1H-indazol-3-yl)-acrylate (143 mg, 0.614 mmol) in methanol (10 mL) is added nickel chloride.6 hydrate (73.0. mg, 0.307 mmol), and further thereto is added sodium borohydride (93 mg, 2.46 mmol) under ice-cooling over a period of 0.5 hour. The mixture is stirred at room temperature for 4.5 hours. After the reaction is completed, the solvent is evaporated under reduced pressure. Water is added to the residue, and the mixture is extracted with ethyl acetate. The organic layer is washed with a saturated brine, and dried over anhydrous magnesium sulfate. The solvent is evaporated under reduced pressure, and the obtained residue is purified by silica gel column chromatography (n-hexane/ethyl acetate=3/1) to give the title compound (122 mg, yield: 85%).

$^1$H-NMR (CDCl$_3$) acrylate δ: 2.89 (2H, dd, J=8.0, 7.4 Hz), 3.30 (2H, dd, J=8.0, 7.4 Hz), 3.70 (3H, s), 3.97 (3H, s), 6.73 (1H, d, J=7.5 Hz), 7.06 (1H, dd, J=8.1, 7.5 Hz), 7.28 (1H, dd, J=8.1, 0.3 Hz), 10.06 (1H, brs)

Reference Example 120

3-(7-Methoxy-1H-indazol-3-yl)propanoic acid

To a solution of methyl 3-(7-methoxy-1H-indazol-3-yl)-propanoate (140 mg, 0.596 mmol) in tetrahydrofuran (2 mL) is added a 6N aqueous sodium hydroxide solution (2 ml), and the mixture is stirred at room temperature overnight. The reaction solution is washed with diethyl ether, and the aqueous layer is acidified with 6N hydrochloric acid, and the mixture is extracted with diethyl ether. The organic layer is dried over anhydrous magnesium sulfate, and the solvent is evaporated under reduced pressure to give the title compound (123 mg, yield: 94%).

$^1$H-NMR (CDCl$_3$) δ: 2.89 (dd, 2H, J=8.0, 7.4 Hz), 3.30 (dd, 2H, J=8.0, 7.4 Hz), 3.70 (s, 3H), 3.97 (s, 3H), 6.73 (d, 1H, J=7.5 Hz), 7.06 (dd, 1H, J=8.1, 7.5 Hz), 7.28 (dd, 1H, J=8.1, 0.3 Hz), 10.06 (brs, 1H).

Reference Example 121 tert-Butyl
[2-(7-methoxy-1H-indazol-3-yl)ethyl]carbamate

Under nitrogen atmosphere, to a solution of 3-(7-methoxy-1H-indazol-3-yl)propanoic acid (86.4 mg, 0.392 mmol) in toluene (5 mL)-tert-butanol (2.5 mL) are added triethylamine (80.0 μL, 0.574 mmol) and diphenylphosphoryl azide (110 μL, 0.510 mmol), and the mixture is stirred at room temperature for 2 hours. The mixture is stirred at 60° C. for 1 hour, and further stirred at 100° C. for 5 hours. The mixture is allowed to cool to room temperature, and thereto is added a saturated aqueous sodium hydrogen carbonate solution, and the mixture is extracted with ethyl acetate. The organic layer is dried over anhydrous magnesium sulfate, and the solvent is evaporated under reduced pressure. The obtained residue is purified by silica gel column chromatography (n-hexane/ethyl acetate=3/1) to give the title compound (94.3 mg, yield: 82%).
$^1$H-NMR (CDCl$_3$) δ: 1.43 (s, 9H), 3.17 (dd, 1H, J=12, 6.6 Hz), 3.62 (dd, 1H, J=12, 5.9 Hz), 3.98 (s, 3H), 5.08 (brs, 1H), 6.74 (d, 1H, J=7.5 Hz), 7.04 (dd, 1H, J=8.1, 7.5 Hz), 7.27 (d, 1H, J=8.1 Hz), 10.19 (brs, 1H).

Reference Example 122 tert-Butyl
[2-(7-hydroxy-1H-indazol-3-yl)ethyl]carbamate

To a solution of tert-butyl [2-(7-methoxy-1H-indazol-3-yl)ethyl]-carbamate (91.8 mg, 0.315 mmol) in dichloromethane (1 mL) is added a solution of boron tribromide (1.0 M dichloromethane solution, 0.95 mL, 0.95 mmol) under nitrogen atmosphere, and the mixture is refluxed for 2.5 hours. The reaction solution is cooled with ice, and thereto is added dropwise methanol (3 ml), and the mixture is stirred at room temperature for 2 hours. The solvent is concentrated under reduced pressure to give a crude phenol product.
To a solution of the crude phenol product in acetonitrile (3.5 mL) are added triethylamine (100 μL, 0.717 mmol) and di-t-butyl bicarbonate (72.4 μL, 0.315 mmol) under nitrogen atmosphere, and the mixture is stirred at room temperature for 0.5 hour. Water is added to the reaction solution, and the mixture is extracted with ethyl acetate. The organic layer is washed with a saturated brine, and dried over anhydrous magnesium sulfate. The solvent is evaporated under reduced pressure, and the obtained residue is purified by silica gel column chromatography (n-hexane/ethyl acetate=2/1) to give the title compound (46.0. mg, yield: 54% (2 steps)).
$^1$H-NMR (DMSO-d$_6$) δ: 1.37 (s, 9H), 2.96 (dd, 2H, J=8.1, 7.1 Hz), 3.24–3.30 (m, 2H), 6.63 (d, 1H, J=7.2 Hz), 6.85 (dd, 1H, J=8.0, 7.2 Hz), 6.88 (t, 1H, 5.7 Hz), 7.10 (d, 1H, J=8.0 Hz), 9.98 (brs, 1H), 12.65 (brs, 1H).

Reference Example 123 tert-Butyl (2-{7-[(1S)-1-methyl-2-morpholin-4-yl-2-oxoethoxy]-1H-indazol-3-yl}ethyl)carbamate The title compound is obtained in a similar manner to Reference Example 84.
$^1$H-NMR (CDCl$_3$) δ: 1.41 (s, 9H), 1.68 (d, 3H, J=6.7 Hz), 3.17 (t, 2H, J=6.4 Hz), 3.43–3.47 (m, 1H), 3.56–3.64 (m, 9H), 5.28 (q, 1H, J=6.7 Hz), 5.22 (m, 1H), 6.72 (d, 1H, J=7.6 Hz), 7.01 (dd, 1H, J=8.1, 7.6 Hz), 7.33 (d, 1H, J=8.1 Hz).

Reference Example 124

(2-{7-[(1S)-1-Methyl-2-morpholin-4-yl-2-oxoethoxy]-1 H-indazol-3-yl}-ethyl)amine The title compound is obtained in a similar manner to Reference Example 106.
$^1$H-NMR (CDCl$_3$) δ: 1.69 (d, 3H, J=6.7 Hz), 3.10–3.18 (m, 4H), 3.42–3.46 (m, 1H), 3.56–3.64 (m, 7H), 5.15 (q, 1H, J=6.7 Hz), 6.72 (d, 1H, J=7.6 Hz), 7.02 (dd, 1H, J=8.1, 7.6 Hz), 7.33 (d, 1H, J=8.1 Hz).

Example 186

(2S)-2-{[3-(2-{[(2R)-2-Hydroxy-2-pyridin-3-yl-ethyl]amino}ethyl)-1H-indazol-7-yl]oxy}propanoic acid The title compound is obtained in a similar manner to Example 183.
$^1$H-NMR (CD$_3$OD) δ: 1.71 (d, 3H, J=6.8 Hz), 3.33–3.36 (m, 1H), 3.39–3.43 (m, 2H), 3.49 (dd, 1H, J=12.8, 3.1 Hz), 3.53–3.63 (m, 2H), 5.02 (q, 1H, J=6.8 Hz), 5.25 (dd, 1H, J=9.8, 3.1 Hz), 6.75 (d, 1H, J=7.6 Hz), 7.05 (dd, 1H, J=8.1, 7.6 Hz), 7.33 (d, 1H, J=8.1 Hz), 7.90 (dd, 1H, J=7.3, 6.1 Hz), 8.43 (d, 1H, J=8.0 Hz), 8.74 (d, 1H, J=5.3Hz), 8.85 (s, 1H).

Reference Example 125

2-{[tert-Butyl(dimethyl)silyl]oxy}-6-nitroaniline

The title compound is obtained in a similar manner to Reference Example 107.
$^1$H-NMR (CD30D) δ: 0.28 (s, 6H), 1.04 (s, 9H), 6.29 (brs, 2H), 6.53 (dd, 1H, J=8.8, 7.5 Hz), 6.89 (dd, 1H, J=7.5, 1.3 Hz), 7.75 (dd, 1H, J=8.8, 1.4 Hz).

Reference Example 126

3-{[tert-Butyl(dimethyl)silyl]oxy}benzen-1,2-diamine

To a solution of 2-{[tert-butyl(dimethyl)silyl]oxy}-6-nitroaniline (8.5 g, 31.7 mmol) in tetrahydrofuran (100 mL) is added a 10% palladium on carbon (50% wet, 8.2 g), and the mixture is vigorously stirred under hydrogen atmosphere at room temperature for one hour. The catalyst is removed by filtration, and the filtrate is concentrated under reduced pressure. The obtained residue is purified by silica gel column chromatography (ethyl acetate/n-hexane=1/5, 1/3 and 1/1) to give the title compound as brown oil (6.95 g, yield: 92%).
$^1$H-NMR (CD$_3$OD) δ: 6.56 (t, 1H, J=8.0 Hz), 6.37 (dd, 1H, J=8.0, 1.3 Hz), 6.34 (dd, 1H, J=8.0, 1.3 Hz), 3.15 (brs, 4H), 1.02 (s, 9H), 0.24 (s, 6H).

Reference Example 127

7-{[tert-Butyl(dimethyl)silyl]oxy}1H-benzimidazole

To 3-{[tert-butyl(dimethyl)silyl]oxy}benzene-1,2-diamine (4.27 g, 17.9 mmol) is added diethoxymethyl acetate (8.7 g, 53.6 mmol), and the mixture is stirred at room temperature for 5 hours. The precipitated white solid is collected by filtration, and the filtrate is further stirred at room temperature for 12 hours. The precipitated white solid is collected by filtration, and washed with a small amount of hexane. The filtrate is concentrated under reduced pressure, ant the obtained residue is purified by silica gel column chromatography (ammonic chloroform) to give the title compound as white solid (1.89 g, yield: 43%).

$^1$H-NMR (CD$_3$OD) δ: 9.16 (brs, 1H), 7.98 (s, 1H), 7.44 (brs, 1H), 7.13 (t, 1H, J=8.1 Hz), 6.73 (d, 1H, J=8.6 Hz), 1.05 (s, 9H), 0.29 (s, 6H).

Reference Example 128

(4-{[tert-Butyl(dimethyl)silyl]oxy}-1H-benzimidazol-1-yl)acetonitrile

The title compound is obtained in a similar manner to Reference Example 108.

$^1$H-NMR (CD$_3$OD) δ: 7.85 (s, 1H), 7.25 (t, 1H, J=8.0 Hz), 7.06 (dd, 1H, J=8.0, 0.8 Hz), 6.80 (dd, 1H, J=8.0, 0.8 Hz), 5.05 (s, 2H), 1.06 (s, 9H), 0.29 (s, 6H).

Reference Example 129

[2-(4-{[tert-Butyl(dimethyl)silyl]oxy}-1H-benzimidazol-1-yl) ethyl]amine

The title compound is obtained in a similar manner to Reference Example 109 except that a 10% palladium on carbon (50% wet) is used instead of active Raney-nickel.

$^1$H-NMR (CD$_3$OD) δ: 7.87 (s, 1H), 7.14 (t, 1H, J=8.0 Hz), 7.01 (dd, 1H, J=8.0, 0.7 Hz), 6.72 (dd, 1H, J=8.0, 0.7 Hz), 4.21 (t, 2H, J=5.9 Hz), 3.15 (t, 2H, J=5.9 Hz), 1.06 (s, 9H), 0.30 (s, 6H).

Example 187

(1R)-2-[(2-{4-[(1S)-1-Methyl-2-morpholin-4-yl-2-oxoethoxy]-1H-benzimidazol-1-yl}ethyl)amino]-1-pyridin-3-ylethanol The title compound is obtained in a similar manner to Reference Examples 61, 111 and 112 and Example 119.

$^1$H-NMR (CD$_3$OD) δ: 1.67 (d, 1H, J=6.4 Hz), 3.40–3.45 (m, 1H), 3.58–3.98 (m, 11H), 5.04–5.06 (m, 2H), 5.46 (d, 1H, J=8.3 Hz), 5.63 (q, 1H, J=6.4 Hz), 7.11 (d, 1H, J=7.9 Hz), 7.62 (t, 1H, J=8.0 Hz), 7.71 (d, 1H, J=8.3 Hz), 8.16 (dd, 1H, J=7.4, 6.1 Hz), 8.80 (d, 1H, J=7.9 Hz), 8.87 (d, 1H, J=5.4 Hz), 9.04 (s, 1H), 9.66 (s, 1H).

Example 188

(2S)-2-{[1-(2-{[(2R)-2-Hydroxy-2-pyridin-3-yl-ethyl]amino}ethyl)-1H-benzimidazol-4-yl]oxy}propanoic acid The title compound is obtained in a similar manner to Example 120.

$^1$H-NMR (CD$_3$OD) δ:1.74 (d, 3H, J=6.8 Hz), 3.30–3.37 (m, 3H), 3.52 (dd, 1H, J=12.6, 3.2 Hz), 3.72–3.83 (m, 2H), 5.18 (q, 1H, J=6.8 Hz), 5.29 (dd, 1H, J=9.7, 3.0 Hz), 7.07 (dd, 1H, J=6.4, 2.3 Hz), 7.53–7.58 (m, 2H), 7.97 (dd, 1H, J=7.9, 5.7 Hz), 8.52 (d, 1H, J=8.1Hz), 8.77 (d, 1H, J=5.3 Hz), 8.87 (s, 1H), 9.39 (s, 1H).

Experiment 1

Human β3, β2 and β1-receptor stimulation test

Human β3-receptor-stimulating activity was studied using SK-N-MC cell line, i.e., cells permanently expressing human β3- and human β1-receptors (SK-N-MC cells, purchased from Dainippon Pharmaceutical Co., Ltd.), and human β2- and β1-receptor-stimulating activities were studied using THP-1 cell line, i.e., cells expressing both human β2- and β1-receptors (THP-1 cells, purchased Dainippon Pharmaceutical Co., Ltd.).

The β3-receptor stimulating activity of a test compound ($10^{-9}$ to $10^{-5}$ M) was studied using as an index cyclic AMP (hereinafter, referred to as cAMP) producing activity of SK-N-MC cells at almost confluent in the presence of a β1-receptor inhibitor ((±)-2-hydroxy-5-(2-((2-hydroxy-3-(4-(1-methyl-4-(trifluoromethyl)-1H-imidazol-2-yl)phenoxy)propyl)-amino)ethoxy)benzamide methanesulfonate, CGP-20712A (Sigma-Aldrich), $10^{-6}$M), wherein said SK-N-MC cells were seeded into a 96-well plate at a cell density of $2\times10^4$ cells/well and had been cultured for 3 days. The β2-receptor-stimulating activity of a test compound was studied by stimulating floating THP-1 cells ($2.5\times10^5$ cells) with a test compound in the presence of a β1-receptor inhibitor (the above-mentioned CGP-20712A, $10^{-6}$ M), and the β1-receptor stimulating activity was studied by stimulating floating THP-1 cells ($2.5\times10^4$ cells) with a test compound in the presence of a β2-receptor inhibitor ((R*,S*)-(±)-1-((2,3-dihydro-7-methyl-1H-inden-4-yl)oxy)-3-((1-methylethyl)-amino)-2-butanol hydrochloride, ICI-118551 (Sigma-Aldrich), $10^{-8}$M), and both activities were evaluated with using as an index cAMP producing activity thereof. The cAMP production in the cells was measured by ELISA method.

The action potency of each compound was evaluated by calculating EC$_{50}$ value ($-\log_{10}$ EC$_{50}$=pD$_2$) and intrinsic activity (%) from the dose-response curve thus obtained, wherein the responses to $10^{-6}$ M isoproterenol, $10^{-5}$ M salmeterol and $10^{-5}$ M isoproterenol were counted as 100% for β3-receptor-stimulating activity, β2-receptor-stimulating activity and β1-receptor-stimulating activity, respectively, and comparing them. It was confirmed that the present compound exhibits a selective stimulating activity on human β3-receptor.

For example, the EC$_{50}$ value of β3-stimulating activity of the compound of Example 2 was 48 nM while the β1- and β2-stimulating activities thereof were not observed up to a maximum concentration of 10 μM.

Experiment 2

Effect of a medicament on autonomic beat of the excised right atrium specimen based on β1-adrenoceptor-stimulating activity (study on positive chronotropic action)

The heart of Hartley guinea pig was excised, and a right atrium specimen was prepared therefrom and the experiment was carried out thereon according to Magnus method. The specimen was hung at 34° C. in Krebs-Henseleit solution to which a mixed gas of 95% oxygen and 5% carbon dioxide was aerated, and loaded so that the maximum resting tension became about 0.5 g. The autonomic beat of the right atrium was detected through a pressure transducer, and the tension and the beat were continuously recorded onto a linear recorder. A medicament was cumulatively added every time the beat became plateau. With counting the maximum increase in the beat by isoproterenol as 100%, the ratio of the maximum increase in the beat by a medicament to that of isoproterenol was calculated, and the potency of a medicament was evaluated in terms of EC$_{50}$ value, which was a concentration of the medicament to be required for increasing the beat by 50% of the maximum increase of the beat by said medicament.

In order to show the divergence between β3-stimulating activity/β1-stimulating activity in the experimental results, the $EC_{50}$ value of positive chronotropic action of the test compound of Examples obtained in Experiment 2 was divided by the $EC_{50}$ value of human β3-stimulating activity of said compound obtained in Experiment 1, which is the main activity in Experiment 1. The results are expressed by relative values, which are calculated by counting the value of the reference compound (AJ 9677) as 1.

As shown below, the compound of the feature [1] as defined herein before, especially the compound of the feature [2], exhibited a high divergence between β3-stimulating activity and β1-stimulating activity even in the evaluation system using tissues, as compared to the reference compound (AJ 9677) which was disclosed in JP-A-11-255743.

Relative divergence between $EC_{50}$ value of human β3-stimulating activity and $EC_{50}$ value of positive chronotropic effect of some compounds of the Examples (relative values when the value of the reference compound (AJ 9677) is counted as 1)

The compound of Example 14:

| | |
|---|---|
| The compound of Example 14: | 68 |
| The compound of Example 73: | 77 |
| The compound of Example 76: | 300 |
| The compound of Example 114: | 230 |
| The compound of Example 121: | 78 |
| The compound of Example 150: | 470 |
| The compound of Example 154: | 90 |
| Reference compound (AJ 9677): | 1 |

INDUSTRIAL APPLICABILITY

The indole, indazole, and benzazole derivatives of the formula (I) and a pharmaceutically acceptable salt thereof exhibit excellent β3-adrenoceptor-stimulating activity, and are useful as a medicament for treatment of obesity, hyperglycemia, diseases caused by increased intestinal motility, frequent urination, urinary incontinence, depression, bilestone, or disease caused by increased biliary tract motility.

The invention claimed is:

1. A compound of the formula (I):

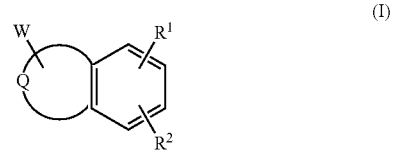

(I)

wherein W is a group of the following formula (VIII) binding to any possible position on Q;

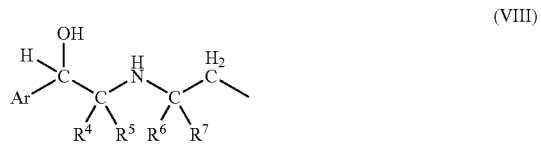

(VIII)

Q is, together with W, a group of the formula: —C(W)=C($R^{3A}$)—N($R^3$)— or —C($R^{3A}$)=C(W)—N($R^3$);

$R^{3A}$ is independently a hydrogen atom or an optionally substituted lower alkyl group;

$R^4$, $R^5$, $R^6$, and $R^7$ are independently a hydrogen atom or an optionally substituted lower alkyl group;

$R^1$ is a group of the formula: —X—$R^{1e}$—C(=O)NR$^{1a}$R$^{1b}$, —X—$R^{1e}$—C(=O)OR$^{1a}$ or —X—$R^{1d}$ in which X is —O—, —S—, or —SO$_2$N(R$^{1c}$)—, and $R^{1e}$ is a direct bond or an optionally substituted lower alkylene group, $R^{1a}$, $R^{1b}$, and $R^{1c}$ are independently a hydrogen atom, an optionally substituted lower alkyl group, an optionally substituted aralkyl group, an optionally substituted aryl group, or an optionally substituted cycloalkyl group;

$R^{1d}$ is a hydrogen atom, an optionally substituted lower alkyl group, an optionally substituted phenyl group, or an optionally substituted cycloalkyl group;

$R^2$ is a hydrogen atom, a halogen atom, an optionally substituted lower alkyl group, an optionally substituted lower alkenyl group, an optionally substituted amino group, a hydroxy group, a lower alkoxy group, or $R^3$ is a hydrogen atom or an optionally substituted lower alkyl group, or $R^1$ and $R^3$ may combine each other and form a divalent group of the formula: —X—$R^{1e}$—C(=O)— (provided that the bond at the carbonyl side of the above formula binds to the atom to which $R^3$ of the compound of the formula (I) attaches);

Ar is a group of the following formula (XIII);

(XIII)

(in which $R^{17}$ is a hydrogen atom, a halogen atom, or a cyano group);

or a pharmaceutically acceptable salt thereof.

2. The compound according to claim 1, wherein $R^1$ is a group of the formula: —X—$R^{1e}$—C(=O)NR$^{1a}$R$^{1b}$ or the formula: —X—$R^{1e}$—C(=O)OR$^{1a}$, or $R^1$ and $R^3$ may combine each other and form a divalent group of the formula: —X—$R^{1e}$—C(=O)—, wherein X is a group of the formula: —O— or —S—, and $R^{1e}$ is a group of the formula: —CR$^{1f}$R$^{1g}$—, wherein $R^{1f}$ and $R^{1g}$ are independently a hydrogen atom, an optionally substituted lower alkyl group, an optionally substituted cycloalkyl group, an optionally substituted aryl group, or an optionally substituted aralkyl group, or both may combine each other, and with the carbon atom to which they bond, form an optionally substituted cycloalkane ring, provided that both $R^{1f}$ and $R^{1g}$ are not simultaneously a hydrogen atom, or a pharmaceutically acceptable salt thereof.

3. The compound according to claim 1 or claim 2, which is a compound of the formula (I'):

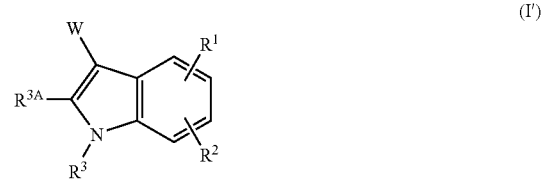

(I')

wherein $R^1$, $R^2$, $R^3$, $R^{3A}$, and W are as defined in claim 1, or a pharmaceutically acceptable salt thereof.

4. The compound according to claim 3, wherein $R^1$ binds to the 5-, 6- or 7-position of the indole ring of the compound of the formula (I'), and $R^2$ is a hydrogen atom, or a pharmaceutically acceptable salt thereof.

5. The compound according to claim 3, wherein $R^2$ is a group other than a hydrogen atom, and one of $R^1$ and $R^2$ binds to the 6-position of the indole ring of the compound of the formula (I'), and the other binds to the 7-position thereof, or a pharmaceutically acceptable salt thereof.

6. The compound according to claim 1, wherein Ar is a group selected from the following substituents:

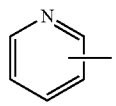

or a pharmaceutically acceptable salt thereof.

7. The compound according to claim 1, wherein $R^1$ is a group of the formula: —X—$R^{1e}$—C(=O)$NR^{1a}R^{1b}$ or —X—$R^{1e}$—C(=O)$OR^{1a}$;

X is —O—;

$R^{1a}$, and $R^{1b}$ when it exists, are independently selected from
  (i) a hydrogen atom,
  (ii) an unsubstituted lower alkyl group,
  (iii) a lower alkyl group being substituted by one or more substituents, which are the same or different, and said substituent(s) are selected from a carboxyl group, a lower alkoxycarbonyl group, an amino group, a hydroxy group, an alkoxy group, a mercapto group, an alkylthio group, a carbamoyl group, an indolyl group, a guanidino group, an imidazolyl group, and a phenyl group optionally being substituted by a hydroxy group, or a pharmaceutically acceptable salt thereof.

8. The compound according to claim 2, wherein $R^1$ is a group of the formula: —X—$CR^{1f}R^{1g}$—C(=O)$OR^{1a}$, or a pharmaceutically acceptable salt thereof.

9. The compound according to claim 2, wherein X is a group of the formula: —O—, or a pharmaceutically acceptable salt thereof.

10. A pharmaceutical composition comprising as an active ingredient the compound as set forth in claim 1, or a pharmaceutically acceptable salt thereof.

11. A method for treatment of obesity, hyperglycemia, frequent urination, or urinary incontinence which comprises administering to a patient in need an effective amount of the compound as set forth in claim 1, or a pharmaceutically acceptable salt thereof.

* * * * *